US008815175B2

(12) United States Patent
Bryer et al.

(10) Patent No.: US 8,815,175 B2
(45) Date of Patent: Aug. 26, 2014

(54) INTEGRATED METER FOR ANALYZING BIOLOGICAL SAMPLES

(75) Inventors: Philip Bryer, Tarzana, CA (US); Irving Lee, Palo Alto, CA (US); Stephen J. Schoenberg, Upper Moutere (NZ); Lloyd M. Berken, Fremont, CA (US); Jean-Pierre Giraud, Paris (FR)

(73) Assignee: Abbott Diabetes Care Inc., Alameda, CA (US)

( * ) Notice: Subject to any disclaimer, the term of this patent is extended or adjusted under 35 U.S.C. 154(b) by 755 days.

(21) Appl. No.: 12/488,181

(22) Filed: Jun. 19, 2009

(65) Prior Publication Data

US 2009/0270765 A1 Oct. 29, 2009

Related U.S. Application Data

(63) Continuation-in-part of application No. 11/535,985, filed on Sep. 28, 2006, now Pat. No. 7,922,971.

(60) Provisional application No. 60/741,019, filed on Nov. 30, 2005, provisional application No. 61/168,549, filed on Apr. 10, 2009.

(51) Int. Cl.
*G01N 21/75* (2006.01)
*C12Q 1/68* (2006.01)
*G01N 15/06* (2006.01)
*A61B 5/00* (2006.01)

(52) U.S. Cl.
USPC ............ 422/410; 422/50; 422/68.1; 600/300; 600/583

(58) Field of Classification Search
CPC ............ A61B 5/1411; A61B 5/15146; A61B 2562/0295; A61B 5/14532; A61B 5/157; A61B 5/15142; A61B 5/151; A61B 5/150022; A61B 5/150297; A61B 5/150549; A61B 5/150618; A61B 5/150625; A61B 5/150717; A61B 5/15111; A61B 5/15113; A61B 5/15117; C12Q 1/006; C12Q 1/005; C12Q 1/54; G01N 27/327; G01N 27/3272; G01N 33/48; G01N 35/00663; G01N 33/4875; G01N 33/54386
USPC .............. 422/50, 68.1; 436/95, 128; 600/300, 600/583
See application file for complete search history.

(56) References Cited

U.S. PATENT DOCUMENTS

| | | | |
|---|---|---|---|
| 4,895,147 A | 1/1990 | Bodicky et al. |
| 5,279,294 A | 1/1994 | Anderson et al. |
| 5,487,748 A | 1/1996 | Marshall et al. |
| 5,971,941 A | 10/1999 | Simons et al. |
| 6,129,823 A | 10/2000 | Hughes et al. |
| 6,315,738 B1 | 11/2001 | Nishikawa et al. |
| 6,377,894 B1 | 4/2002 | Deweese et al. |
| 6,541,216 B1 | 4/2003 | Wilsey et al. |
| 6,561,989 B2 | 5/2003 | Whitson |
| 6,670,115 B1 | 12/2003 | Zhang |
| 6,783,502 B2 | 8/2004 | Orloff et al. |
| 6,939,450 B2 | 9/2005 | Karinka et al. |
| 7,118,667 B2 | 10/2006 | Lee |
| 7,299,081 B2 | 11/2007 | Mace et al. |
| 2002/0002344 A1 | 1/2002 | Douglas et al. |
| 2003/0068666 A1 | 4/2003 | Zweig |
| 2003/0191415 A1 | 10/2003 | Moerman et al. |

(Continued)

*Primary Examiner* — Dean Kwak
(74) *Attorney, Agent, or Firm* — Edward J. Baba; Bozicevic, Field & Francis LLP

(57) ABSTRACT

Analyte monitoring devices and methods therefore are provided. The devices integrate various functions of analyte monitoring, e.g., sample acquisition and testing.

22 Claims, 83 Drawing Sheets

(56) References Cited

U.S. PATENT DOCUMENTS

| | | |
|---|---|---|
| 2003/0209451 A1 | 11/2003 | Dineen et al. |
| 2003/0211619 A1 | 11/2003 | Olson et al. |
| 2003/0212345 A1* | 11/2003 | McAllister et al. ........... 600/584 |
| 2004/0134779 A1 | 7/2004 | Hsu et al. |
| 2005/0234368 A1* | 10/2005 | Wong et al. .................. 600/583 |
| 2005/0277850 A1 | 12/2005 | Mace et al. |
| 2006/0094985 A1 | 5/2006 | Aceti et al. |
| 2006/0229532 A1 | 10/2006 | Wong et al. |
| 2007/0149897 A1 | 6/2007 | Ghesquiere et al. |
| 2007/0173739 A1 | 7/2007 | Chan |
| 2007/0287191 A1 | 12/2007 | Stiene et al. |
| 2008/0039946 A1 | 2/2008 | Zucherman et al. |
| 2008/0039949 A1 | 2/2008 | Meesenburg et al. |
| 2008/0167578 A1 | 7/2008 | Bryer et al. |
| 2009/0321287 A1 | 12/2009 | List et al. |

* cited by examiner

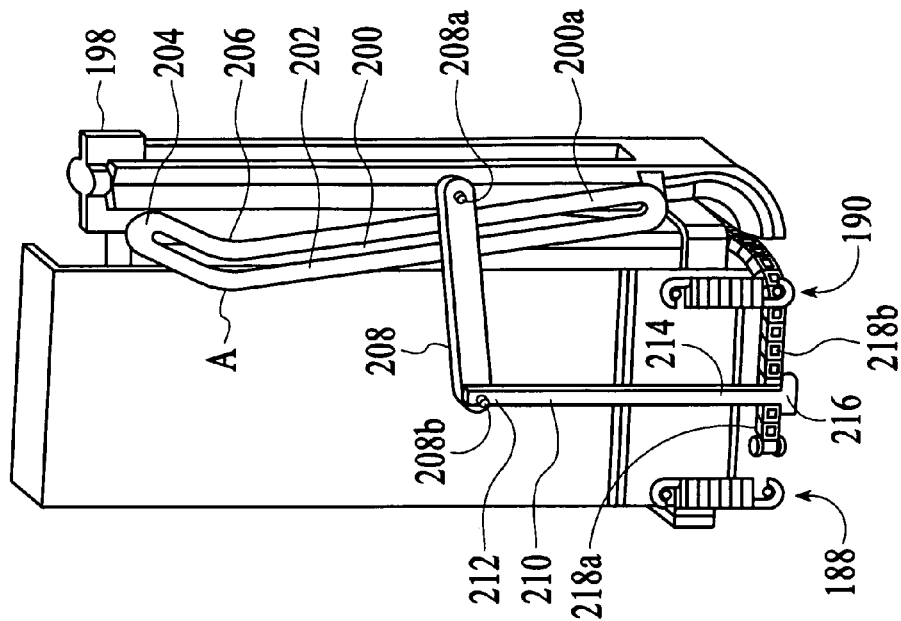
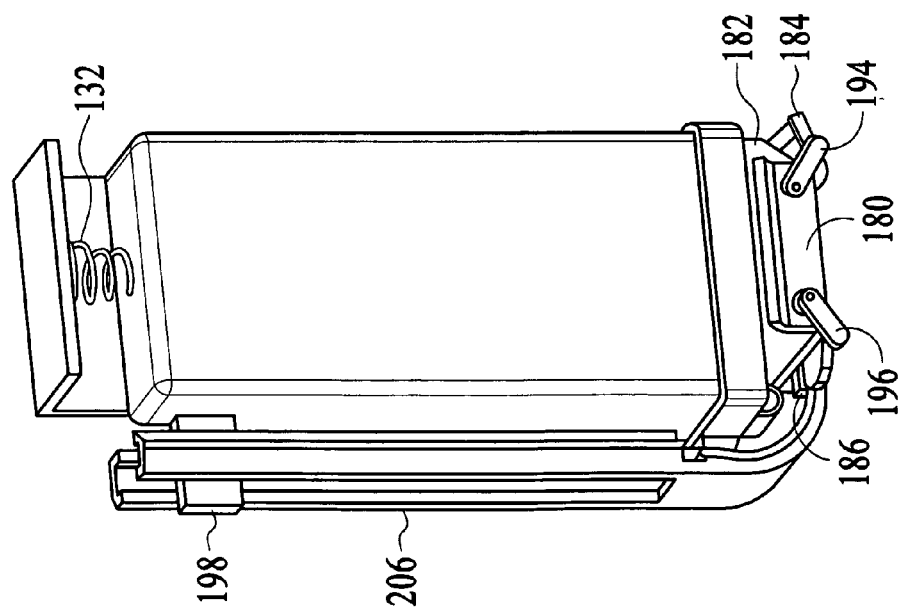
FIG.5D
FIG.5C

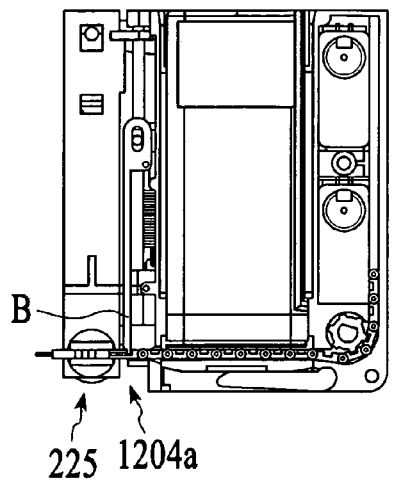
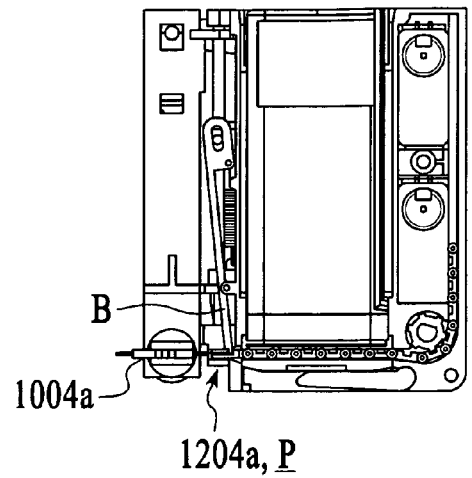
FIG.7E    FIG.7F
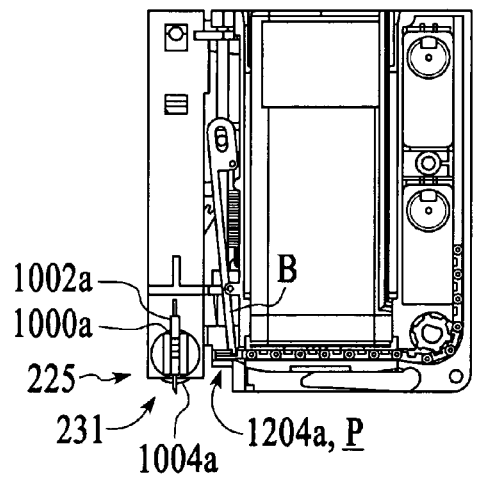
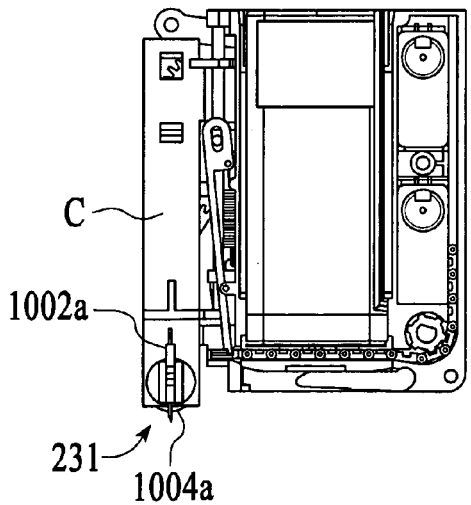
FIG.7G    FIG.7H

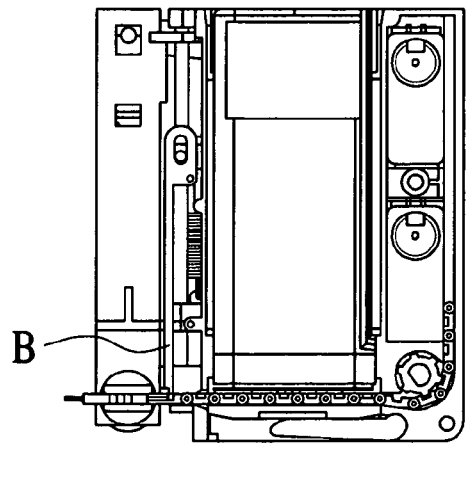
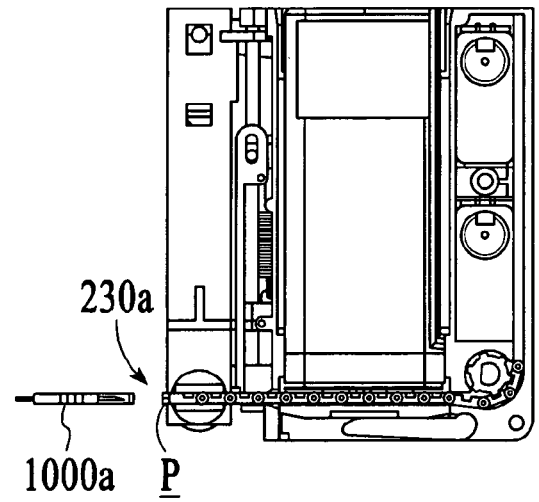
FIG.7M
FIG.7N
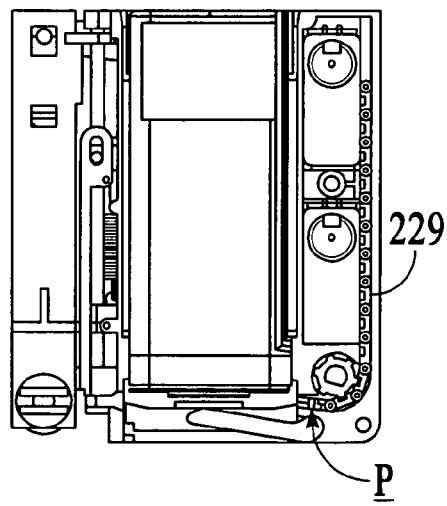
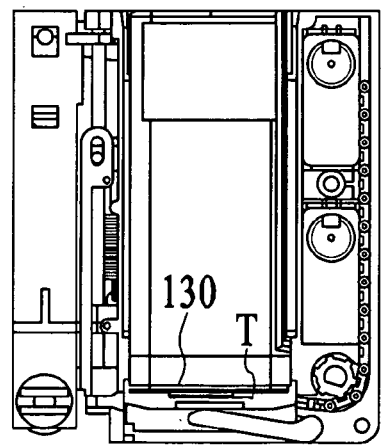
FIG.7O
FIG.7P

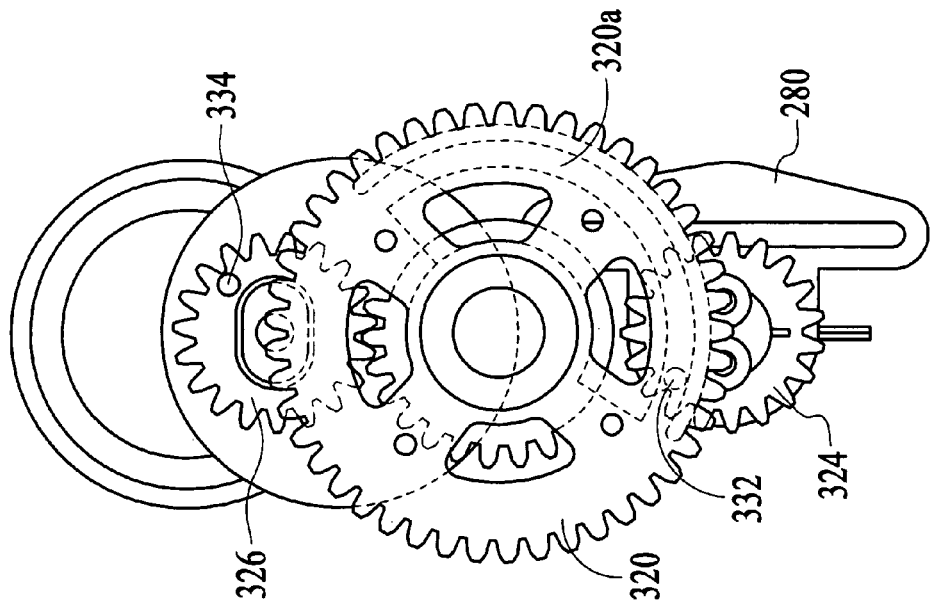
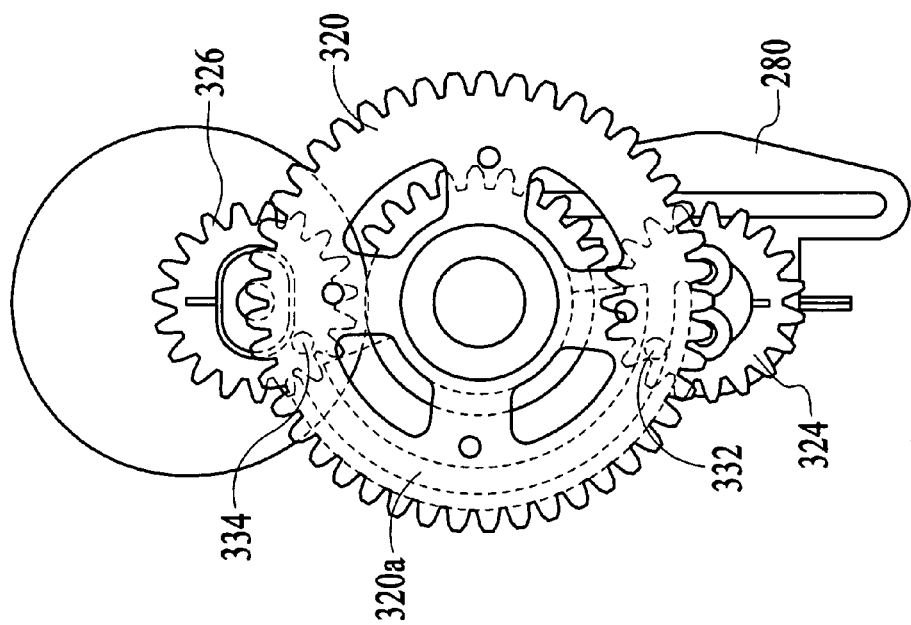

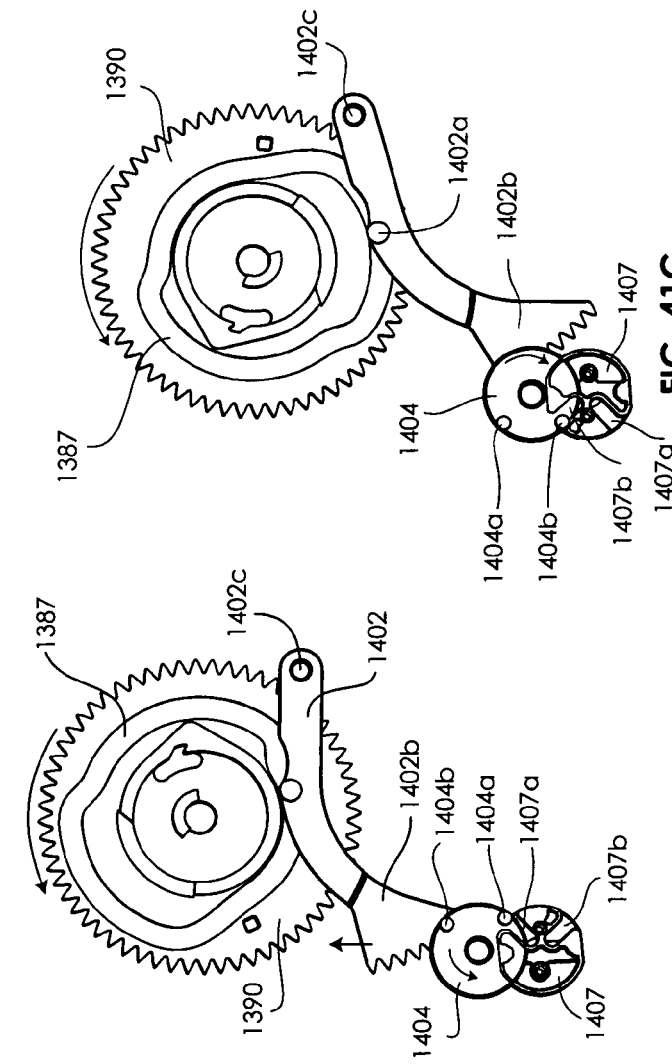
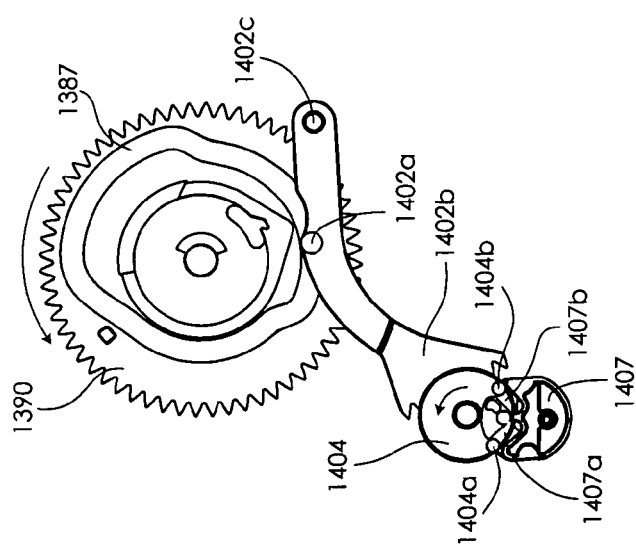

INTEGRATED METER FOR ANALYZING BIOLOGICAL SAMPLES

PRIORITY

This application is a continuation-in-part of U.S. patent application Ser. No. 11/535,985, filed Sep. 28, 2006, and claims the benefit of priority to U.S. provisional patent application Nos. 60/741,019, filed Nov. 30, 2005, and 61/168,549, filed Apr. 10, 2009, which are hereby incorporated by reference.

BACKGROUND OF THE INVENTION

1. Field of the Invention

This invention relates to the field of medical diagnostic devices.

2. Discussion of the Art

The prevalence of diabetes is increasing markedly in the world. At this time, diagnosed diabetics represent about 3% of the population of the United States. It is believed that the actual number of diabetics in the United States is much higher. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse some of the effects of diabetes.

Analyte, e.g., glucose, monitoring devices known in the art have operated on the principle of taking blood from an individual by a variety of methods, such as by means of a needle or a lancet. The individual then coats a paper strip carrying reagents with the blood, and finally inserts the blood coated strip into a blood glucose meter for measurement of glucose concentration by optical or electrochemical techniques.

Medical devices of the prior art for monitoring the level of glucose in the blood stream have required that an individual have separately available a needle or a lancet for extracting blood from the individual, test strips carrying reagents for bringing about a chemical reaction with the glucose in the blood stream and generating an optical or electrochemical signal, and a blood glucose, meter for reading the results of the reaction, thereby indicating the level of glucose in the blood stream. The level of glucose, when measured by a glucose, meter, is read from the strip by an optical or electrochemical meter.

It is desired to simplify the systems, devices, and methods for determining the level of an analyte such as glucose in a body fluid such as blood. In particular, it is desired to integrate the operations of extracting a sample of blood by means of a needle or a lancet, applying the sample of blood to a reagent-bearing test strip, reading the result of a glucose, monitoring test, and discarding the used needle or lancet and test strip in a safe and efficient manner.

Certain patents describe devices that can perform steps of determining the concentration of glucose in the blood stream. For example, U.S. Pat. No. 5,632,410 discloses a sensor-dispensing instrument for handling a plurality of fluid sensors (i.e., test strips). However, this patent fails to include a lancing device for puncturing the skin of a patient in order to extract a sample of blood. U.S. Pat. No. 6,908,008 discloses an apparatus that includes a dispenser comprising a housing having a chamber; a means for retaining a plurality of test strips in a substantially moisture-proof, air-tight first position; and a means for opening the chamber and moving one of the plurality of test strips translationally from a first position inside of the chamber to a second position at least partially outside of the chamber, wherein the opening of the chamber and the moving of the one test strip is achieved by a single mechanical motion; and an electrochemical analyzing means for analyzing a biological fluid. However, like, U.S. Pat. No. 5,632,410, this patent fails to simplify the testing process, e.g., this patent fails to include a lancing device for puncturing the skin of a patient in order to extract a sample of blood.

In addition, U.S. Pat. No. 5,035,704 discloses a blood sampling mechanism including a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, means for testing the blood sample, means for defining a blood sampling station at which the blood sample is obtained, means for defining a blood testing station at which the blood sample is tested by said blood sample testing means, and means for conveying said test pad from said blood sampling station after the blood sample has been obtained to said blood testing station. The dermis-piercing member and test pad are, however, entirely separate components in this system (see also WO 03/082091).

U.S. Pat. No. 5,971,941 discloses a blood sampling apparatus for sampling blood from the skin of a patient for analysis. The apparatus includes a cartridge and a housing with a driver. The cartridge has a cartridge case, lancet, and a compartment associated with the cartridge case for receiving blood. The lancet is housed in the cartridge case and operatively connected thereto such that it is drivable to extend outside the cartridge case through a lancing opening for lancing the skin to yield blood. The housing has a driver for urging the lancet to extend outside the cartridge case. During lancing, the cartridge may be detachably held in the housing such that the cartridge can be disassociated from the driver after sampling blood. The U.S. Pat. No. 5,971,941 patent discloses that material around a lancet aperture in a cartridge case soaks up blood after lancing (see also U.S. Pat. No. 5,279,294). This does not bring the absorbent material to the center of the sample, and when only a small amount of blood is available such as is often the case in alternate site testing away from fingertips, then testing may be unreliable, may need to be repeated far too often, or may simply require testing at the fingertips. Application of sample fluid to a capillary end leading to reagent material involves careful manual alignment. A manual actuation step is also involves in getting the lancet to protrude from the cartridge.

WO 2004/041082 discloses a device for use with a body fluid sampling device for extracting bodily fluid from an anatomical feature. The device comprises a cartridge having a plurality of cavities. The device may include a plurality of penetrating members each at least partially contained in the cavities of the cartridge wherein the penetrating members are slidably moved to extend outward from openings on the cartridge to penetrate tissue. The device may also include a plurality of analyte detecting members and a plurality of chambers. Each chamber may be associated with one of the cavities, the chambers positioned along an outer periphery of the cartridge, wherein at least one of the analyte detecting members forms a portion of one wall of one of the plurality of chambers.

SUMMARY OF THE INVENTION

It would be desirable to develop a medical diagnostic device that (1) stores and dispenses lancets and sensors as integrated STRIPLETS™, test elements having a body configured as a lancet at one and a test strip at the opposing end or having each coupled directly thereto, (2) forms an opening with the lancet in the skin of a patient to enable a sample of biological liquid to emerge from the patient, (3) reorients the STRIPLET™ for collecting the sample of biological liquid from the patient emerging from the opening in the skin by means of the test strip, (4) analyzes the sample of biological liquid to determine a characteristic of the biological liquid, and (5) ejects the used STRIPLET™ in a safe manner. It would also be desirable to develop a medical diagnostic device that is small in size, reliable to use, and provides accurate results, even when only a small volume of sample of biological liquid is collected.

An analyte monitoring apparatus is provided. An example is a glucose monitoring apparatus. The apparatus includes a housing with a user interface having one or more switches or a display or both. One or more analyte testing STRIPLETS™ are contained within a cartridge loaded within the housing.

A STRIPLET™ is an element which includes both a test strip portion and a lancet portion. A STRIPLET™ is also referred to herein as an analyte testing structure. These portions may be relatively opposed, e.g., extending about 180 degrees from each other, or extending at another angle from zero to 360 degrees. The lancet portion may couple to the test strip portion as a two-piece device, or each may couple with the ends of a central body as a three-piece device. Throughout the following description, the terms STRIPLET™ and test strip may be used interchangeably at times.

A lancing and testing port is defined in the housing for permitting a STRIPLET™ to contact a lancing site outside the housing. A set of mechanical components serve to load a STRIPLET™ for a lancing and testing process, advance the STRIPLET™ for lancing through the port at a lancing site proximate to the port, and reorient and advance the STRIPLET™ for testing at the lancing site also through the port. An analyzer determines an analyte level, e.g., a glucose level, of a body fluid, e.g., blood, applied to the test sensor from the lancing site.

The monitoring apparatuses are configured for analysis (e.g., concentration determination) of an analyte in a sample of body fluid, where in certain embodiments the apparatuses are configured to determine the concentration of an analyte in a small volume of sample, e.g., less than about 1 microliter, e.g., less than about 0.5 microliters, e.g., less than about 0.2 microliters, e.g., about 0.1 microliters or less. The monitoring apparatuses may be configured for analysis of an analyte in a volume of sample by, for example, coulometry, amperometry, and/or potentiometry. In certain embodiments, the monitoring apparatuses are configured for optical analysis of an analyte in a sample.

A cartridge that is coupled within a compartment of the housing may contain several STRIPLETS™. As used herein, the terms "cartridge", "storing/dispensing assembly or sub-assembly", "assembly for storing and dispensing test strips" mean a mechanism that is capable of both (a) storing a plurality of test strips in a magazine and (b) advancing the test strips, one at a time, from the magazine to a lancing/collecting assembly. The cartridge may include one or more guide rails or inserts for relative positioning within the housing with respect to the set of mechanical components. The guide rail has a stopping point which precisely locates the cartridge relative to the housing where the cartridge remains upon advancing the STRIPLET™ from the cartridge. A seal is provided at the cartridge's STRIPLET™-dispensing end for maintaining the STRIPLETS™ within the cartridge free from exposure to ambient air. The seal may be configured to be released temporarily to permit loading of a STRIPLET™ from the cartridge to within the apparatus for a lancing and testing process. The seal may be elastomeric and/or include a bellows. In this sense, a bellows may be understood as a container which is deformable in such a way as to alter its volume, or a portion of a container that includes a pleated or expansible part and/or a length or direction adjustable element, which may be tubular or connecting one plane; in collapsible devices or applications permitting good sealing. The cartridge may include a biasing member for providing the STRIPLETS™ at a loading end of the cartridge. One or more structural supports or inserts may be included within the cartridge for structural support of the STRIPLETS™ within the cartridge, and also for desiccating an interior of the cartridge to keep the STRIPLETS™ substantially free of moisture. The one or more inserts may include a hard plastic insert for providing the structural support and a desiccating plastic insert for providing the desiccating. Desiccants may also be provided separately.

The set of mechanical components includes a turret 225 including a STRIPLET™ slot 299 for holding the STRIPLET™ during reorientation which includes rotation of the STRIPLET™. The STRIPLET™ slot may be coupled with a cam that oscillates, and in certain embodiments about a point of unstable equilibrium, although in a particular embodiment having a localized point of stability at or near its center or somewhere within its range of motion, between points corresponding to different orientations of the STRIPLET™ for lancing and testing.

The STRIPLETS™ may further include a lancet cap which covers the protruding lancet. A lancet cap mechanism or compartment may serve to remove the lancet cap, e.g., by grabbing it more tightly than it is being held covering the lancet, when the lancet cap is positioned into the compartment. The lancet cap compartment may provide a space and a frictional force for holding the lancet cap during a lancing and testing process, and may provide the lancet cap back to recover the lancet for safe ejection of a used STRIPLET™.

The set of mechanical components may include first and second primary component sets. The first primary component set includes a first set of gears within the housing, which, along with a cartridge housing and tub combination, a STRIPLET™ pusher, a STRIPLET™ track or chain, a rotatable turret 225 including STRIPLET™ slot 299, and an ejection port in the housing, are respectively for unsealing the tub from the cartridge housing, advancing a STRIPLET™ to the turret, and ejecting the STRIPLET™ after testing. The second primary component set includes a second set of gears within the housing, which, along with a lever arm or blade and mating lancet cap contour, the turret, and a carriage which contains the turret, are respectively for arming/disarming (also referred to herein as uncapping/capping) the lancet by removing/replacing (uncapping/capping) the lancet cap over the lancet, flipping or reorienting the STRIPLET™ between lancing and testing, and performing both lancing and testing through the lancing and testing port when a user provides the lancing site proximate to the port. The primary component sets provide various sub-assemblies or subsets with associated componentry which perform these functions, where certain components contribute to more than one sub-assembly.

The arming/uncapping function includes removing the optional lancet cap which may involve the first primary component set in an embodiment wherein the pusher couples with the lancet cap and pulls both the lever arm and lancet cap away from the STRIPLET™ in a retreating motion. The disarming may include replacing the lancet cap for safe ejection of a used testing STRIPLET™ through a separate STRIPLET™ ejection port or through the same lancing and testing port. The pusher may contact and move the STRIPLET™ along the STRIPLET™ track until the STRIPLET™ is disposed within the turret, while both the lancing and the testing may occur by movement of the carriage relative to the rest the apparatus. The lancing and the testing may occur by same or similar movements of the carriage due to the reorienting of the STRIPLET™ by rotating the turret by 180 degrees, or by whatever angle at which the testing component and lancing component of the STRIPLET™ are relatively disposed. The reorienting of the STRIPLET™ may include rotating and/or flipping the STRIPLET™. A transmission system may be included for orienting a lancing/collecting assembly in a first position, whereby the lancet end of the STRIPLET™ can be used to form an opening in the skin of a patient, and in a second position, whereby the test sensor end of the STRIPLET™ can be used to collect a sample of biological liquid from the patient. As used herein, the expression "lancing/collecting assembly" or "lancing/sensing assembly" means a mechanism that is capable of both (a) forming an opening in the skin of a patient and (b) collecting a sample of biological liquid emerging from that opening.

An analyte, e.g., glucose, monitoring apparatus is further provided including a user interface coupled with a housing including one or more switches or a display or both. Multiple analyte, e.g., glucose, testing STRIPLETS™ include both a lancet and an analyte test sensor. A cartridge contains multiple STRIPLETS™ for loading into the housing within a cartridge compartment, wherein the cartridge includes at least one guide rail for relative positioning within the housing. The seal generally maintains the STRIPLETS™ within the cartridge free from exposure to ambient air, and is configured for releasing the seal temporarily to permit loading of a STRIPLET™ for a lancing and testing process. One or more lancing and testing ports are defined in the housing for permitting the STRIPLET™ to contact a lancing site outside the housing. A set of mechanical components load a STRIPLET™ for a lancing and testing process, advance the STRIPLET™ for lancing at a lancing site, and also advance the STRIPLET™ for testing at said lancing site, via the one or more lancing and testing ports. An analyzer determines an analyte, e.g., glucose, level of a body fluid applied to the test sensor from the lancing site.

The seal may be elastomeric and/or include a bellows. The guide rail may have a stopping point which precisely locates the cartridge relative to the housing. The cartridge may remain stationary relative to the housing due to the guide rail and stopping point when the seal is temporarily broken for loading the STRIPLET™. The cartridge may include a biasing member for urging the STRIPLETS™ to be loaded from the loading end of the cartridge. One or more structural supports and/or inserts within the cartridge may be for structural support of the STRIPLETS™ within the cartridge, and/or for desiccating an interior of the cartridge to keep the STRIPLETS™ substantially free of moisture. These may include a hard plastic insert for providing said structural support and a desiccating plastic insert for providing the desiccating.

A further analyte monitoring apparatus is provided with a housing having a user interface that includes one or more switches or a display or both. Multiple analyte testing STRIPLETS™ that include both a lancet and a test sensor are contained within a cartridge that is loaded into the housing within a cartridge compartment. One or more structural supports or inserts are provided within the cartridge for structural support of the STRIPLETS™ within the cartridge, and for desiccating an interior of the cartridge to keep the STRIPLETS™ substantially free of moisture. One or more lancing and testing ports are defined in the housing for permitting the STRIPLET™ to contact a lancing site outside the housing. A set of mechanical components automatically load the STRIPLET™ for a lancing and testing process, advance the STRIPLET™ for lancing and for testing at a lancing site upon reorienting via the one or more lancing and testing ports. An analyzer determines an analyte level, e.g., a glucose level, of a body fluid applied to the test sensor from the lancing site.

The one or more structural supports or inserts include a hard plastic insert for providing structural support and a desiccating plastic insert for providing desiccation. The cartridge may include one or more guide rails for relative positioning within the housing. The guide rail may have a stopping point which precisely locates the cartridge relative to the housing, such that the cartridge remains stationary relative to the housing when the seal is temporarily broken for loading a STRIPLET™ for lancing and testing. The seal generally maintains the STRIPLETS™ within the cartridge free from exposure to ambient air, and is configured for releasing temporarily to permit loading of a STRIPLET™ for a lancing and testing process. This apparatus can include other features described elsewhere hereinabove or below.

A further analyte monitoring apparatus is provided which includes many of the features already recited hereinabove. A set of mechanical components includes first and second subsets respectively including first and second sets of gears. The first subset, along with a lancet cap compartment, a STRIPLET™ track or chain and a rotatable slot, are respectively for arming/disarming the lancet, loading a STRIPLET™ for a lancing and testing process, and reorienting the STRIPLET™ between lancing and testing for performing both lancing and testing through a lancing and testing port when a user provides the lancing site proximate to the port. The second mechanical subset includes a second set of gears within the housing, which, along with a pusher, are for advancing the STRIPLET™ though the port to the lancing site for both lancing and testing upon reorienting.

Alone or in combination with one or more other features recited above and/or below herein, an assembly is also provided for storing and dispensing test strips, wherein each test strip includes a lancet-containing portion and a sensor-containing portion. The assembly includes an exterior cover, an interior housing, a platform for containing a biasing element, an insert for securing the biasing element, a test strip track for providing a guide path for an assembly for forming an opening in the skin of a patient and collecting a sample of biological liquid emerging from the skin of the patient, a biasing member for urging the test strips toward the test strip track, and an element for advancing a test strip from the assembly to the assembly for forming an opening in the skin of a patient and collecting a sample of biological liquid emerging from the skin of the patient.

The STRIPLETS™ are advanced, one at a time, to the assembly for forming an opening in the skin of a patient and collecting a sample of biological liquid emerging from the skin of the patient by a pushing element. A seal ensures a substantially moisture-tight, air-tight condition in the assembly for storing and dispensing a plurality of test strips. A bellows or elastomerically-composed seal ensures a substantially moisture-tight, air-tight condition in the assembly for storing and dispensing test strips. A door ensures a substantially moisture-tight, air-tight condition in the assembly for storing and dispensing test strips.

In further embodiments, an apparatus is provided whereby a test strip or a lancet is applied through a testing or lancing port, followed by reorienting and ejection through an ejection port. According to one of these embodiments, an analyte monitoring apparatus includes a housing; a user interface coupled with the housing including one or more switches or a display or both; one or more analyte test strips; a testing port defined in the housing for permitting the strip to contact a testing site outside the housing; an ejection port separate from the testing port for disposing of the strip after testing; a set of mechanical components for loading a strip for a testing process, for advancing the strip for testing through said testing port at the testing site proximate to the port, for reorienting the strip after testing, and for ejecting the strip through the ejection port; and an analyzer for determining a glucose or other analyte level of a body fluid applied to the test strip from the lancing site.

A cartridge containing a plurality of strips may be received within a slot or internal compartment within the housing. A seal may generally maintain the strips within the cartridge free from exposure to ambient air, and may be configured for releasing the seal temporarily to permit loading of a strip for a testing process. The cartridge may have a structural support for the strips within the cartridge. The cartridge may include a desiccating member for keeping the strips substantially free of moisture. The set of mechanical components may include a strip turret for holding the strip at least during the reorienting which includes rotation of the strip in certain embodiments.

In another of these further embodiments, an analyte monitoring apparatus includes a housing; one or more lancets; a lancing port defined in the housing for permitting a lancet to contact a lancing site outside the housing; a separate ejection port for disposing of the lancet after testing; and a set of mechanical components for loading a lancet for a lancing process, for advancing the lancet for lancing through said lancing port at the lancing site proximate to the port, for reorienting the lancet after lancing, and for ejecting the lancet through the ejection port.

The apparatus may further include a user interface coupled with the housing including one or more switches or a display or both; one or more test strips; and an analyzer for determining an analyte level of a body fluid applied to the test strip from the lancing site. The apparatus may also include a cartridge contain a plurality of lancets received within a slot or interior compartment within the housing. The cartridge may include a structural support for the lancets within the cartridge. A set of mechanical components may include a lancet turret for holding the lancet at least during the reorienting which includes rotation of the lancet in certain embodiments.

BRIEF DESCRIPTION OF THE DRAWINGS

FIG. 5A shows the assembly in a sealed condition. FIG. 5B shows the assembly in an unsealed condition.

FIG. 5C is a side view in elevation of one side of one embodiment of an assembly for storing and dispensing test strips suitable for use in the medical diagnostic device.

FIG. 5D is a side view in elevation of the other side of the embodiment of the assembly for storing and dispensing the test strips shown in FIG. 7.

In FIG. 10B, the hidden side of a drive gear is shown.

FIGS. 25A-25J, inclusive, are side elevational views illustrating positions of certain gears of a lancing/collecting assembly of a medical diagnostic apparatus of an alternative embodiment during one cycle of operation of the lancing/collecting assembly of the medical diagnostic device of an alternative embodiment.

FIGS. 41A-41C, inclusive, illustrate various stages of other gear positions involved in the reorientation of the STRIPLET™ during the lancing and fluid collecting/sensing functions of the device of FIGS. 36A-36D.

DETAILED DESCRIPTION OF EXEMPLARY EMBODIMENTS OF THE INVENTION

Figure 1:
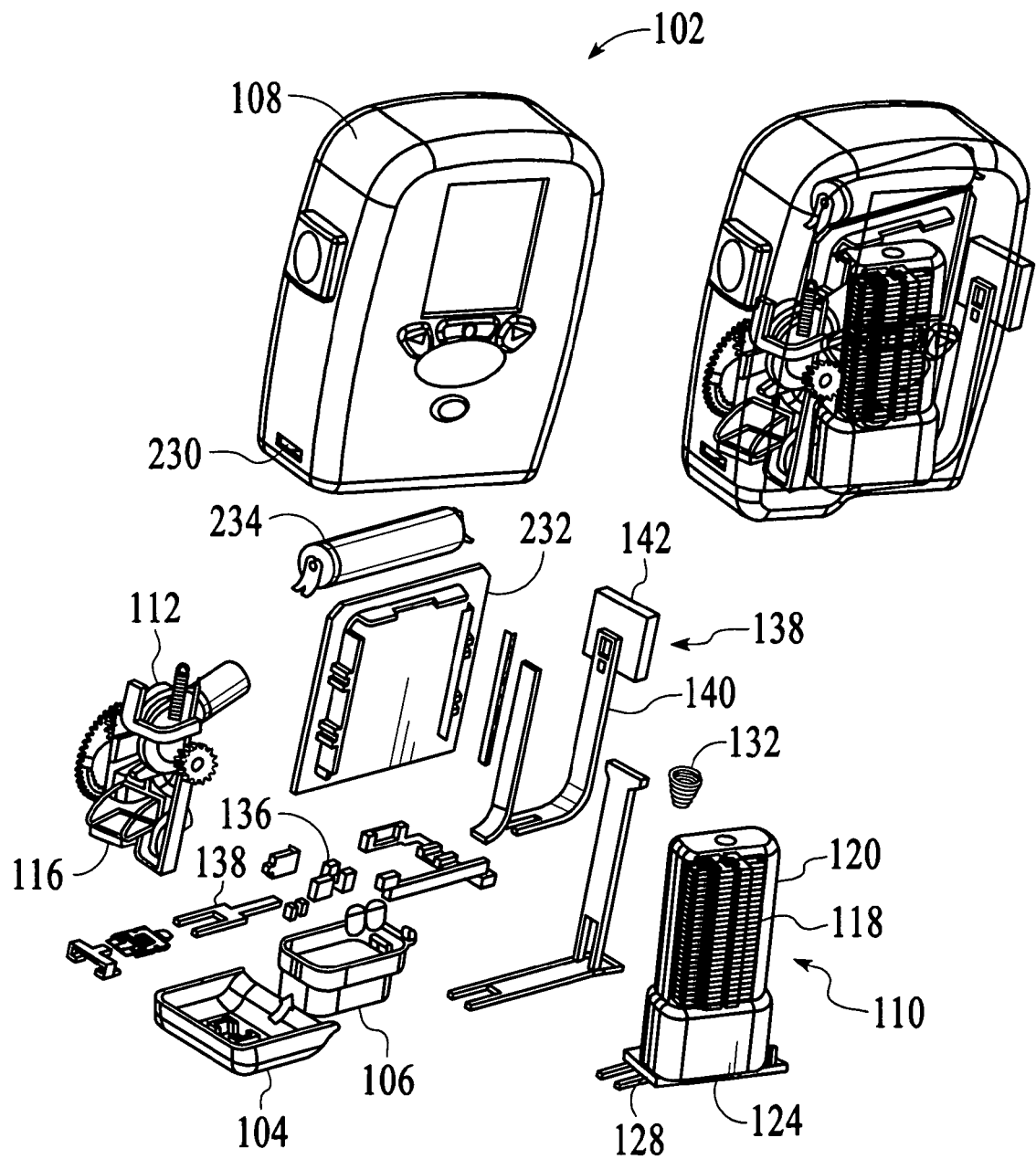
FIG. 1 is an exploded perspective view of one embodiment of the medical diagnostic device.

Referring now to FIGS. 1 and 2A-2C, the medical diagnostic device 100, 100a in accordance with certain embodiments includes a housing 102, 102a. The device 100 may have an end cap 104, a tub 106, and a protective cover 108 for the subsystems and assemblies located with the housing 102, as in the embodiment of FIG. 1. Within the housing 102 is located an assembly for storing and dispensing test strips 110, a lancing/collecting assembly 112, an assembly 114 for removing a protective cover from the tip of a lancet and re-attaching the protective cover to the tip of a used lancet, and an analyzer 116. The end cap 104 has an opening 117, through which a lancet can be projected for forming an opening in the skin of a patient, and through which a sensor can be projected for collecting a sample of biological liquid emerging from the opening in the skin of the patient.

Figure 2A:
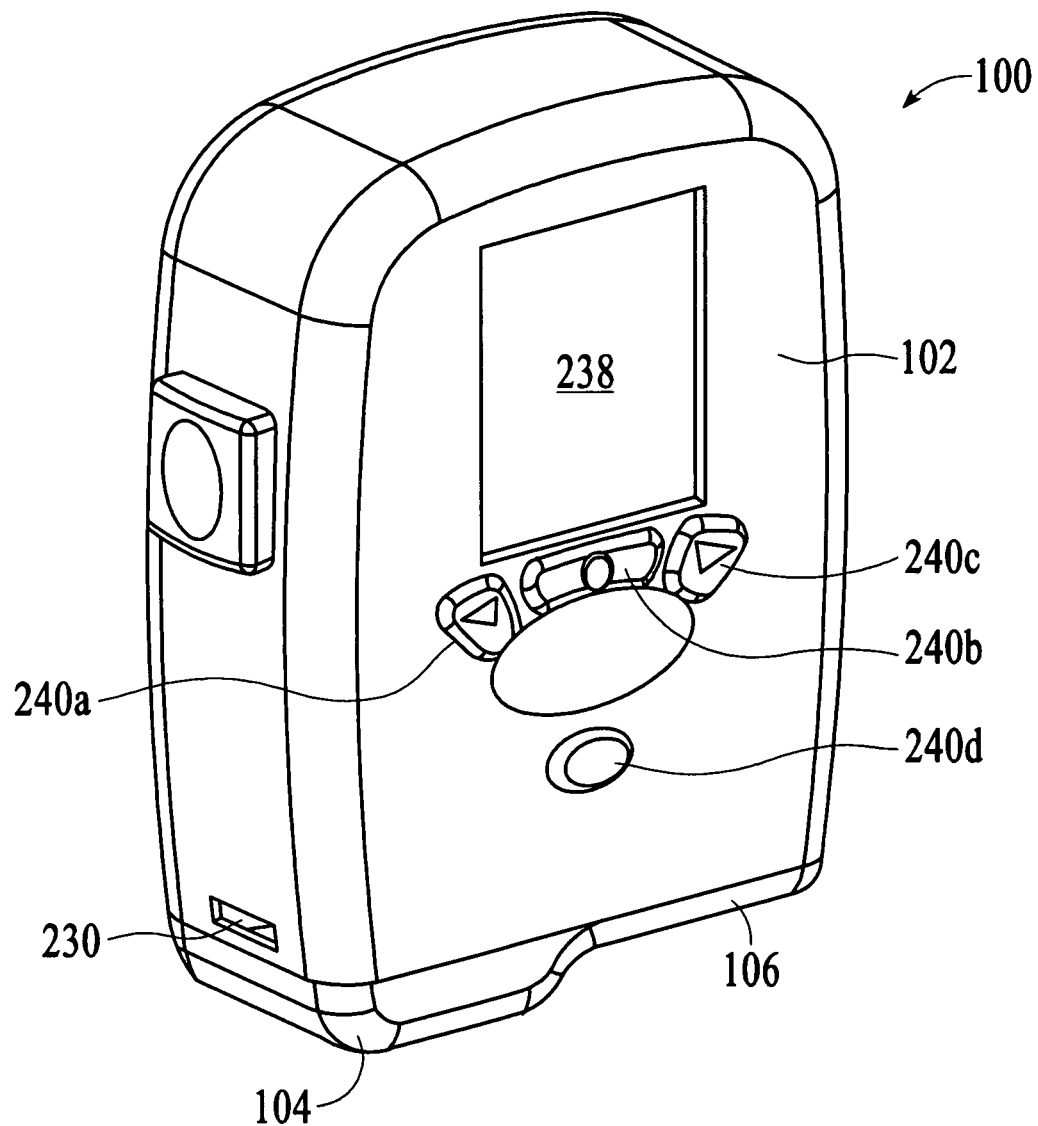
FIG. 2A is a perspective view of the medical diagnostic device with the housing shown attached to an end cap and a tub.
Figure 2C:
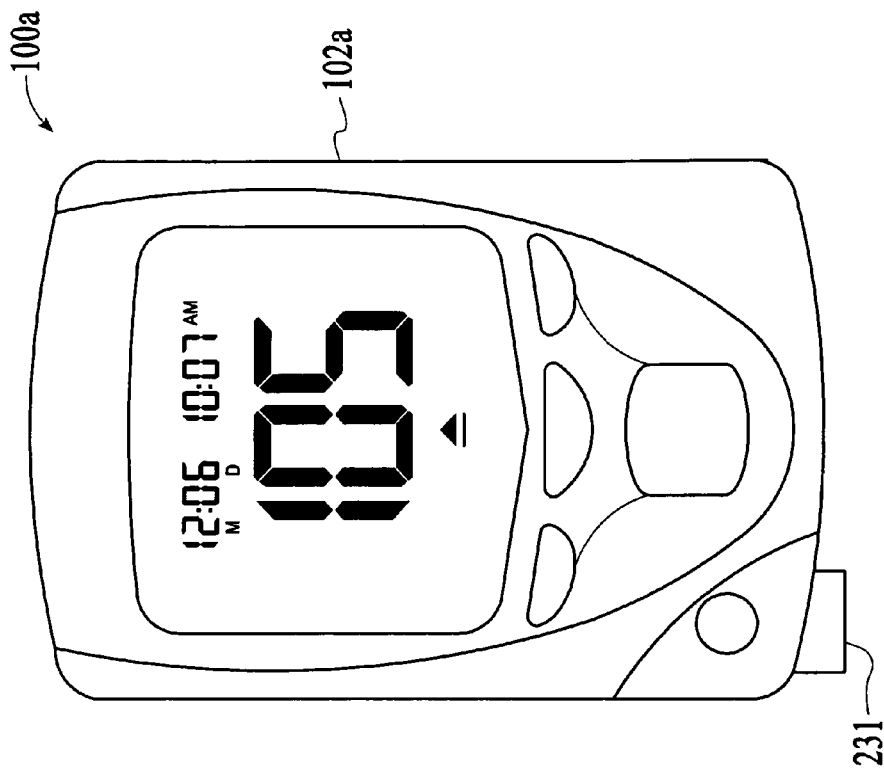
FIG. 2C is a front view illustrating a housing including switches and a display of a user interface of a medical diagnostic apparatus in accordance with an embodiment.
Figure 2B:
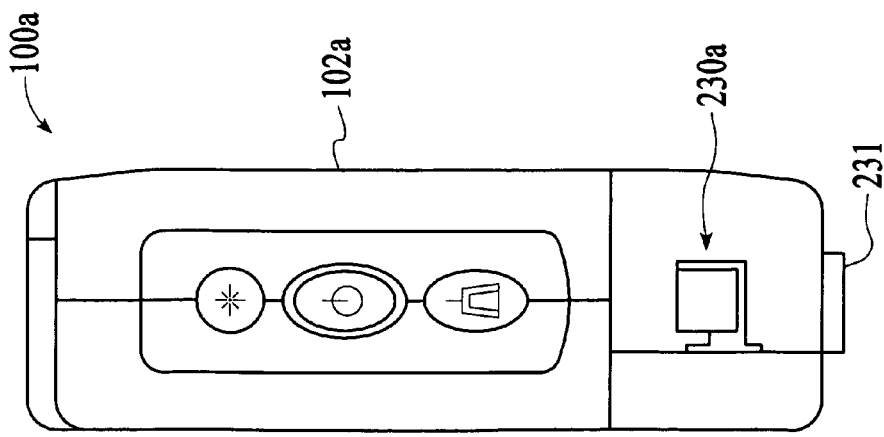
FIG. 2B is a side view illustrating a housing with a port defined therein, and including switches of a user interface, of a medical diagnostic apparatus in accordance with an embodiment.

An ejection port 230 is shown in the illustrations of a medical diagnostic apparatus in accordance with an alternative embodiment FIG. 1 and FIG. 2A, while ejection port 230a is shown in the illustration of the embodiment at FIG. 2B. Although either ejection port 230, 230a may also be used as a lancing and/or testing port, a separate lancing and testing port 231 is provided opening to the bottom of FIGS. 2B and 2C in accordance with an embodiment. In operation (which is described in moiré detail below with reference to FIGS. 7A-7P), the apparatus of an embodiment illustrated at FIGS. 2B-2C lances and tests through port 231, by reorienting a STRIPLET™ within the housing 102a after lancing for testing through the same port 231, and then retracting the STRIPLET™ into the housing after testing, rotating the STRIPLET™ 90 degrees, re-capping the lancet portion for safety, and ejecting the STRIPLET™ through ejection port 230a.

As shown in FIGS. 3A-4D, the assembly for storing and dispensing test strips 110, 110a includes a magazine 118, 118a including a plurality of test strips "TS", each test strip comprising a lancet-containing portion and a sensor-containing portion. Test strips that are suitable for use with a medical diagnostic device in accordance with an embodiment are illustrated in FIGS. 26A-33, inclusive, and described in detail in the text accompanying those figures. The magazine 118, 118a has an exterior cover 120, 120a. The purpose of the exterior cover 120, 120a is to maintain the test strips in a substantially moisture-tight, air-tight condition. Materials that are suitable for forming the exterior cover 120, 120a include rubber and other polymeric materials.

Figure 3A:
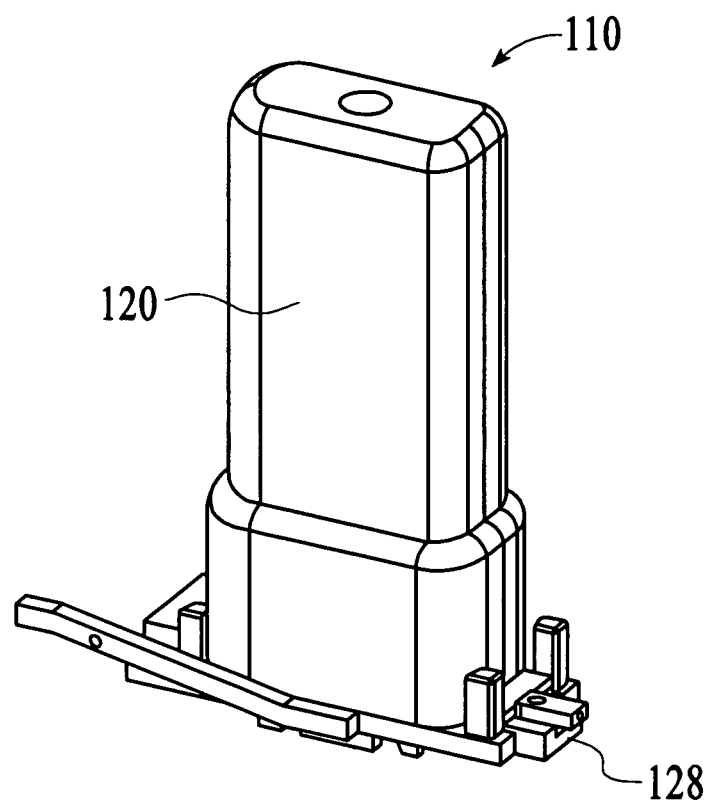
FIG. 3A is a perspective view of one embodiment of an assembly for storing and dispensing the testing STRIPLETS™ suitable for use in the medical diagnostic device in accordance with an embodiment.
Figure 4A:
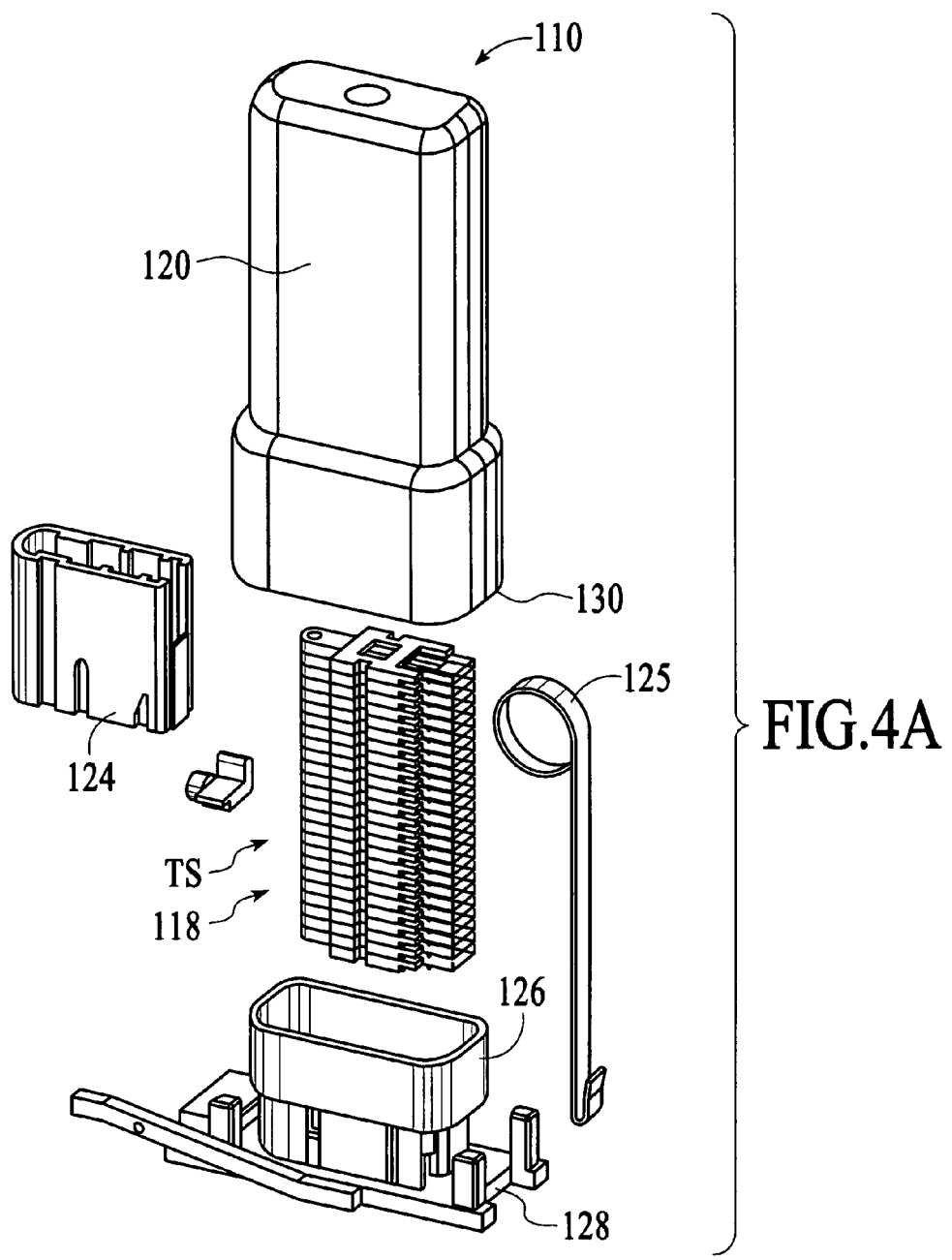
FIG. 4A is an exploded perspective view of the assembly for storing and dispensing test STRIPLETS™ shown in FIG. 3A.
Figure 4B:
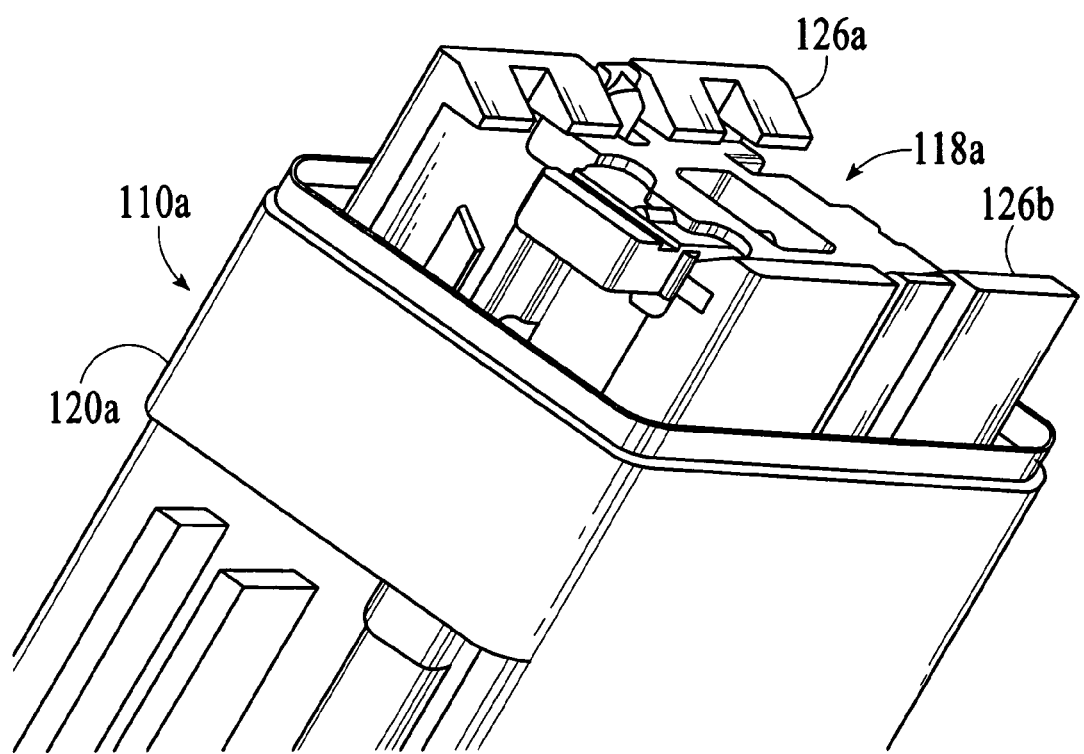
FIG. 4B is a perspective view of a loading end of the cartridge of FIG. 3B.

Inside the exterior cover 120 of FIGS. 3A and 4A is an interior cover 122, which contains a desiccant. The purpose of the interior cover 122 is to provide a second barrier to maintain the test strips in a substantially moisture-tight, air-tight condition. Materials that are suitable for forming the interior cover 122 include polymeric materials impregnated with a desiccant, e.g., plastic impregnated with desiccant. The structure of the interior cover 122 is substantially congruent with the structure of the exterior cover 120. The desiccant absorbs moisture that evades the exterior cover 120. Inside the interior cover 122 is a platform 124 for containing a biasing element 125, e.g., a constant force spring, for urging test strips toward the location in the magazine 118 from which test strips are fed to the lancing/collecting assembly 112. Also inside the interior cover 122 is an insert 126 for securing the biasing element 125. The platform 124 can be filled with a desiccant, in order to enhance moisture resistance of the test strips stored within the assembly 110.

Figure 3B:
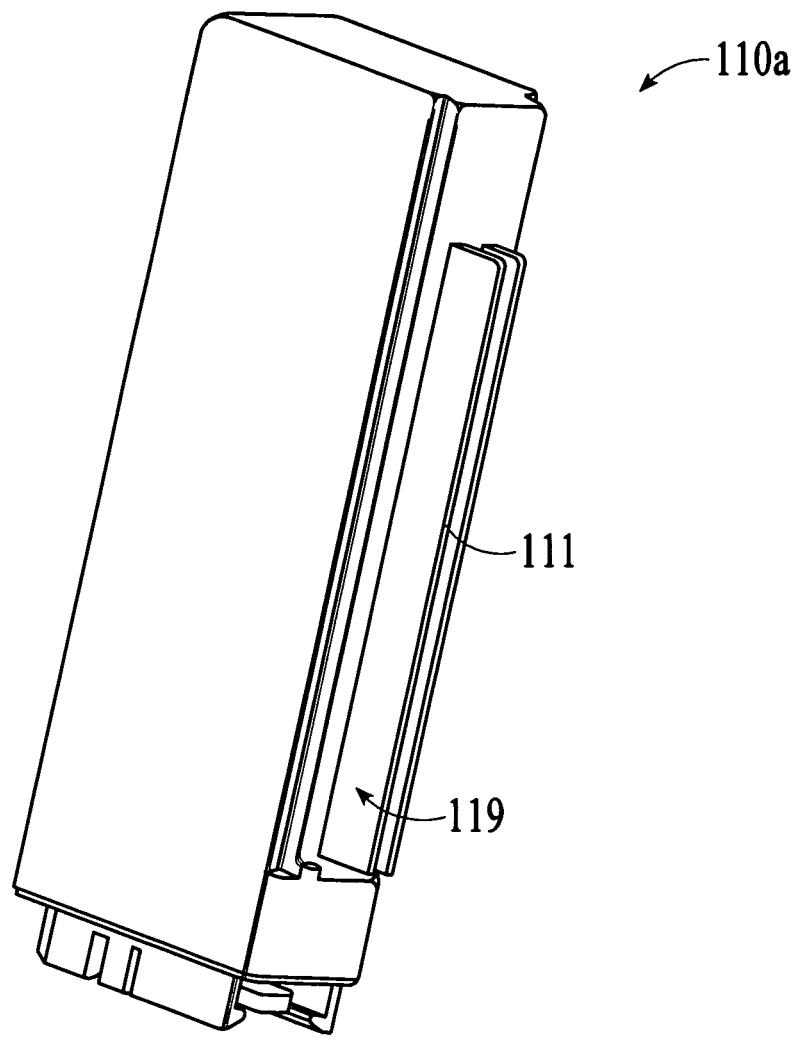
FIG. 3B is a perspective view illustrating another embodiment of a cartridge assembly for storing and dispensing testing STRIPLETS™.
Figure 6A:
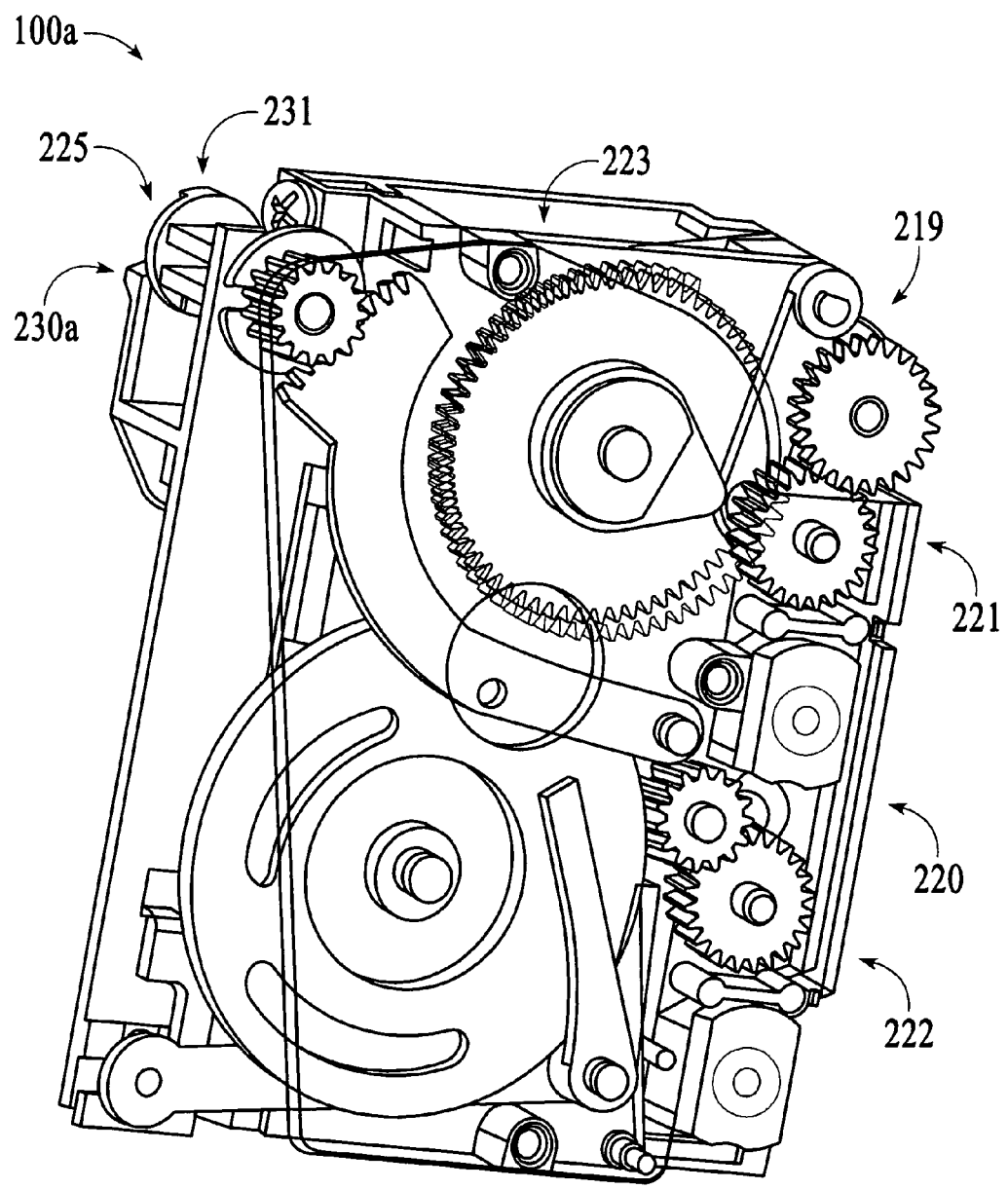
FIG. 6A is a front view of mechanical components of a medical diagnostic apparatus in accordance with an embodiment.

FIG. 3B illustrates a guide rail that moves within a guide track 115 (see FIG. 6C) which is formed as part of the cartridge compartment 123 in the device 100, 100a. The coupling of the guide rail 111 and the guide track 115 permits the cartridge be positioned relative to the device 100, 100a and particularly the mechanical components contained therein which are configured to precisely load, advance and reorient STRIPLETS™ received from the cartridge. At the end of the guide rail 111 is a stopping point 113. The stopping point meets with a complementary point within the guide track 115 at which point the cartridge 110, 110a cannot be advanced deeper into the cartridge slot 123. The walls of the cartridge slot 123 including the guide track 115 and the stopping point 113 precisely position the cartridge 110, 110a relative to the mechanical components of the medical diagnostic device 100, 100a.

In certain embodiments, the stopping point 113 and complementary point within the track just move apart when the tub T is sealed with the cartridge 110, ensuring a good seal. The cartridge remains substantially stationary relative to the apparatus 100, 100a when the tub T is moved away and unsealed from the cartridge to permit a STRIPLET™ to be loaded onto a segment of a track leading to turret 225 (see FIGS. 6A and 7B, for example). By "substantially stationary", a small movement actually occurs due to the loss of contact of the cartridge at the stopping point when the tub T is sealed, ensuring a good seal. The small movement of the cartridge occurs when the tub T is moved until the cartridge contacts the stopping point. This small movement may be a far smaller movement than the movement of the tub T to expose a STRIPLET™ to the guide track segment, which is why the cartridge is deemed to remain "substantially stationary" during the movement of the tub T.

Figure 4C:
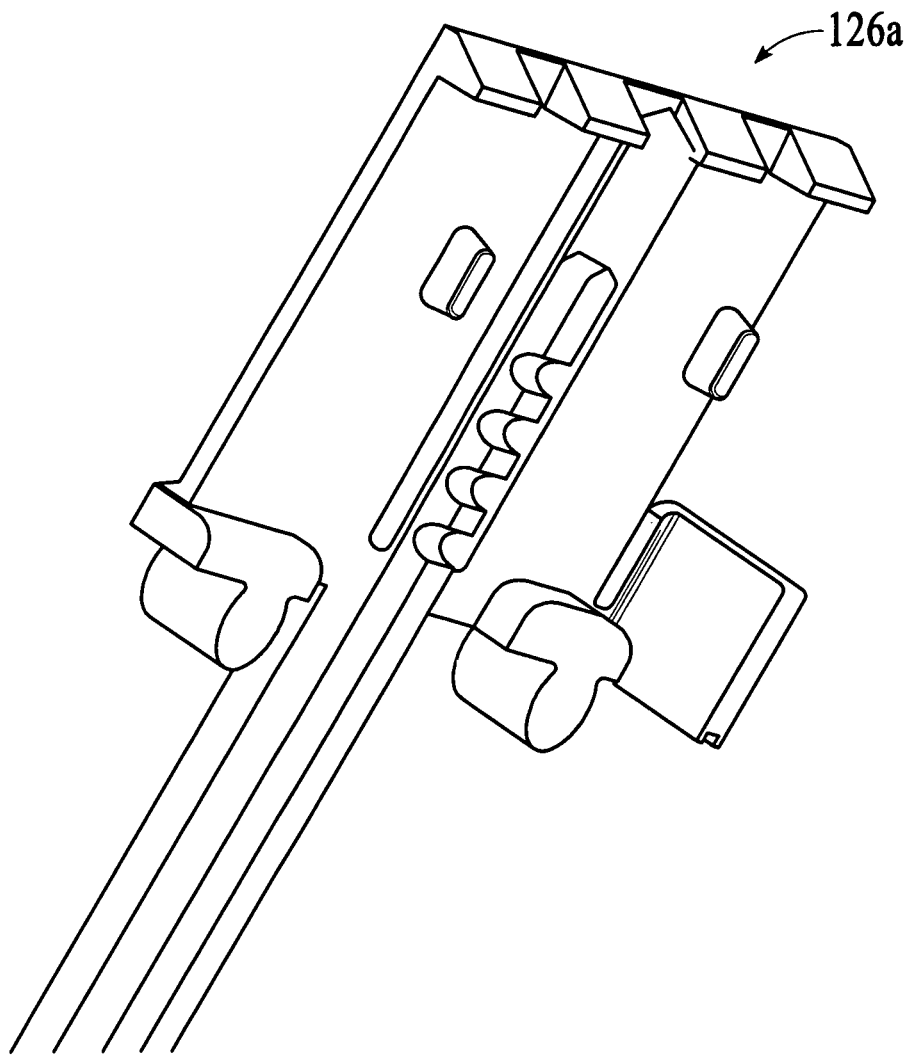
FIG. 4C is a perspective view of an insert or fixed support for structurally supporting and/or desiccating the testing STRIPLETS™ within the cartridge of FIGS. 3B and 4B.
Figure 4D:
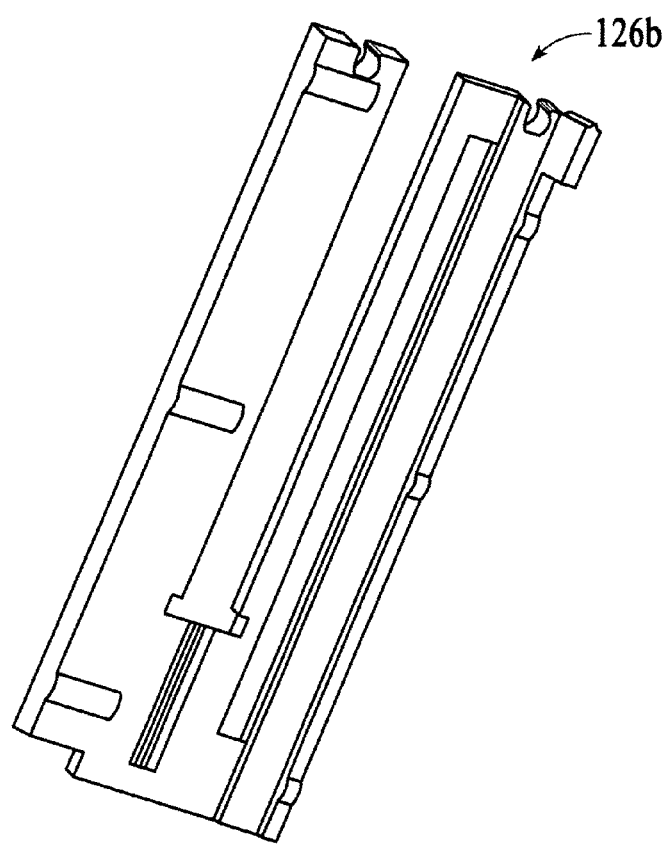
FIG. 4D illustrates a second insert for structurally supporting and/or desiccating the testing STRIPLETS™ within the cartridge of FIGS. 3B and 4B.

The cartridge 110a has inserts or structural supports 126a and 126b in certain embodiments which are illustrated at FIGS. 4C and 4D. The insert 126a of FIG. 4C provides structural support for the testing STRIPLETS™ that are stacked inside the housing cover 120a of cartridge 110a. The other insert 126b of FIG. 4D is made of a desiccating plastic. Insert 126b may provide some structural support or not, and element 126b may provide desiccation without being formed to also provide support, e.g., may be a coating on the wall or a small structure or series of small components interwoven with support 126a, for example. Either or both of the "inserts" 126a and 126b may actually be built-in, e.g., by being molded together with the cartridge body 110, 110a.

Referring back now to FIG. 4A, at least a segment of a test strip track 128 is disposed below the magazine 118, 118a for receiving the test strip from the magazine 118, 118a and for providing a segment of a guide path for a test strip when the test strip is being fed to the lancing/collecting assembly 112. Some of the features shown in FIG. 4A may be present in the embodiment of FIG. 4B even though they are not specifically shown in FIG. 4B. The test strip track 128 also abuts against a seal 130 attached to the bottom end of the magazine 118, 118a. The seal 130 surrounds the bottom end of the magazine 118, 118a and is typically made from a substantially air-impermeable, moisture-impermeable material, such as, for example, rubber or a polymeric material. The combination of the test strip track 128 and the seal 130 provides a substantially moisture-tight, air-tight seal for the magazine 118, 118a. A resilient biasing element 132, e.g., a spring, is positioned exterior to and above the magazine 118, 118a in order to ensure that the magazine 118, 118a can maintain test strips in a substantially moisture-tight, air-tight condition.

Outside of the magazine 118, 118a is a mechanism 134 for feeding test strips to the lancing/collecting assembly 112. This feeding mechanism 134 includes a cam or cam assembly 136 for lifting the magazine 118, 118a, whereby a gap is formed between the seal 130 at the bottom end of the magazine 118, 118a and the test strip track 128. The feeding mechanism 134 further includes a mechanism 138 for advancing a test strip from the magazine 118, 118a to the lancing/collecting assembly 112. The mechanism 138 for advancing a test strip from the assembly for storing test strips and dispensing test strips 110 to the lancing/collecting assembly 112 includes at least one flexible component 140 that translates a force applied from a first direction (e.g., vertically) to a force applied in a second direction (e.g., horizontally) to advance a test strip from the magazine 118, 118a to the lancing/collecting assembly 112. Examples of the at least one flexible component 140 include, for example, a flexible strip or flexible strips of a material, e.g., metal or polymeric material, capable of extending around a corner, i.e., an angle of approximately 90°, or a flexible spring or flexible springs, e.g., formed of metal or a polymeric material, capable of extending around a corner, i.e., an angle of approximately 90°. In order to lift the magazine 118, 118a and advance a test strip out of the magazine 118, 118a and into the lancing/collecting assembly 112, the medical diagnostic device 100 is equipped with a slide 142 to which is attached the at least one flexible component 140, either directly, or indirectly by means of an intermediate connector. The slide 142 is positioned to move along a slot 144 in a wall of the housing 102. The user moves the slide 142 in a direction that results in the cam or cam assembly 136 lifting the magazine 118, 118a. After the magazine 118, 118a is lifted to a sufficient extent, whereby the seal 130 separates from the test strip track 128 to temporarily break the substantially moisture-tight, air-tight seal formed by the test strip track 128 and the seal 130, the at least one flexible component 140 pushes a test strip out of the magazine 118, 118a and into the lancing/collecting assembly 112. In an alternative embodiment, the slide 142 can be eliminated and the aforementioned functions can be performed by a motor located within the housing 102.

Figures 5A, 5B:
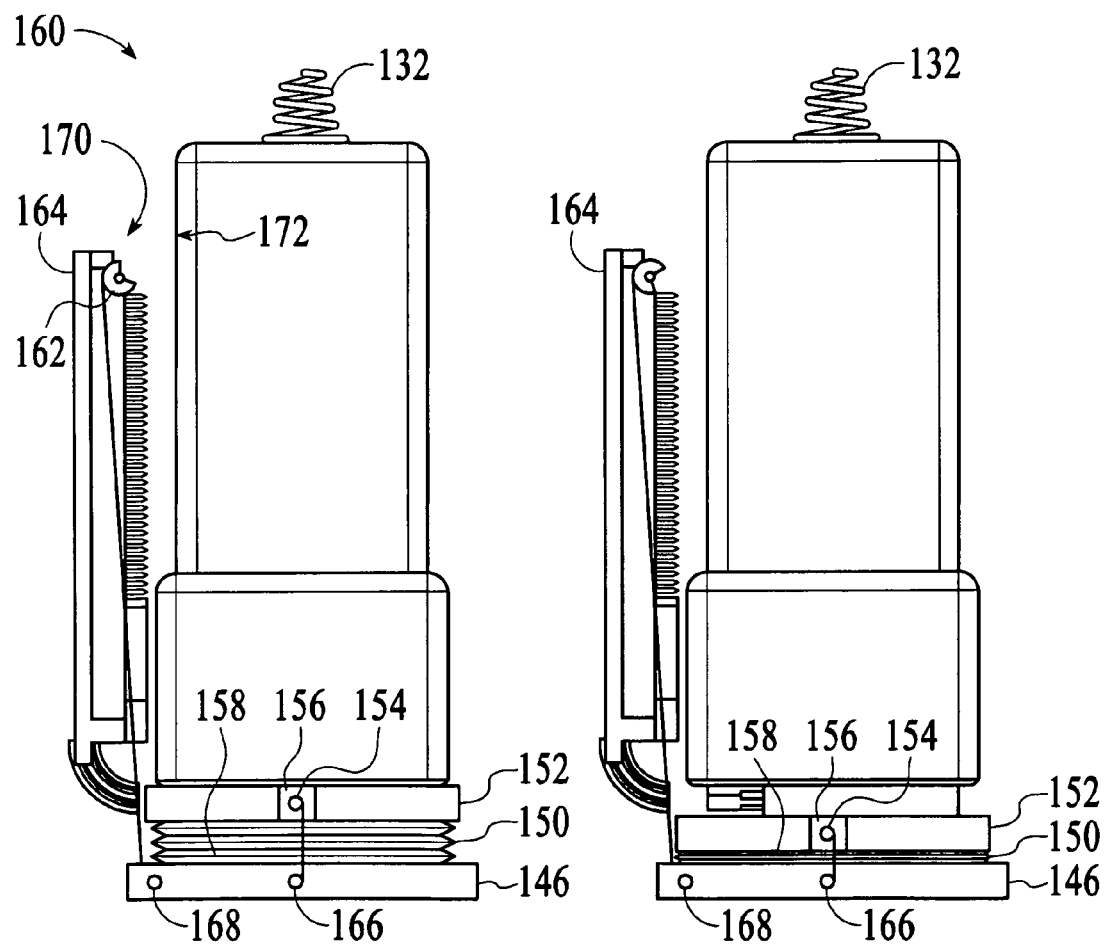
FIGS. 5A and 5B are side views in elevation of one embodiment of an assembly for storing and dispensing the test strips suitable for use in the medical diagnostic device.

FIGS. 5A and 5B illustrate the operation of one alternative for the magazine 118, 118a in which test strips are stored and from which test strips are fed to the lancing/collecting assembly 112. In this embodiment the magazine 118, 118a is mounted on a base 146. The magazine 118, 118a remains immobile throughout the step of feeding a test strip to the lancing/collecting assembly 112. The magazine 118, 118a is not lifted or lowered by a cam or cam assembly to unseal the magazine 118, 118a. An opening in the magazine 118, 118a from which the test strips emerge when fed into the lancing/collecting assembly 112 is maintained in a sealed condition by a bellows 150. The bellows 150 is attached to both the base 146 and a movable element 152, which surrounds the bottom of the magazine 118, 118a. The movable element 152 is of such a shape and dimensions that the movable element 152 fits around the bottom of the magazine 118, 118a to bring about a substantially moisture-tight and air-tight seal of the magazine 118, 118a. The movable element 152 is biased to a position to maintain the substantially moisture-tight, air-tight seal of the magazine 118, 118a. Attached to the movable element 152 is a first post 154, to which is attached one end 156 of a cord 158. The cord 158 is typically made of a metallic material. The other end 160 of the cord 158 is attached to a second post 162, which is attached to a slide 164, which is used for advancing a test strip from the magazine 118, 118a to the lancing/collecting assembly 112. Guide wheels 166, 168 are attached to the base 146 for maintaining the cord 158 in a taut condition. When the slide 164 is in its starting position, the bellows 150 is fully extended, thereby maintaining the magazine 118, 118a in a sealed condition. Furthermore, a pin 170 projecting from the slide 164 orients a recess 172 in the periphery of the second post 162 so as to enable the bellows 150 to be maintained in the fully extended position. When the slide 164 is moved in a direction to advance a test strip from the magazine 118 to the lancing/collecting assembly 112, the pin 170 projecting from the slide 164 orients of the recess 172 in the periphery of the second post 162 so as to cause the movable element 152 to descend and compress the bellows 150, thereby enabling a gap to be formed between the movable element 152 and the bottom of the magazine 118, thereby further enabling a mechanism for advancing a test strip from the assembly for storing test strips and dispensing test strips 110 to the lancing/collecting assembly 112 to advance a test strip through this gap and subsequently into the lancing/collecting assembly 112. Movement of the slide 164 to its starting position raises the movable element 152 to a position whereby the bellows 150 is fully extended so as to maintain the magazine 118 in a substantially moisture-tight, air-tight condition.

FIGS. 5C and 5D illustrate the operation of another alternative for the magazine 118, 118a in which test strips are stored and from which test strips are fed to the lancing/collecting assembly 112. In this embodiment the magazine 118, 118a is mounted on a base 180. The magazine 118, 118a remains immobile throughout the step of feeding a test strip to the lancing/collecting assembly 112. The magazine 118, 118a is not lifted or lowered by a cam or cam assembly to unseal the magazine 118, 118a. An opening 182 in the magazine 118, 118a from which a test strip emerges when fed into the lancing/collecting assembly 112 is maintained in a sealed condition, i.e., a substantially moisture-tight and air-tight condition, by a set of doors 184 and 186. The door 184 is maintained in a closed position by a resilient biasing element 188, e.g., a spring, which resiliently biases the door 184 to the closed position. The door 186 is maintained in a closed position by a resilient biasing element 190, e.g., a spring, which resiliently biases the door 186 to the closed position. The resilient biasing elements 188 and 190 are extended to cause the doors 184 and 186, respectively, to open, whereby a mechanism for advancing a test strip from the assembly for storing test strips and dispensing test strips 110 to the lancing/collecting assembly 112 can advance a test strip from the magazine 118, 118a through the opening 182 to the lancing/collecting assembly 112. The doors 184 and 186 are attached to the base 180 on which the magazine 118, 118a is mounted by hinges 194, 194a and 196, 196a, which enable the doors 184 and 186 to swing from a closed position to an open position, and vice-versa. The resilient biasing elements 188 and 190 are extended by a three-component assembly linked to a slide 198, which is used to open the doors 184 and 186 to enable the advancement of a test strip from the magazine 118, 118a to the lancing/collecting assembly 112. One component of the three-component assembly is a bi-directional rod 200 having a bi-directional slot 202 formed therein. The bi-directional slot 202 receives the pin 170 attached to the slide 198. The pin 170 moves in a slot 206, which restricts the movement of the pin 204 to a single direction. Attached to the bi-directional rod 200 is the second component of the three-component assembly, a rod 208 that extends in a direction substantially perpendicular to the lower end 200a of the bi-directional rod 200. The first end 208a of the rod 208 is securely attached to the bi-directional rod 200, and can only move when the bi-directional rod 200 moves. The third component of the three-component assembly is a rod 210 having a first end 212 pivotally connected to the second end 208b of the rod 208 and a second end 214 having a T-shaped projection 216 thereon that exerts a negligible force upon the resilient biasing elements 188 and 190 when the slide 198 is in its uppermost, or starting, position. In order to cause the doors 184 and 186 to open so that a mechanism for advancing a test strip from the assembly for storing test strips and dispensing test strips 110 to the lancing/collecting assembly 112 can advance a test strip from the magazine 118, 118a to the lancing/collecting assembly 112, the slide 198 is pushed in a direction to cause the pin 170 to move until it reaches a position "A", at which point the bi-directional feature of the bi-directional rod 200 causes the second end 208b of the rod 208 to move upwardly, which, in turn, causes the rod 210 to rise slightly, thereby causing the T-shaped projection 216 to raise an extension 218a of the door 184 and an extension 218b of the door 186, which extends the resilient biasing elements 188 and 190, respectively, thereby causing the doors 184 and 186 to open. When the doors 184 and 186 are open, the mechanism for advancing a test strip from the assembly for storing test strips and dispensing test strips 110 to the lancing/collecting assembly 112 causes a test strip to be fed from the magazine 118, 118a to the lancing/collecting assembly 112. When the slide 198 returns to its starting position, the resilient biasing elements 188 and 190 retract, thereby causing the doors 184 and 186 to close, and, consequently restoring the substantially air-tight, moisture-tight seal between the doors 184 and 186 and the magazine 118, 118a.

For the latter two embodiments, the mechanism for advancing a test strip from the assembly for storing test strips and dispensing test strips 110 to the lancing/collecting assembly 112 can be similar to that shown and described for the first embodiment. In the three embodiments described herein, the mechanism for advancing a test strip from the assembly for storing test strips and dispensing test strips 110 to the lancing/collecting assembly 112 can be separate from the mechanism for unsealing of the magazine 118, 118a or the mechanism for advancing a test strip from the assembly for storing test strips and dispensing test strips 110 to the lancing/collecting assembly 112 can be integrated with the mechanism for unsealing of the magazine 118, 118a.

Figure 23:
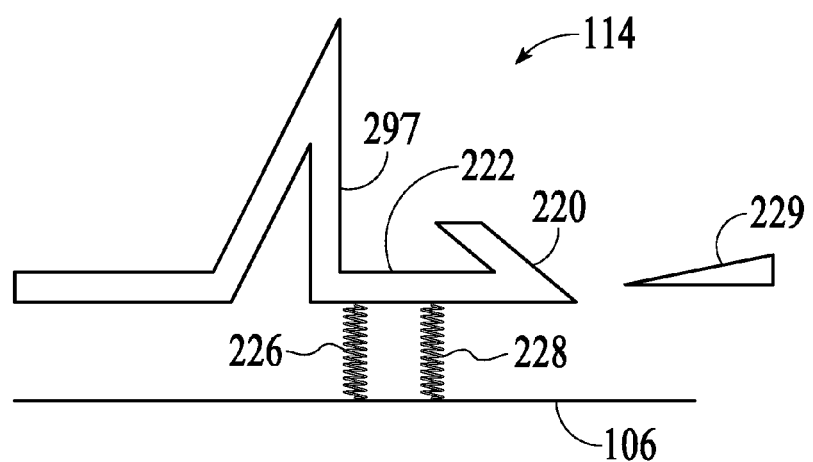
FIG. 23 is a schematic view of a mechanism suitable for use in a medical diagnostic apparatus of an alternative embodiment for removing a protective cover from a lancet and re-attaching the protective cover to the lancet.

Because the lancet of the lancet-containing portion of the STRIPLET™ is furnished with a protective cover, the protective cover must be removed or displaced from the tip of the lancet before the lancet can be used to form an opening in the skin of the patient. Accordingly, the assembly 114 for removing a protective cover from the tip of a lancet and re-attaching the protective cover to the tip of a used lancet is located in a position whereby the assembly 114 can remove the protective cover from the tip of the lancet of the lancet-containing portion of the test strip prior to the lancing step and re-attach the protective cover to the tip of the lancet of the lancet-containing portion of the test strip prior to disposal of the test strip after the test strip has been used. As shown schematically in FIG. 23, the assembly 114 includes a strip of flexible metal comprising a cover-snagging portion 220, a cover-storing portion 222, and a cover-stopping portion 297. The assembly 114 can be positioned between the magazine 118, 118a and the lancing/collecting assembly 112. The assembly 114 is mounted to the tub 106 by one or more resilient biasing elements 226 and 228, e.g., springs, which enable upward and downward movement of the assembly 114. As a test strip is being advanced from the magazine 118, 118a, the test strip slides over the cover-stopping portion 297 and the cover-storing portion 222 until the protective cover is snagged by the cover-snagging portion 220. As the test strip continues to advance to the lancing/collecting assembly, the lancet of the lancet-containing portion of the test strip is separated from the protective cover and the test strip enters the lancing/collecting assembly 112. The protective cover is retained in the cover-storing portion 220. At the completion of the testing procedure, the protective cover is re-attached to the tip of the lancet by moving the test strip toward the assembly 114 or by moving the assembly 114 toward the test strip, whereby the tip of the used lancet re-enters the protective cover. The protective cover is made from a material that can receive the sharp tip of a lancet. The cover-stopping portion 297 stops the protective cover from sliding during re-attachment of the protective cover to the tip of the lancet to facilitate the step of re-attachment. The resilient biasing elements 226 and 228 enable the assembly 114 to move upwardly and downwardly, as required, to remove the protective cover from the tip of the lancet or to re-attach the protective cover to the tip of the lancet. The cover-snagging portion 220 is moved downwardly by a compressing element 229 after the protective cover is re-attached to the tip of the lancet to allow the re-covered test strip to be ejected from the medical diagnostic device 100. A pushing device can be used to push the re-covered test strip out of an ejection port 230 in the housing 102.

Referring again to FIGS. 1 and 2A-2C, a printed circuit board (PCB) assembly 232 for controlling the electromechanical components and the electronic components of the medical diagnostic device 100, 100a is positioned in the housing 102, 102a. At least one battery 234 is included in the housing 102, 102a to provide a source of power for at least one motor 236 that will drive the lancing/collecting assembly 112 and, optionally, to drive one or more additional functional components of the medical diagnostic device 100, including, but not limited to, the assembly 110, 110a for advancing test strips from the magazine 118, 118a to the lancing/collecting assembly 112, the system for arming the lancet, the system for triggering the lancet, and to provide power for the analyzer 116 for determining the parameter of the biological liquid to be measured, storing data collected, activating the display, and other features of the analyzer 116. More than one motor can be employed for carrying out the various mechanical functions described herein. The medical diagnostic device 100, 100a has a display 238, typically a liquid crystal display, for showing the results of the determinations of analytes. The medical diagnostic device 100, 100a typically includes one or more flexible circuits for connecting the PCB assembly 232 to the analyzer 116 and connecting the PCB assembly 232 to the motor or motors. The medical diagnostic device 100 can also include flexible circuits to connect the PCB assembly 232 to one or more sensors to determine the status of the medical diagnostic device 100, 100a. The medical diagnostic device 100, 100a also has various activation buttons 240a, 240b, 240c, and 240d for actuation of various functions of the medical diagnostic device 100, 100a. The medical diagnostic device 100, 100a can also have an alphanumeric keypad for manual input of various parameters related to determination of analytes.

The medical diagnostic device 100, 100a has a depth adjustment control 242. A particularly useful depth adjustment control employs a knob that is rotated to control movement of the end cap 104 or a portion thereof so that the depth of penetration of the lancet of the lancet-containing portion of the test strip can be specified. In another embodiment, a series of caps of different sizes are affixed to the housing at the lancing and testing port to accommodate the different lancing depths that are preferred by different patients or users.

Figure 6B:
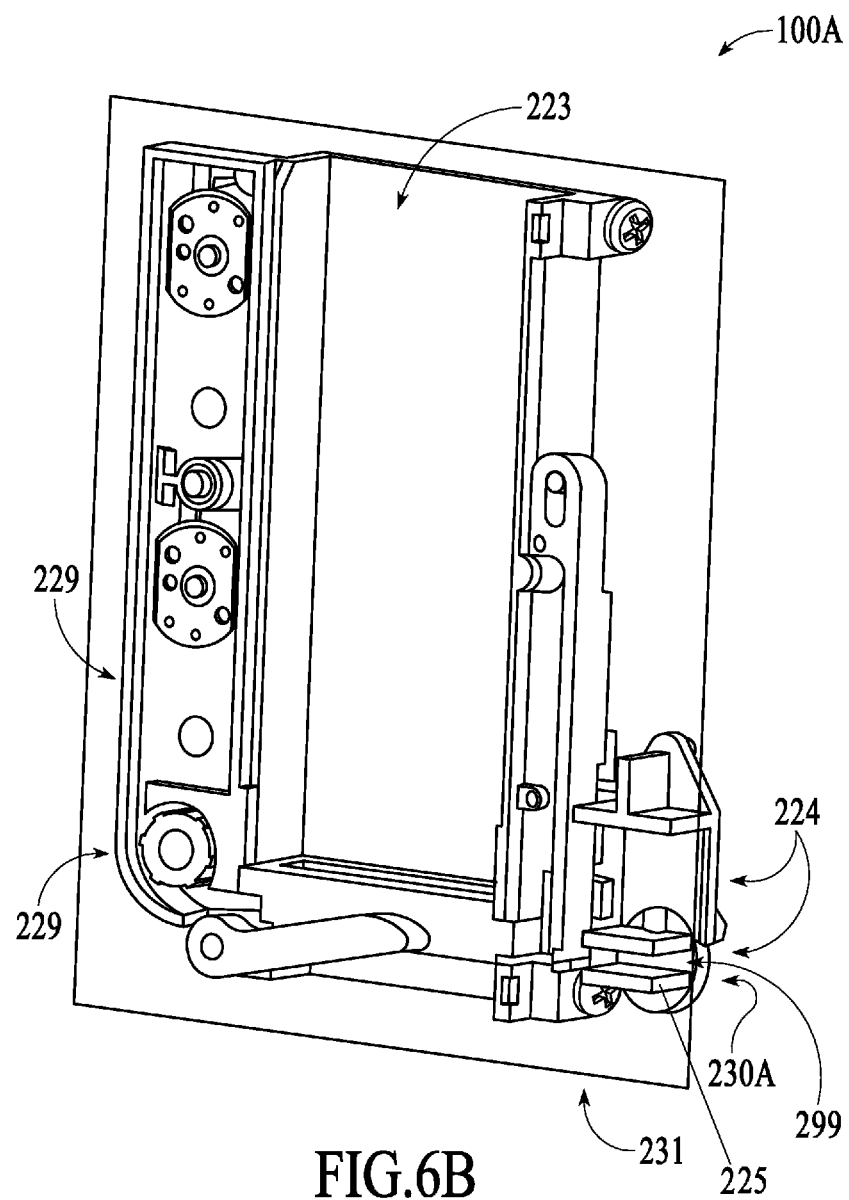
FIG. 6B is a back view of mechanical components of a medical diagnostic apparatus in accordance with an embodiment.
Figure 6C:
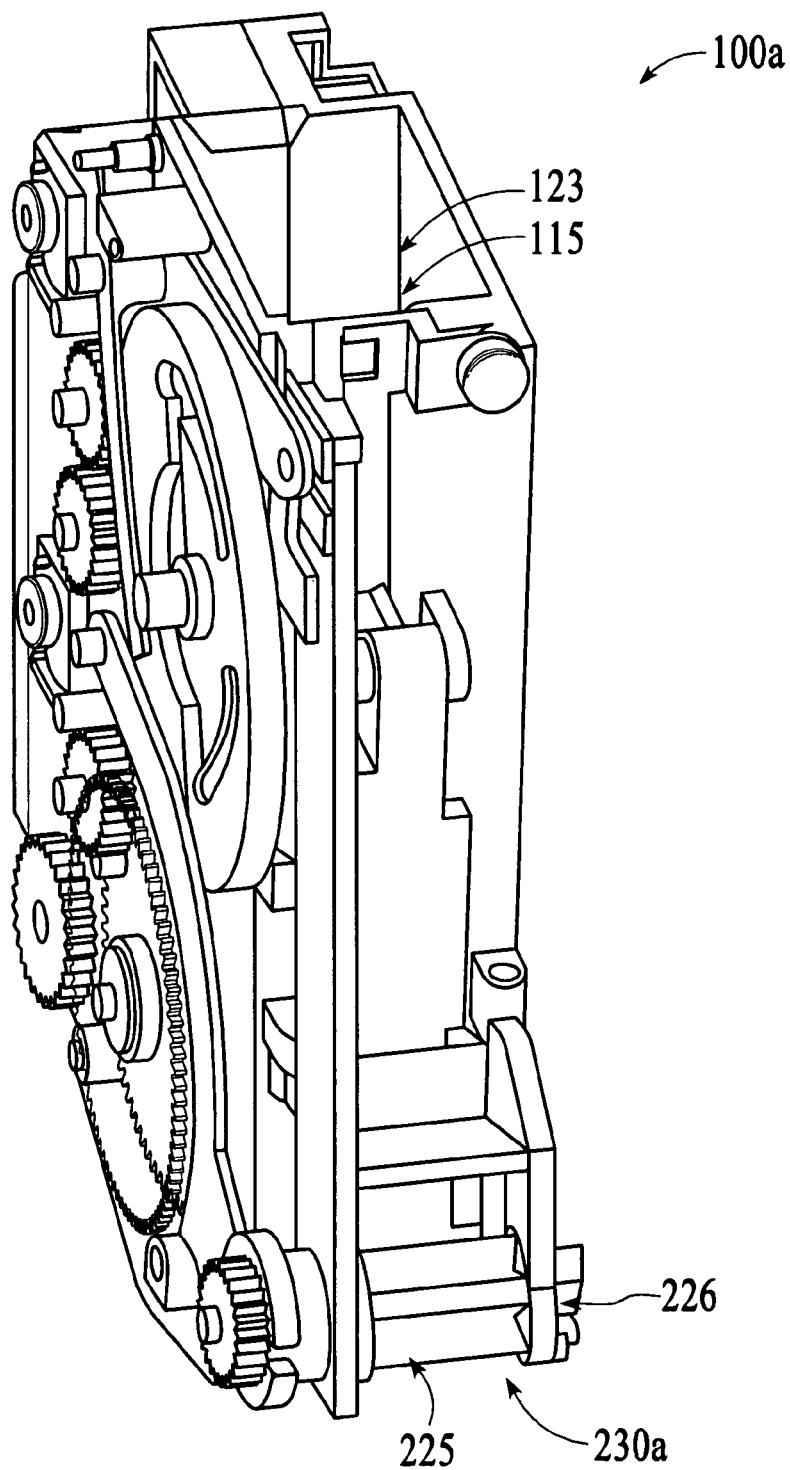
FIG. 6C is a side view of mechanical components of a medical diagnostic apparatus in accordance with an embodiment.
Figure 6D:
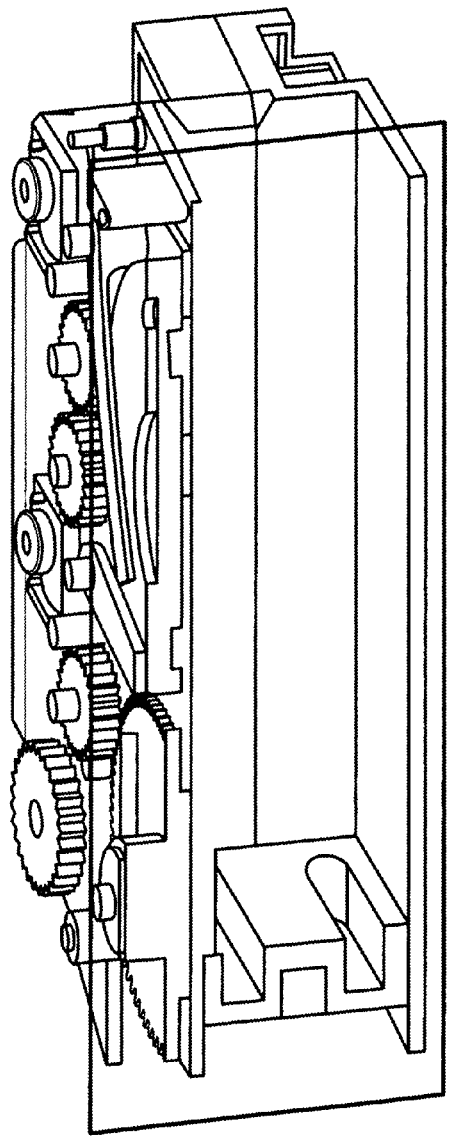
FIG. 6D is an opposite side view to FIG. 6C of mechanical components of a medical diagnostic apparatus in accordance with an embodiment.
Figure 6E:
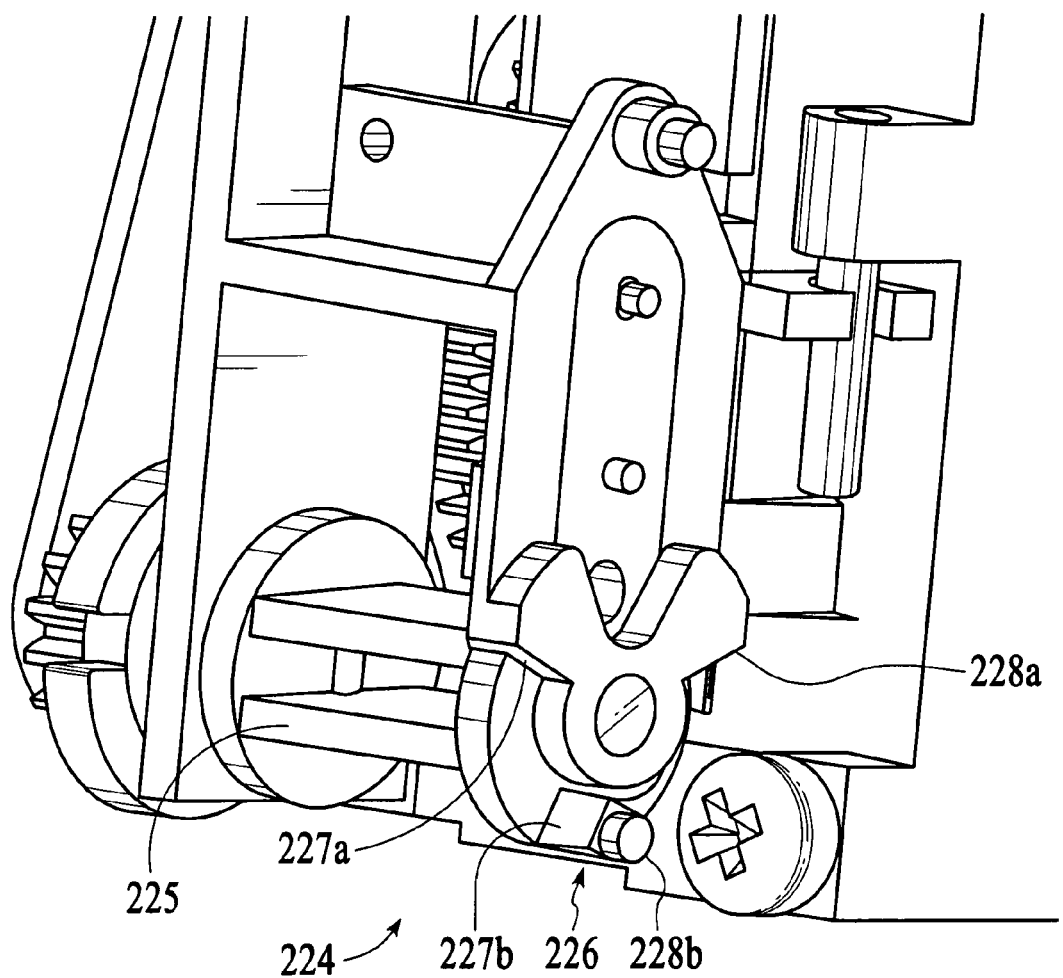
FIG. 6E is a perspective view of a rotatable slot for reorienting a testing STRIPLET™ within a medical diagnostic apparatus in accordance with an embodiment.

FIGS. 6A-6D are front, back, side and opposite side views, respectively, of mechanical components of a medical diagnostic apparatus 100, 100a in accordance with an embodiment, while FIG. 6E is a perspective view of a rotatable turret 225 including a STRIPLET™ slot 299 for reorienting a testing STRIPLET™ within a medical diagnostic apparatus 100, 100a in accordance with an embodiment.

The apparatus shown functions substantially mechanically according to first and second mechanical subsets 219 and 220, respectively, which includes first and second sets of gears 221 and 222, in addition to various cams and levers. There is a cartridge slot defined down the center of the long dimension of the apparatus 100a. A reorientation carriage 224 is shown including turret 225 that rotates according to the movement of a cam 226 that oscillates between points, for example around an unstable equilibrium or other mechanism for urging the rotation of the turret 225 for reorienting the STRIPLET™ between lancing and testing via port 231 and ejecting via port 230a. In an embodiment, the turret 225 is rotated 90 degrees, from an original position that the turret 225 is in when the STRIPLET™ 1000a is loaded, prior to translation through the port 231 of FIG. 6B for lancing, 180 degrees prior to translation through the port 231 for testing, and 90 degrees prior to ejection through port 230a of FIG. 6B. Referring to FIG. 6E, the STRIPLET™ is oriented in a first direction when surfaces 227a and 227b meet for lancing, and the STRIPLET™ is oriented in a second direction for testing, rotated approximately 180 degrees or another angle equal to the angular displacement of the lancet and reagent area of the STRIPLET™, or flipped relative to the first direction, when surfaces 228a and 228b meet. When the STRIPLET™ is in the first direction, it is armed for lancing such that upon advancement through port 231, a lancing site can be pierced. When the STRIPLET™ is reoriented as a result of the functioning of cam 226, the STRIPLET™ is ready to be advanced through the port 231 in the new orientation, so that a test sensor this time extends to touch the bodily fluid exposed at the lancing site due to the lancing. In the position shown in FIG. 6E, a fresh STRIPLET™ may be loaded into the turret 225 from the cartridge, and a used STRIPLET™ may be discarded through ejection port 230a.

Figure 6F:
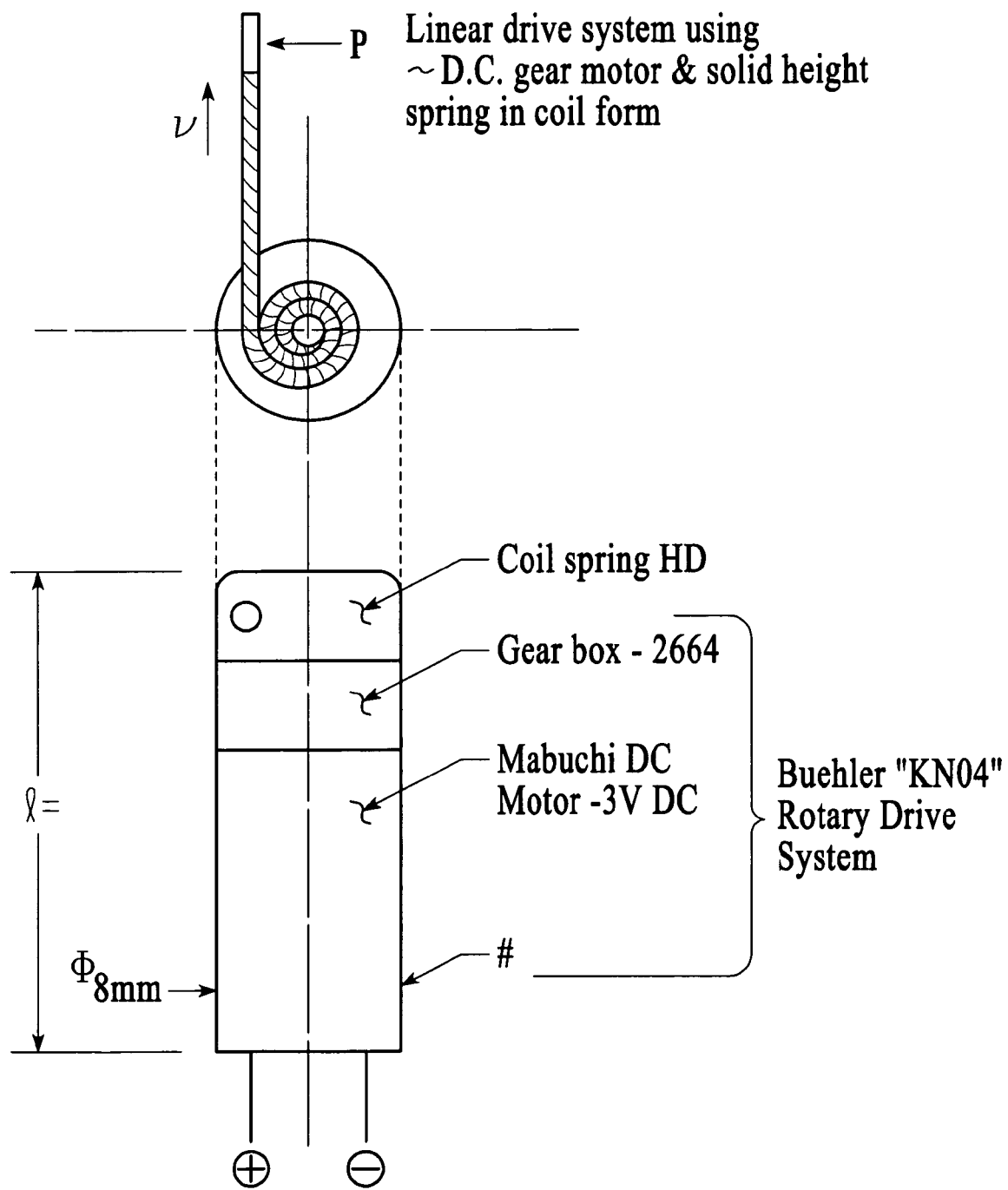
FIG. 6F is a exemplary embodiment illustrating how a pusher P may be advanced and retreated along a guide track for advancing the STRIPLET™ to the turret and arming the lancet, respectively.
Figure 7A:
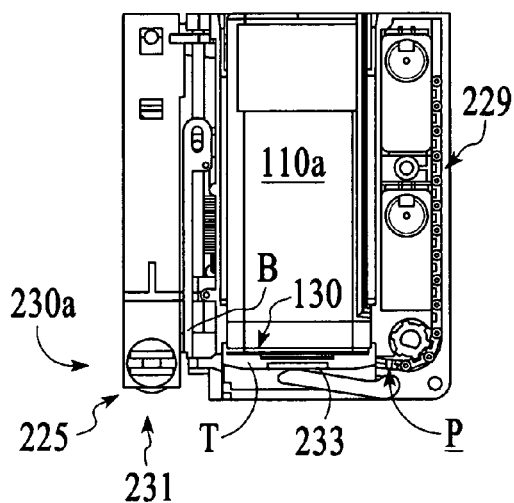
FIGS. 7A-7P illustrate an operational sequence of a medical diagnostic apparatus in accordance with an embodiment.

A track 229 is shown in FIG. 6B along which a pusher P, not shown but which may be a flexible piece such as a uniformly flexible plastic or a chain with a suitable end piece for contacting the STRIPLET™, see FIGS. 7A-7P, moves to advance the STRIPLET™ into the turret 225, or permit it to retreat into the housing 110, 110a. The pusher P may lead a chain drive, or a highly flexible uniform plastic and/or another flexible material such as a metal such as stainless steel. The pusher P and drive mechanism may itself be a single piece or multiple pieces like a chain drive. The flexible pusher mechanism, including the pusher P and the drive mechanism, may wind and unwind from a coil to advance when it unwinds and retreat when it winds. FIG. 6F illustrates this feature. The unwinding coil may follow the track 229 to push the STRIPLET™ through port both when the STRIPLET™ is in a lancing orientation and when the STRIPLET™ is reoriented for testing. FIG. 6F illustrates a Buehler KNO4 rotary drive system, which can be used to provide a linear drive mechanism for advancing a STRIPLET™. The system shown in FIG. 6F includes a DC gear motor (e.g., Mabuchi DC motor-3V DC) and solid height spring in coil form.

The pusher P may also simply extend along a long dimension of the housing and turn at a corner, with the help of a curved inner wall surface such that the track 229 is formed between an outer wall of the housing or a proximate attachment thereto and the curved inner wall surface. The pusher P may even bend around two or three corners of the housing, and may be condensed in various ways when it is in the retreated position so that it is long enough to extend sufficiently when advancing the STRIPLET™ and yet is maintained inside the housing out of the way of other components when retreated.

In operation, the pusher P moves along track 229 and meets with a loaded STRIPLET™ pushing it into the turret 225. The STRIPLET™ is rotated 90 degrees and advanced through port 231 for lancing. The STRIPLET™ retreats some and is rotated or flipped by reorientation mechanism 224, including cam 226, as the STRIPLET™ remains within the slot 229 of turret slot 225. The STRIPLET™ is reoriented by 180 degrees, or another angle equal to the angle between the lancet and testing area of the strip portion of the STRIPLET™, so that it can advanced again through the port 230a so that test sensor end 1002 of the STRIPLET™ now exits port 230a and bodily fluid, e.g., blood, is applied for testing a body analyte, e.g., glucose, level such as a blood glucose, or ketone or other analyte level. After testing, the STRIPLET™ is rotated 90 degrees or whatever the angle between the ejection port and the lancing and testing port relative to the rotational center of the turret or STRIPLET™, and is ejected through port 231 with lancet cap covering lancet for safety. The pusher P may be used a second time for assisting in the ejecting of the used and recapped STRIPLET™ 1000a.

Figure 6G:
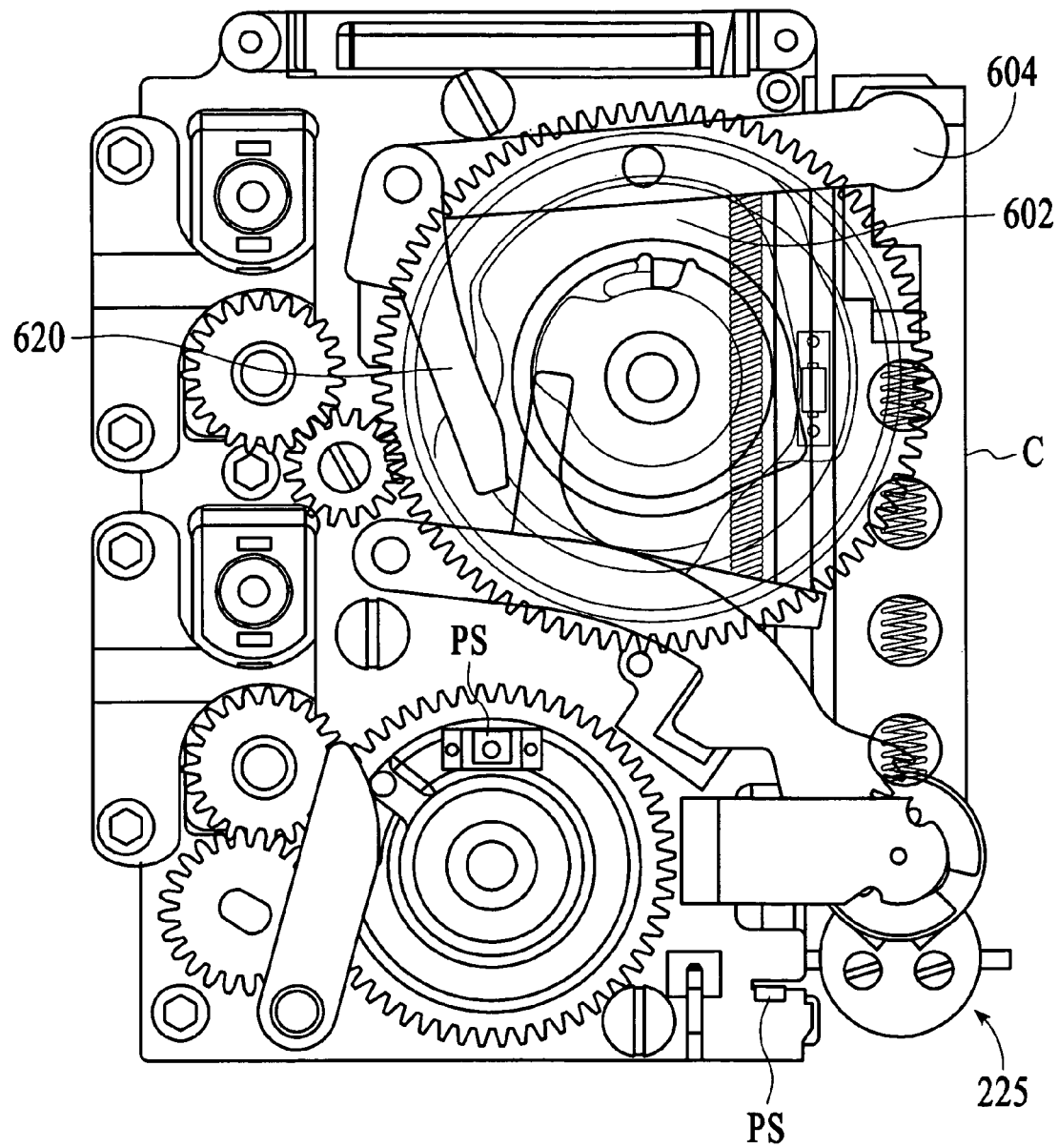
FIG. 6G illustrates an exemplary embodiment showing a side view with some transparencies of mechanical components of an integrated meter.

FIG. 6G illustrates an exemplary embodiment showing a side view with some transparencies of mechanical components of an integrated meter. A main gear 602 or drive gear 602 is shown partially transparent for illustration. Gear 602 is coupled with a cam which is not visible in FIG. 6G, but which controls cam follower 604. A carriage C is shown including a turret 225, and these components are further illustrated at FIGS. 7A-7P and described below. FIG. 6G also illustrates multiple photosensors PS that are used for monitoring various movements and status of a lancing and testing process performed with the integrated meter. Optical signals are received at photosensors PS, which may or may not also emit optical signals that are reflected back, for providing information to a microprocessor and/or other meter control circuitry.

Figure 6H:
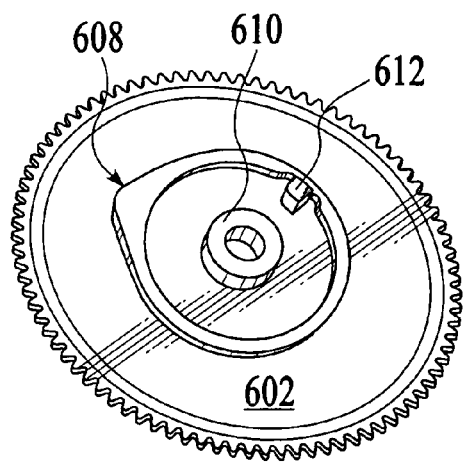
FIGS. 6H-6I illustrate front and back views of a main drive gear of an integrated meter according to an embodiment.
Figure 6I:
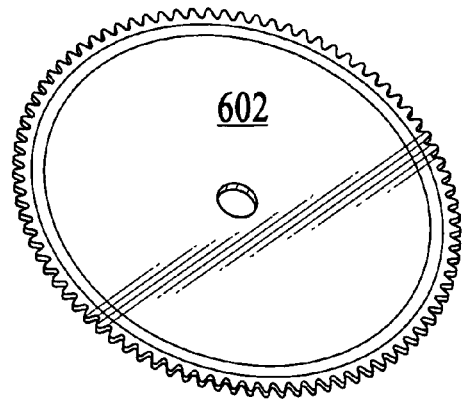

FIGS. 6H-6I illustrate front and back views of a main drive gear of an integrated meter according to an embodiment. The front of the main gear 602 includes a central ring-like portion that has a nub 608, and a hook 610 and post 612 for a clock spring (not shown). When the nub 608 is at about the 7 o-clock position, nub 608 causes lever 620 to rotate clockwise releasing a disk gear 630 or cam gear 630.

Figure 6L:
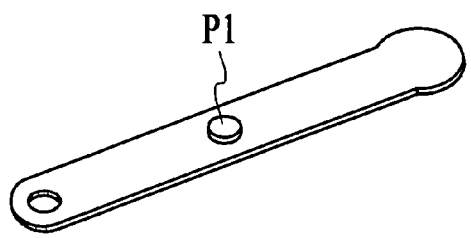
FIGS. 6L-6M illustrates front and back views of cam follower of an integrated meter according to an embodiment.
Figure 6M:
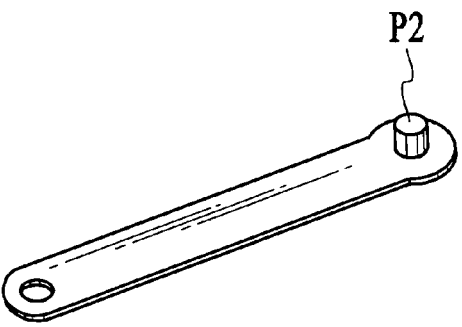
Figure 6J:
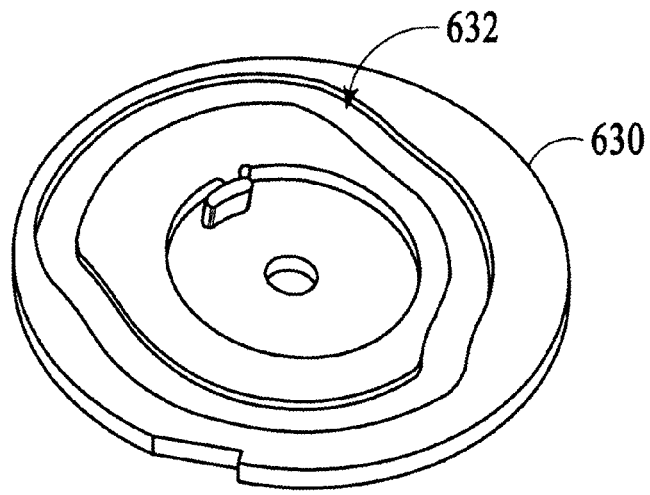
FIGS. 6J-6K illustrate front and back view of a disk or cam gear of an integrated meter according to an embodiment.
Figure 6K:
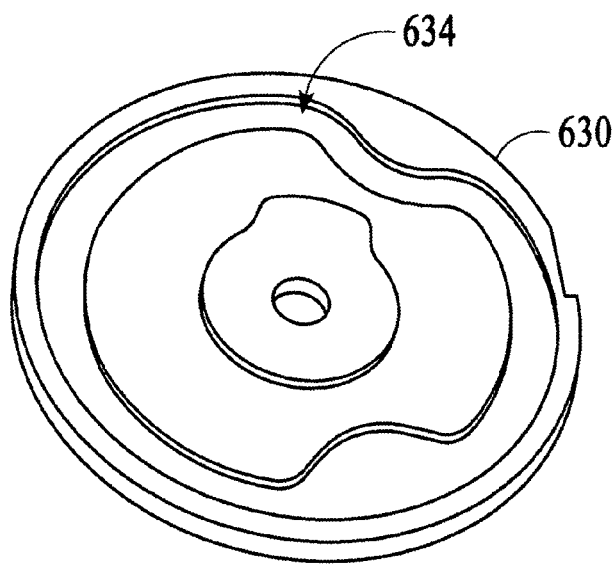

FIGS. 6J-6K illustrate front and back views of the disk gear 630 or cam gear 630 of an integrated meter according to an embodiment. The clock spring interfaces between the main gear 602 and the cam gear 630. Two cam paths 632 and 634 are defined in the cam gear, one or either side.

FIGS. 6L-6M illustrates front and back views of cam follower 604 of an integrated meter according to an embodiment. Cam follower 604 includes pivots P1 and P2 which follow cam paths 632 and 634.

FIGS. 7A-7P illustrate an operational sequence of a medical diagnostic apparatus in accordance with an embodiment. FIG. 7A shows the medical diagnostic apparatus of this embodiment. The turret 225 is shown with the positions of lancing and testing port 231 and ejection port 230a pointed out. Track 229 has a chain therein which is led by pusher P. The cartridge 110a is closed with seal 130 in place sealed with a tub T. Seal 130 may utilize an o-ring type seal. Tub T includes centering element 233, which centers a next STRIPLET™ for precision loading onto track 229 for permitting the STRIPLET™ and pusher P to be precisely relatively disposed. A blade B is also illustrated awaiting its time to move downwardly for uncapping a lancet of a STRIPLET™ 1000a.

Figure 7B:
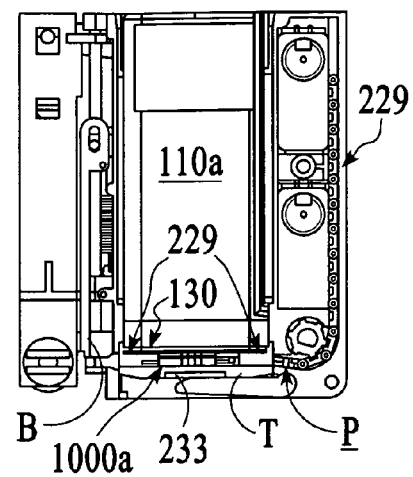

FIG. 7B shows the tub T moved down breaking the seal 130 with tub T to expose a STRIPLET™ 1000a. The STRIPLET™ 1000a is loaded from the cartridge 110a onto track 229 guided by centering element 233. The tub T may include a guide platform for positioning a STRIPLET™ while retreating from the cartridge 110a. The STRIPLET™ may therefore be loaded with precision onto the guide track segment from which a pusher P matches a contour of the lancet end of the STRIPLET™ and advance the STRIPLET™ into the turret 225.

Figure 7C:
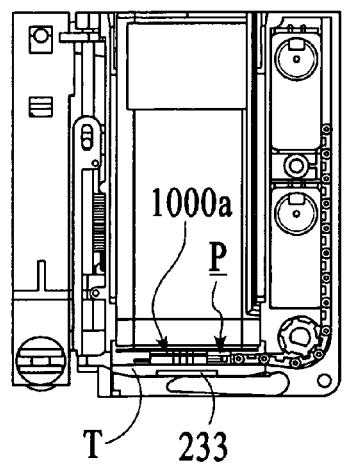
Figure 7D:
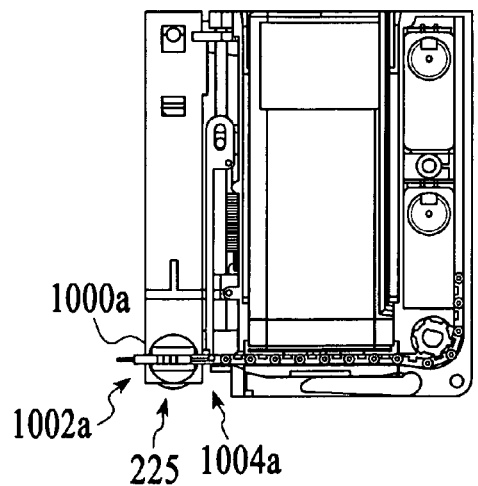

FIG. 7C shows the pusher P advanced to meet the STRIPLET™1000a. The tub T continues to be in the downward position while the track 229 is exposed. FIG. 7D shows the pusher P after having pushed the STRIPLET™ 1000a into turret 225. The strip end 1002a of the STRIPLET™ 1000a is pushed through first, while the lancet end 1004a of the STRIPLET™ 1000a is behind. At FIG. 7E, a blade B or decapping lever moves down to engage the lancet cap 1204a. A ridge on the lancet cap 1204a allows a contour of the blade B to couple therewith. The chain retracts as shown in FIG. 7F rotating the blade B slightly to permit the lancet cap 1204a to move rearward along with the chain and pusher P so that the lancet cap 1204a becomes removed from the lancet end 1004a of the STRIPLET™ 1000a which remains in position in the turret 225.

Referring to FIG. 7G, now that the lancet cap 1204a is removed and retracted fully from the STRIPLET™ 1000a, the turret 225 is rotated 90 degrees. This 90 degree rotation of the STRIPLET™ 1000a orients the STRIPLET™ 1000a with lancet 1004a first and strip 1002a behind, for being advanced through port 231 for lancing.

FIG. 7H illustrates a lancing position as the carriage C is moved relative to the rest of the meter apparatus for lancing. Alternatively, a mechanism for pushing only the STRIPLET™ downward or only a turret section of the carriage downward may be provided.

Figure 7I:
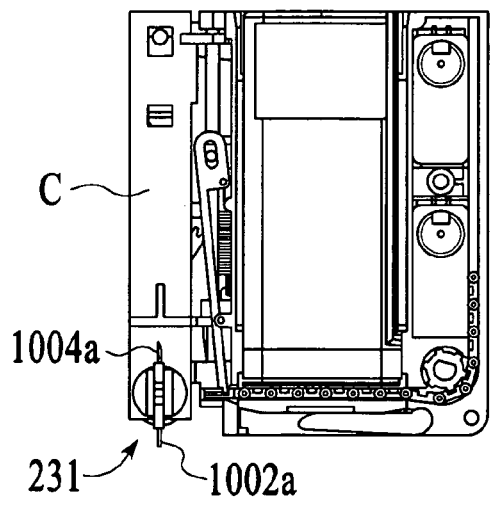

Referring to FIG. 7I, the carriage C is moved back upward after the lancing or piercing of the skin of a diabetic at a lancing site. The turret 225 is rotated 180 degrees preparing for sensing. Note that the strip end 1002a is shown in FIG. 7I pointing toward port 231, while in FIGS. 7G and 7H, the lancet end 1004a was pointing toward port 231.

Figure 7J:
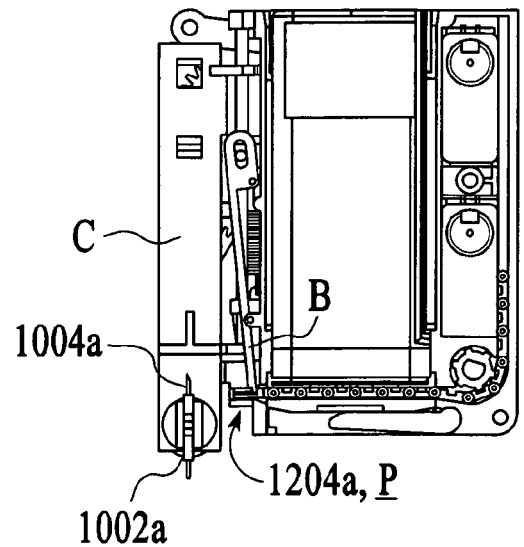

FIG. 7J illustrates how the carriage C is again moved downward this time for permitting body fluid appearing at the lancing site to be applied to the strip 1002a. Note that the lancet cap 1204a, blade B, and pusher P each remain in position while the lancing and testing occurs. The pusher P is overlapped with the cap 1204a, such that the blade holds both the cap 1204a and pusher P in place.

Figure 7K:
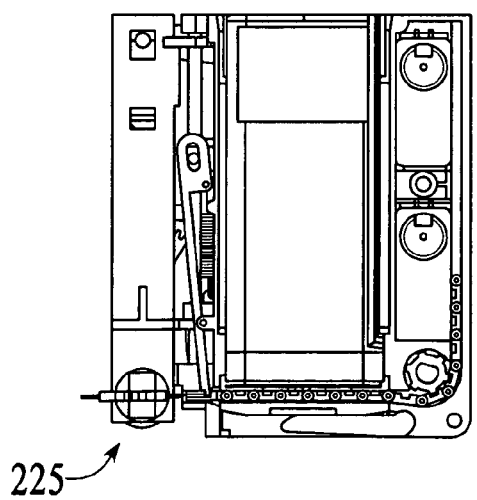
Figure 7L:
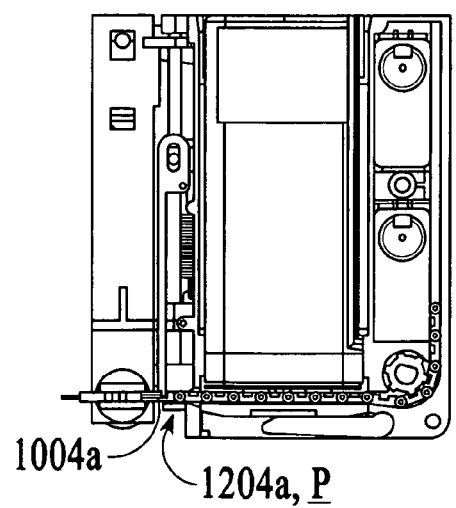
Figure 8:
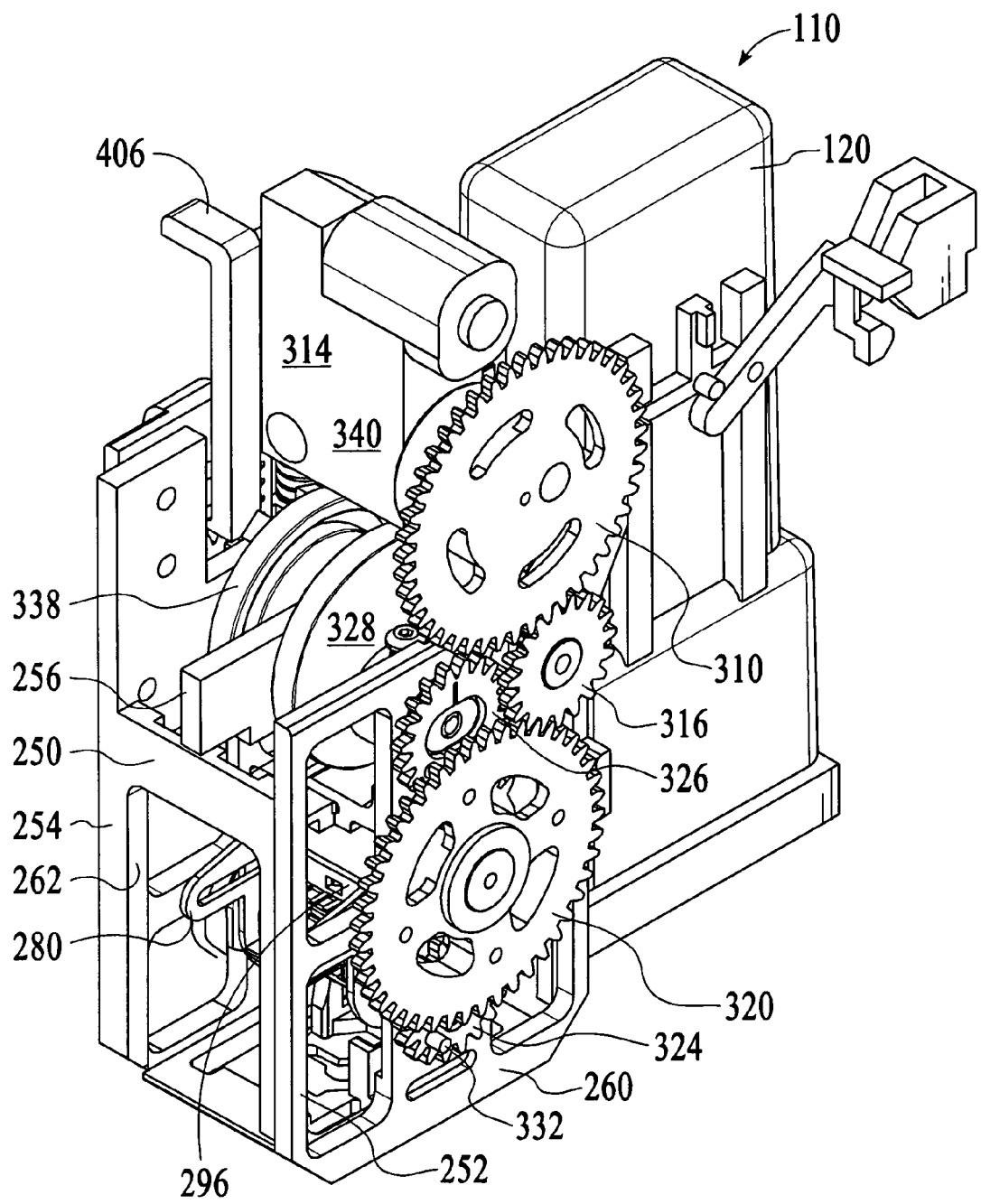
FIG. 8 is a perspective view of the lancing/collecting assembly of a medical diagnostic apparatus in accordance with an alternative embodiment.
Figure 9:
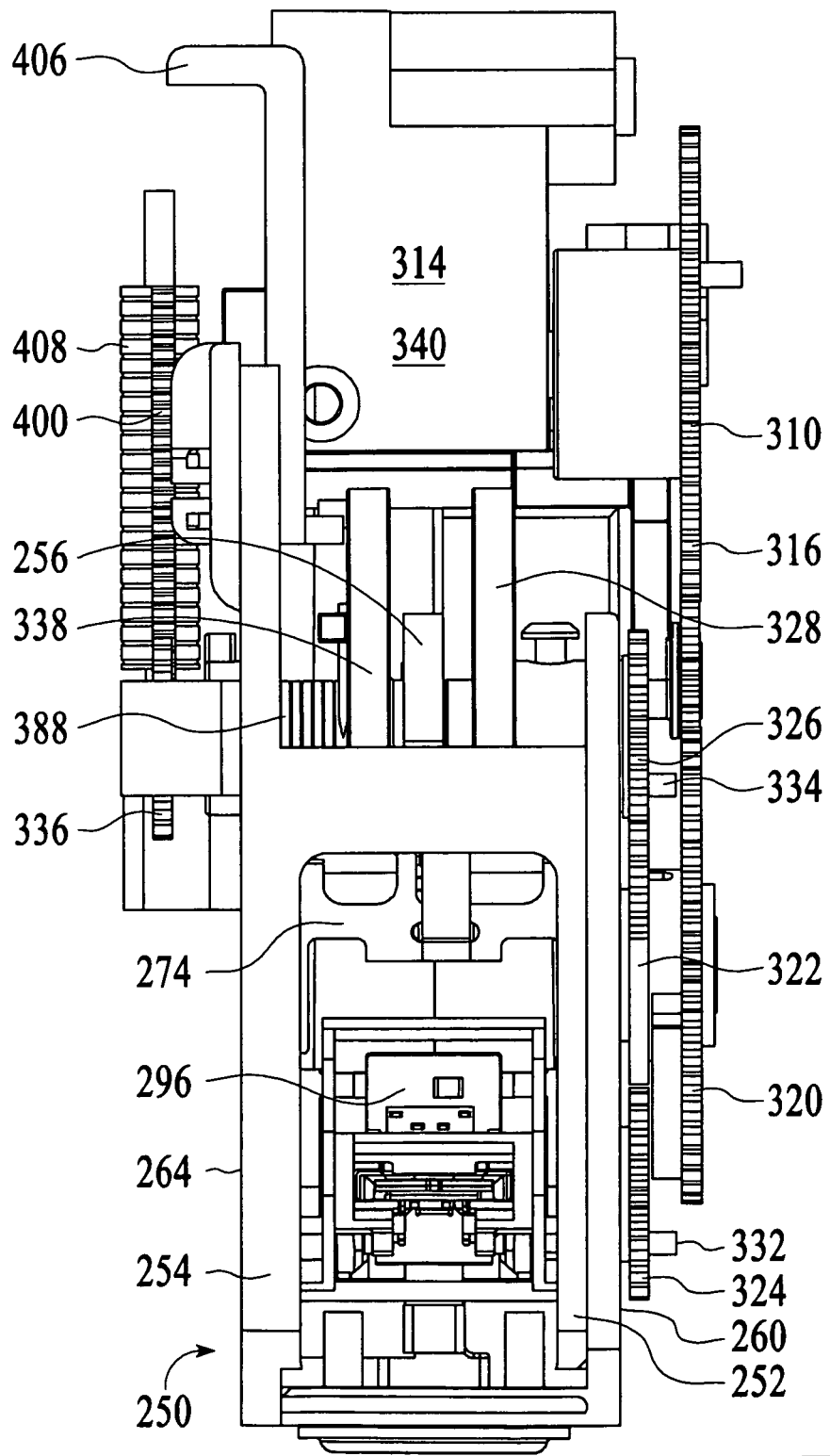
FIG. 9 is a front view in elevation of a medical diagnostic apparatus with a housing shown attached to an end cap and a tub.
Figure 10A:
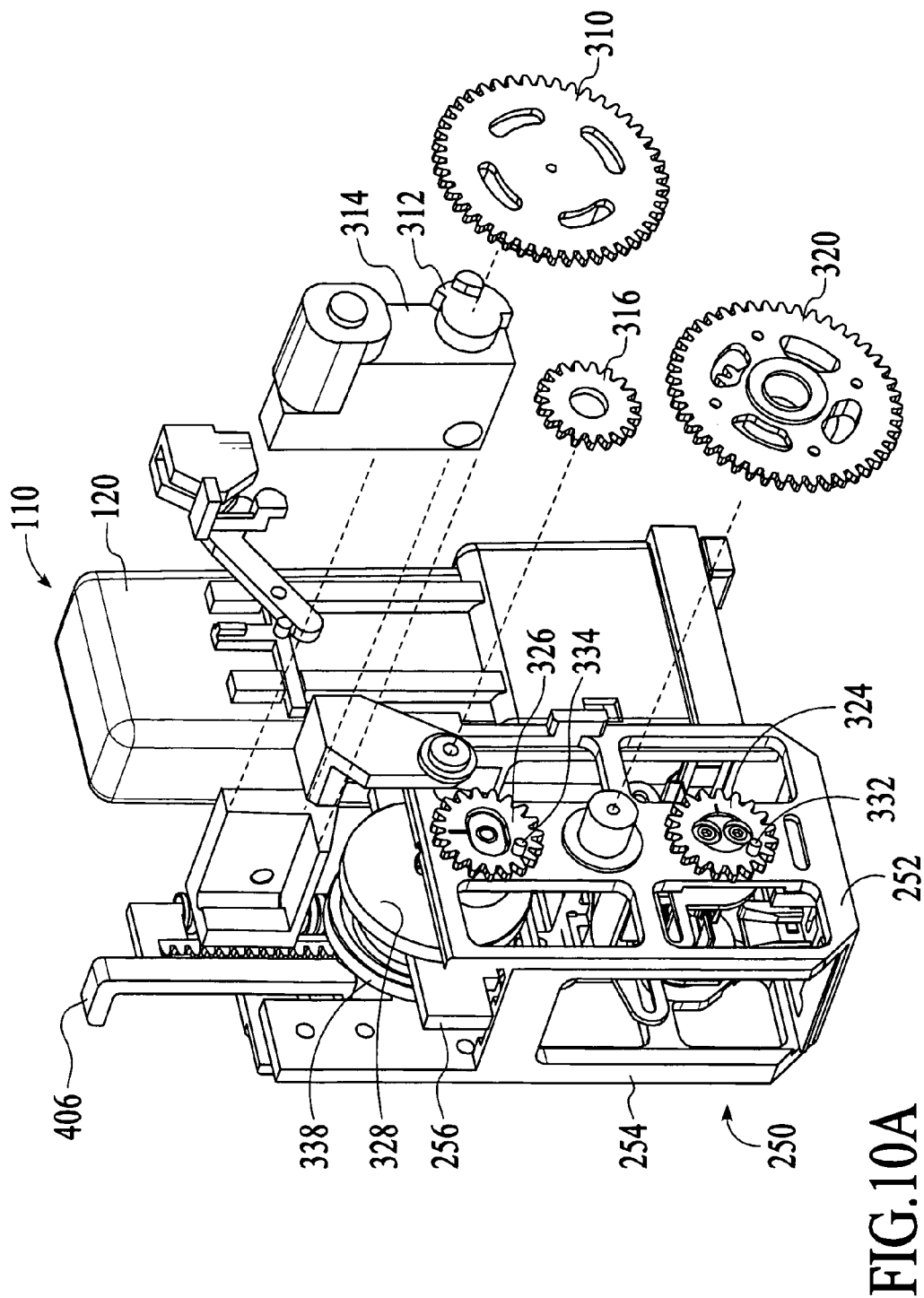
FIGS. 10A and 10B are exploded perspective views of the lancing/collecting assembly of the medical diagnostic apparatus in accordance with an alternative embodiment.
Figure 10B:
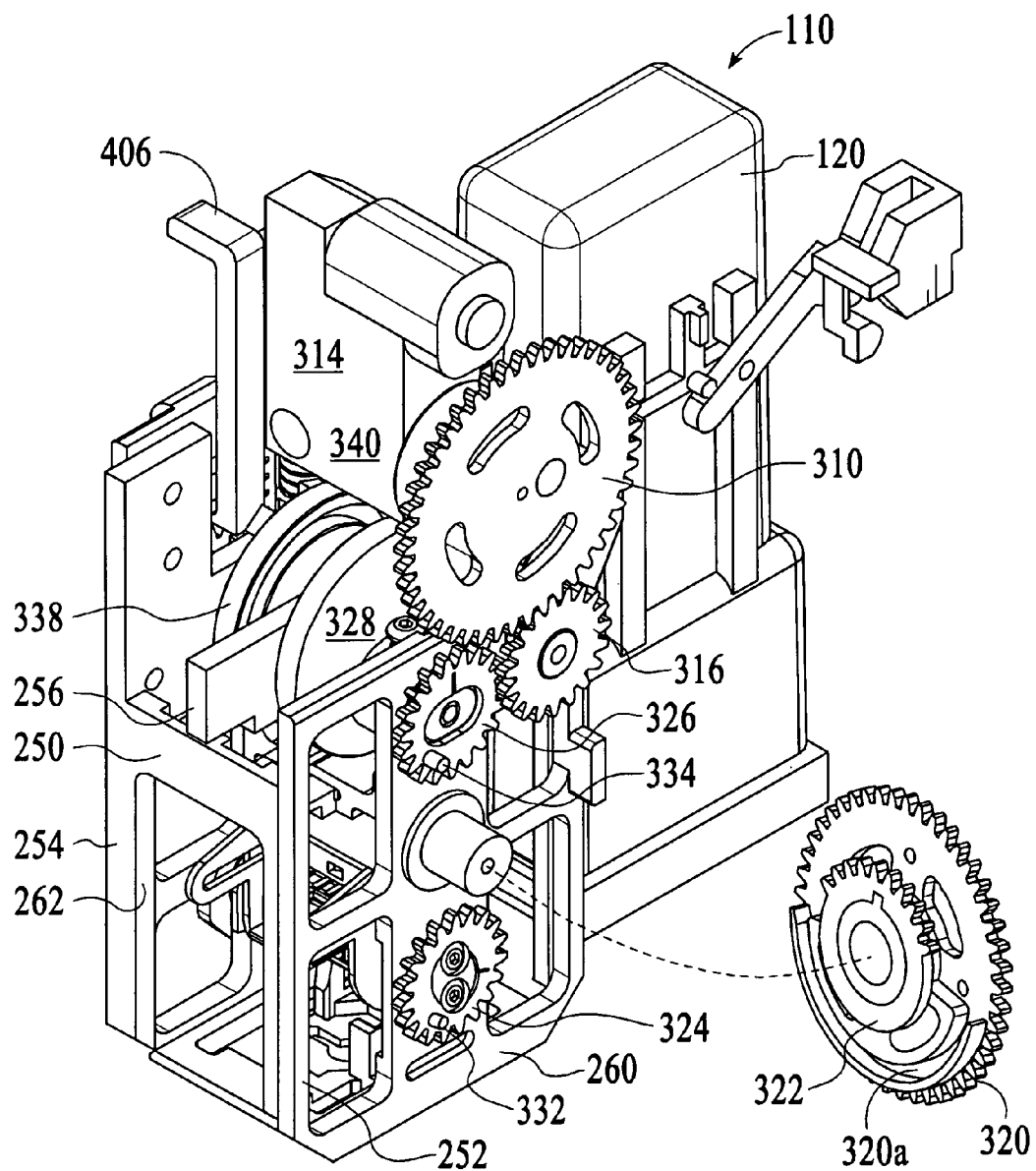
Figure 11:
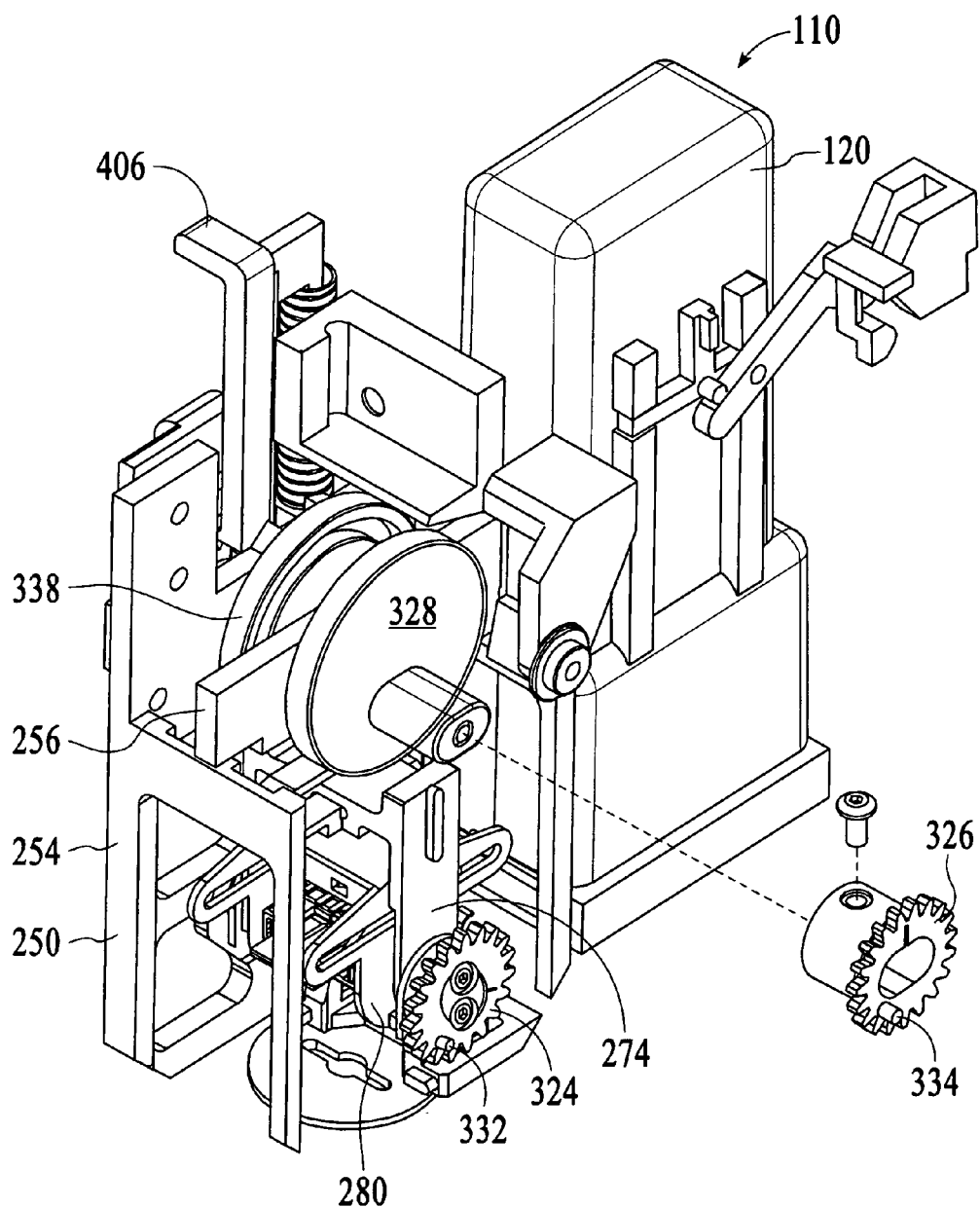
FIG. 11 is another exploded perspective view of a lancing/collecting assembly of a medical diagnostic apparatus in accordance with an alternative embodiment. In this view, part of the frame is shown as being broken away.
Figure 12:
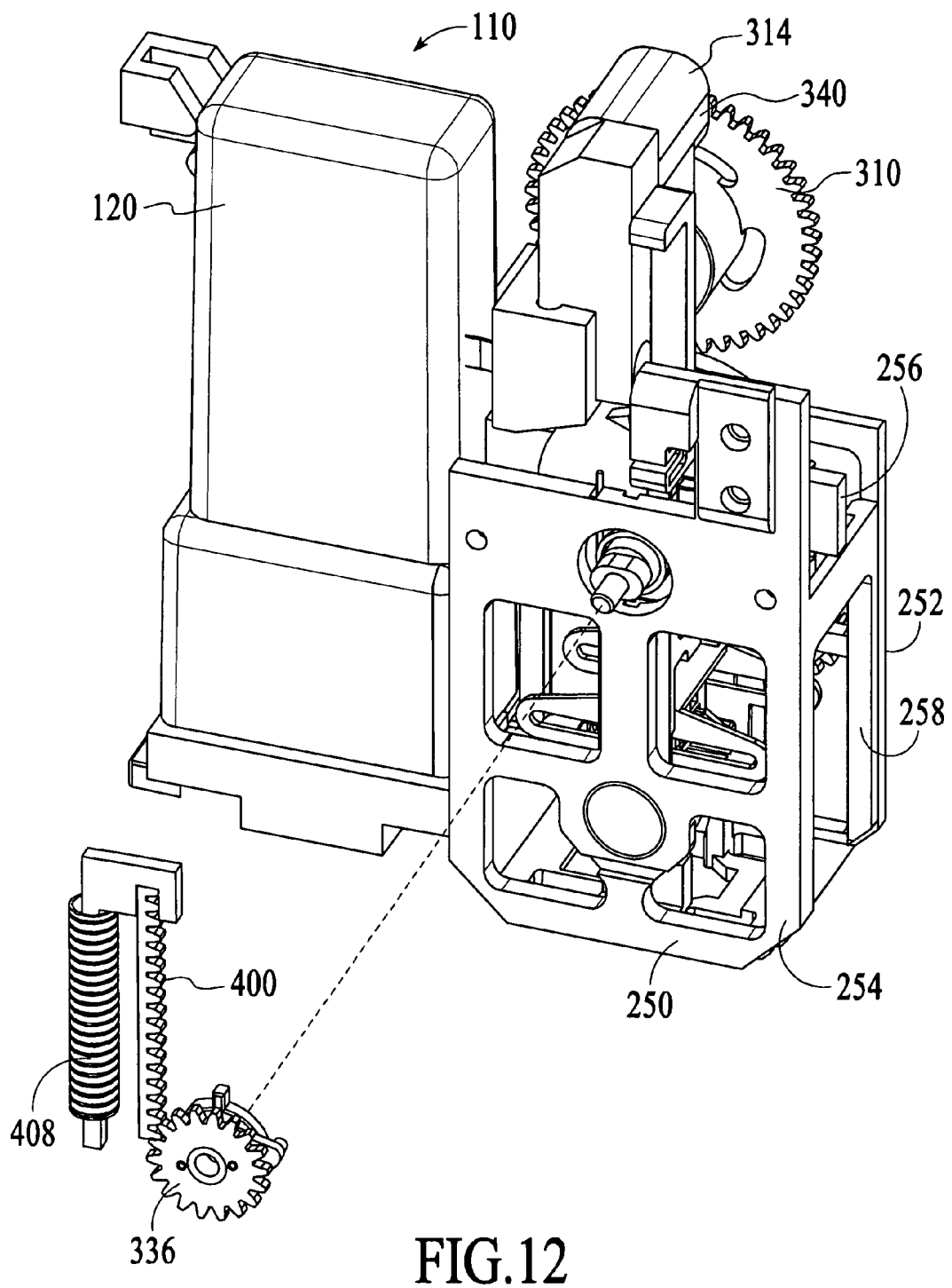
FIG. 12 is another exploded perspective view of a lancing/collecting assembly of a medical diagnostic apparatus of an alternative embodiment. This view shows a side of the lancing/collecting assembly not shown in FIGS. 8, 10A, 10B, and 11.
Figure 13:
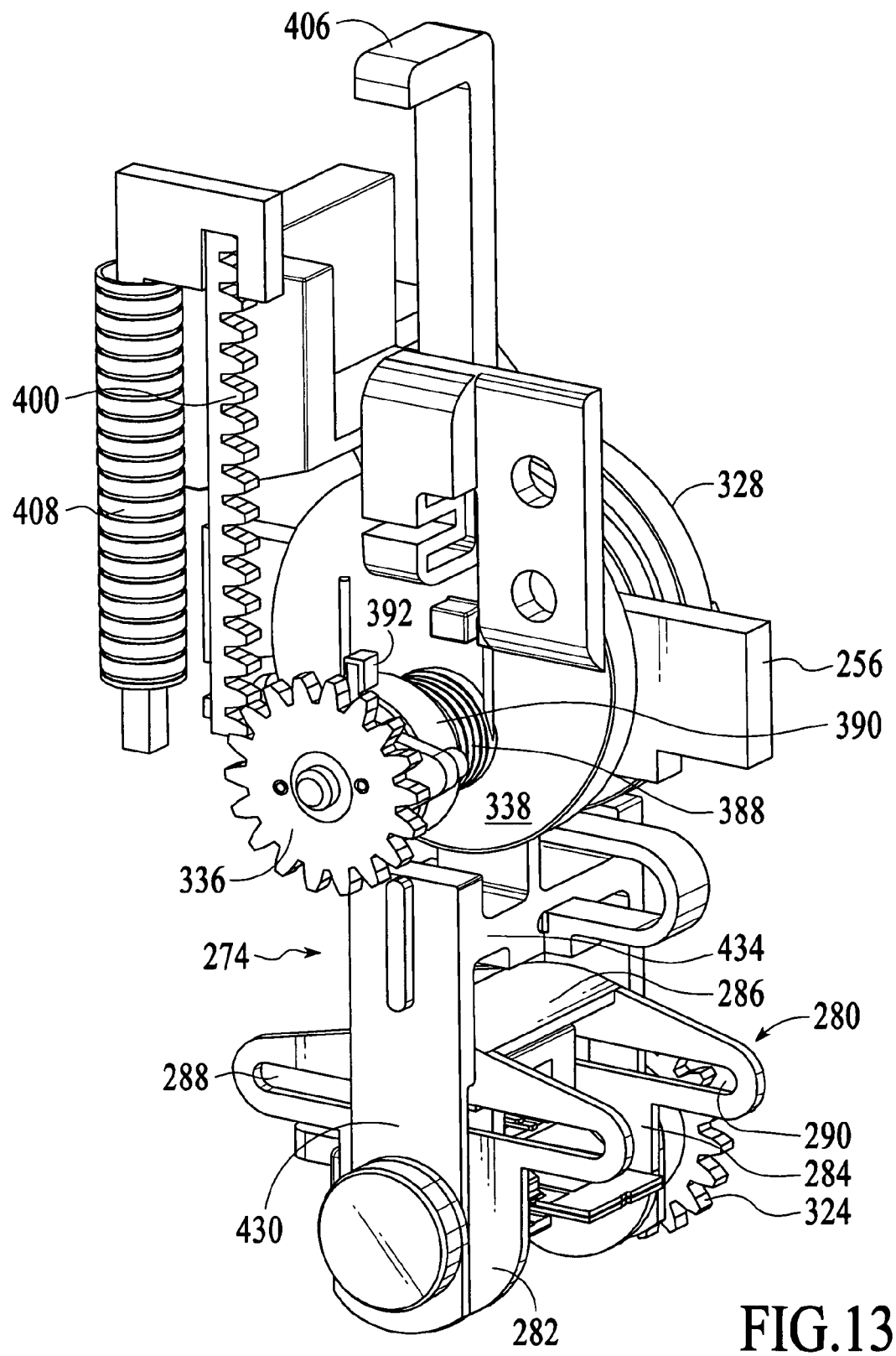
FIG. 13 is another exploded perspective view of a lancing/collecting assembly of a medical diagnostic apparatus of an alternative embodiment. This view shows a side of a lancing/collecting assembly not shown in FIGS. 8, 10A, 10B, and 11. In this view, the frame has been removed.
Figure 14:
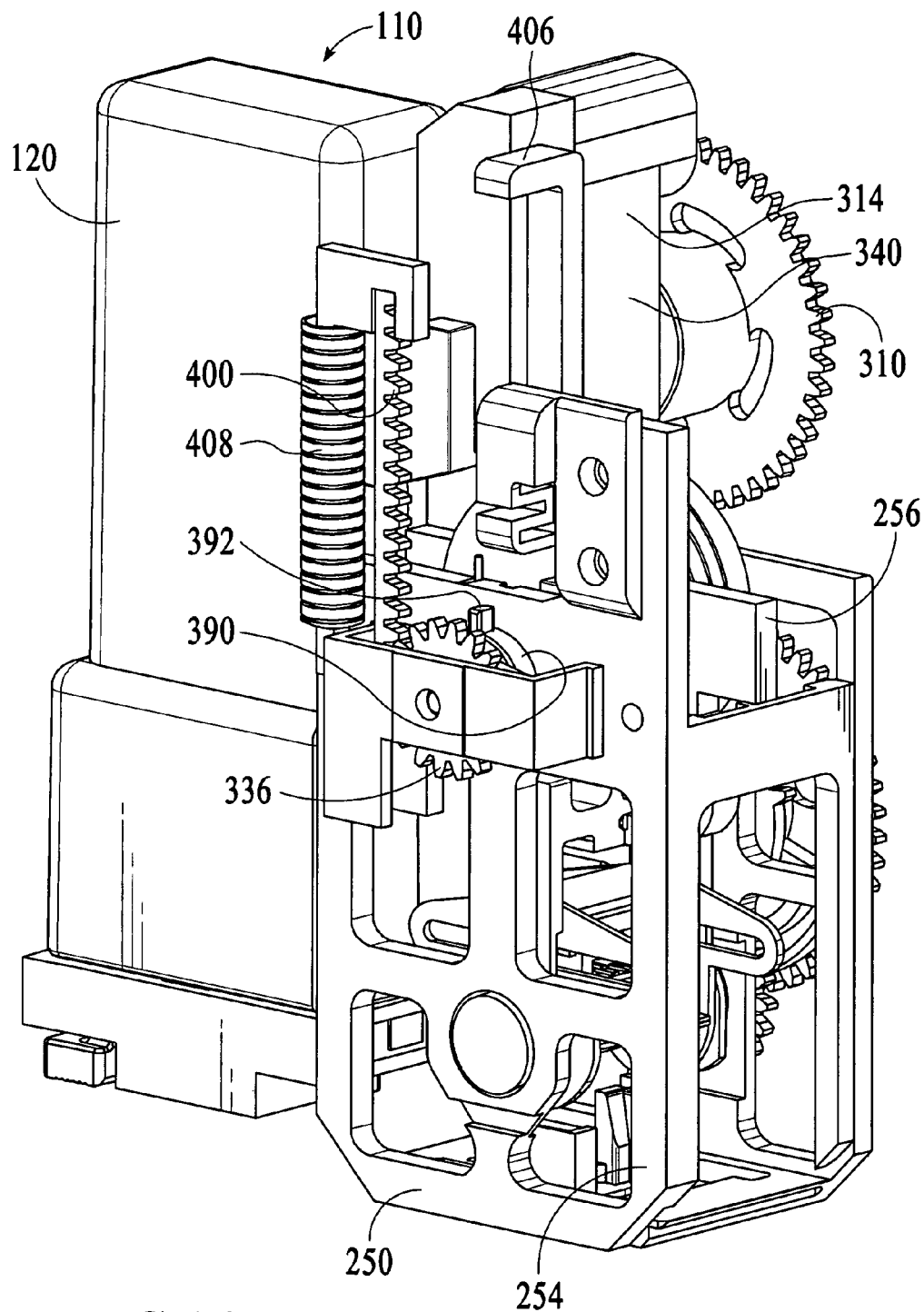
FIG. 14 is a perspective view of a side of a lancing/collecting assembly of a medical diagnostic apparatus of an alternative embodiment not shown in FIGS. 8, 10A, 10B, and 11. In this view, the frame is included.
Figure 15:
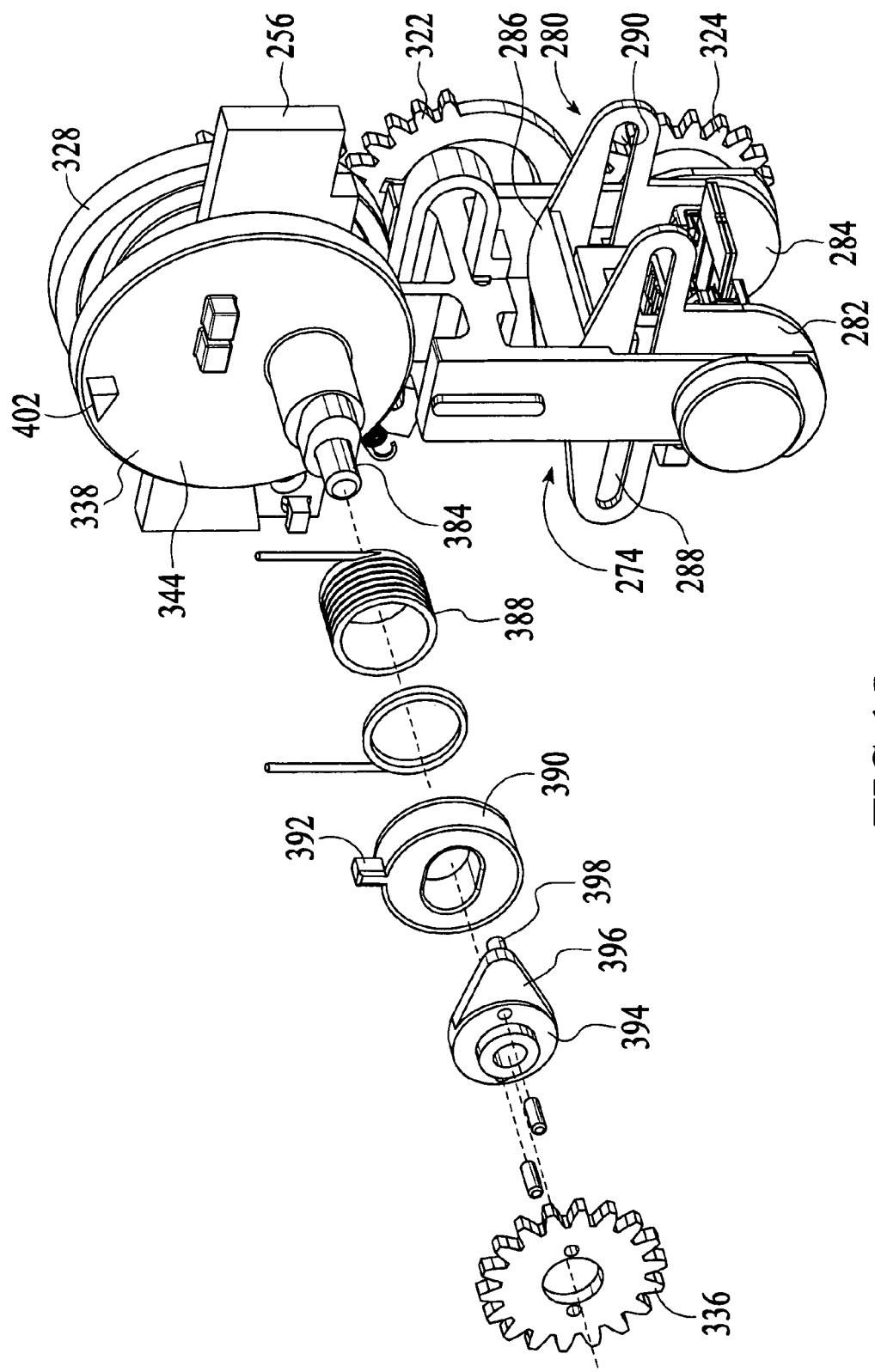
FIG. 15 is an exploded perspective view of one side of a lancing/collecting assembly of a medical diagnostic apparatus of an alternative embodiment. In this view, the components required for arming the lancet are displayed without any obscuring barrier.
Figure 16:
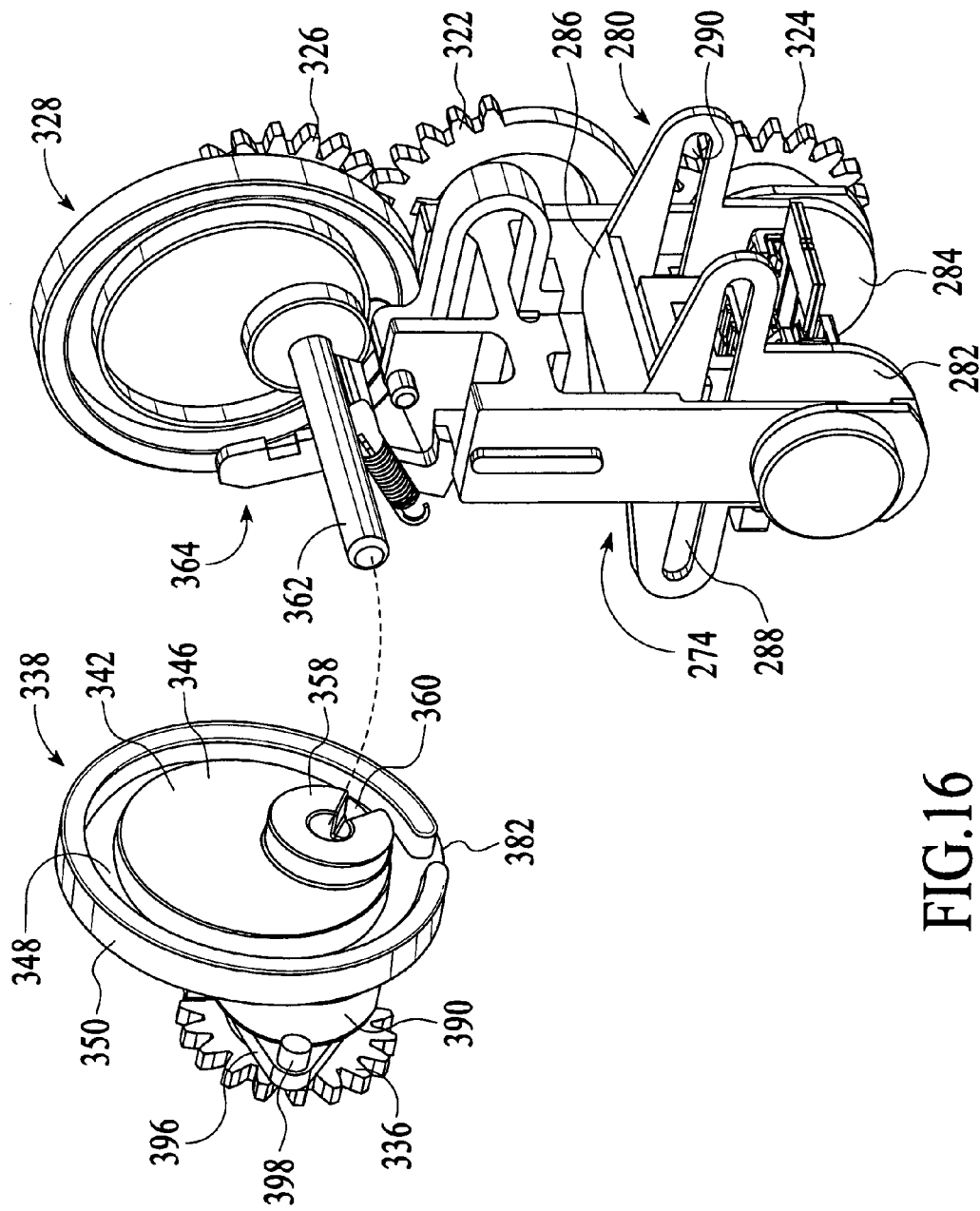
FIG. 16 is an exploded perspective view of selected components of a lancing/collecting assembly of a medical diagnostic apparatus of an alternative embodiment.

FIG. 7K shows the carriage C moved back upward, and the turret 225 having been rotated 90 degrees from when the body fluid was being applied to the strip 1002a. Now at FIG. 7L, the pusher P pushers the cap 1204a back onto the lancet end 1004a.

The STRIPLET™ may protrude from the housing when loaded into the turret 225. The port 231 and 230a may be configured with a slot or may be two ends of a same cavity that curves around the two sides of the housing shown. In this way, the carriage C. advances the STRIPLET™ for lancing and testing, and the turret 225 may remain translationally fixed relative to the carriage C. The turret 225 may alternatively move to expose either end of the STRIPLET™ through either port. In another embodiment, the carriage C does not move, while the turret 225 translates to expose the ends of the STRIPLET™ in turn through port 231.

FIG. 7M shows the uncapping lever or blade B moved back up disengaging from the lancet cap 1204a and pusher P. FIG. 7N shows the ejecting of the STRIPLET™ 1000a. The pusher P is shown after having advanced to push the STRIPLET™ 1000a through port 230a.

At FIG. 7O, the pusher P is retracted back to the start position on the track 229 that it was in at FIG. 7A. Now the pusher P is out of the way of the tub T, which can move back up as shown at FIG. 7P and meet again with seal 130 to protect the STRIPLETS™ from ambient air and moisture until a next testing is to be performed.

Referring now to FIGS. 8-12, inclusive, the lancing/collecting assembly 112 includes a frame 250 having two upright members 252 and 254 and a horizontal member 256. The upright member 252 has an inner face 258 and an outer face 260. The upright member 254 has an inner face 262 and an outer face 264. The inner face 258 and the outer face 260 are bounded by a top edge 266a, a bottom edge 266b, and two side edges 266c and 266d. The inner face 262 and the outer face 264 are bounded by a top edge 268a, a bottom edge 268b, and two side edges 268c and 268d. The inner face 258 has a track 270 and the inner face 262 has a track 272 for guiding the movement of a cam follower 274. The inner faces 258 and 262 of the upright members 252 and 254, respectively, of the frame 250 face one another. The horizontal member 256 of the frame 250 has a top edge 276a, a bottom edge 276b, two side edges 276c, 276d, and two faces 276e, 276f. One of the faces 276e of the transverse member 256 of the frame 250 faces one of the upright members 252 of the frame 250 and the other face 276f of the horizontal member 256 of the frame 250 faces the other of the upright members 254 of the frame 250.

Referring now to FIGS. 11, 13, and 15-22, inclusive, the lancing/collecting assembly 112 includes a cradle 280. The purpose of the cradle 280 is to hold a test strip during both the lancing step and the sample collecting step, which are carried out by the medical diagnostic device 100. Another purpose of the cradle 280 is to orient a test strip during the lancing step and the sample collecting step so that the lancet of the lancet-containing portion of the test strip can form an opening in the skin of the patient during the lancing step and the sensor of the sensor-containing portion of the test strip can collect the sample of biological liquid emerging from the opening in the skin of the patient during the sample collecting step. In the embodiment shown in FIGS. 1-22, inclusive, the cradle 280 also holds the test strip during the analyzing step. The cradle 280 includes two upright members 282 and 284 and a transverse member 286. The transverse member 286 of the cradle 280 connects the two upright members 282 and 284 of the cradle 280. The upright member 282 of the cradle 280 has a slot 288 formed therein, and the upright member 284 of the cradle 280 has a slot 290 formed therein. The slots 288 and 290 receive an L-shaped element 292 and 294, respectively, formed on a carrier 296. The L-shaped element 292 has a foot 292a and a leg 292b. The L-shaped element 294 has a foot 294a and a leg 294b. The foot 292a of the L-shaped element 292 and the foot 294a of the L-shaped element 294 are capable of sliding in the slots 288 and 290, respectively, of the cradle 280 during the lancing step and the sample collecting step so that the lancet of the lancet-containing portion of the test strip can form an opening in the skin of the patient during the lancing step and the sensor of the sensor-containing portion of the test strip can collect the sample of biological liquid emerging from the opening in the skin of the patient during the collecting step. The sliding motion of the foot 292a and the foot 294a is brought about by the movement of the cam follower 274 during the lancing step and during the sample collecting step. The upright member 282 of the cradle 280 further contains a track 298 formed therein, and the upright member 284 of the cradle 280 further contains a track 300 formed therein, each of which tracks 298 and 300 is of a size suitable for holding a test strip during the lancing and collecting functions of the medical diagnostic device, and in the embodiment shown in FIGS. 1-22, inclusive, the analyzing function.

The function of the carrier 296 is to house the electrical components and electronic components for completing a circuit when the test strip has received a sample of biological liquid from the patient. FIGS. 19-22, inclusive, shows how the carrier 296 receives and holds a test strip. The carrier 296, which is shown as a six-sided element, has a first L-shaped element 292 formed in one side 296a and a second L-shaped element 294 formed in an opposing side 296b, which L-shaped elements 292 and 294 are received by the slots 288 and 290, respectively, in the cradle 280. The leg 292b of the L-shaped element 292 and has a pin 292c, which pin 292c fits into and rotates in an aperture of the cam follower 274. Similarly, the leg 294b of the L-shaped element 294 and has a pin 294c, which pin 294c fits into and rotates in an aperture of the cam follower 274. The electrical and electronic components of the carrier 296, and the types of analyses that can be performed by the carrier 296 are described in detail in U.S. Pat. Nos. 6,299,757 and 6,616,819, the entireties of which are incorporated herein by reference.

Referring now to FIGS. 8-22, inclusive, the lancing/collecting assembly 112 includes a transmission system, including gears for (1) enabling operation of components required for a lancing operation for forming an opening in the skin of a patient, (2) collecting the sample of biological liquid emerging from the opening in the skin of the patient formed by the lancing operation, and (3) positioning a test strip during the analyzing operation. It should be noted that other configurations of gears, racks, can be used in place of the configuration shown in FIGS. 8-22, inclusive. It should be noted that transmission systems that utilize components other than gears can be used. The transmission system of the lancing/collecting assembly comprising the gears shown in FIGS. 8-22, inclusive, can be replaced in whole or in part by subsystems involving one or more racks and one or more pinions. Two important features of the medical diagnostic device 100 are that movement of the cam follower 274 can be effected in two directions, the directions being separated by approximately 180°, and that the cradle 280 or equivalent be capable of being rotated approximately 180° from a first position to a second position, the first position and the second position being separated by approximately 180°. As used herein, the expression "approximately 180°" means an angle ranging from about 160° to 200°, such as angles equal to or close to 180°.

Devices for mechanical transmission of power, or "mechanisms", constitute the basic units from which all kinds of devices are built. Every mechanism consists of individual elements whose movements in relation to one another are "positive", i.e., the motion of one element produces an accurately determinable and definable motion of every individual point of the other elements of that mechanism. Numerous combinations and modifications are possible, but only certain basic types of mechanisms will be noted here:

(1) Screw mechanism: When a screw spindle is rotated, the element attached to the nut will move in the longitudinal direction of the screw. Conversely, if the nut is rotatably mounted in the frame of the mechanism and driven, the screw spindle will move longitudinally.

(2) Linkage or crank mechanism: The characteristic element is the crank, which is rotatably mounted on a frame and is usually so designed that it can perform complete revolutions. Its motion is transmitted through the coupler (or connecting rod) to the lever (or rocker arm), likewise rotatably mounted, but not performing complete revolutions. Alternatively, instead of being connected to a lever, the coupler may be attached to a sliding element, e.g., a piston.

(3) Pulley mechanism: Connection between pulleys on their respective shafts is effected by flexible elements (belts, ropes).

(4) Ratchet mechanism: This serves to arrest a motion or to produce an intermittent rotation in the driven element. The pawl allows the ratchet wheel to rotate in one direction only, preventing rotation in the opposite direction by engaging the specially shaped teeth on the wheel.

(5) Gear mechanism: This type of mechanism, which is used extensively herein, transmits rotary motion from one shaft to another, usually in conjunction with a change in rotational speed and torque. In a gear mechanism of the usual type, the transmission is effected by the meshing of gear teeth, but in a friction-gear mechanism, this positive drive is replaced by frictional contact of wheels or rollers.

(6) Cam mechanism: This type of mechanism, which is used extensively herein, involves a cam mounted on a frame. The cam is driven and thereby moves a follower, which performs a desired predetermined motion depending on the shape of the cam.

Further information relating to the foregoing mechanisms can be found in The Way Things Work, Volume 2, Simon and Schuster (New York: 1971), pages 198-217, incorporated herein by reference.

Referring now to FIGS. 8-22, inclusive, a motor gear 310 is attached to a gear shaft 312 from the motor 314. The motor gear 314 drives an idler gear 316. The combination of motor gear 310 and idler gear 316 drives a first drive gear 320, which is attached to a second drive gear 322. As shown in FIGS. 8-22, inclusive, the first drive gear 320 is circular and has a greater diameter than the second drive gear 322. The second drive gear 322 is capable of driving both a gear 324 for rotating the cradle 280 and a gear 326 for rotating an index cam 328. The first drive gear 320 has teeth surrounding the entire periphery thereof. The second drive gear 322 is a sector gear, and contains teeth on only a portion of the periphery thereof. The first driven gear 324 is included for rotating the cradle 280. The second driven gear 326 is included for rotating the index cam 328. Both the first driven gear 324 and the second driven gear 326 have teeth surrounding the entire periphery thereof. The first driven gear 324 has a locking pin 332 projecting from the major surface thereof that faces the first drive gear 320. Similarly, the second driven gear 326 has a locking pin 334 projecting from the major surface thereof that faces the first drive gear 320. The locking pins 332 and 334 perform a variety of locking functions during the operation of the lancing/collecting assembly 112. The first drive gear 320 has a slot 320a formed therein for retaining the locking pins 332 and 334 during the operation of the lancing/collecting assembly 112. FIGS. 25A-25J, inclusive, show and TABLE 1 describes the positions of the locking pins 332 and 334 during one cycle of the medical diagnostic device 100.

TABLE 1

| FIG. | Activity | Position of cradle | Position of locking pin 332 of first driven gear 324 | Position of locking pin 334 of second driven gear 326 |
|---|---|---|---|---|
| 25A | Loading test strip | Horizontal | Free of slot 320a in drive gear 320 | In slot 320a in drive gear 320 |
| 25B | Lancing | Vertical (lancet facing down) | Free of slot 320a in drive gear 320 | In slot 320a in drive gear 320 |
| 25C | Disengaging first driven gear 324 | Substantially vertical (sensor facing down) | Entering slot 320a in drive gear 320 | In slot 320a in drive gear 320 |
| 25D | Capturing locking pin 334 of second driven gear 326 | Substantially vertical (sensor facing down) | Entering slot 320a in drive gear 320 | In slot 320a in drive gear 320 |
| 25E | Engaging second driven gear 326 | Substantially vertical (sensor facing down) | In slot 320a in drive gear 320 | Exiting slot 320a in drive gear 320 |
| 25F | Indexing (maximum depth) | Substantially vertical (sensor facing down) | In slot 320a in drive gear 320 | Free of slot 320a in drive gear 320 |
| 25G | Disengaging second driven gear 326 | Substantially vertical (sensor facing down) | In slot 320a in drive gear 320 | Entering slot 320a in drive gear 320 |
| 25H | Capturing locking pin 334 of second driven gear 326 | Substantially vertical (sensor facing down) | In slot 320a in drive gear 320 | Entering slot 320a in drive gear 320 |
| 25I | Engaging first driven gear 324 | Substantially vertical (sensor facing down) | Exiting slot 320a in drive gear 320 | In slot 320a in drive gear 320 |
| 25J | Loading test strip | Horizontal | Free of slot 320a in drive gear 320 | In slot 320a in drive gear 320 |

A lancing gear 336 is included for arming and firing a lancing cam 338. A gearbox 340 is also shown. The gearbox 340 contains those components that enable the second drive gear 322 to switch from driving the first driven gear 324, i.e., the gear for rotating the cradle 280, to driving the second driven gear 326, i.e., the gear for rotating the index cam 328. The gearbox 340 also contains those components that enable the drive gears to reverse their direction of rotation.

The lancing cam 338 is shown as having major surfaces that are circular in shape. The lancing cam 338 has an inner face 342 and an outer face 344. The inner face 342 contains a cylindrical element 346 formed thereon in such a manner that a circular path 348 is formed between the cylindrical element 346 and the peripheral edge 350 of the lancing cam 338. A pin 352 formed on a projection 354 on the cam follower 274 travels along this circular path 348 in order to enable the cam follower 274 to move in the direction desired for the particular operation being undertaken. Further projecting from the cylindrical element 346 of the inner face 342 is a substantially cylindrical projection 358 having a recess 360 formed in the periphery thereof. The purpose of the cylindrical projection 358 is to support one end of an axle 362 that traverses the distance between the lancing cam 338 and the index cam 328.

The purpose of the recess 360 in the cylindrical projection 358 is to receive a lock 364 to prevent the force of gravity from drawing the lancing cam 338 and the index cam 328 downwardly when the lancing cam 338 and the index cam 328 are not being operated. The lock 364 includes a hook portion 366, a resilient biasing element-retaining portion 368, and a cam-supporting portion 370. A resilient biasing element 372, e.g., a spring, one end of which is secured to the resilient biasing element-retaining portion 368 and the other end of which is secured to the frame 250, biases the lock 364 to the locked position. The lock 364 is released to enable movement of the lancing cam 338 and the index cam 328 merely by causing either the lancing cam 338 or the index cam 328 to be rotated a few degrees. The force generated by such rotation is sufficient to overcome the biasing force of the resilient biasing element 372.

The peripheral edge 350 of the lancing cam 338 has a portion 382 cut out to enable the pin 352 formed on the projection 354 of the cam follower 274 to enter the circular path 348 surrounding the cylindrical element 346 on the inner face 342 of the lancing cam 338. The lancing cam 338 has a lancing camshaft 384 projecting from the outer face 386 of the lancing cam 338. The lancing camshaft 384 is positioned eccentrically with respect to the outer face 386 of the lancing cam 338. Positioned on the lancing camshaft 384 is a torsion spring 388, which has the function of storing sufficient energy to enable the lancet of the lancet-containing portion of the test strip to be fired with sufficient force to form an opening in the skin of the patient. Located on the lancing camshaft 384, but facing the outer face 264 of the upright member 254 of the frame 250 is a ring 390 having a pin 392 projecting from the peripheral surface thereof. Adjacent to the ring 390 is a spring winder 394, which is permanently attached to the lancing gear 336. The spring winder 394 is cylindrical in shape and has an element 396 projecting from the periphery thereof. A pin 398 for contacting the pin 392 projecting from ring 390 projects from the end of the element 396. Upon rotation of the lancing gear 336 by a lancing rack 400, the lancing gear 336 drives the spring winder 394, whereby the element 396 brings about rotation of the ring 390 by means of rotating the pin 392 projecting from the periphery of the ring 390. After the ring 390 is rotated approximately 340-360°, a locking tab 402 on the face 344 of the lancing cam 338 abuts a locking tab 404 positioned on a trigger 406, thereby arming the medical diagnostic device 100. The teeth of the lancing gear 336 are capable of meshing with the teeth of the lancing rack 400.

In order to trigger the medical diagnostic device 100 so that the lancet of the lancet-containing portion of the test strip can form an opening in the skin of the patient and can subsequently be retracted from the opening so formed, the user merely actuates the trigger 406, such as, for example, by pushing a button, whereby the locking tab 404 disengages from the locking tab 402, and the energy stored in the torsion spring 388 causes the lancet of the lancet-containing portion of the test strip to be fired and subsequently retracted. Attached to one end of the lancing rack 400 is a lance return spring 408. During the lancing step, as the lancing rack 400 drives the lancing gear 336, the lance return spring 408 is expanded. The energy stored in the expanded lance return spring 408 is sufficient to enable retraction of the lancet of the lancet-containing portion of the test strip.

As described earlier with respect to the interaction between the cradle 280, the carrier 296, the L-shaped elements 292 and 294, the lancet-containing portion of the test strip, and the sensor-containing portion of the test strip, the lancet of the lancet-containing portion of the test strip is moved toward the skin of the patient to form an opening in the skin of the patient by means of movement of the cam follower 274, which causes the foot 292a of the L-shaped element 292 and the foot 294a of the L-shaped element 294, both of which are attached to the carrier 296, to slide in the slots 288 and 290, respectively, of the cradle 280. In the lancing step, the cam follower 274 is driven by the lancing cam 338.

The lancing cam 338 engages a pin 352 on the cam follower 274 when the cradle 280 is in either of two vertical positions (the position required for lancing the skin of a patient and the position required for collecting a sample of biological liquid from the patient). Because these positions are 180° apart, there are two engagement surfaces on opposite ends of the cradle 280. The sliding of the L-shaped elements 292 and 294 of the carrier 296 in slots 288 and 290 of the cradle 280 produces the required motions for forming an opening in the skin of the patient and collecting a sample of biological liquid from the opening formed in the skin of the patient.

The index cam 328 is shown as having major surfaces that are circular in shape. The index cam 328 has an inner face 410 and an outer face 412. The inner face 410 contains a cylindrical element 414 formed thereon in such a manner that a circular path 416 is formed between the cylindrical element 414 and the peripheral edge 418 of the index cam 328. A pin 420 formed on a projection 422 on the cam follower 274 travels along this circular path 416 in order to enable the cam follower 274 to move in the direction desired for the particular operation being undertaken. Further projecting from the cylindrical element 414 of the inner face 410 is a substantially cylindrical projection 424 having a recess 426 formed in the periphery thereof. The purpose of this cylindrical projection 424 is to support one end of an axle 362 that traverses the distance between the lancing cam 338 and the index cam 328. The index cam 328 has an index camshaft 428. The index camshaft 428 is positioned eccentrically with respect to the outer face 412 of the index cam 328.

After an opening is formed in the skin of the patient during the lancing step, and after the lancet-containing portion of the test strip is retracted, the test strip is oriented so that the sensor-containing portion of the test strip can collect a sample of biological liquid emerging from the opening in the skin of the patient. In the embodiment of the lancing/collecting assembly 112 shown herein, the mechanical transmission system orients the test strip by rotating the cradle 280 approximately 180° so that the sensor-containing portion of the test strip faces the opening in the skin of the patient. The mechanical transmission system then causes the index cam 328 to advance the test strip to the opening in the skin of the patient through the opening 117 in the end cap 104. Unlike the lancing step, no arming step or trigger step is required. However, the test strip moves in the same manner as it did during the lancing step, namely, the mechanical transmission system causes the index cam 328 to move the cam follower 274, which in turn causes the L-shaped elements 292 and 294 to slide in the slots 288 and 290 in the cradle 280, thereby enabling the sensor of the sensor-containing portion of the test strip to contact the sample of biological liquid emerging from the opening in the skin of the patient. The sensor of the sensor-containing portion of the test strip receives a sufficient quantity of the sample to carry out a determination of the analyte. In the embodiment of the lancing/collecting assembly 112 shown herein, the carrier 296 is designed to carry out the determination of the analyte. During the assay or after the completion of the assay, the cradle 280 is rotated 90° by the mechanical transmission system to position the test strip for re-attaching the protective cover to the used lancet of the lancet-containing portion of the test strip, removing the used test strip from the lancing/collecting assembly 112, and disposing of the used test strip through an ejection port 230 in the housing 102.

The cam follower 274 is a substantially U-shaped element having two upright members 430 and 432 that are connected by a transverse member 434. The upright member 430 has an aperture 436 into which the pin 292c projecting from the leg 292b of the L-shaped element 292 on the carrier 296 is received. The upright member 432 has an aperture 442 into which the pin 294c projecting from the leg 294b of the L-shaped element 294 on the carrier 296 is received. The upright member 430 of the cam follower 274 is disposed between the upright member 448 of an L-shaped projection 450 of the cradle 280 and the upright member 282 of the cradle 280. Similarly, the upright member 432 of the cam follower 274 is disposed between the upright member 454 of an L-shaped projection 456 of the cradle 280 and the upright member 284 of the cradle 280. Rotation of the pins 292c and 294c in the apertures 436 and 442, respectively, make it possible for the lancing/collecting assembly 112 to achieve all of the positions required to carry out the operations needed to (a) receive a test strip from the assembly for storing and dispensing test strips 110, (b) form an opening in the skin of the patient, (c) collect a sample of biological liquid emerging from the skin of the patient, and (d) remove the test strip form the lancing/collecting assembly 112.

Figure 17:
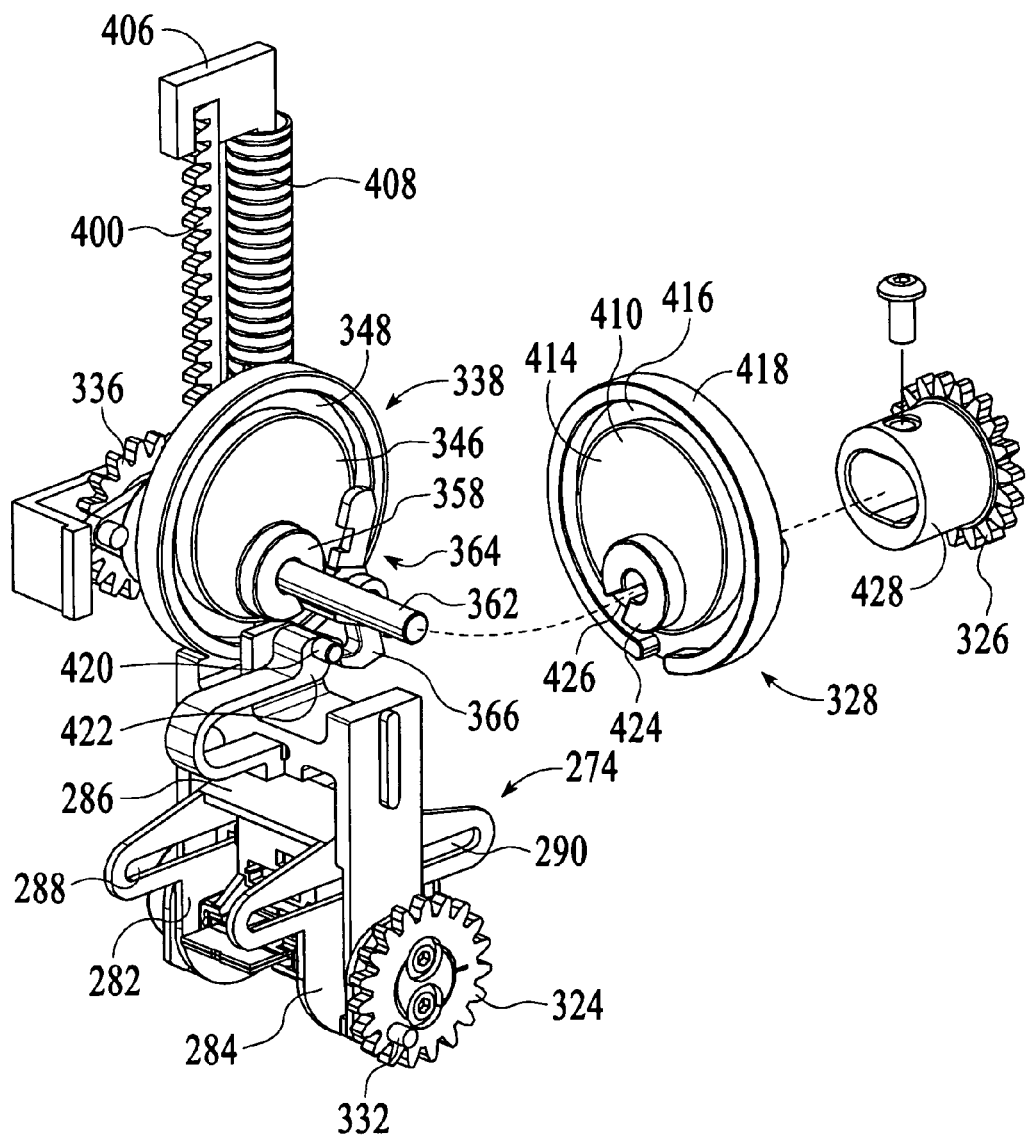
FIG. 17 is another exploded perspective view of selected components of a lancing/collecting assembly of a medical diagnostic apparatus of an alternative embodiment. This view shows a side of the lancing/collecting assembly not shown in FIG. 16.
Figure 18:
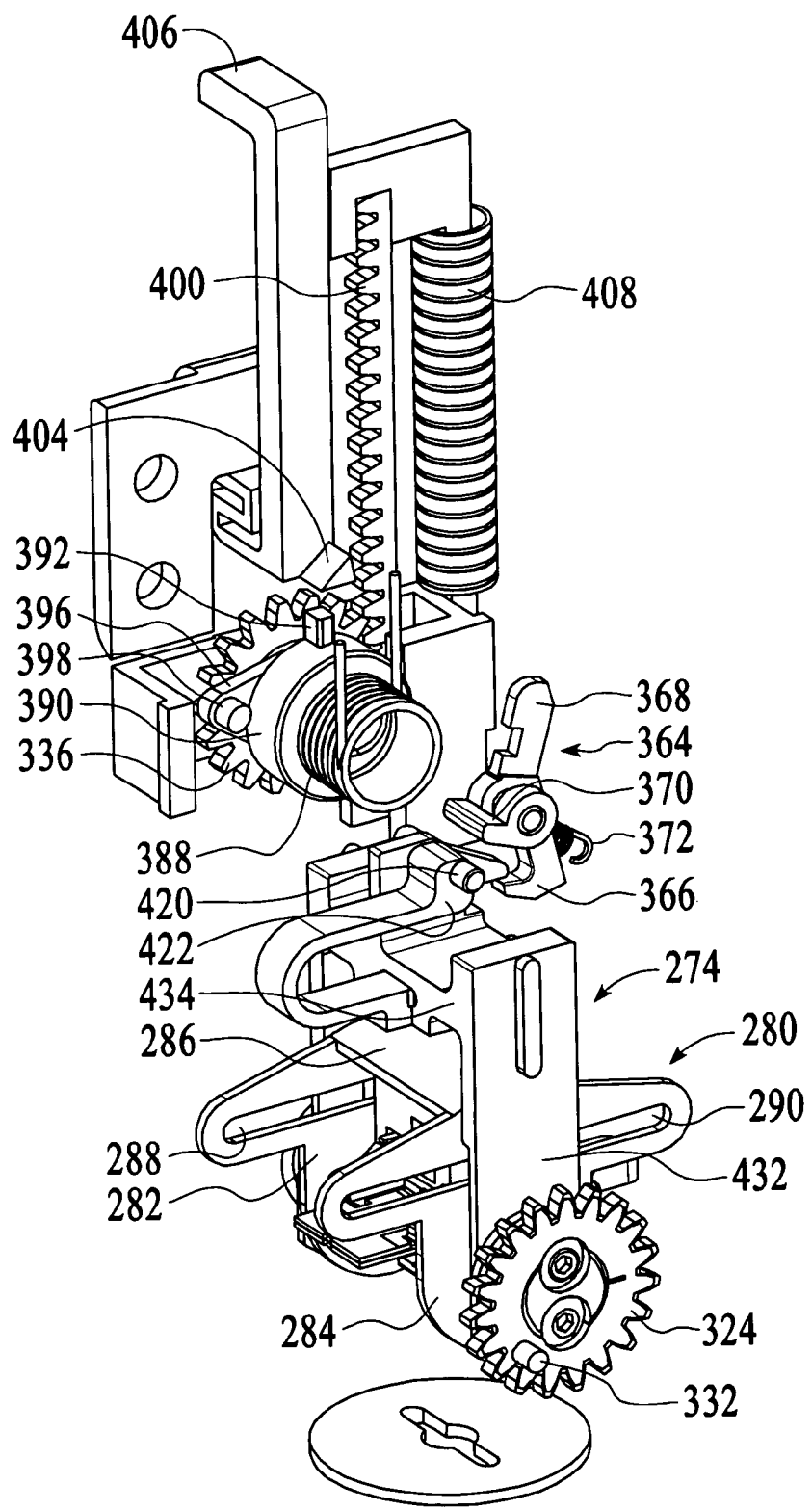
FIG. 18 is a perspective view of selected components for arming the lancet of a lancing/collecting assembly of a medical diagnostic apparatus of an alternative embodiment.
Figure 19:
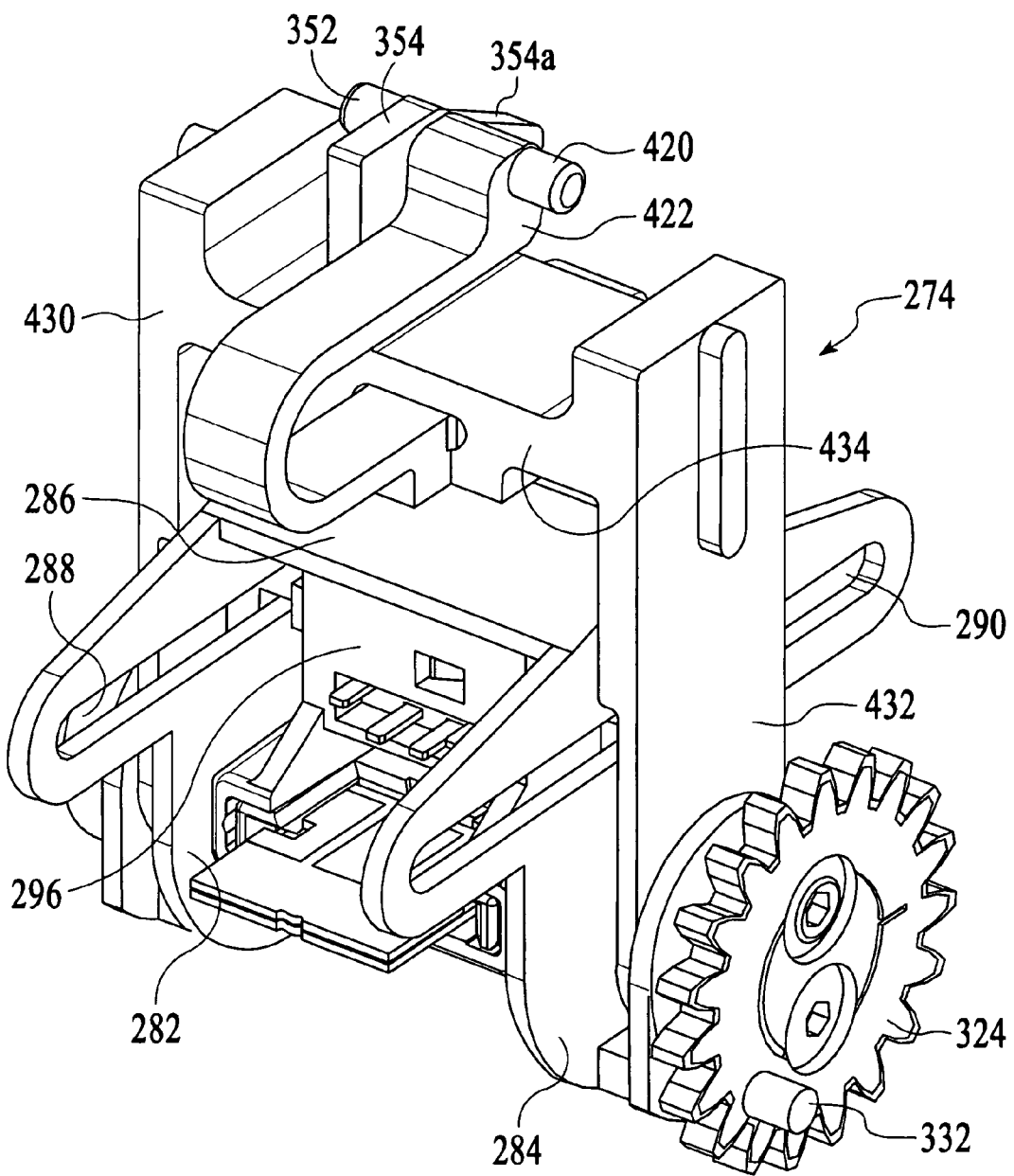
FIG. 19 is a perspective view of selected components of a lancing/collecting assembly of a medical diagnostic apparatus of an alternative embodiment.
Figure 20:
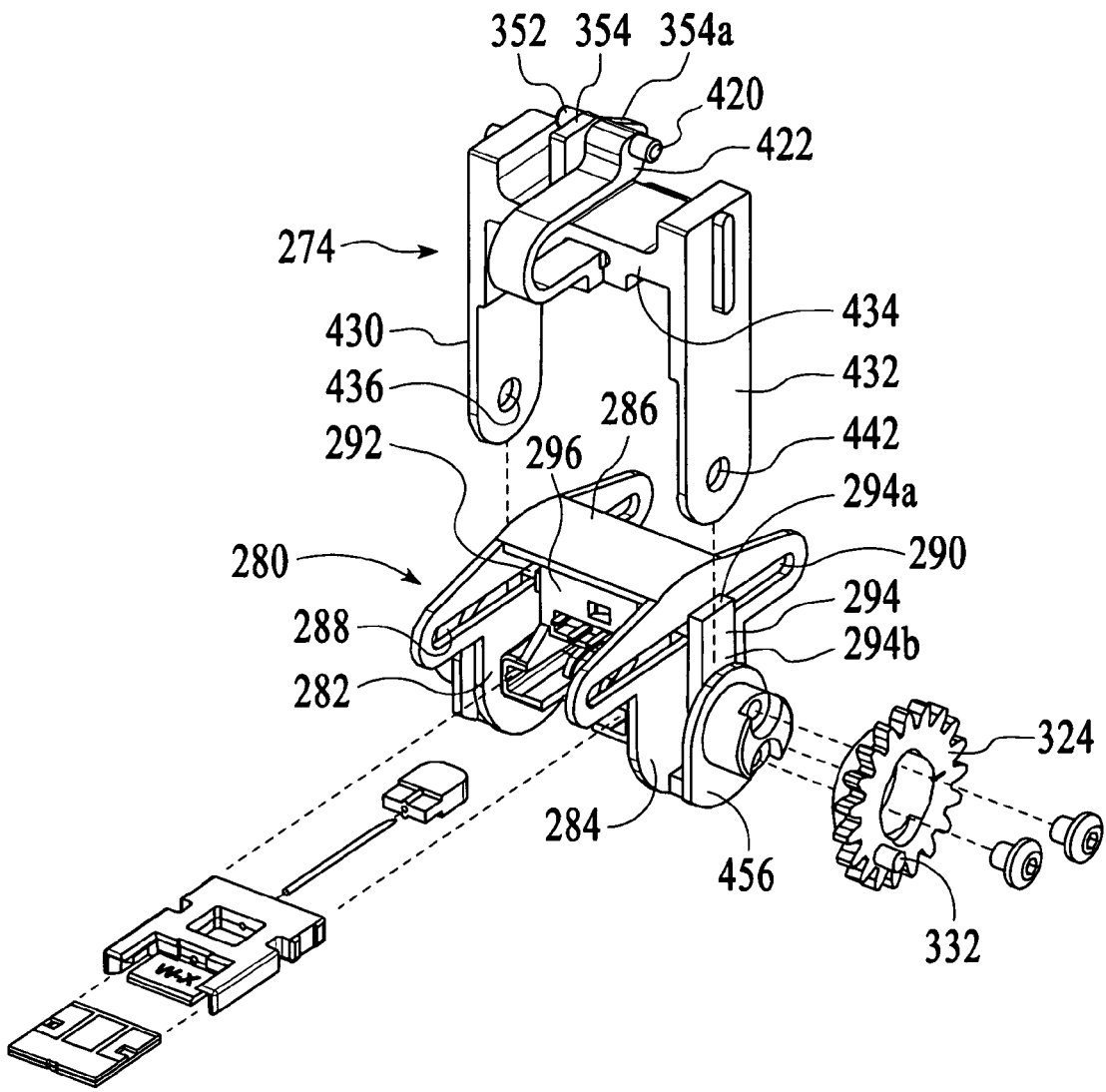
FIG. 20 is an exploded perspective view of selected components of a lancing/collecting assembly of a medical diagnostic apparatus of an alternative embodiment.
Figure 21:
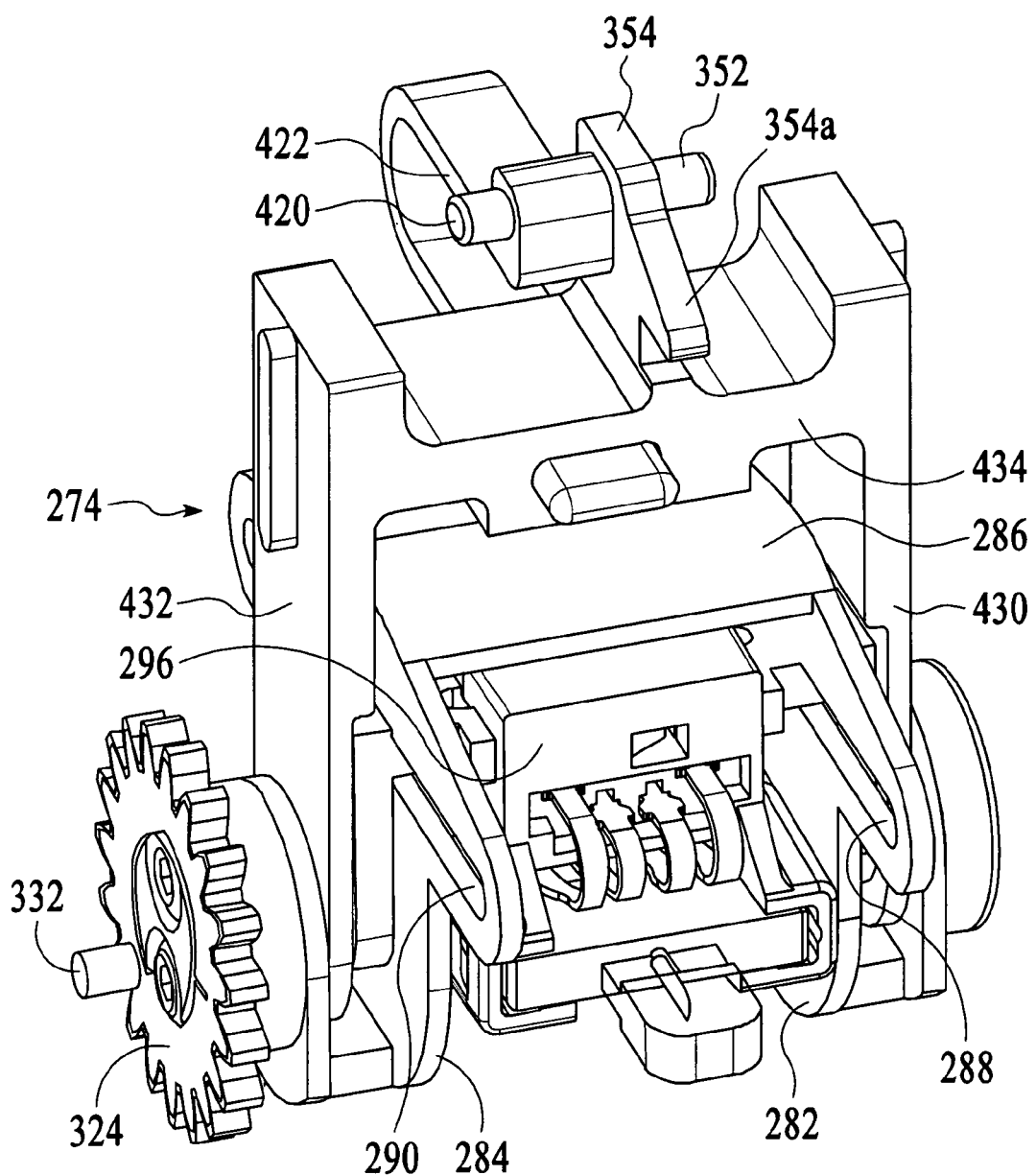
FIG. 21 is another perspective view of selected components of a lancing/collecting assembly of a medical diagnostic apparatus of an alternative embodiment. This view shows a side of the assembly not shown in FIG. 19.
Figure 22:
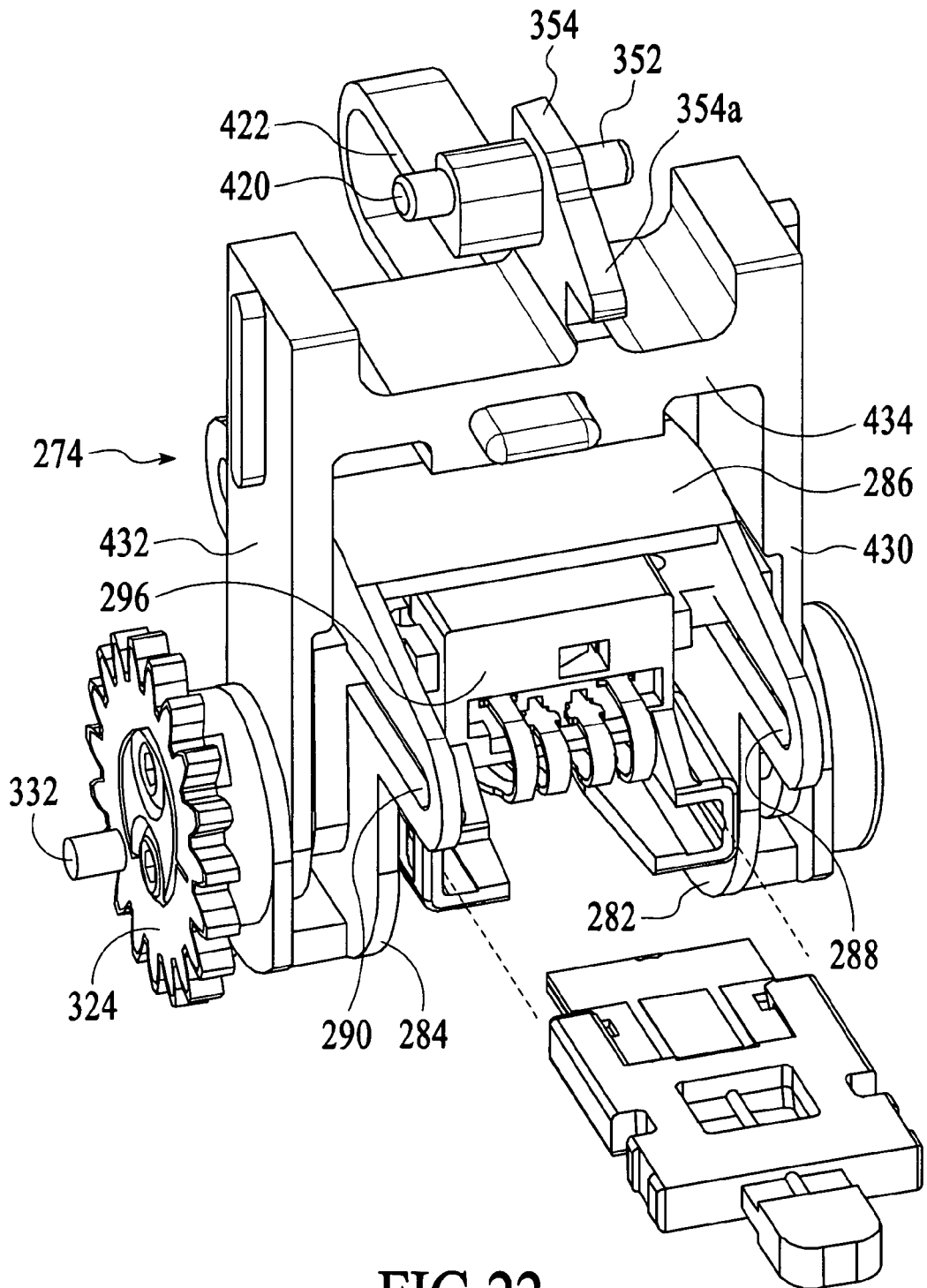
FIG. 22 is another perspective view of selected components of a lancing/collecting assembly of a medical diagnostic apparatus of an alternative embodiment. This view shows a side of the assembly not shown in FIG. 19.

As shown in FIG. 17, the projection 422 on the cam follower 274 is flexible and the projection 354 on the cam follower 274 is rigid. The flexible projection 422 is in the shape of the letter U. However, such a shape is merely a matter of choice and other shapes can be selected. For example, the projecting element can be diamond-shaped. The flexibility of the projection 422 enables the test strip to comply with the opening formed in the skin of the patient to facilitate collection of the sample of biological liquid. The rigid projection 354 is adjacent to the flexible projection 422. The lack of flexibility of the projection 354 enables the motion of the lancet of the lancet-containing portion of the test strip to be fixed, thereby allowing uniform puncturing of the skin of the patient during the lancing step. A nose portion 354a projecting from the projection 354 receives one end of the resilient biasing element 372, which locks the lancing cam 338 and the index cam 328 when these cams are not in operation.

The medical diagnostic device 100 can also include a mechanism for ejecting used test strips from the cradle 280. This mechanism can be operated by employing a user-actuated pushing assembly or a motor-actuated pushing assembly to push a used test strip out of the cradle 280 and out of the ejection port 230 of the housing 102.

To operate the lancing/collecting assembly, a motor can be used to apply a rotating drive input. Alternatively, any rotating drive source could be used, e.g., manual input by the user.

The lancing/collecting assembly 112 can be armed by actuating a slide 460 positioned in a slot in a side of the housing 102. The slide 460 is connected to the lancing rack 400 by means of a connector. In order to arm the lancet of the lancet-containing portion of the lancing/collecting assembly, the user need only move the slide 460 in the appropriate direction until the locking tab 404 on the trigger 406 abuts the locking tab 402 on the lancing cam 338. In an alternative embodiment, the slide 460 can be replaced by a motor capable of driving the lancing rack 400 in the appropriate direction.

Figure 24:
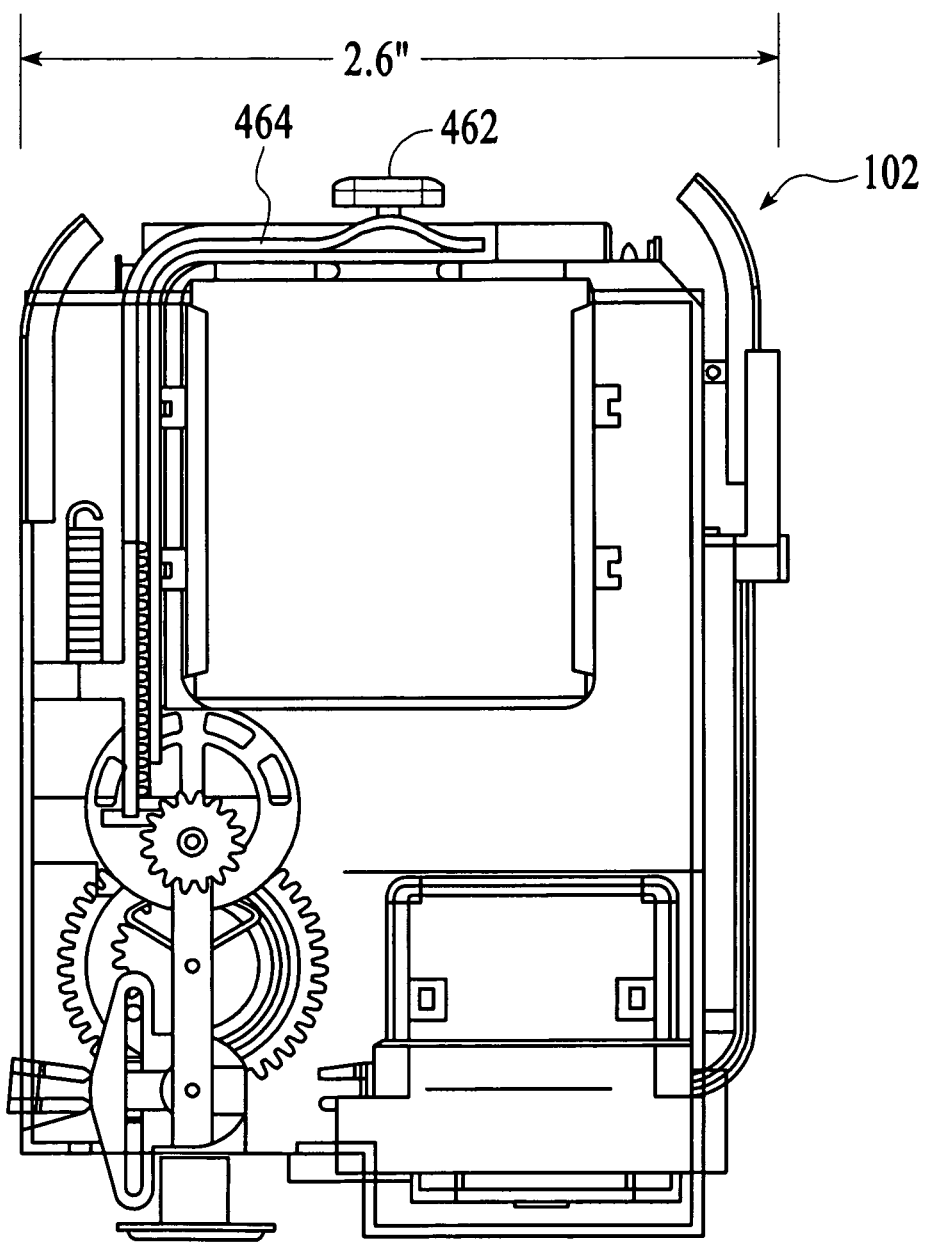
FIG. 24 is side view in elevation of a medical diagnostic apparatus of an alternative embodiment showing the position of a push-button suitable for triggering the lancing step of the method of an alternative embodiment.
Figure 25B:
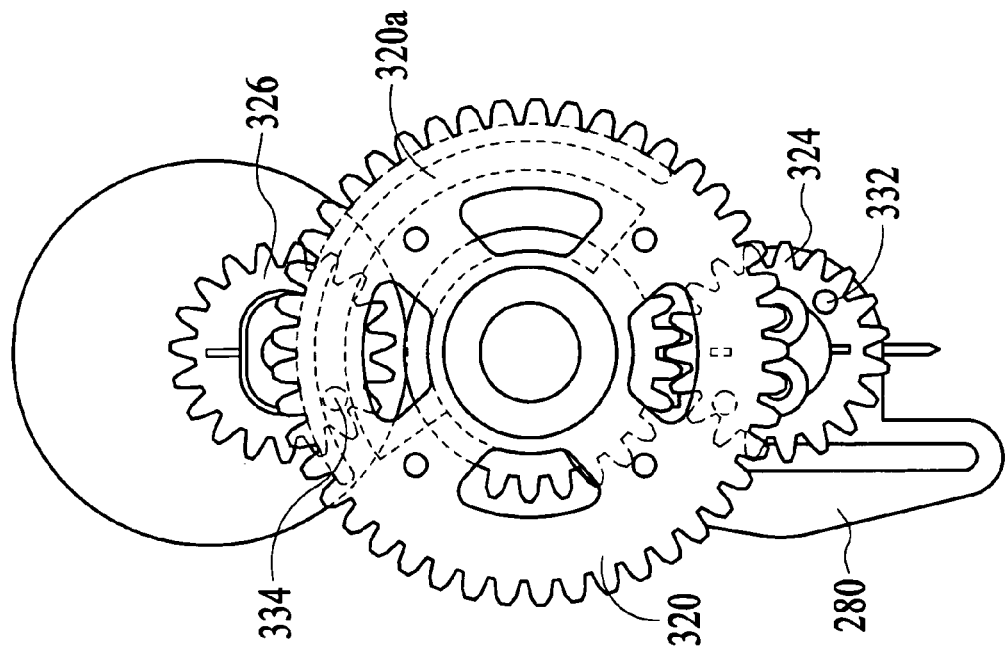
Figure 25A:
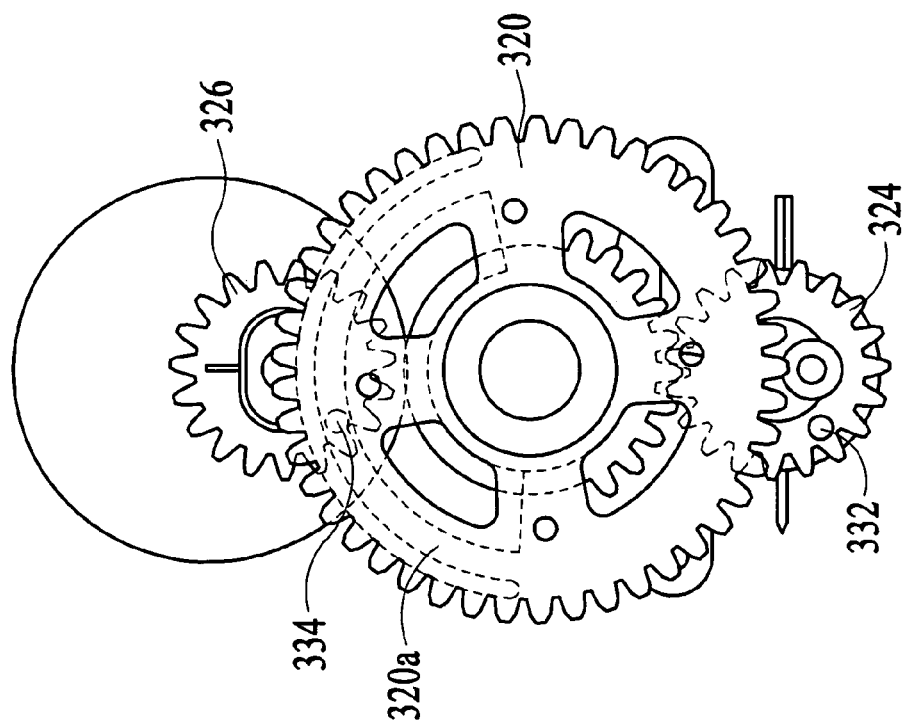
Figure 25D:
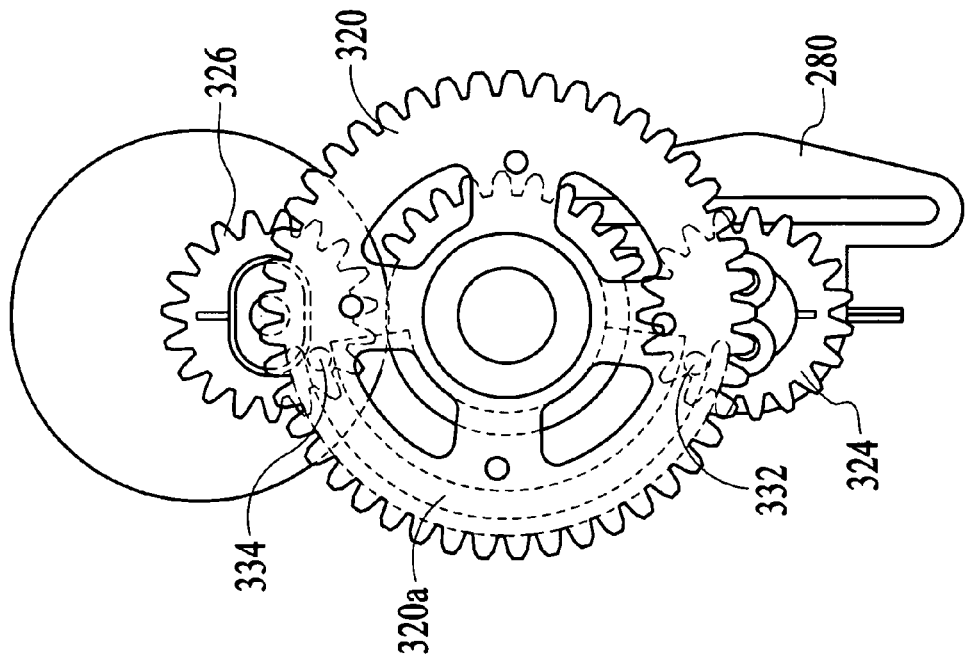
Figure 25C:
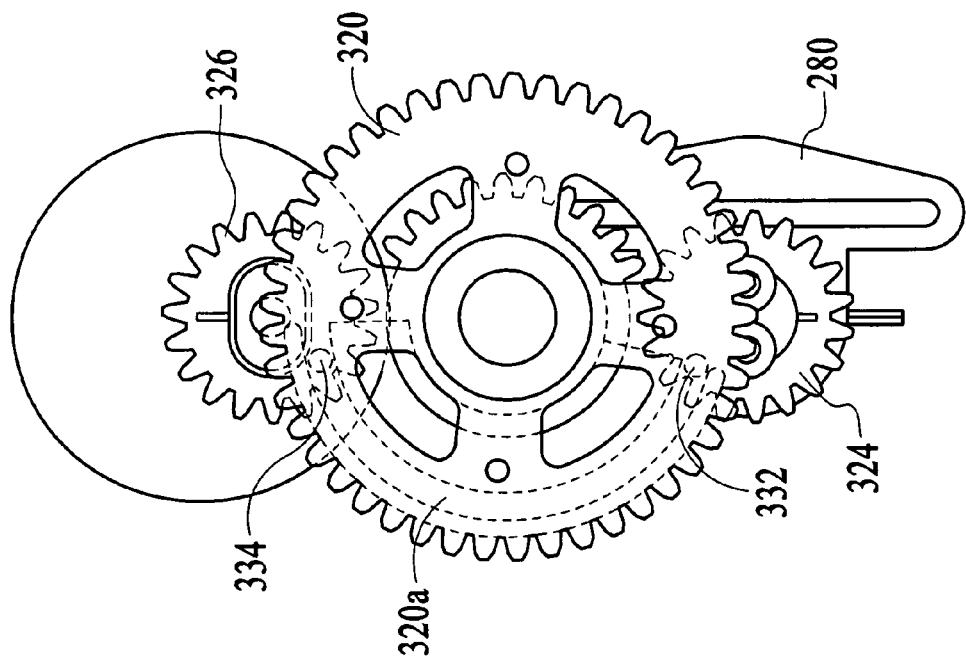
Figure 25H:
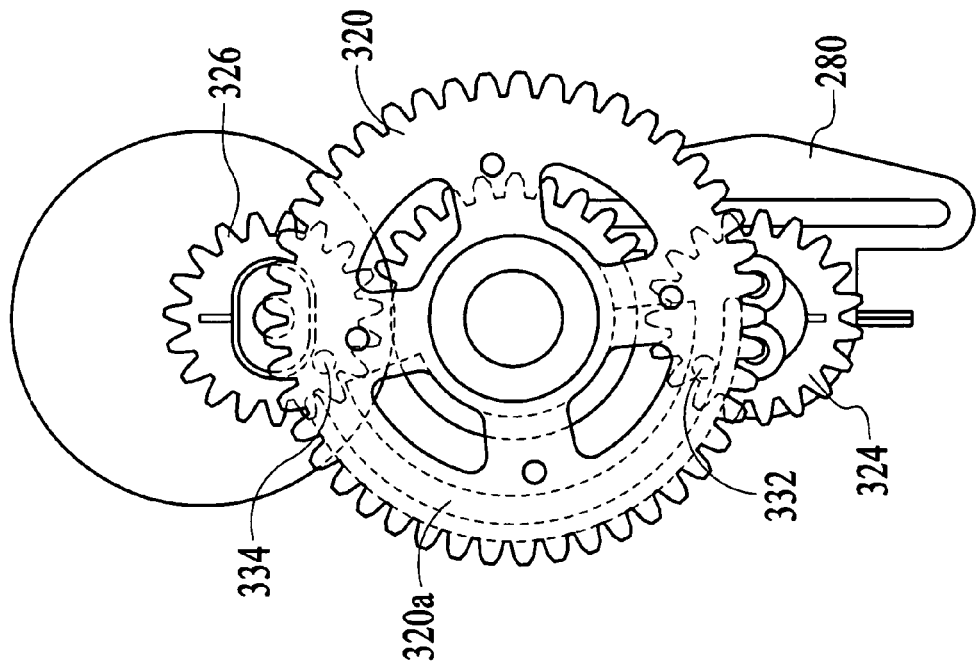
Figure 25G:
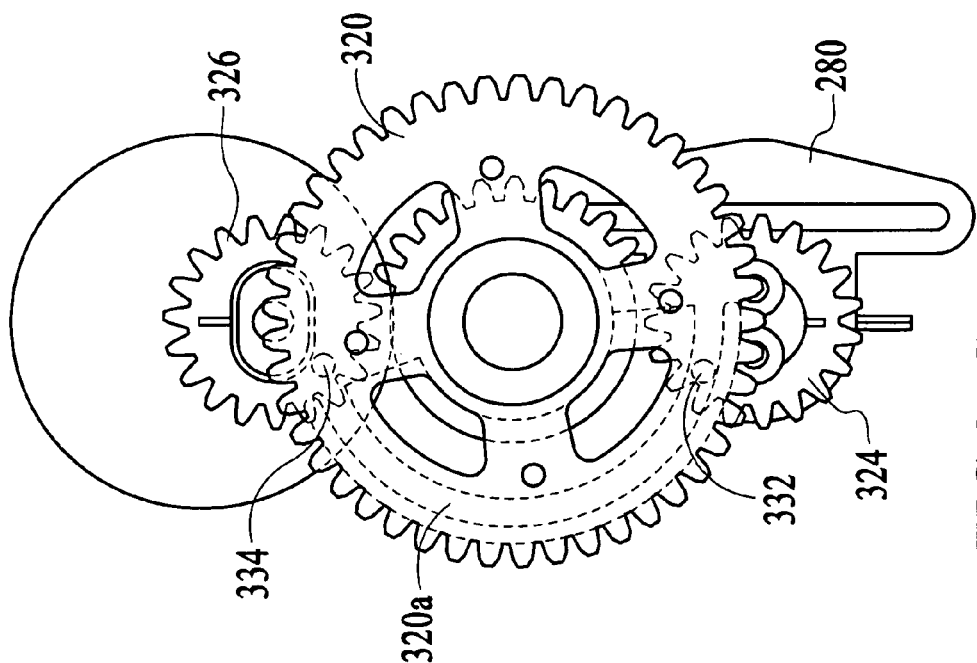
Figure 25J:
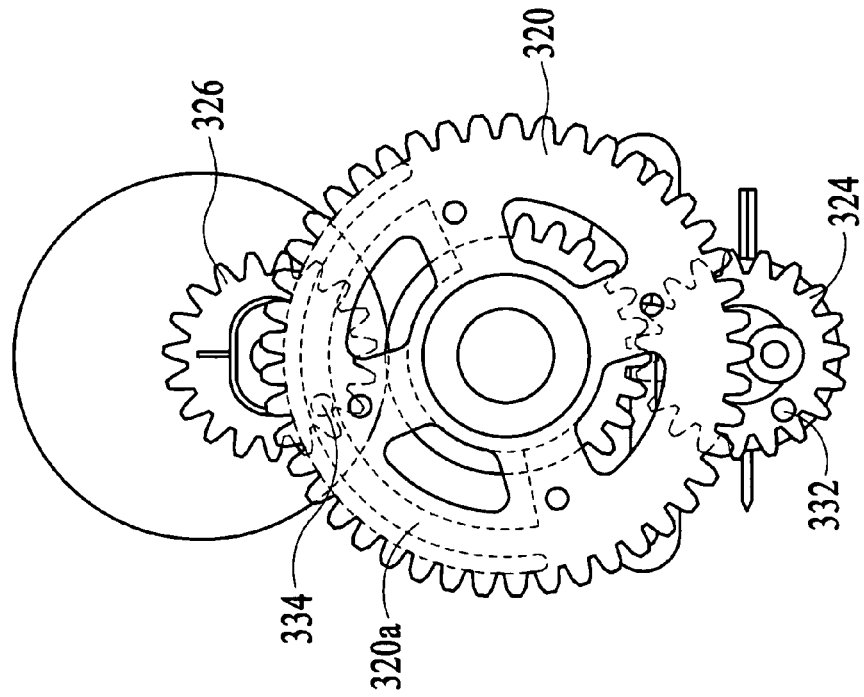
Figure 25I:
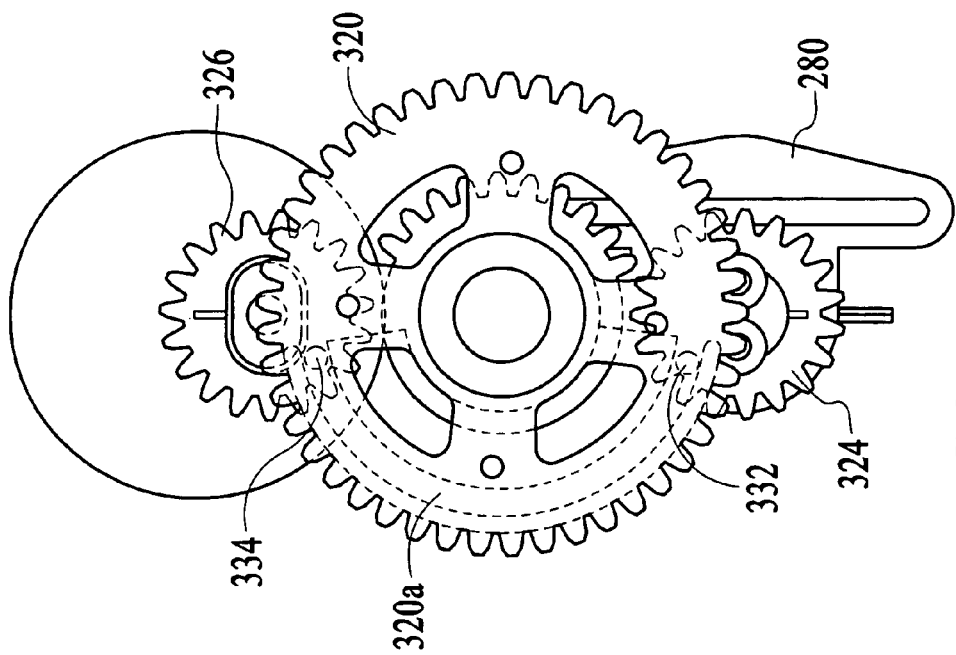

The trigger 406 of the lancing/collecting assembly 112 can be actuated by a push-button 462 positioned at the proximal end of an elongated element 464 that carries the locking tab 404, as shown in FIG. 24.

Figure 26A:
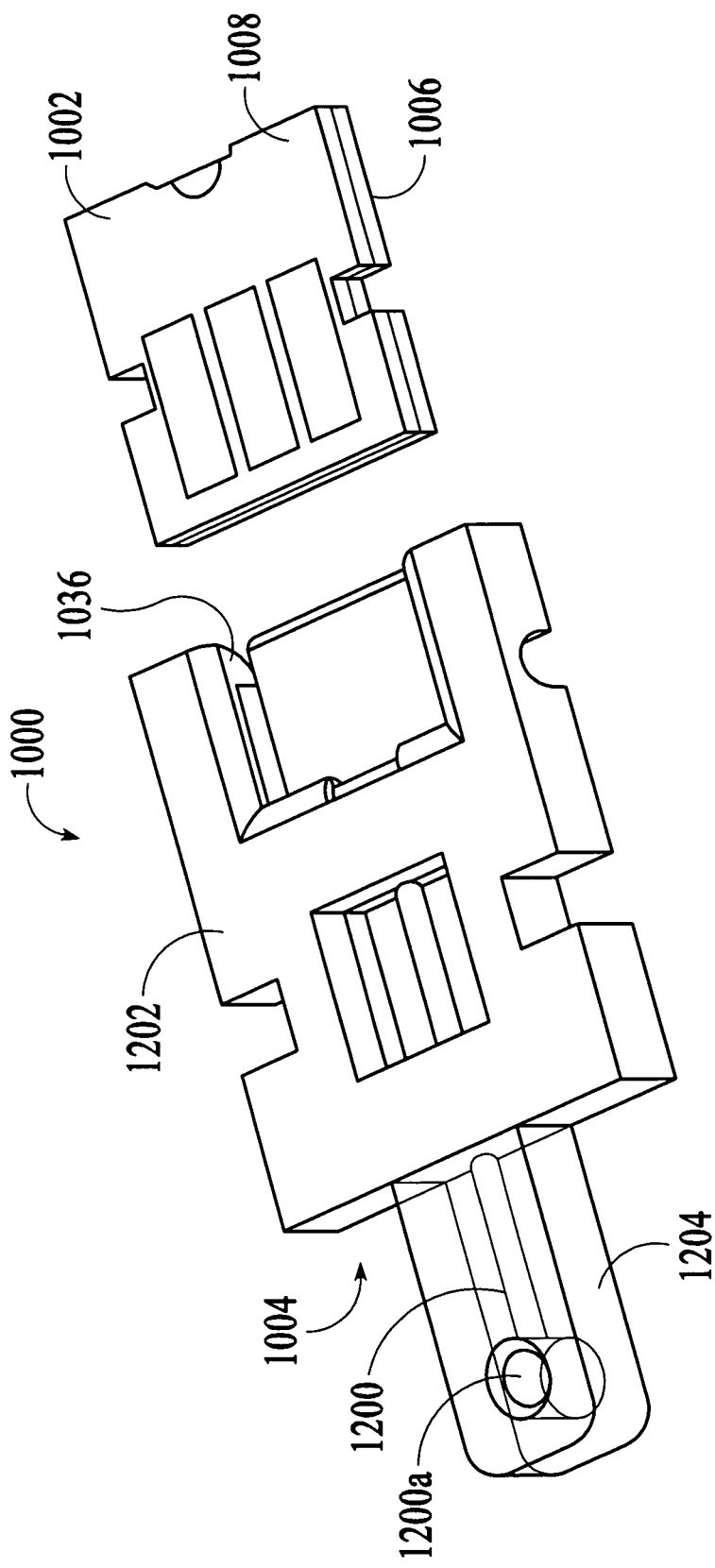
FIG. 26A is an exploded perspective view of one embodiment of the test strip of an embodiment, showing the lancet bearing a removable protective cover.
Figure 26B:
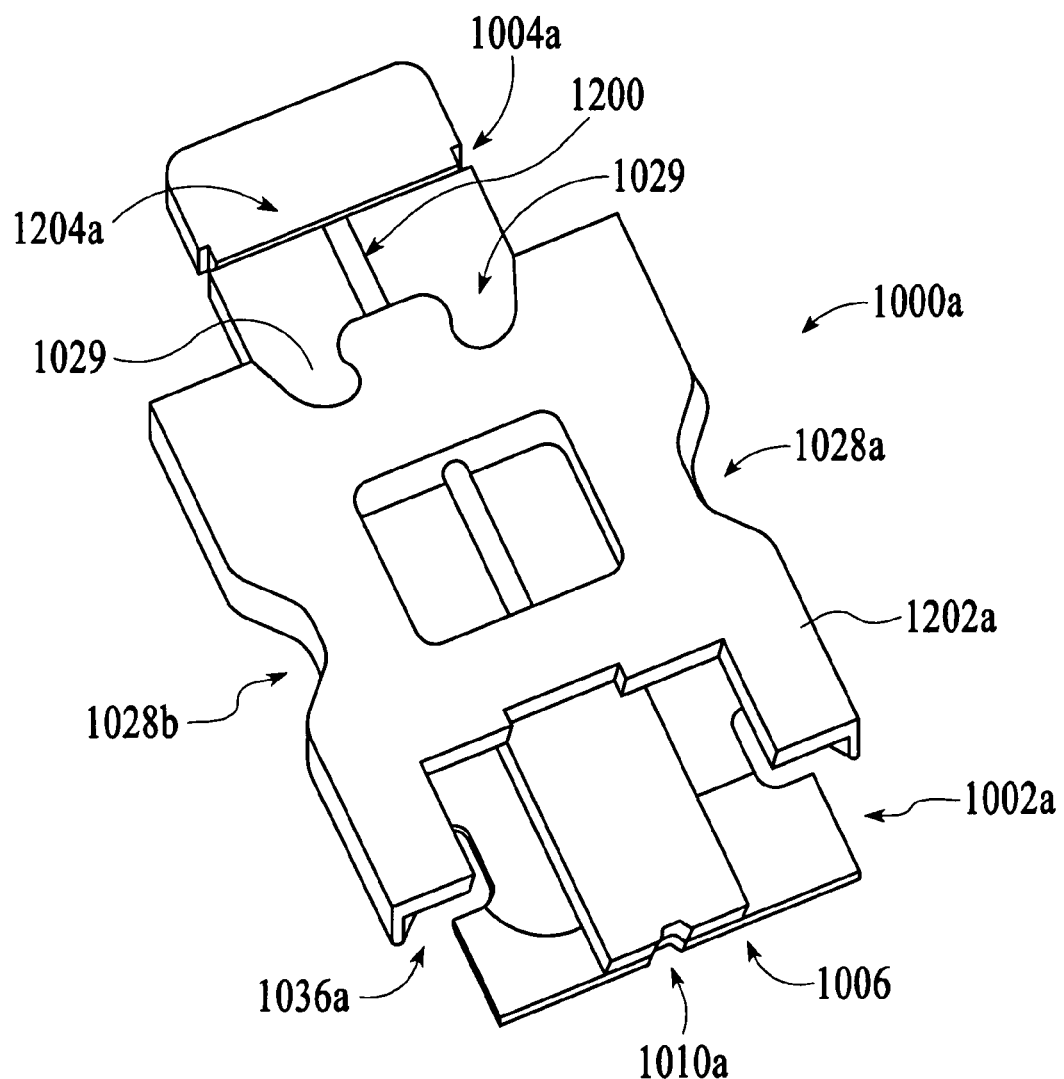
FIG. 26B is a perspective view of a testing STRIPLET™ in accordance with an embodiment.

In order to make effective use of the medical diagnostic device described above, a novel testing and lancing element, i.e., a STRIPLET™, was developed. As shown in FIGS. 26A-26B, STRIPLET™ 1000, 1000a has a sensor-containing portion 1002, 1002a and a lancet-containing portion 1004, 1004a. Referring specifically to FIGS. 26A-26B, an integrated lancet and testing STRIPLET™ 1000, 1000a is provided for measuring a body analyte, e.g., glucose, level in a diabetes care regimen. A lancet body 1202, 1202a includes a test strip receiving end 1036, 1036a and a lancet end. A lancet 1200 is coupled with and protruding from the lancet end and secured by a lancet cap 1204, 1204a. A test strip 1002, 1002a is coupled to the test strip receiving end 1036, 1036a of the lancet body 1202, 1202*a* having multiple electrodes and assay chemistry for testing an analyte, e.g., glucose, level of an applied body fluid. The test strip 1002, 1002*a* and lancet 1200 are relatively disposed at different ends of the STRIPLET™ 1000, 1000a for providing both lancing and application of body fluid at a lancing site by reorienting and advancing the STRIPLET™ 1000, 1000a within the meter after lancing to contact a sample receiving portion of the test strip precisely at the lancing site.

The reorienting may include rotating the STRIPLET™ 1000, 1000a when the lancing site remains approximately at the predetermined location relative to the meter for application of body fluid to the sample receiving portion of the test strip 1002, 1002*a*. The test strip 1002, 1002*a* and lancet 1200 may be symmetrically disposed at opposite ends of the lancet body 1202, 1202*a*. The reorienting may include rotating and/ or flipping the STRIPLET™ 1000, 1000a when the lancing site remains approximately at the predetermined location relative to the meter for application of body fluid to the sample receiving portion 1010*a* of the test strip 1002, 1002*a*.

The lancet body 1202, 1202*a* may include a pair of relatively disposed recesses 1028*a*, 1028*b* for respectively positioning the test strip via a spring-loaded ball and detent mechanism (not shown) for lancing and application of body fluid at a same lancing/testing site. The recesses 1028*a*, 1028*b* may be trapezoidally-shaped, as in FIG. 26B.

The lancet cap 1204*a* of FIG. 26B includes two elastomeric arms 1029, although there may be one or more than two, that couple with defined cutouts in the lancet body 1202*a* for snapping the cap 1204*a* into and out of mating relationship with the lancet body 1202*a* by respective application of sufficient coupling and separation force.

Figure 26C:
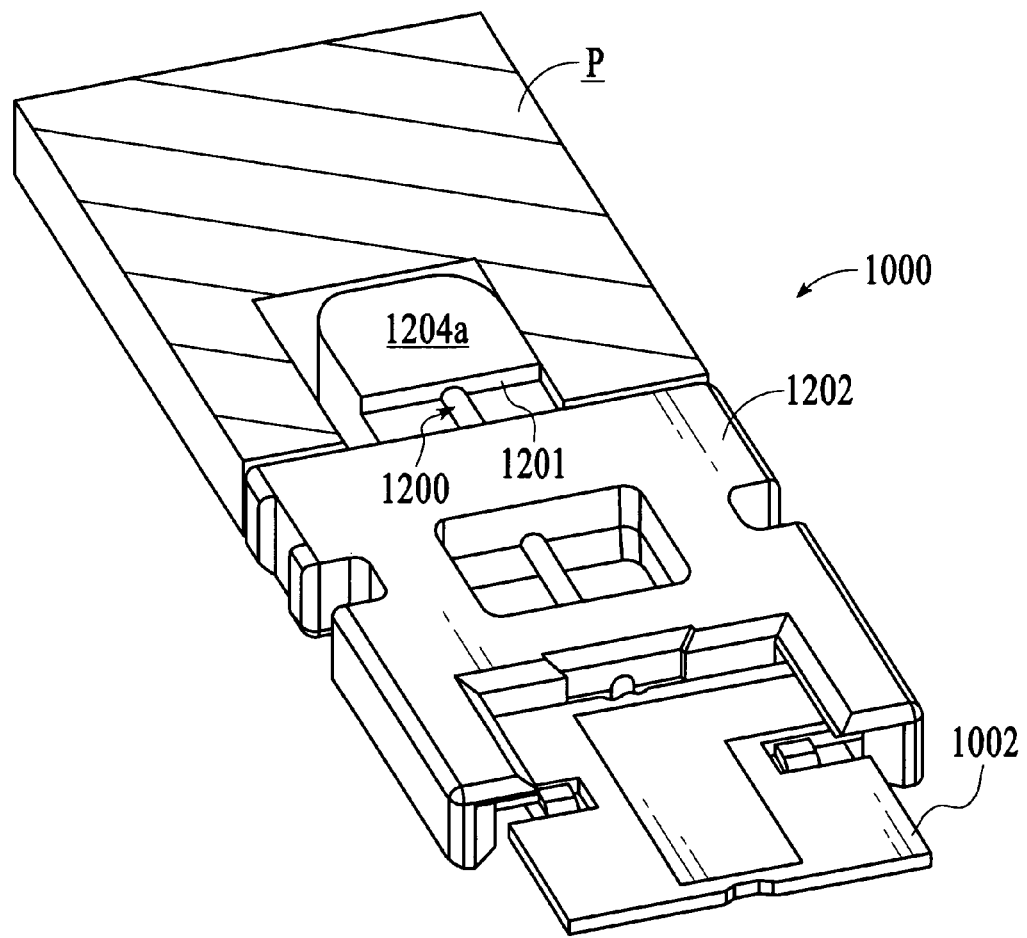
FIG. 26C is a perspective view of a testing STRIPLET™ coupled with a pusher P which serves both to advance the STRIPLET™ and in combination with a lever arm B in one embodiment also serves to arm the lancet by removing lancet cap in a retreating motion of the coupled-together blade B, cap and pusher P.
Figure 27:
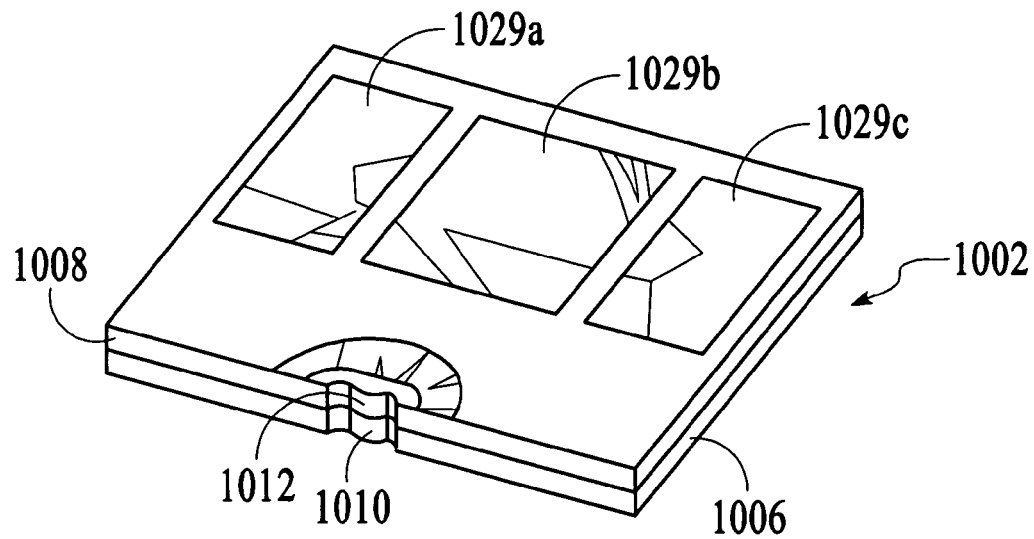
FIG. 27 is a perspective view of the sensor-containing portion of the embodiment of the test strip shown in FIG. 26.

Referring for a moment to FIG. 26C, a STRIPLET™ 1000 is shown including a lancet body 1202, test strip 1002 coupled with the lancet body 1202, and a lancet cap 1204*a* protecting a lancet 1200 which is also coupled to the lancet body 1202. The pusher P of FIGS. 7A-7P is shown coupled with the STRIPLET™ 1000. The pusher P has a U-shape in FIG. 26C, and may have any of a variety of shapes that fit somewhat snugly such as to overlap the lancet cap 1204*a* at least through the plane of a mating contour 1201 of the lancet cap 1204*a*. Although not shown in FIG. 26C, the pusher may have a corresponding contour to the mating contour 1201 of the lancet cap 1204*a*. When the blade B of FIGS. 7A-7P is disposed in mating relation with the mating contour 1201 of the lancet cap 1204*a*, the pusher P is also coupled, via its own corresponding contour or sufficient friction, with the blade B and/or with the lancet cap 1204*a*. This permits a retreating motion of the pusher P to bring the lancet cap 1204*a* with it away from the lancet body 1202 of the STRIPLET™ 1000 for arming the lancet 1200 while the STRIPLET™ 1000 is disposed in the turret 225 shown in FIGS. 7A-7P. Although not shown, a chain or other flexible component may be attached to the pusher P for advancing and retreating the pusher P, e.g., as illustrated in one example at FIG. 6F.

Figure 31:
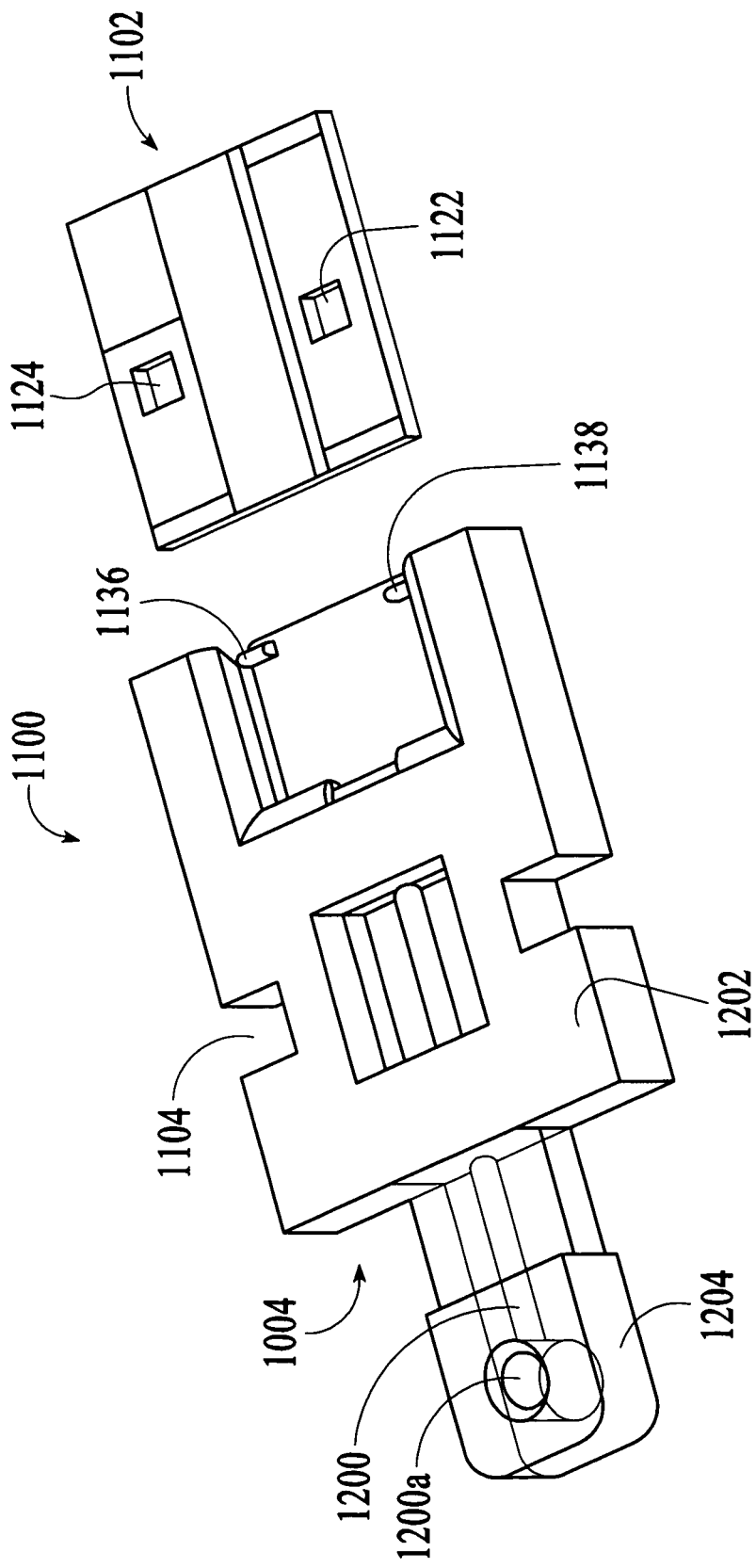
FIG. 31 is an exploded perspective view of still another embodiment of the test strip of an alternative embodiment, showing the lancet bearing a removable protective cover.

The lancet body 1202, 1202*a* and test strip 1002, 1002*a* of FIGS. 26A, 26B or see specifically FIG. 31, may include at least two teeth 1136, 1138 that fit corresponding slots 1122, 1124 for coupling the lancet body 1202, 1202*a* and test strip 1002, 1002*a*, 1102 together, and the lancet body 1202, 1202*a* has the teeth and the test strip 1002, 1002*a*, 1102 has the corresponding slots 1122, 1124.

Figure 28:
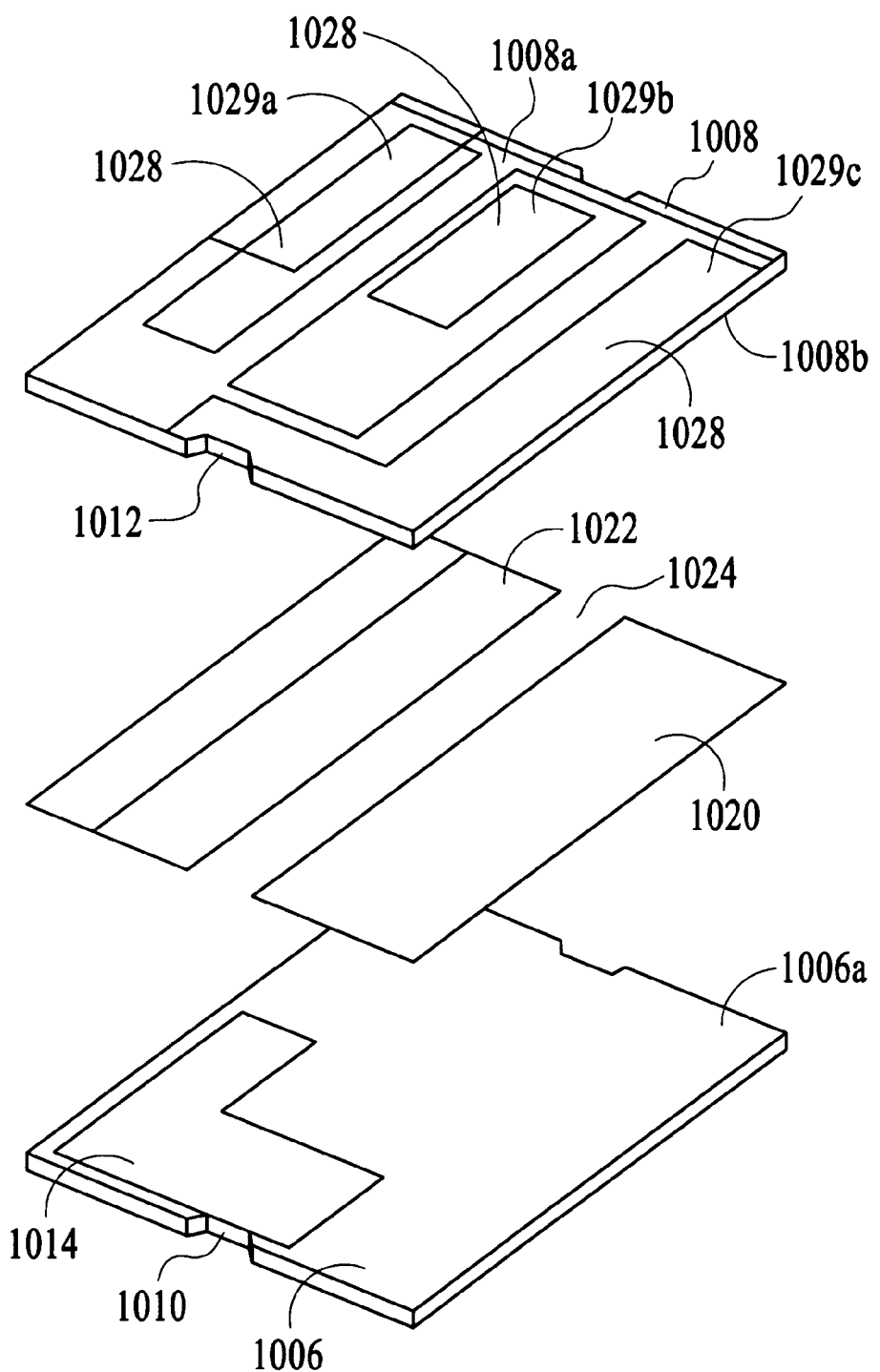
FIG. 28 is an exploded perspective view of the sensor-containing portion of the test strip shown in FIG. 27. In this view, the recesses for tabs of the lancet-containing portion of the test strip are not shown.

The test strip 1002, 1002*a*, 1102 may include a base 1006 and a cover 1008 as illustrated at FIG. 28. The base 1006 may have a layer of electrically conductive material applied to one major surface thereof 1006*a*, while the cover 1008 may have a working electrode and a trigger electrode applied to one major surface 1008*b* thereof. The base 1006 may be adhered to the cover 1008 by a layer of electrically conductive adhesive and/or a layer of non-conductive adhesive 1020, 1026. The sensor-containing portion may include a sample flow channel, and a working electrode and a trigger electrode may be positioned in the flow channel. The cover 1008 may include at least one electrical passageway running from an inner face to an outer face and/or a slot formed therein to attach the sensor-containing portion to a tab in the lancet-containing body. The base may include an opening formed therein to attach the sensor-containing portion to a tab in the lancet-containing body.

The base 1006 or the cover 1008 has a recess 1010, 1010*a*, 1012 formed in an edge thereof that forms the sample receiving portion of the test strip. The recess 1010, 1010*a*, 1012 may have a hydrophilic material applied thereto. The lancet 1200 may be positioned approximately 180° from the recess 1010, 1010*a*, 1012. Electrical contact pads may be on one major surface of the cover 1006 and/or base 1008. The cover 1006 may include a layer of electrically conductive or semiconductive material, such as carbon. The trigger electrode may include carbon.

In one embodiment, the sensor-containing portion 1002 includes a base 1006 and a cover 1008. As shown in FIGS. 26-29B, inclusive, both the base 1006 and the cover 1008 are substantially rectangular in shape, although other shapes may be used. In this substantially rectangular embodiment, the base 1006 has two major surfaces 1006*a*, 1006*b* and four edges 1006*c*, 1006*d*, 1006*e*, and 1006*f* (see FIG. 28). The cover 1008 has two major surfaces 1008*a*, 1008*b* and four edges 1008*c*, 1008*d*, 1008*e*, and 1008*f*. The base 1006 has a recess 1010 formed in one edge thereof, and the cover 1008 has a recess 1012 formed in one edge thereof. The surfaces of these recesses 1010 and 1012 bear a hydrophilic material in order to enable the sample of biological liquid to have greater affinity for the recesses 1010 and 1012 than if the recesses were not bearing a hydrophilic material. The base 1006 and the cover 1008 may be made from an electrically non-conducting material, e.g., an insulating material that is not capable of carrying substantial electric charge or current. Examples of materials usable include polyesters, polyethylene (both high density and low density), polyethylene terephthalate, polycarbonate, vinyls, and the like. The material may be treated with a primer or other such coating to improve the adhesion of the electrodes thereon. In certain embodiments, the base and/or cover is made from a hydrophobic polymeric material, e.g., "MELINEX" polymer, or the like.

The base 1006 bears a layer of electrically conductive material 1014 on the major surface thereof facing the cover 1008. Conductive material that may be used include gold, carbon, platinum, ruthenium dioxide, palladium, and conductive epoxies, such as, for example, ECCOCOAT CT5079-3 Carbon-Filled Conductive Epoxy Coating (available from W. R. Grace Company, Woburn, Mass.), Ag/AgCl, Ag/AgBr, as well as other materials known to those skilled in the art. For example, the embodiment of FIG. 6A may include Ag/AgCl. This electrically conductive material functions as a dual-purpose reference/counter electrode. The major surface of the cover 1008 facing the base 1006 bears a layer of electrically conductive material 1016 in a first area, which layer of electrically conductive material constitutes a working electrode, and a layer of electrically conductive material 1018 in a second area, which layer of electrically conductive material constitutes a trigger electrode. The major surface of the cover 1008 facing the base 1006 also bears a layer of non-conductive adhesive 1020 in a first area and layer of non-conductive adhesive 1022 in a second area to bond the cover 1008 to the base 1006. The layers of non-conductive adhesive 1020, 1022 also function to space the cover 1008 from the base 1006 so that a channel 1024 running along the center of the sensor-containing portion 1002 of the test strip 1000 is formed. A layer of electrically conductive adhesive 1026 enables the transfer of signal from the major surface 1006*a* of the base 1006 to the major surface 1008*b* of the cover 1008. The layer of electrically conductive adhesive 1026 can be made from a pressure-sensitive adhesive doped with an electrically conductive material, e.g., carbon. The layer of electrically conductive adhesive 1026 may be any suitable thickness, e.g., 0.002 inch.

At least one electrical passageway 1028 enables the transfer of signal from the major surface 1008*b* of the cover 1008 to the major surface 1008*a* of the cover 1008. An electrical passageway is a passageway formed in the cover 1008. The at least one electrical passageway 1028 is filled with electrically conductive material, such as, for example, carbon. The benefit resulting from the use of one or more electrical passageways is that all of the contact pads 1029*a*, 1029*b*, 1029*c* of the sensor-containing portion 1002 of the test strip 1000 can be positioned on one major surface of the cover 1008 of the test strip 1000.

Figure 29A:
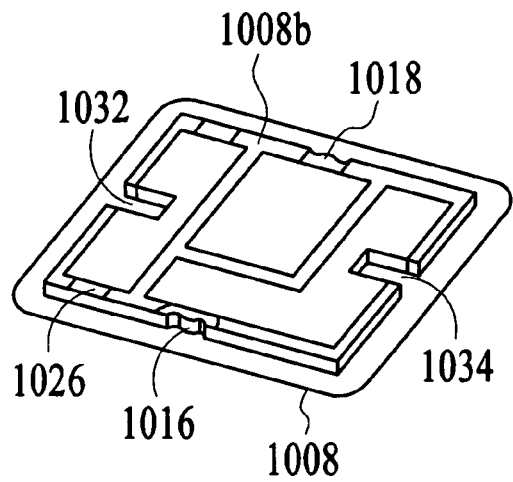
FIG. 29A is a perspective view of the inner face of the cover of the sensor-containing portion of the test strip shown in FIG. 26. In this embodiment, the recesses for tabs of the lancet-containing portion of the test strip are shown.
Figure 29B:
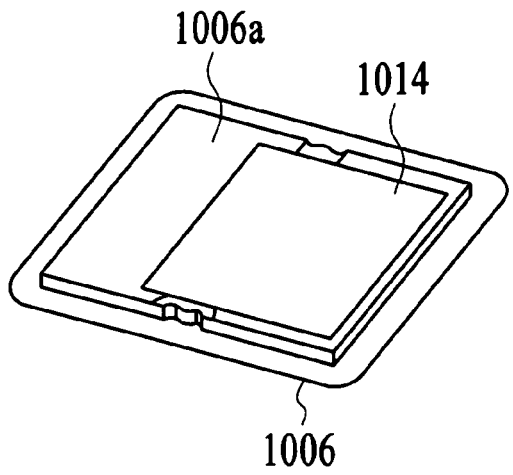
FIG. 29B is a perspective view of the inner face of the base of the sensor-containing portion of the test strip shown in FIG. 26.
Figure 29C:
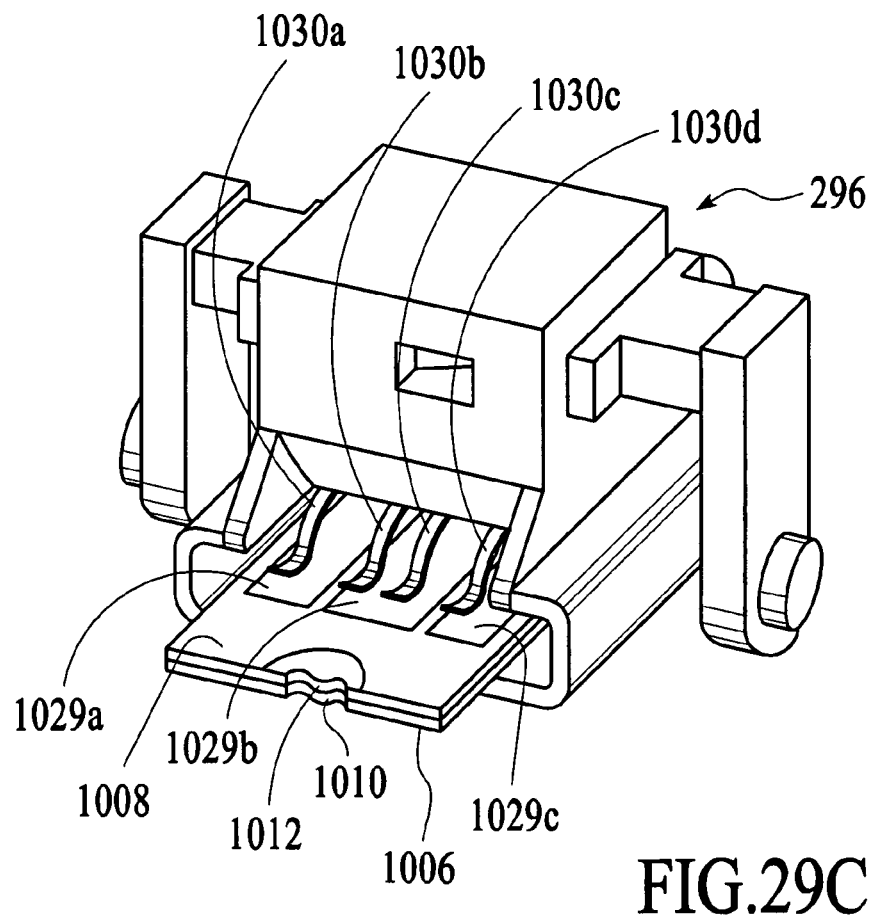
FIG. 29C is a perspective view of the test strip of FIG. 26 inserted into the analyzer of the medical diagnostic device of an alternative embodiment.

While not critical, it is advantageous that the dimensions of the sensor-containing portion 1002 of the test strip 1000 be as small as possible in order to reduce the size of the assembly 110 and reduce the volume of sample required to carry out a test. Typical dimensions of the base 1006 and cover 1008 are approximately 6 mm×6 mm x<2 mm. Typical dimensions of the electrodes and typical dimensions of a sample flow channel 1024 are described in U.S. Pat. Nos. 6,229,757 and 6,616,819, incorporated herein by reference. When the sample of biological liquid is introduced at the hydrophilic recesses 1010, 1012, the liquid is easily drawn up into the channel 1024, along which the liquid flows by means of capillary attraction. The major surface 1008*a* of the cover 1008 not facing the base 1006 has electrical contact pads 1029*a*, 1029*b*, 1029*c* exposed, which electrical contact pads 1029*a*, 1029*b*, 1029*c* are in contact with the contact leads 1030*a*, 1030*b*, 1030*c*, 1030*d* of the carrier 296, as shown in FIG. 29C. The cover 1008 also has two recesses 1032, 1034 in the edges perpendicular to the edge having the sample uptake recess 1012. The function of these recesses 1032, 1034 in the sides is to securely attach the sensor-containing portion 1002 of the test strip 1000 to the lancet-containing portion 1004 of the test strip 1000, which holds the lancet in place. As shown in FIG. 26, the tabs 1036 and 1038 project downwardly from the lancet-containing portion 1004 of the test strip 1000 toward the recesses 1032, 1034 in the edges of the sensor-containing portion 1002 of the test strip 1000.

A meter or other electrical device may use an electrical connector, which is configured to couple with and contact the contact pads at the end of a sensor. The meter may include a potentiostat or other component to provide a potential and/or current for the electrodes of the sensor. If configured for optical analysis, at least one light source may be provided, including componentry for measuring a property of the light as it impinges the sample, e.g., reflectance, absorbance, etc. The meter also typically includes a processor (e.g., a microprocessor or hardware) for determining the concentration of an analyte from the signals from the sensor. The meter also includes a display or port for coupling a display to the sensor. The display displays the signals from the sensor and/or results determined for the signals from the sensor including, for example, the concentration of an analyte, and/or the exceeding of a threshold of the concentration of an analyte (including, for example, hypo- or hyperglycemia). Furthermore, the meter may be configured to indicate to the user, via, for example, an audible, visual, or other sensory-stimulating alarm, when the level of the analyte is at or near a threshold level. For example, an alarm system may be included. For example, if glucose, is monitored then an alarm may be used to alert the user to a hypoglycemic or hyperglycemic glucose level and/or to impending hypoglycemia or hyperglycemia. The electrical connector employs contact leads that provide electrical connection between the sensor and the meter. The leads have proximal ends to physically contact the contact pads and distal ends to connect to any attached meter. The end of the sensor that has the contact pads can be slid into or mated with the electrical connector by placing the sensor into a slide area, which provides a support for and retains the sensor. It is important that the contact leads of the electrical connector make electrical contact with the correct pads of the sensor so that the working electrode and counter electrode(s) are correctly coupled to the meter. In certain embodiment of the medical diagnostic device 100 described herein, the carrier 296 substantially performs the aforementioned functions of the meter that is described in U.S. Pat. No. 6,616,819.

Figure 30A:
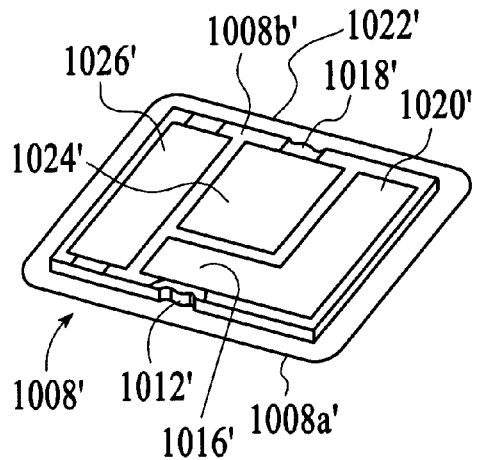
FIG. 30A is a perspective view of the inner face of the cover of another embodiment of the sensor-containing portion of the test strip of an alternative embodiment.
Figure 30B:
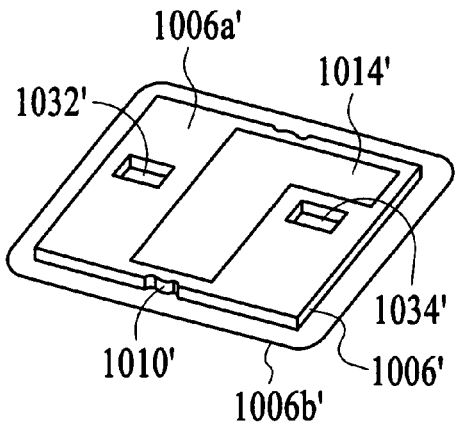
FIG. 30B is a perspective view of the inner face of the base of the sensor-containing portion of the test strip shown in FIG. 30A. In this embodiment, the openings for tabs of the lancet-containing portion of the test strip are shown.
Figure 30C:
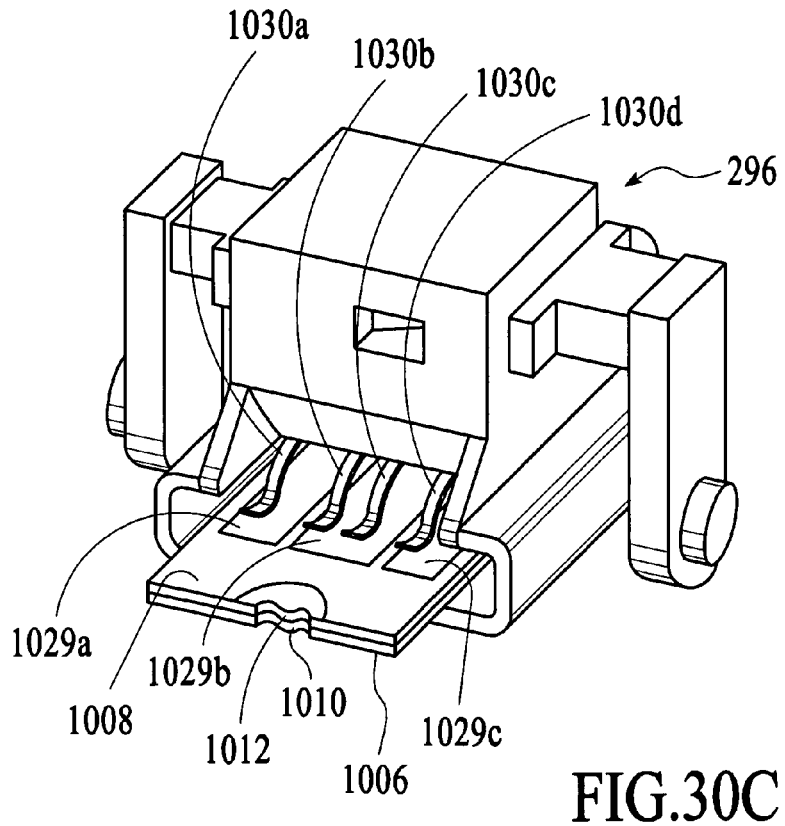
FIG. 30C is a perspective view of the test strip made from the base shown in FIG. 30A and the cover shown in FIG. 30B inserted into the analyzer of the medical diagnostic device of an alternative embodiment.

In another embodiment, the sensor-containing portion 1002' includes a base 1006' and a cover 1008'. As shown in FIGS. 30A-30C, inclusive, both the base 1006' and the cover 1008' are substantially rectangular in shape, but other shapes may be employed. In this embodiment, the base 1006' has two major surfaces 1006*a'*, 1006*b'* and four edges 1006*c'*, 1006*d'*, 1006*e'*, and 1006*f'*. The cover 1008' in this embodiment has two major surfaces 1008*a'*, 1008*b'* and four edges 1008*c'*, 1008*d'*, 1008*e'*, and 1008*f'*. The base 1006' has a recess 1010' formed in one edge thereof, and the cover 1008' has a recess 1012' formed in one edge thereof. The surfaces of these recesses 1010' and 1012' bear a hydrophilic material in order to enable the sample of biological liquid to have greater affinity for the recesses 10100', 1012' than if the recesses were not bearing a hydrophilic material.

The base 1006' bears a layer of electrically conductive material 1014' (for example, Ag/AgCl) on the major surface thereof facing the cover layer 1008'. This electrically conductive material functions as a dual purpose reference/counter electrode. The major surface of the cover 1008' facing the base 1006' bears a layer of electrically conductive material 1016' in a first area, which layer of electrically conductive material constitutes a working electrode, and a layer of electrically conductive material 1018' in a second area, which layer of electrically conductive material constitutes a trigger electrode. The major surface of the cover 1008' facing the base 1006' also bears a layer of non-conductive adhesive 1020' in a first area and layer of non-conductive adhesive 1022' in a second area to bond the cover 1008' to the base 1006'. The layers of non-conductive adhesive 1020', 1022' also function to space the cover 1008' from the base 1006' so that a channel 1024' running along the center of the sensor-portion 1002' of the test strip 1000' is formed. A layer of conductive adhesive 1026' enables the transfer of signal from the major surface 1006*a'* of the base 1006' to the major surface 1008*b'* of the cover 1008'. The layer of electrically conductive adhesive 1026' can be made from a pressure-sensitive adhesive doped with an electrically conductive material, e.g., carbon. The layer of electrically conductive adhesive 1026' typically has a thickness of about 0.002 inch.

At least one electrical passageway 1028' enables the transfer of signal from the major surface 1008*b'* of the cover 1008' to the major surface 1008*a'* of the cover 1008'. An electrical passageway 1028' is a passageway formed in the cover 1008'. The at least one electrical passageway 1028' is filled with electrically conductive material, such as, for example, carbon. The benefit resulting from the use of one or more electrical passageways is that all of the contacts of the sensor-containing portion of the test strip can be positioned on one major surface of the cover of the test strip. The electrical passageways 1028' are identical to or substantially similar to the electrical passageways 1028 previously described and shown in FIG. 28.

Figure 32:
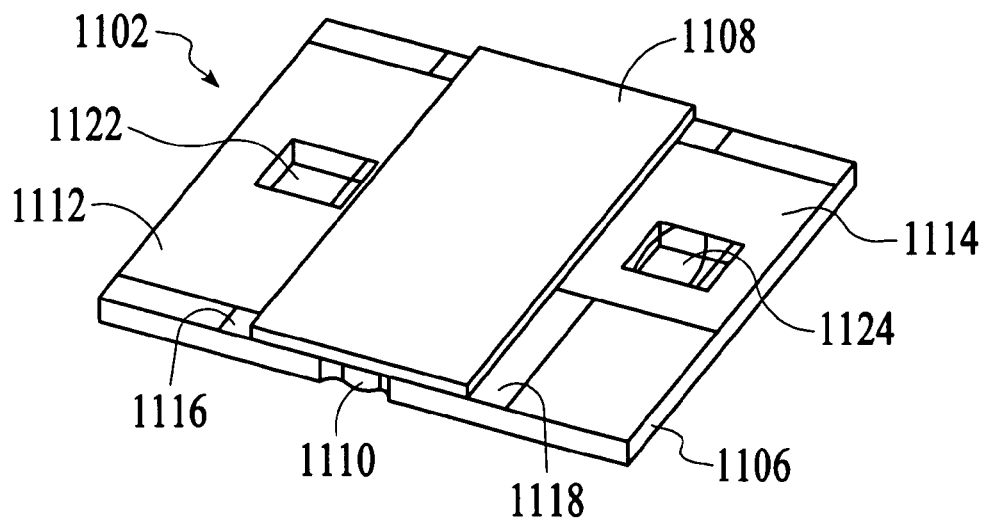
FIG. 32 is a perspective view of the sensor-containing portion of the test strip shown in FIG. 31.

While not critical, it is advantageous that the dimensions of the sensor-containing portion 1002' of the test strip 1000' be as small as possible in order to in order to reduce the size of the magazine 118 and reduce the volume of sample required to carry out a test. Typical dimensions of the base 1006' and cover 1008' are about 6 mm×6 mm x<2 mm. Typical dimensions of the electrodes and typical dimensions of channels 1024' that may be used are described in U.S. Pat. Nos. 6,229,757 and 6,616,819, incorporated herein by reference. When the sample of biological liquid is introduced at the sample receiving area, e.g., hydrophilic recesses 1010' and 1012', if present, the sample is easily drawn up into the channel 1024', along which the sample flows by means of capillary attraction. The major surface of the cover 1008' not facing the base 1006' has electrical contact pads 1029a', 1029b', 1029c' exposed, which electrical contact pads 1029a', 1029b', 1029c' are in contact with the contact leads 1030a, 1030b, 1030c, 1030d of the carrier 296, as shown in FIG. 30C. The base 1006' also has two openings 1032', 1034' formed therein on either side of one leg of the L-shaped electrode 1014'. The function of these openings 1032', 1034' is to securely attach the sensor-containing portion 1002' of the test strip 1000' to the lancet-containing portion, which holds the lancet in place. When the sensor-containing portion of the test strip has recesses in the sides of the cover, as shown in FIGS. 26 and 29A, the tabs of the lancet-containing portion of the test strip project downwardly, in the manner of the tabs of the lancet-containing portion shown in FIG. 26. When the sensor-containing portion of the test strip has openings in the base, as shown in FIGS. 30B, 31, and 32, the tabs of the lancet-containing portion of the test strip project upwardly, in the manner of the tabs of the lancet-containing portion shown in FIG. 31. The test strip 1000' of this embodiment can employ the same carrier 296 that can be used with the embodiment of the test strip 1000 previously described and the same type of meter as described in U.S. Pat. No. 6,616,819.

Figure 33:
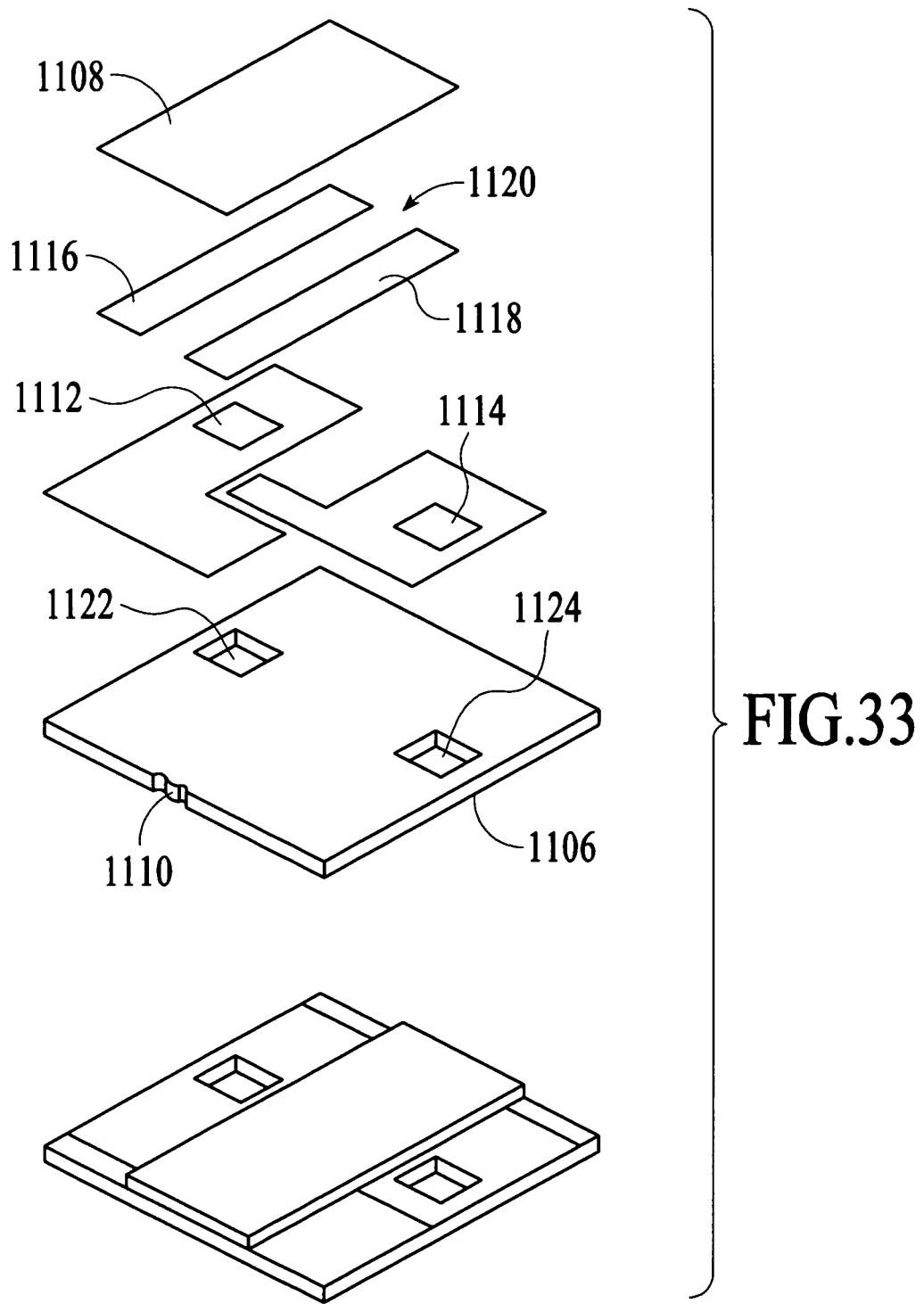
FIG. 33 is an exploded perspective view of the sensor-containing portion of the test strip shown in FIG. 31.

In still another embodiment, as shown in FIGS. 31-33, inclusive, a test strip 1100 includes a sensor-containing portion 1102 and a lancet-containing portion 1104. The sensor-containing portion 1102 includes a base 1106 and a cover 1108. The base 1106 is substantially rectangular in shape and has two major surfaces 1106a, 1106b and four edges 1106c, 1106d, 1106e, and 1106f. The base 1106 has a recess 1110 formed in one edge thereof. The surface of this recess 1110 bears a hydrophilic material in order to enable the sample of biological liquid to have greater affinity for the recess 1110 than if the recess were not bearing a hydrophilic material.

On one major surface of the base 1106 is a layer of electrically conductive material 1112 in a first area and a layer of electrically conductive material 1114 in a second area. The first area constitutes the working electrode and the second area constitutes the trigger electrode. The cover 1108 is separated from the base 1106 by layers 1116, 1118 of non-conductive adhesive applied to the base 1106 and cover 1108 in such a manner that a channel 1120 forming a sample flow path is created. This channel 1120 runs along the center of the sensor-portion 1102 of the test strip 1100. The cover 1108 is made of an electrically conductive material (such as, for example, vinyl having an electrically conductive material, e.g., Ag/AgCl, thereon) and functions as a dual purpose reference/counter electrode. When a sample of biological liquid is introduced at the hydrophilic recess 1110, the sample is easily drawn up into the channel 1116, along which the sample flows by means of capillary attraction. Portions of the electrically conductive material of the base 1106 function as electrical contact pads. The base 1106 has two openings 1122, 1124 formed therein on either side of the cover 1108. The function of these openings 1122, 1124 is to securely attach the sensor-containing portion 1102 of the test strip 1100 to the lancet-containing portion 1104, which holds the lancet in place. This embodiment does not require a conductive adhesive or electrical passageways to carry out determination of analytes.

The test strip 1100 of this embodiment can employ the same carrier 296 that can be used with the embodiments of the test strips 1000, 1000' previously described and the same type of meter as described in U.S. Pat. No. 6,616,819, which is incorporated by reference.

Below a sample application well or zone of a test strip may be a wicking membrane that is striped with various reagents to create various reagent, capture and/or eluate zones. A hemolysis reagent zone may be positioned below a sample application zone. The hemolysis reagent zone may include a hemolysis reagent that is striped, such as absorbed, confined, or immobilized, on a wicking membrane of the test strip. A small amount of hemolysis reagent, such as about 1 to about 2 or about 3 microliters, for example, is sufficient for striping the wicking membrane such that the hemolysis reagent zone is sufficiently confined on the test strip. Any reagent or combination of reagents suitable for hemolysis, and the consequent liberation of hemoglobin, can be used. By way of example, an ionic detergent, such as sodium dodecyl sulfate (SDS), a non-ionic detergent, such as a octylphenol ethylene oxide condensate or octoxynol-9 or t-octylphenoxypoly-ethoxy-ethanol, sold under the name, Triton X-100, and commercially available from Sigma Chemical or Sigma-Aldrich Co., or a hypotonic solution, may be used as a hemolysis reagent.

A glycated hemoglogin capture zone may be disposed downstream relative to the hemolysis zone. By way of example, any chemical reagent comprising at least one boron ligand, such as phenyl boronate or other boron affinity chemistry used in the above-referenced Glycosal test, or such as m-aminophenylboronic acid, such as that of a gel that is immobilized on cross-linked, beaded agarose, any antibody, such as anti-HbA1c antibody available from a number of sources, any immunoassay reagent, any chemical reagent including at least one binding ligand, such a boronic acid involving boron binding ligands, and the like, and any combination thereof, that is suitable for the binding of glycated hemoglobin to the capture zone 222, such as via covalent bonds, for example, or the capture of glycated hemoglobin in capture zone 222, may be used. A hemolysis layer/zone and a glycated hemoglobin capture zone can be integrated to form an integrated reagent zone.

A lancet 1200 can be integrated directly into the sensor-containing portion 1002, 1002', 1102 of the test strip. Alternatively, the sensor-containing portion 1002, 1002', 1102 of the test strip can be attached to the lancet-containing portion of the test strip. The medical diagnostic device 100 can have an alignment feature to ensure that movement, e.g., rotation, of the test strip during use does not result in misalignment of the sample application zone of the test strip. The alignment feature can be provided by springs associated with the carrier 296.

The lancet-containing portion 1004 shown in FIG. 26 can be used with, or can be modified to be used with, any of the sensor-containing portions 1002, 1002', and 1102 described herein. For example, the tabs for connecting the lancet-containing portion to the sensor-containing portion can be modified to project upwardly to enable the lancet-containing portion to be used with a sensor-containing portion having openings in the base, rather than recesses in the sides of the base and the cover. It should be noted that other embodiments of the lancet-containing portion can be used with any of the sensor-containing portions 1002, 1002', and 1102 described herein. As shown in FIG. 26, the lancet-containing portion 1004 is shown as having a lancet-containing body 1202. The lancet 1200 is held in the lancet-containing body 1202. The lancet-containing body 1202 can be attached to the sensor-containing portion 1002 by tabs 1036, 1038 or can be attached to the sensor-containing portion 1002', 1102 by tabs 1136, 1138. When the sensor-containing portion of the test strip has recesses in the sides of the cover, as shown in FIGS. 26 and 29A, the tabs 1036, 1038 of the lancet-containing portion of the test strip project downwardly, in the manner of the tabs of the lancet-containing portion shown in FIG. 26. When the sensor-containing portion of the test strip has openings in the base, as shown in FIGS. 30B, 31, and 32, the tabs 1136, 1138 of the lancet-containing portion of the test strip project upwardly, in the manner of the tabs of the lancet-containing portion shown in FIG. 31. Any suitable dimensions of the lancet-containing body may be employed, and in certain embodiments the lancet-containing body 1202 of the lancet-containing portion 1004 is 10 mm×8 mm×1.5 mm. Typical dimensions of the protective cover 1204 for the lancet 1200 are 3 mm×1.4 mm. Typical dimensions of the needle for forming the lancet 1200 are 28 to 30 gauge, 10 mm total length, 3.5 mm exposed length.

A lancet 1200 for puncturing the skin to obtain a sample of biological liquid includes a sharp metal component (needle) that is maintained in a sterile condition until the moment of use. In addition, an ideal lancet 1200 is disposable with minimum possibility of an injury subsequent to the initial use. The lancet 1200 includes a substantially cylindrical needle having a sharp end and an opposing end which may be a blunt end. The tip 1200*a* of the lancet 1200, i.e., the sharp end, has a protective cover 1204 that ensures sterility of the lancet 1200. The protective cover 1204 is also designed to be re-attached to the tip 1200*a* of the lancet 1200 for safe disposal. The blunt end can be embedded into the lancet-containing body 1202 by insert molding or adhesive. In one embodiment, the lancet-containing body 1202 includes a polymeric material molded into a substantially rectangular shape.

The tip 1200*a* of the lancet 1200 and as much of the lancet 1200 as is expected to puncture the skin of the patient can embedded in the protective cover 1204, e.g., a polymeric plug, which may be an elastomeric plug, e.g., thermoplastic elastomeric, silicone, plug. In this configuration, ionizing radiation can be used to sterilize the lancet 1200 and the elastomer will prevent subsequent contamination. Embedding the piercing portion (tip) 1200*a* of the lancet 1200 in a soft material does not damage the delicate tip 1200*a* of the lancet 1200 but forms a tight seal that allows for sterilization (such as by irradiation) and the preservation of that sterile condition. Such a protective cover 1204 can be removed from the piercing portion of the lancet 1200 either by pulling the protective cover 1204 off the tip 1200*a* of the lancet 1200 or by fully piercing the protective cover 1204 and allowing the protective cover 1204 to cover a more proximal part of the lancet 1200.

The nature of the thermoplastic elastomer (TPE) eliminates the necessity of relocating the tip 1200*a* of the used lancet 1200 precisely into the hole originally occupied by the tip 1200*a* of the unused lancet 1200. Relocation of the tip 1200*a* of the lancet 1200 at any position in the thermoplastic elastomeric protective cover 1204 is sufficient to prevent the tip 1200*a* of the lancet 1200 from being exposed after the test strip is ejected from the medical diagnostic device 100.

Thermoplastic elastomers (TPE) are easily processed rubbery materials. They can be easily formed in various shapes. If a sharp lancet 1200 is embedded into a piece of thermoplastic elastomer, and then irradiated by either gamma radiation or electron beam radiation of sufficient energy, the lancet 1200 is rendered sterile, and because the thermoplastic elastomer forms a tight seal, the lancet 1200 remains sterile for a relatively long period of time.

If the protective cover 1204 made is made of thermoplastic elastomer, and the thermoplastic elastomer is at least partially enveloped by a more rigid material, the protective cover 1204 acts more like a rigid body, but keeps the desired features of the thermoplastic elastomer. Configurations of this design might include the lamination of thermoplastic elastomer between thin layers of rigid plastic or metal or the coextrusion of thermoplastic elastomer with a more rigid polymer. The cross-section of such a coextruded profile can be circular, rectangular, or any other shape that renders it useful. Such a combination of thermoplastic elastomer and rigid material can be provided with features such that the combination is allowed to slide proximally on the shaft of the lancet 1200, eventually exposing the tip 1200*a* of the lancet 1200 for lancing. After the lancet 1200 is used, the subassembly can be slid distally and the connection between the protective cover 1204 and the lancet 1200 changed such that the protective cover 1204 cannot return to a position that exposes the tip 1200*a* of the lancet 1200.

It should be noted that all of the embodiments of the test strip shown herein are characterized by having the tip 1200*a* of the lancet 1200 of the lancet-containing portion 1004 of the test strip located 180° from the uptake recess of the sensor-containing portion 1002, 1002', 1102 of the test strip. Such positioning renders the test strips suitable for use with the medical diagnostic device.

The test strips and the magazines 118 containing a plurality of test strips can be made by the following process: To prepare the lancet-containing portion 1004 of a test strip, unfinished lancets are provided. These unfinished lancets are ground and cut to 10 mm. The ground, cut lancets 1200 are then molded into a plastic body 1202 to form the lancet-containing portion 1004 of the test strip. To prepare the sensor-containing portion 1002, 1002', 1102 of the test strip, the electrodes are printed onto the backing or cover, the appropriate reagents (discuss these) are coated over the electrodes, and the cards of sensor-containing portions 1002, 1002', 1102 are singulated to form individual sensor-containing portions 1002, 1002', 1102. The individual sensor-containing portions 1002, 1002', 1102 are combined with the lancet-containing portions 1004 to form completed test strips. Pluralities of test strips are then loaded into magazines 118.

The sensors described herein may be configured for analysis of an analyte in a small volume of sample by, for example, coulometry, amperometry, and/or potentiometry. The sensors may also be configured for optical analysis. The sensors may be configures to determine analyte concentration in about 1 µL or less of sample, e.g., 0.5 µL or less of sample e.g., 0.25 µL or less of sample e.g., 0.1 µL or less of sample. The chemistry of the sensors generally includes an electron transfer agent that facilitates the transfer of electrons to or from the analyte. One example of a suitable electron transfer agent is an enzyme which catalyzes a reaction of the analyte. For example, glucose, oxidase or glucose, dehydrogenase, such as pyrroloquinoline quinone glucose, dehydrogenase (PQQ), may be used when the analyte is glucose. Other enzymes may be used for other analytes. Additionally to or alternatively to the electron transfer agent, may be a redox mediator. Certain embodiments use a redox mediator that is a transition metal compound or complex. Examples of suitable transition metal compounds or complexes include osmium, ruthenium, iron, and cobalt compounds or complexes. In these complexes, the transition metal is coordinatively bound to one or more ligands, which are typically mono-, di-, tri-, or tetradentate. The redox mediator may be a polymeric redox mediator or a redox polymer (i.e., a polymer having one or more redox species). Examples of suitable redox mediators and redox polymers are disclosed in U.S. Pat. Nos. 6,338,790; 6,229, 757; 6,605,200 and 6,605,201, which are incorporated by reference.

The sensor also includes a sample chamber to hold the sample in electrolytic contact with the working electrode. In certain embodiments, the sample chamber may be sized to contain no more than about 1 µL of sample, e.g., no more than about 0.5 µL, e.g., no more than about 0.25 µL, e.g., no more than about 0.1 µL of sample.

The magazines 118 can be prepared by first molding the desiccants into platforms. Resilient biasing elements and the platforms are then assembled into the housings of the magazines. The magazines are then packed and shipped.

Figure 34:
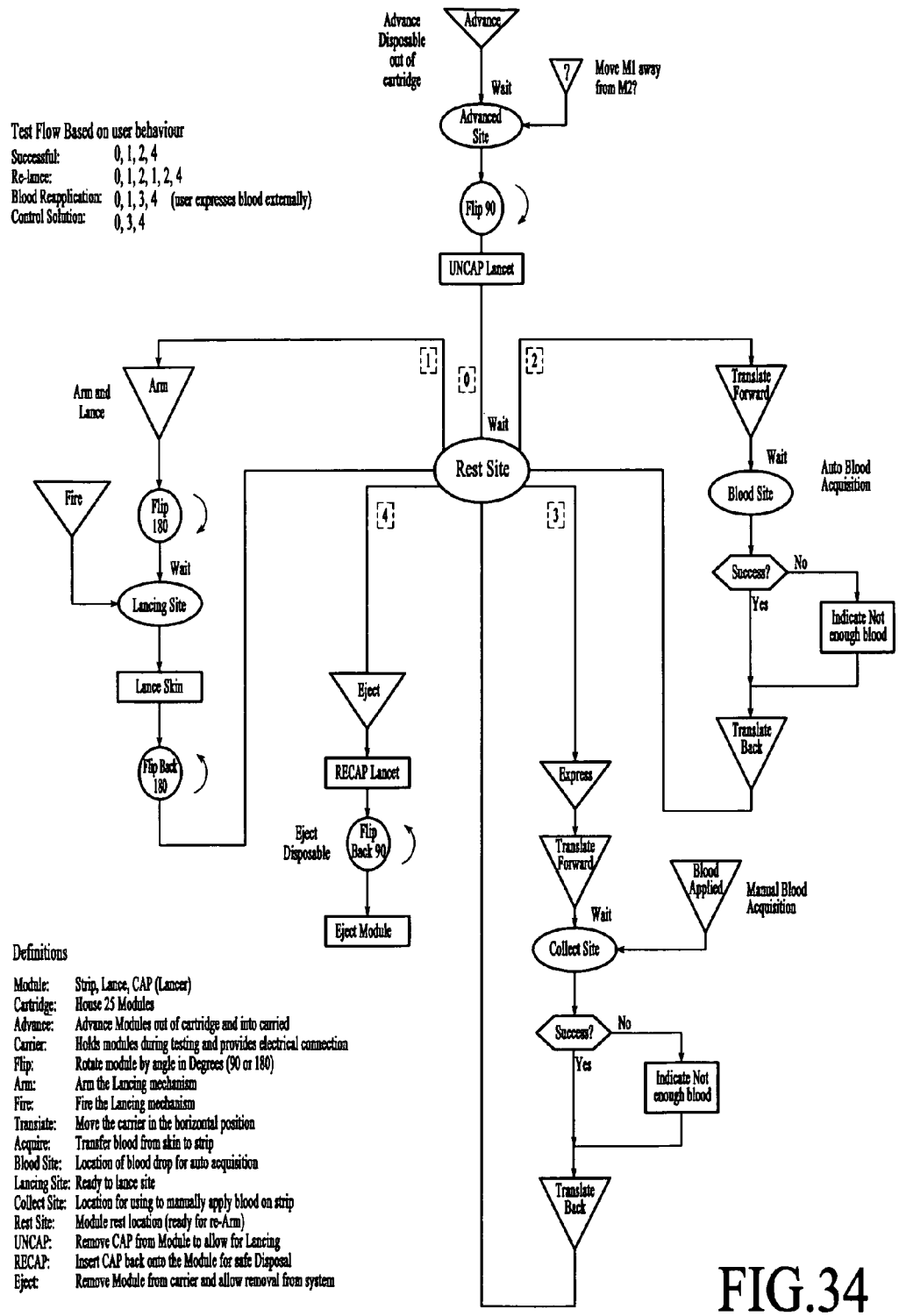
FIG. 34 is a flow chart illustrating the operations of the medical diagnostic device of an alternative embodiment.

Embodiments for operating the medical diagnostic device 100 to dispense a test strip, form an opening in the skin of a patient to obtain a sample of biological liquid, collect a sample of biological liquid from the patient, analyze the sample of biological liquid collected from the patient, and dispose of the used test strip will now be described. FIG. 34 also depicts the operational steps in a flow chart. In most places above and below herein, the reference numerals ending with "a" are left off for convenience, although most reference numerals having a corresponding numeral ending in "a" is intended to have the corresponding numeral there, and such are hereby incorporated there.

Referring now to FIGS. 1-7, the assembly 110 for storing and dispensing a plurality of STRIPLETS™ is inserted into the housing 102 of the medical diagnostic device 100. The housing has a door through which the assembly 110 can be introduced to the proper position in the interior of the housing 102. The door is on the side of the housing 102 opposite the display 238. The door can be mounted by means of at least one hinge or can be mounted by a snap-fit feature.

For the sake of simplification, the STRIPLET™ will be the test strip shown in FIGS. 26A-B. Other test strips described can be used in place of the STRIPLET™ shown in FIG. 26A-26B. Each STRIPLET™ 1000, 1000a in the assembly 110 has a lancet-containing portion and a sensor-containing portion 1002. The lancet-containing portion 1004 of the STRIPLET™ 1000 has a protective cover 1204 to render the tip 1200a of the lancet 1200 sterile and prevent the tip 1200a of the lancet 1200 from causing an unwanted puncture. The sensor-containing portion 1002 of the STRIPLET™ 1000 emerges first from the magazine 118. In order to feed a STRIPLET™ 1000 from the magazine 118 to the cradle 280 of the lancing/collecting assembly 112, the lowermost STRIPLET™ 1000 in the assembly 110 is fed from the assembly 110 to the cradle 280 of the lancing/collecting assembly 112.

In order to advance a STRIPLET™ 1000 from the magazine 118 to the cradle 280 of the lancing/collecting assembly 112, the user causes the slide 142 to move in the required direction. Movement of the slide 142 alone, or in combination with another feature, enables the magazine 118 to become unsealed, so that a test strip 1000 can be removed from the magazine 118. When the magazine 118 is unsealed, the mechanism for advancing a STRIPLET™ 1000 from the assembly for storing and dispensing test strips 1000 to the lancing/collecting assembly 112 advances a STRIPLET™ 1000 into the cradle 280 of the lancing/collecting assembly 112 and positions the STRIPLET™ 1000 so that proper lancing, collecting of sample of biological liquid, and analyzing of the collected sample can be carried out. Prior to the lancing step, the protective cover 1204 of the lancet 1200 is removed, either before the STRIPLET™ 1000 is positioned in the cradle 280 or after the STRIPLET™ 1000 is positioned in the cradle 280. The assembly 114 for removing a protective cover 1204 from the tip 1200a of a lancet 1200 and re-attaching the protective cover 1204 to the tip 1200a of a used lancet 1200 retains the protective cover 1204 for subsequent re-attachment to the tip 1200a of the lancet 1200 of the lancet-containing portion 1004 of the STRIPLET™ 1000 after the lancing step, the collecting step, and the analyzing step are completed.

After STRIPLET™ 1000 has been fed into the cradle 280, the medical diagnostic device 100 causes the STRIPLET™ 1000 to be oriented in such a manner that the lancet 1200 may be introduced into the skin of a patient. In many embodiments, such an orientation step is carried out by a motor. In these embodiments, the PCB assembly 232 can be programmed so that orientation is carried out accurately and reliably. Such an orientation step is carried out by having the transmission system rotate the cradle 280 of the lancing/collecting assembly 112 about 90° (clockwise or counter-clockwise), so that the tip 1200a of the lancet 1200 faces the opening in the end cap 104, so that when the medical diagnostic device 100 is placed against the skin of the patient, the tip 1200a of the lancet 1200 will be facing the skin of the patient.

Then, the lancing/collecting assembly 112 is armed. Movement of the slide 460 causes a sufficient amount of energy for lancing and retracting to be stored in the torsion spring 388. Appropriate movement of the slide 460 causes the locking tab 402 to abut the locking tab 404 to arm the lancing/collecting assembly 112. In an alternative embodiment, the lancing/collecting assembly 112 can be armed by means of a motor, thereby eliminating the need for the slide 460.

After the lancing/collecting assembly 112 is armed, the medical diagnostic device 100 is placed against the skin of the patient in such a manner that the opening in the end cap 104 overlies the position where the patient desires to puncture the skin. When the patient is ready to trigger the lancet 1200, the patient actuates the trigger 406, to disengage the locking tab 402 from the locking tab 404, thereby allowing the carrier 296 to traverse the slots 288 and 290 in the cradle 280 and move rapidly toward the skin of the patient, whereby the lancet 1200 in the lancet-containing portion 1004 of the STRIPLET™ 1000 causes an opening to be formed in the skin of the patient. Immediately after the opening is formed in the skin of the patient, the carrier 296 is retracted by the action of the lancing cam 338, whereupon the lancet 1200 of the lancet-containing portion 1004 of the STRIPLET™ 1000 moves away from the skin of the patient. Meanwhile, the sample of biological liquid is caused to emerge from the opening formed in the skin of the patient The medical diagnostic device 100 then causes the STRIPLET™ 1000 to be oriented in such a manner that the sensor-containing portion 1002 of the STRIPLET™ 1000 can be placed in contact with the sample of biological liquid emerging from the opening in the skin of the patient. For this step, the cradle 280 is rotated 180° so that the sensor-containing portion 1002 of the STRIPLET™ 1000 directly overlies the biological liquid.

The medical diagnostic device 100 then enables the index cam 338 to move the cam follower 274 so that the carrier 296 can traverse the slots 288 and 290 to move toward the opening in the skin of the patient so that the sensor-containing portion 1002 of the STRIPLET™ 1000 is able to collect biological liquid emerging from the opening in the skin of the patient. The carrier 296 and the movements thereof can be designed so that the carrier 296 can move toward and away from the skin in such a manner that a suitable quantity of biological liquid is collected. The flexibility of the flexible component 422 of the cam follower 274 assists in obtaining a sample of biological liquid from the opening in the skin of the patient.

The sample of biological liquid enters the sample application zone of the sensor-containing portion 1002 of the test strip 1000, i.e., the recesses 1010, 1012 formed in an edge of the test strip 1000. The sample of biological liquid travels along the sample flow channel 1024 to the area where the reagents are disposed. The appropriate reaction occurs, thereby activating the electronics and bringing about a reading of the concentration of the analyte, which reading is shown in the display. If insufficient quantity of the sample of biological liquid is drawn in the initial lancing step, the user can actuate a retesting procedure before actuating the analyzing step, whereby the test is aborted so that the user can re-arm the lancing mechanism and begin again.

The sensor-containing portion 1002 of the test strip 1000 collects a sufficient quantity of sample of biological liquid to allow analysis of the sample of biological liquid. After a sufficient amount of sample of biological liquid is collected, the carrier 296, the electrical components of which are in electrical contact with the contacts of the sensor-containing portion 1002 of the test strip 1000, measures the quantity of analyte in the sample by means of an electrochemical analyzer. By this process, the sample of biological liquid is analyzed to determine at least one characteristic of the sample of biological liquid.

After the sample of biological liquid is analyzed, the protective cover 1204 is re-attached to the tip 1200a of the lancet 1200 of the lancet-containing portion 1004 of the test strip 1000. After the protective cover 1204 is re-attached, the re-covered test strip 1000 is ejected from the port 230 in the housing 102.

FIG. 34 is a flow chart that illustrates various steps of a method in accordance with several embodiments. As shown in FIG. 34, there are five basic components of the method. Component 0 involves advancing the test strip from the magazine 118 into the cradle 280, removing the protective cover 1204 from the lancet 1200, and rotating the cradle 280 to position the lancet 1200 for entering the skin of the patient. It should be noted that the protective cover 1204 could be removed from the lancet 1200 prior to rotating the cradle 280 into position for lancing. Component 1 involves arming and triggering the lancet 1200. Component 2 involves indexing the test strip so that the sensor portion of the test strip can obtain blood from the opening formed in the skin in Component 1. Component 3 involves collecting blood from the opening formed in the skin in Component 1. Component 4 involves reattaching the protective cover 1204 to the lancet 1200 and ejecting the used test strip from the medical diagnostic device 100.

Figure 35A:
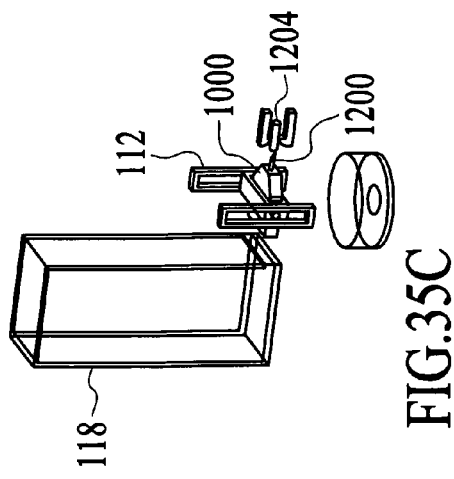
FIGS. 35A-35M, inclusive, are schematic views illustrating the positions of the lancing/collecting assembly of an alternative embodiment during one cycle of operation of the medical diagnostic device of an alternative embodiment.
Figure 35B:
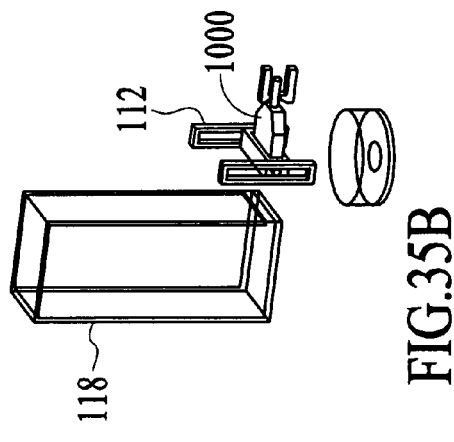
Figure 35C:
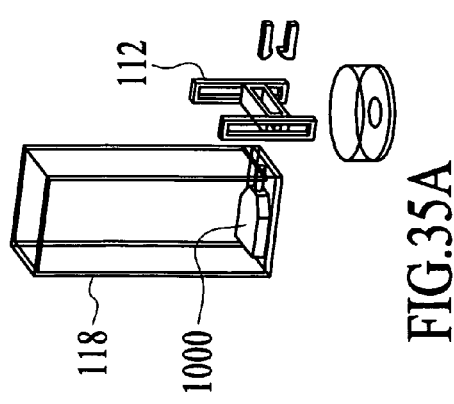
Figure 35D:
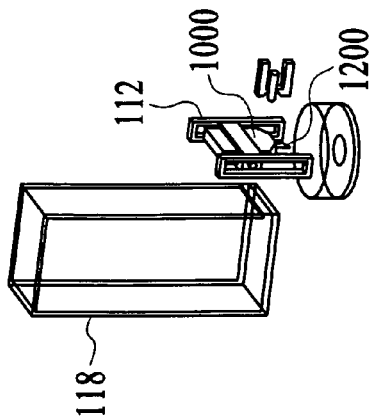
Figure 35E:
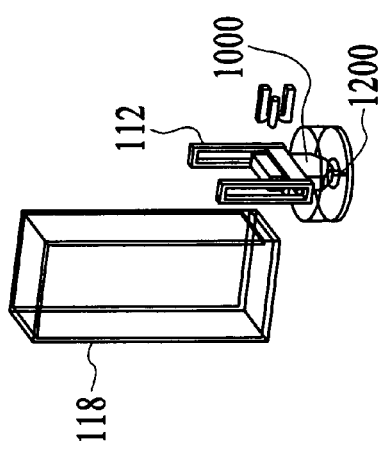
Figure 35F:
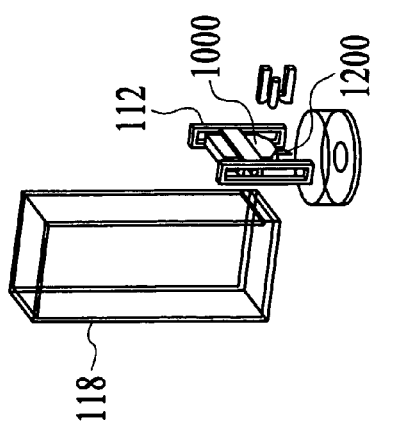
Figure 35G:
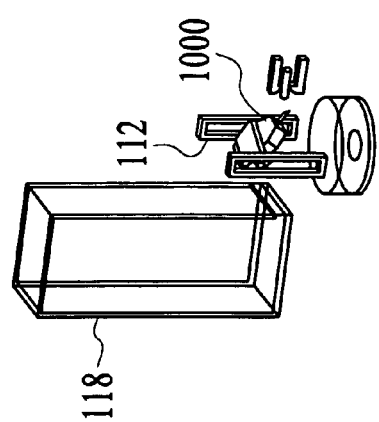
Figure 35H:
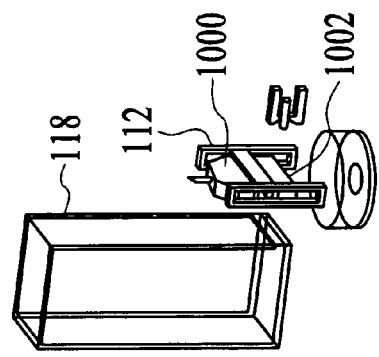
Figure 35I:
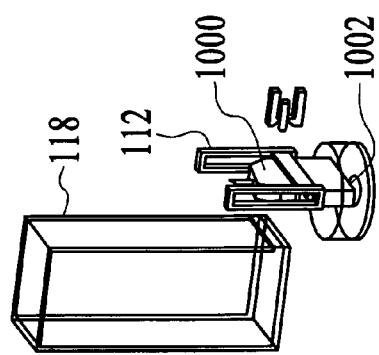
Figure 35J:
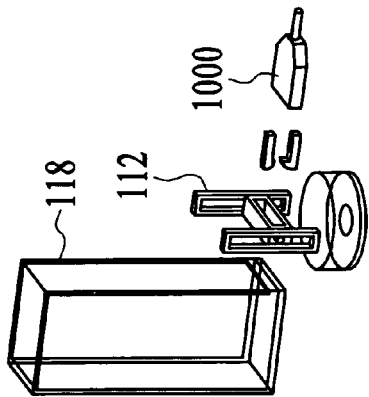
Figure 35K:
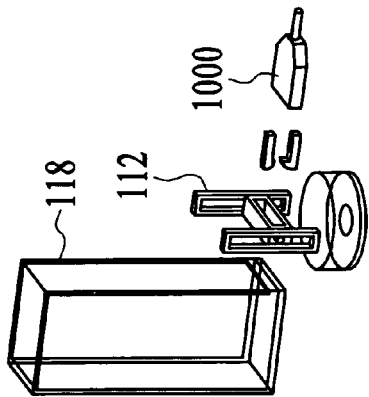
Figure 35L:
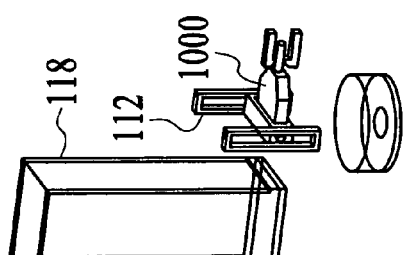
Figure 35M:
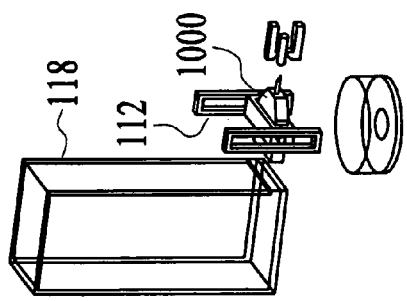

FIG. 35A through FIG. 35M, inclusive, illustrate in schematic form one way of carrying out a method according to embodiments herein. For the sake of simplification, the test strip will be the test strip shown in FIG. 26. Other test strips described can be used in place of the test strip shown in FIG. 26. FIG. 35A shows a test strip 1000 in the magazine 118. FIG. 35B shows the test strip 1000 advanced from the magazine 118 and inserted into the lancing/collecting assembly 112, which is represented schematically by two parallel upright elements, each element having a slot formed therein. FIG. 35C shows the protective cover 1204 being removed from the lancet 1200 of the test strip 1000. It should be noted that the protective cover 1204 could be removed before the test strip 1000 is inserted into the lancing/collecting assembly 112. FIG. 35D shows the test strip 1000 rotated 90° so that the lancet 1200 is in position for lancing the skin of the patient. FIG. 35E shows that the lancet 1200 has entered the skin of the patient. FIG. 35F shows that the lancet 1200 has been retracted from the skin of the patient. FIG. 35G shows that the test strip 1000 is being rotated 180° so that the sensor-containing portion 1002 can collect biological liquid emerging from the opening formed in the skin of the patient. FIG. 35H shows that the sensor-containing portion 1002 of the test strip 1000 is ready to be indexed so that the sensor-containing portion 1002 can collect biological liquid emerging from the opening formed in the skin of the patient. FIG. 35I shows the sensor-containing portion 1002 of the test strip 1000 contacting the biological liquid emerging from the skin of the patient. FIG. 35J shows that the test strip 1000 is being rotated 90° so that the test strip 1000 will come into the proper in position for being ejected from the medical diagnostic device. FIG. 35K shows the test strip 1000 in position for ejection from the medical diagnostic device 100. FIG. 35L shows the protective cover 1204 being reattached to the lancet 1200. FIG. 35M shows the test strip 1000 being ejected from the medical diagnostic device 100.

FIGS. 36-40 and the accompanying description are directed to another "point and shoot" medical diagnostic device 1300 of the present invention which has certain components and functions similar to many of those of the previously described device. By point and shoot, it is meant that a user places the meter on the skin location chosen for fluid/blood extraction, and is merely required to push a button to activate the device and then simply wait for the meter to make the measurement and report blood glucose level.

The following description first provides a discussion of the top-level componentry of device 1300 followed by a more detailed description of the various sub-assemblies of the device and how they interface with a STRIPLET™ cartridge, such as cartridge 1450 described below with respect to FIGS. 39A and 39B.

FIGS. 36A-36F provide various views of the top-level componentry of diagnostic device 1300. The exterior of device 1300 includes front and back housings 1302, 1304 and battery compartment/cartridge door 1306. The collective housing contains a primary component assembly 1328 of mechanical and electronic components, including but not limited to various components for directly interfacing with the STRIPLET™ cartridge (not shown), gears and motors for moving and orienting the STRIPLETS™ to various operative positions, and various printed circuit boards having circuitry for storing electronic data and running software programs for controlling and operating the device and measuring the target analyte in the extracted bodily fluid.

Figure 36A:
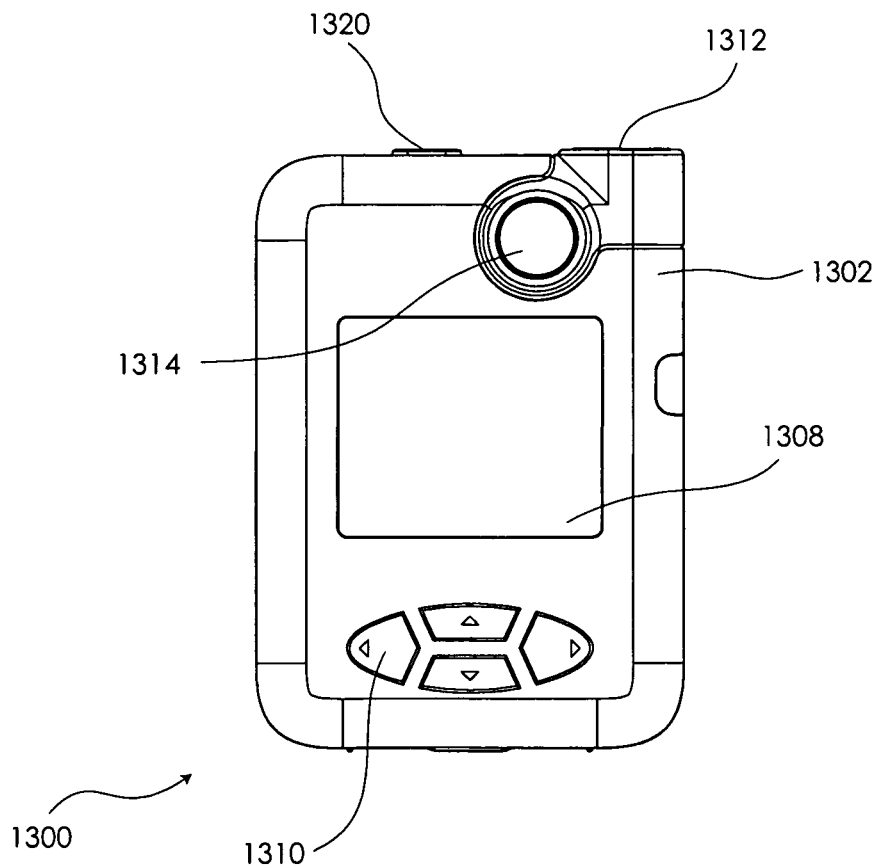
FIGS. 36A-36D, inclusive, are front planar, front perspective, rear perspective and exploded views of another embodiment of a medical diagnostic device of the present invention.
Figure 36B:
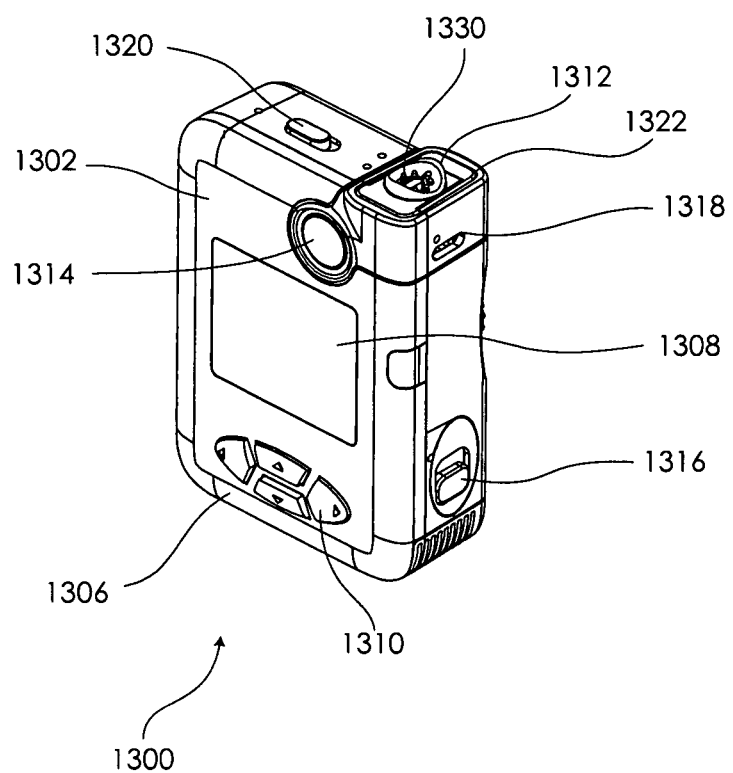
Figure 36C:
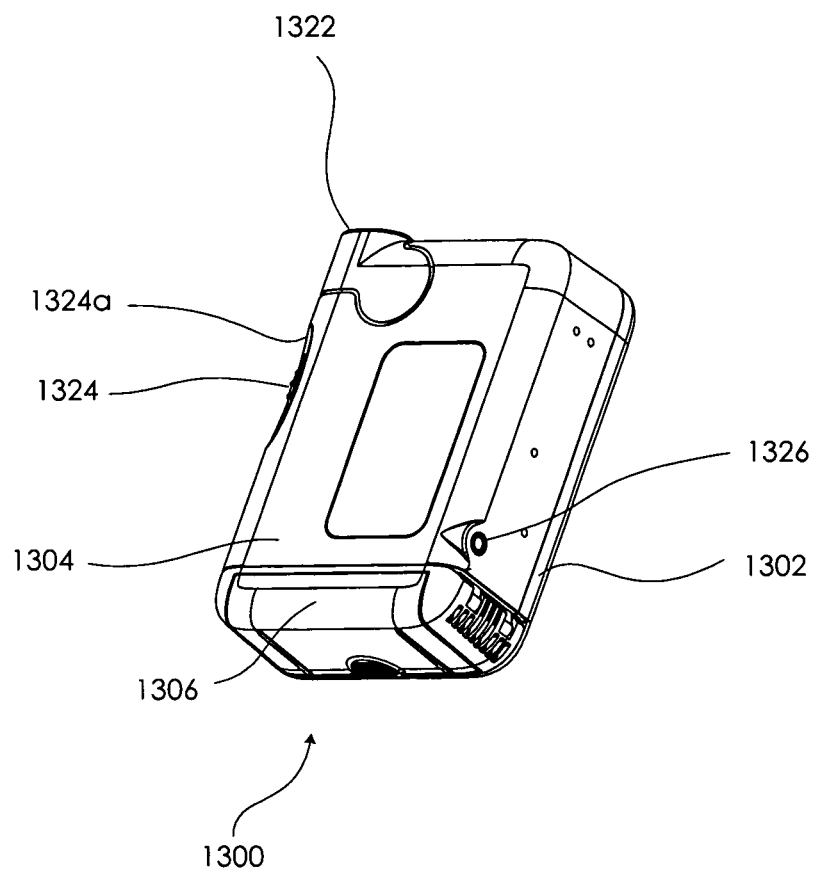
Figure 36D:
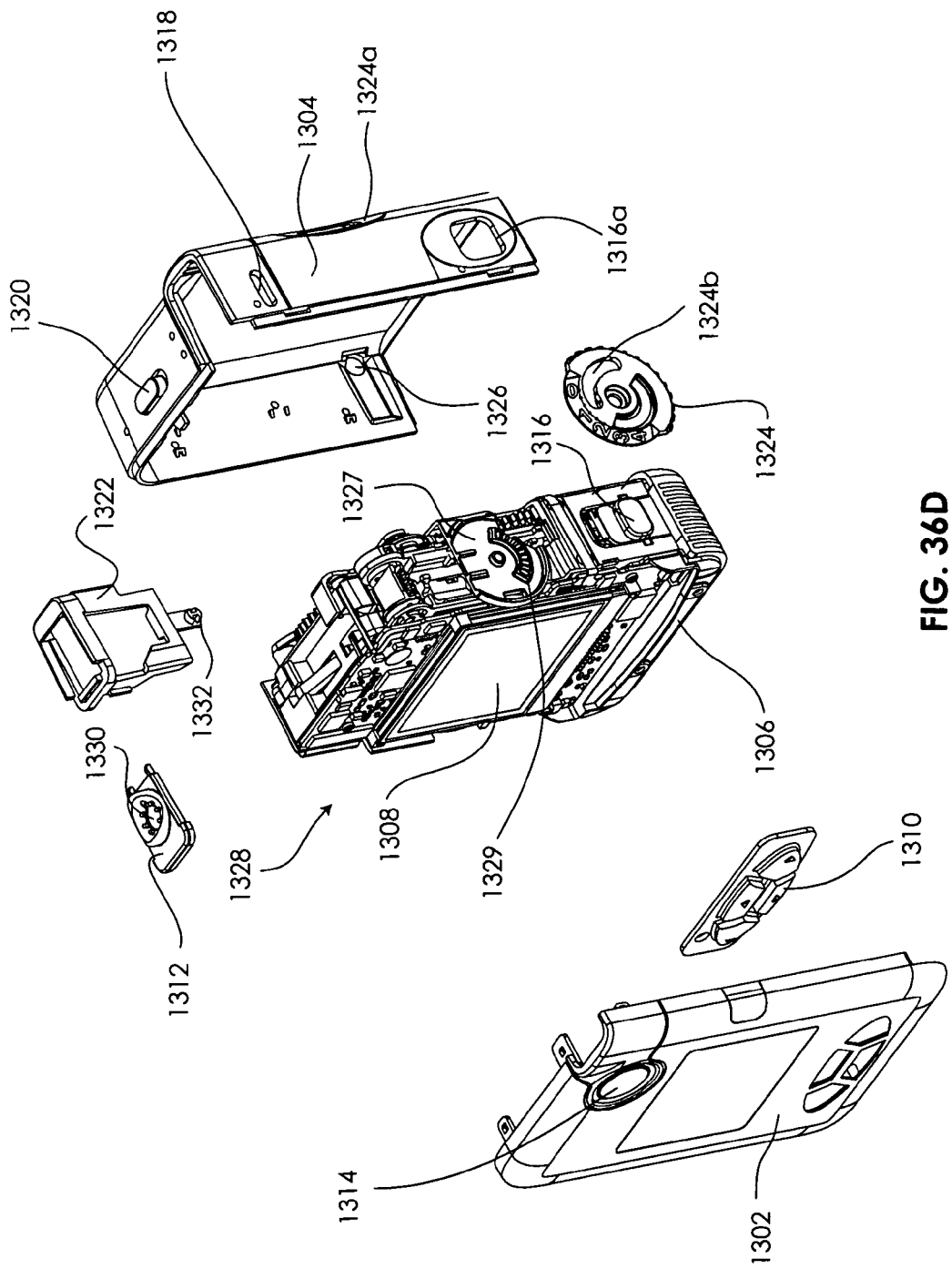
Figure 36E:
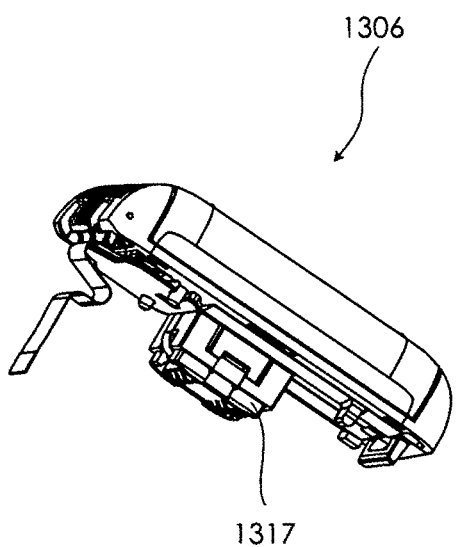
FIGS. 36E and 36F are perspective and exploded views, respectively, of the top cover of the device of FIGS. 36A-36D.
Figure 36F:
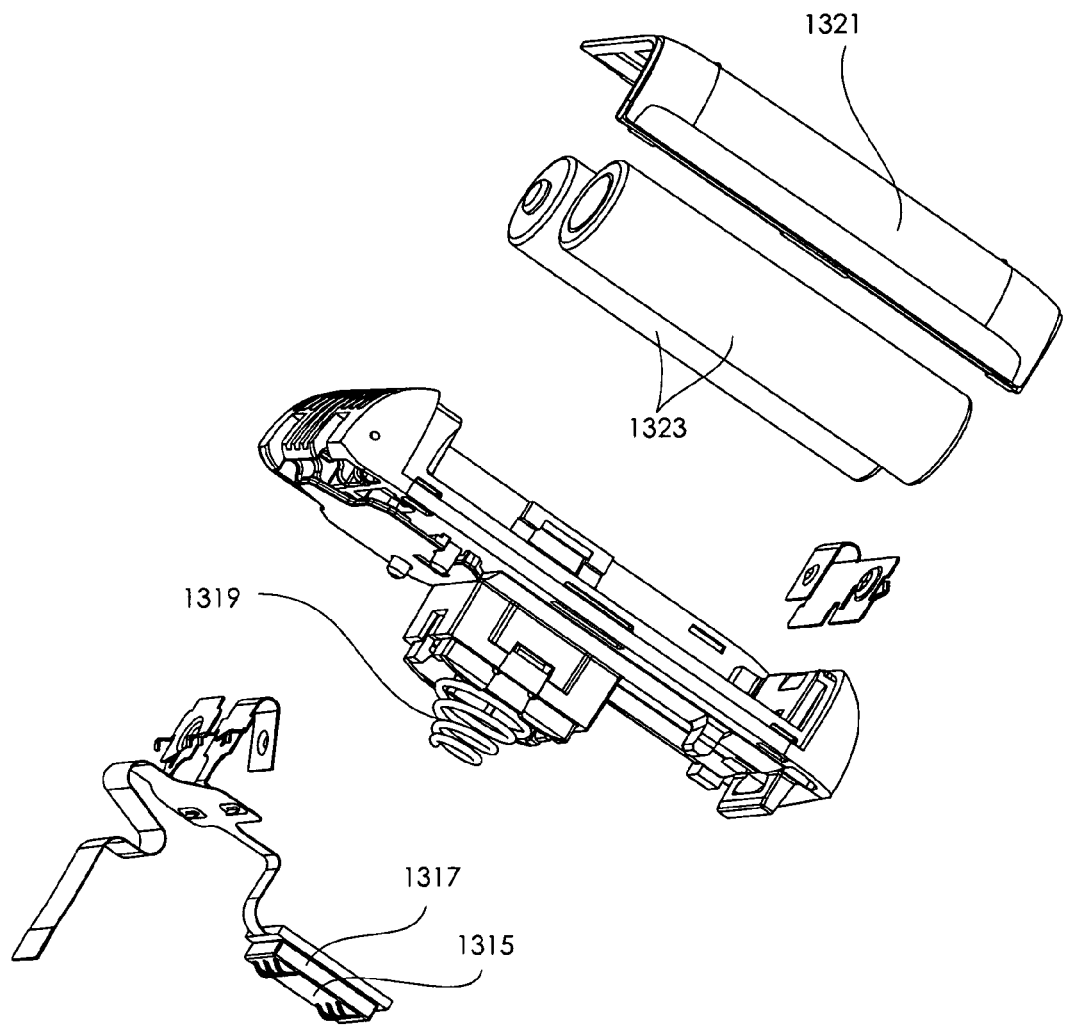

Front housing 1302 frames a display 1308, a navigation keypad 1310 and a trigger button 1314 which enable a user to interface with and operate the device. Back housing 1304 frames various apertures including aperture 1316a for receiving a cartridge door release latch 1316, a STRIPLET™ ejection slot 1318, an electronic communications port 1326 by which an on-board microprocessor (not shown) is accessed for programming, software download and off-board control, and a recessed aperture 1324a for receiving a thumb wheel 1324 for adjusting the depth of expression cap 1312, here in the form of a contoured finger pad and described in greater detail below. Back housing 1304 also provides an electrical switch 1320 to disable or "lock" the meter against accidental button pushes when not in active use. Cartridge door 1306 opens to an interior compartment of the device in which a replaceable STRIPLET™ cartridge (not shown) resides and is mechanically and electronically nested within primary component assembly 1328. As shown in FIGS. 36E and 36F, the door structure contains a spring-loaded piston 1315 which resides within the rectangular frame 1317. A coil spring 1319 biases piston 1325 which in turn, when door 1306 is closed on the cartridge, biases the cartridge downward, either against a tub (described in greater detail below) to create a hermetic seal at the cartridge's STRIPLET-disposing end or against stops within assembly 1328 or cavity 1345 when the tub is in a lowered position. The spring loaded piston 1315 simultaneously serves as the electrical contact interface to the cartridge. Housed within door 1306 under cover 1321 are batteries 1323 which provide power to the electronics and electronic motors which operate the device.

The top end of the collective device housing provides expression cap 1312 for engaging with a finger or other lancing site on the user's body to facilitate the expression of bodily fluid, e.g., blood, from the skin. A small aperture 1330 resides within expression cap 1312 through which STRIPLETS™ are advanced and retracted for their lancing and sampling functions. The expression cap resides within and is carried by a frame structure 1322 which mates with the STRIPLET™ dispensing end of the STRIPLET™ cartridge, and is mechanically coupled to thumb wheel 1324. Rotating thumb wheel 1324 adjusts the vertical height of expression cap 1312 relative to the STRIPLET™ when in a lancing position. As the lancing stroke of the STRIPLET™ is fixed, adjusting the relative height of the expression pad adjusts the location of the skin surface relative to the lance stroke allowing variable lancing depths to accommodate, for example, blood extraction at different sites on the body which may require varying lancing depths.

Figure 37A:
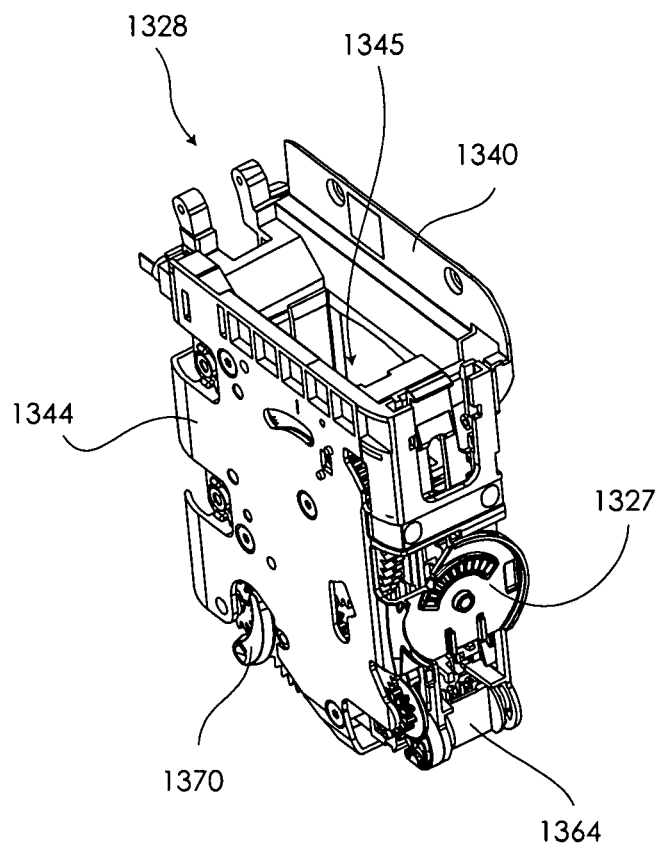
FIGS. 37A-37C, inclusive, are perspective, side and exploded views, respectively, of the primary component assembly of the device of FIGS. 36A-36D.
Figure 37B:
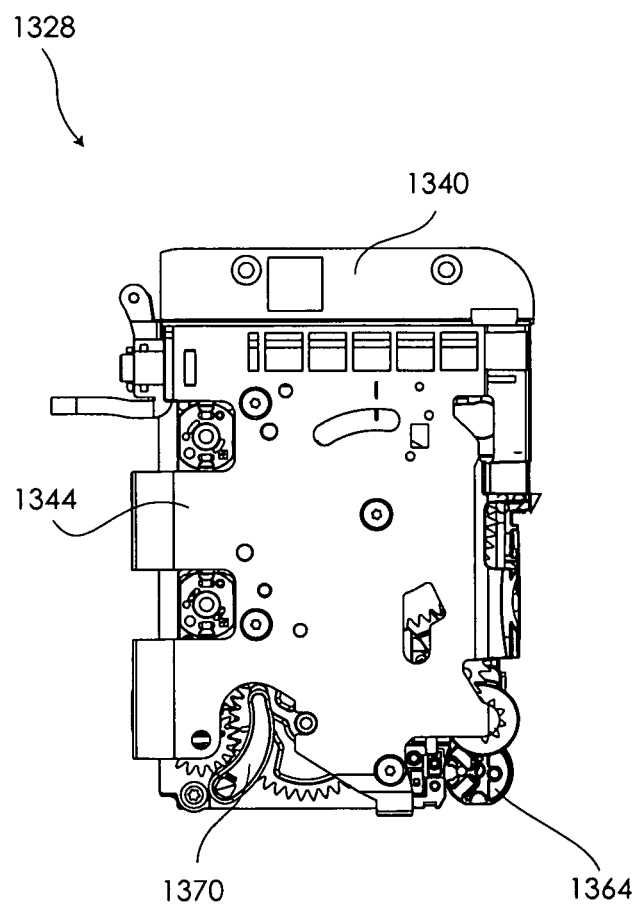
Figure 37C:
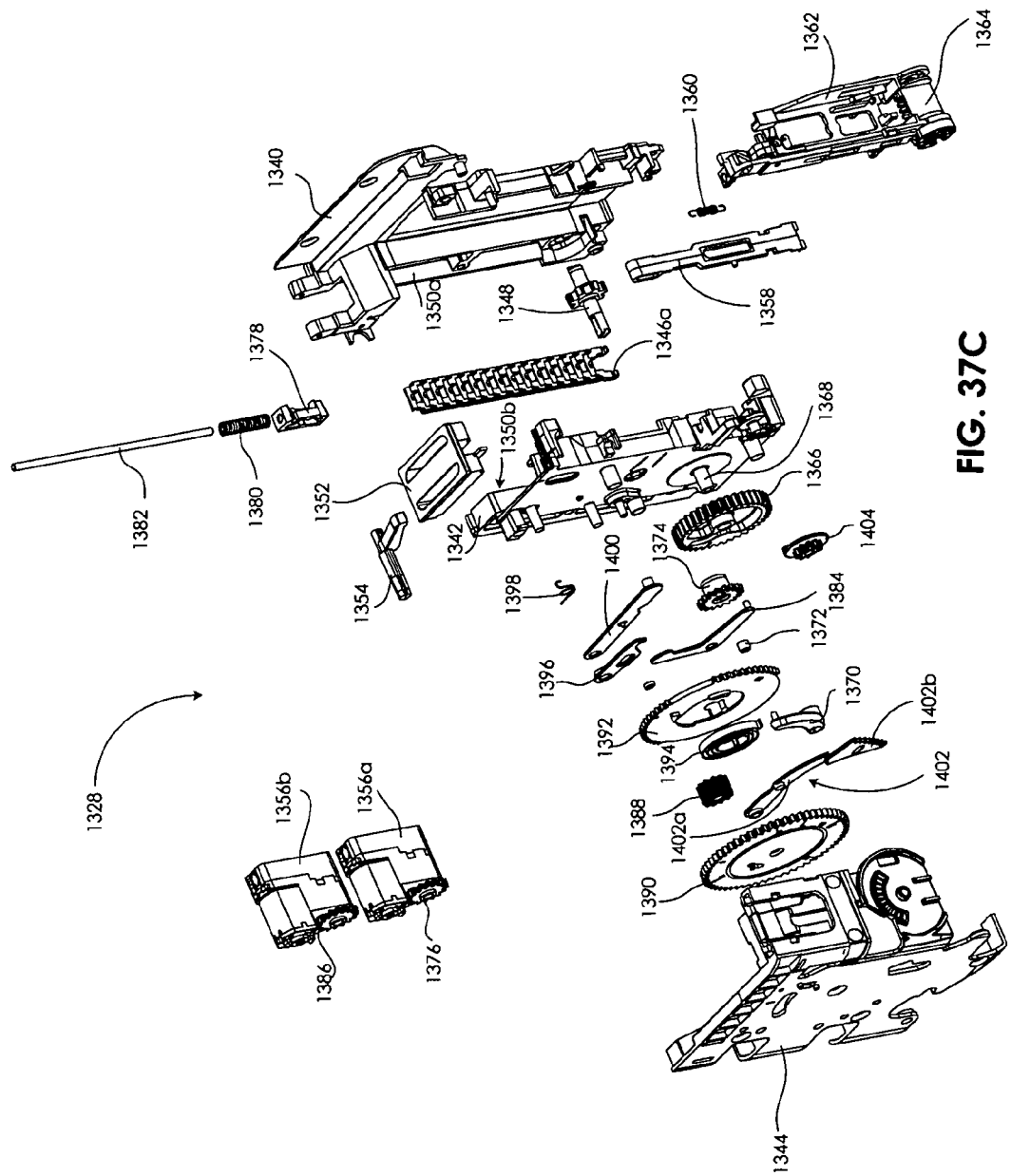
Figure 39A:
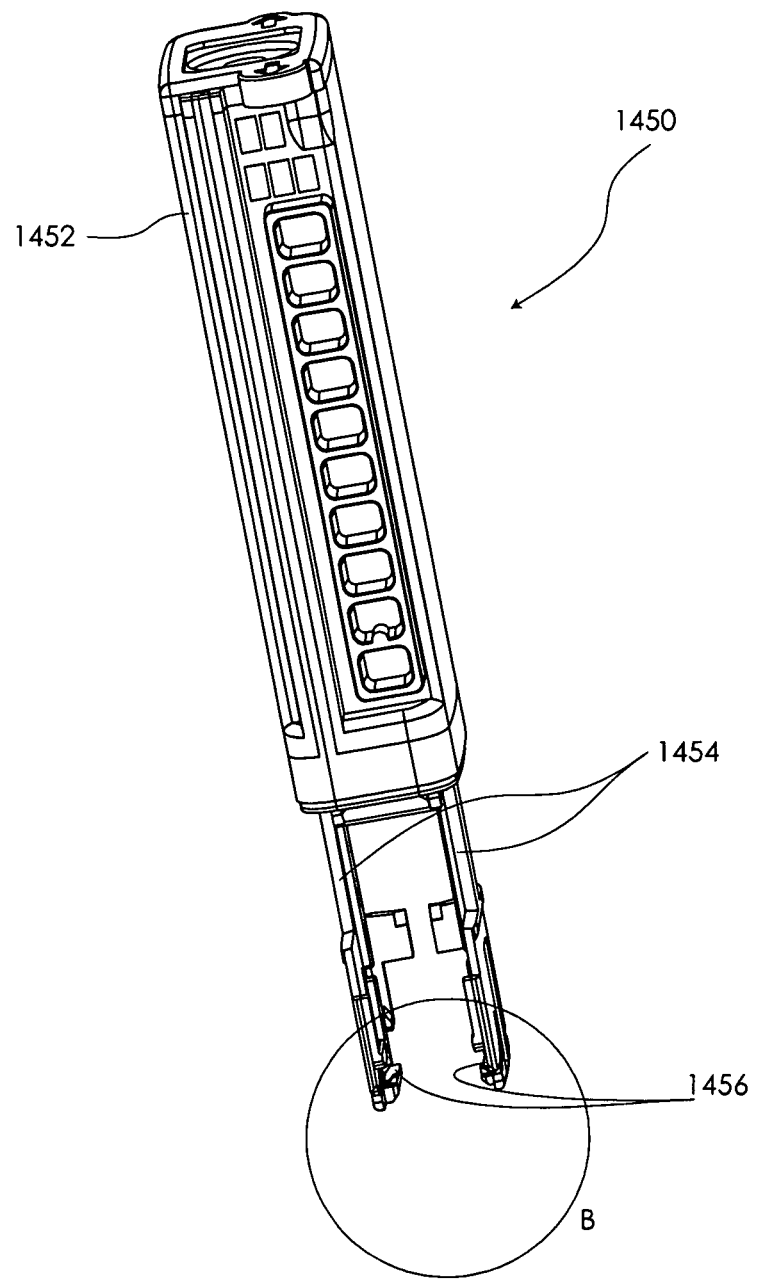
FIGS. 39A and 39B, inclusive, are perspective views, respectively, of a STRIPLET™ cartridge usable with the device of FIGS. 37A-37C and an enlargement of a distal end thereof.
Figure 39B:
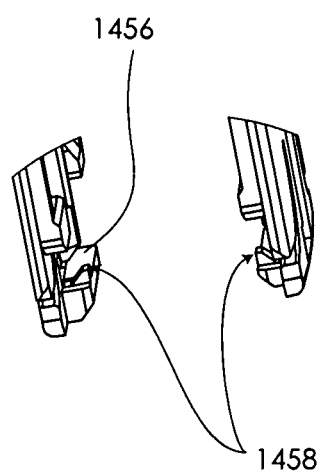

Prior to further describing the details of the internal mechanisms of component assembly 1328 and the various sub-assemblies therein, the basic functions of the STRIPLET™ cartridge are identified, and an exemplary STRIPLET™ cartridge 1450 suitable for use with the medical diagnostic device of FIGS. 37A-37C is described with respect to FIGS. 39A and 39B.

As discussed at least in part above, the basic functions of the STRIPLET™ cartridges of the present invention include: (a) providing a hermetically sealed container which protects STRIPLETS™ contained within from moisture; (b) positioning the contained STRIPLETS™ relative to the STRIPLET™ manipulating mechanism within the device; (c) guiding individual STRIPLETS™ sequentially into a position in which they are fed into the device's STRIPLET™ manipulating mechanisms; (d) spring loading each STRIPLET™ as it is moved within the device mechanisms; (e) containing structural members made of desiccant material which perform the integrated function of protecting STRIPLETS™ from moisture as well as guiding the STRIPLETS™; (f) containing locking features which prevent the STRIPLETS™ from accidental ejection due to shock or vibration loading; (g) interfacing with the device to ensure that the STRIPLETS are correctly oriented for feeding into the manipulating mechanisms; (h) interfacing with reference surfaces within the device to establish a datum plane for STRIPLET™ motion; and (i) containing an on-board active means, sometimes referred to as a "smart chip", for communicating data to the device, including but not limited to STRIPLET™ serial and batch numbers, calibration information, date and time of manufacture, expiration date, and the number of unused STRIPLETS™ remaining in the cartridge.

Referring now to FIGS. 39A and 39B, an exemplary STRIPLET™ cartridge 1450 usable with medical diagnostic device 1300 is described. Cartridge 1450 includes a cartridge body or vial 1452, often referred to as a STRIPLET™ magazine, containing a plurality of STRIPLETS™ and parallel guide rails or inserts 1454 which maintain the orientation of the STRIPLETS™ for feeding to the device. The STRIPLETS™ are retained within cartridge 1450 by opposing spring-loaded forces from the top and bottom ends of the cartridge. When door 1306 of device 1300 is closed on the nested cartridge, a constant-force spring mechanism (i.e., piston 1325 which is biased by coil spring 1319 in FIG. 36F) biases the cartridge and continuously forces the STRIPLETS™ toward the dispensing end of the cartridge. The distal ends of guide rails 1454 have spring-loaded, inwardly extending end features or protrusions 1456 (best viewed in FIG. 39B) which provide the cartridge "floor" and apply an upward force on the STRIPLETS™ prior to being fed from the cartridge. The end features 1456 are configured so that an advance chain and associated STRIPLET™ pusher of the meter, described in greater detail below, enter from one side of cartridge body 1452, engage with the cap that covers the lancing end of each STRIPLET™, and then push a single STRIPLET™ out of the cartridge while the remaining stacked STRIPLETS™ are retained within the cartridge. Structures 1456 each provide a triangular-shaped depression or "shark tooth" feature 1458 which mates with a corresponding indentation on respective sides of the interfaced STRIPLET™. This mating engagement protects the STRIPLET™ from being knocked out of the cartridge should the cartridge be dropped or jarred. "Shark teeth" 1458 are configured to flex outwardly, or perpendicular to the direction of STRIPLET™ advance, to release the interfaced STRIPLET™ as it is pushed out of the cartridge.

The primary component assembly 1328 and the various sub-assemblies therein and the manner in which they interface with the STRIPLET™ cartridge are now described in greater detail with respect to FIGS. 37A-37E, which provide perspective, side and exploded views, respectively, of assembly 1328, and with respect to FIGS. 38A-38F, which provide various exploded views of the sub-assembly components therein. In the description that follows, the individual components within assembly 1328 are identified and their interconnecting structures briefly described, followed by a more expansive description of the various sub-assemblies formed by the components and of their respective functions. It should be noted that some of the components have overlapping functions and contribute to the functioning of more than one sub-assembly.

Figure 38A:
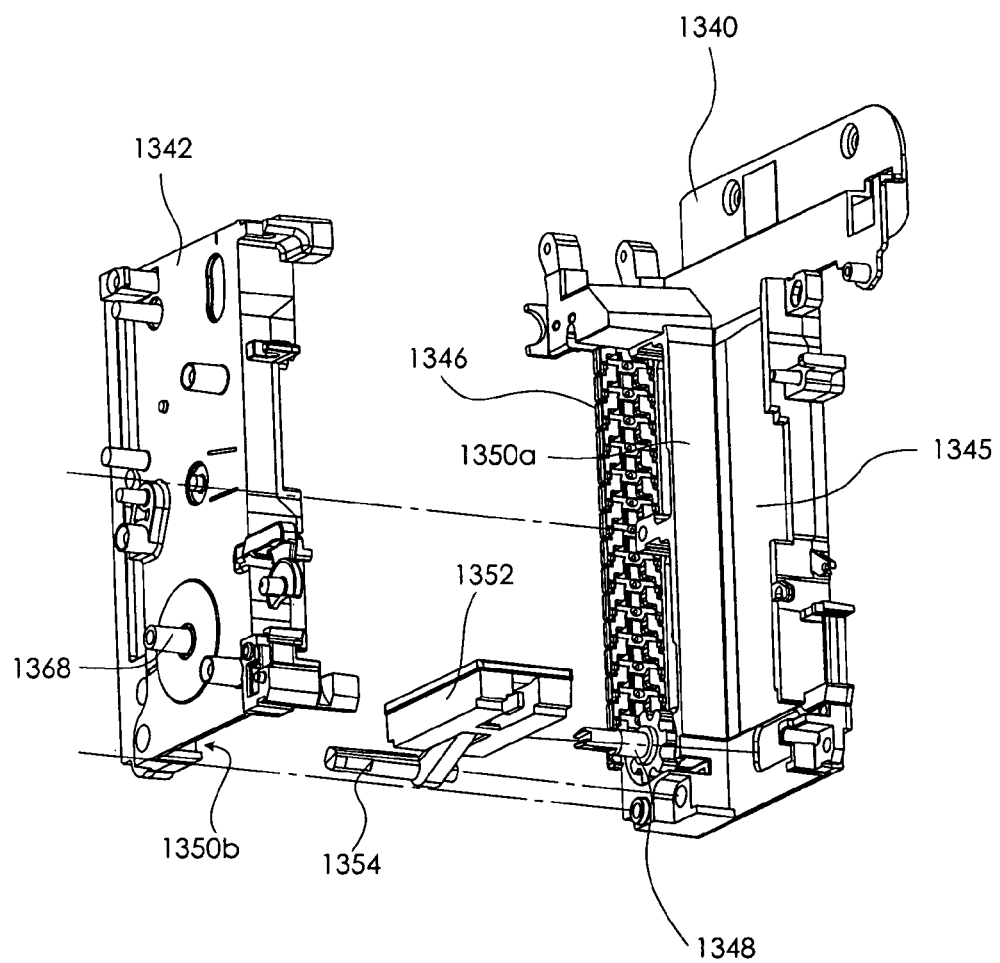
FIGS. 38A-38G, inclusive, are exploded perspective views of various sub-assemblies of the primary component assembly of FIGS. 37A-37C.

Assembly 1328 includes three structural frames or walls, front chassis 1340, rear chassis 1342 and gear retaining plate 1344, which hold a plurality of functional or moveable components between them. As best illustrated in FIGS. 37A and 38A, front and rear chasses 1340, 1342 define an internal cavity 1345 for receiving a STRIPLET™ cartridge (not shown) and further house between them various components which retain the STRIPLET™ cartridge and/or directly handle and move the individual STRIPLETS™ from the STRIPLET™ cartridge.

These components include an advance chain 1346 positioned within opposing guides or tracks 1350a, 1350b extending from opposing walls of front and rear chasses 1340, 1342, respectively. Best viewed in FIG. 37C, advance chain 1346 has a distal end piece 1346a configured for engaging the bottommost STRIPLET™ within a STRIPLET™ cartridge. An involute sprocket 1348 is configured to engage with chain 1346 to advance and retract it within tracks 1350a, 1350b. Positioned just below the bottom end of the STRIPLET™ cartridge (not shown) is a tub 1352 consisting of a flat, continuous surface which, when pressed against the cartridge's elastomeric seal, as described above with respect to cartridge 110 (see FIG. 4A), provides a hermetic seal, thereby protecting the STRIPLETS™ from environmental humidity. A rotary lever arm lift 1354 positioned under and coupled to tub 1352 also extends between the two chassis. Activation of lever arm 1354 lifts and applies a force at the geometric center of the bottom of tub 1352 thereby lifting it perpendicular to the cartridge seal perimeter through a distance equal to at least one STRIPLET™ thickness and with such force as to compress the cartridge's elastomeric seal to provided hermetic sealing of the STRIPLET™ magazine. Reversal of this motion releases the seal against the cartridge. When a STRIPLET-loaded cartridge is inserted into the meter and the cartridge door closed, the cartridge inserts 1454 pass into clearance grooves (not shown) within the tub 1352. Even in the dropped or unsealed position, the tub surface is higher than the top of the retaining "shark teeth" 1458 within protrusions 1456 of the cartridge insert rails 1454, so that the STRIPLETS™ may slide out of the cartridge. When the tub 1352 is lifted to seal the cartridge, the inserts 1454 simply pass deeper into the tub clearance grooves. Thus, once the cartridge is inserted into the meter and the cartridge door closed, the "shark teeth" are no longer engaged with the STRIPLETS™.

Figure 38B:
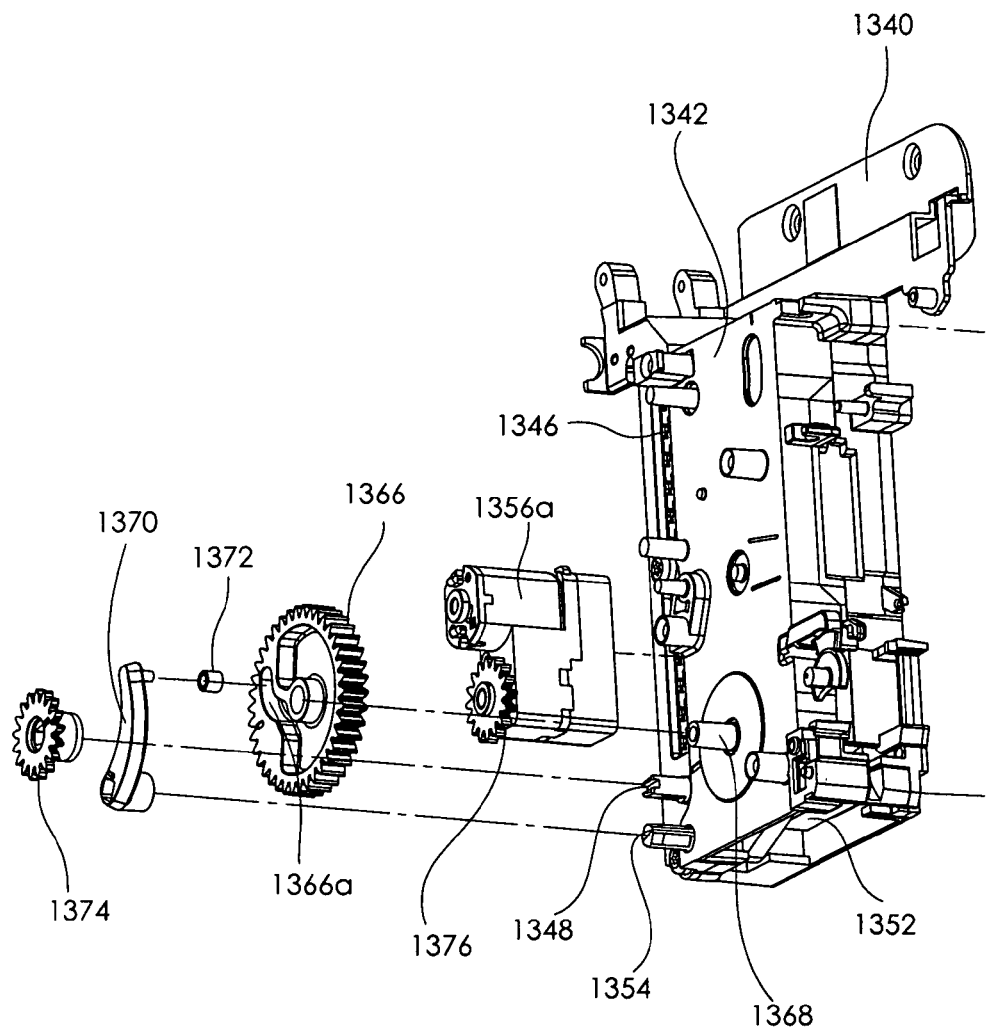
Figure 38C:
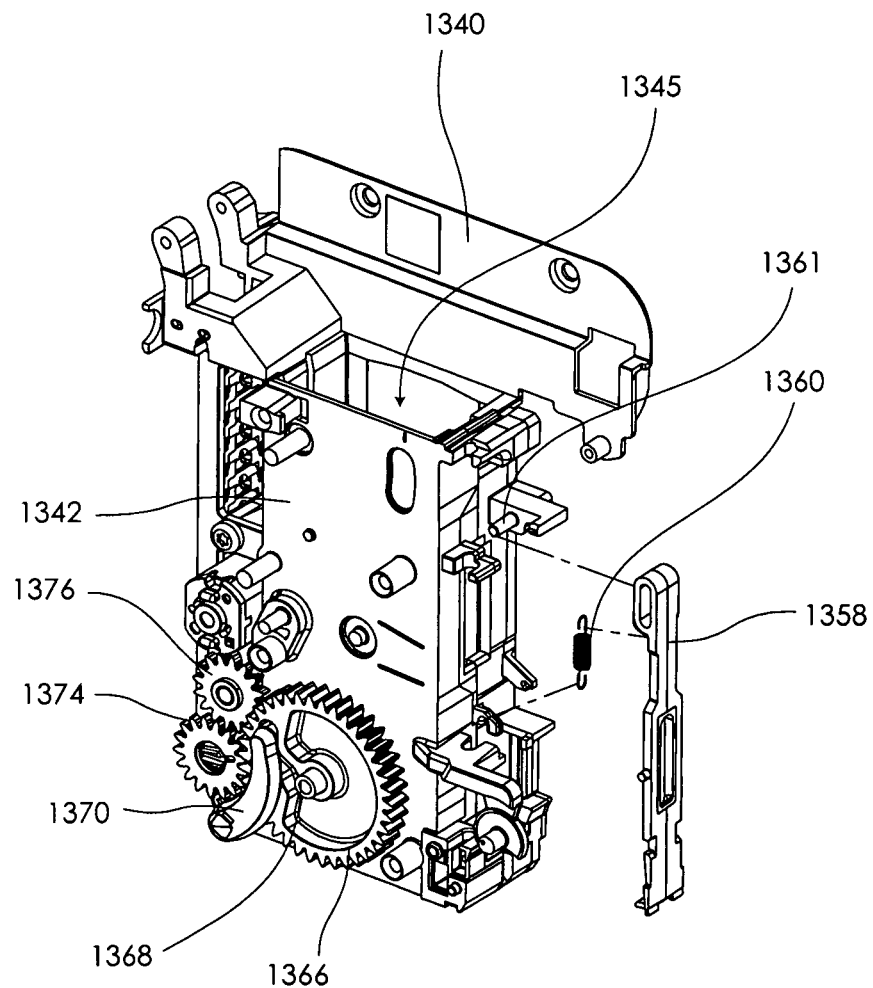
Figure 38D:
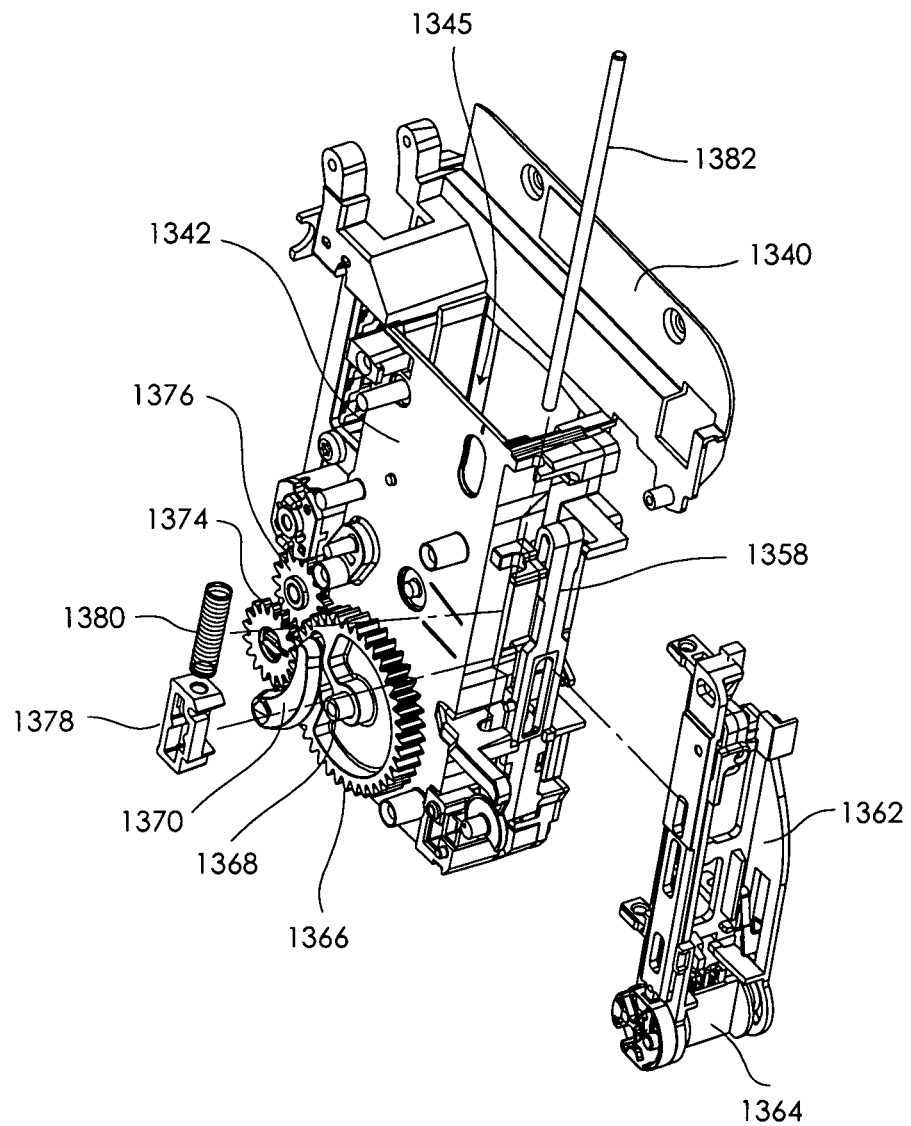

As illustrated in FIGS. 38C and 38D, positioned adjacent a side seam of the front and rear chassis 1340, 1342 when joined is another lever arm 1358. Lever arm 1358 functions to pull the lancet cap off of the STRIPLET™ lancet immediately prior to its use and to push the lancet cap back onto the STRIPLET™ lancet immediately after its use. As best illustrated in FIG. 38C, a spring 1360 is connected between a top portion of lever arm 1358 and a side wall of the conjoined chasses to bias the uncapping lever down against the cap of the next-to-be-used STRIPLET™ (not shown) thereby locking the lever end into a depression within the STRIPLET™ cap so that the cap may be pulled off and pushed onto the lancet. Positioned in front of uncap lever arm 1358, as shown in FIG. 38D, is a carriage assembly 1362 slidable mounted on a guide rail 1382. Carriage 1362 carries, orients and moves the STRIPLET™ through the various motions required to extract body fluid and sense the targeted analyte. At a distal end of the carriage is a turret 1364 which has a rotating slot for receiving and retaining a STRIPLET™. Now referring to the components retained between rear chassis 1342 and a gear retention plate 1344, there are provided two electric motors 1356a, 1356b, each of which operates a plurality of gears to carry out all of the steps during the point and shoot operation of the device. The first motor 1356a drives the gears responsible for lifting the tub and sealing the cartridge, advancing the STRIPLETS™ from the cartridge into the turret, in part, uncapping the STRIPLETS™ prior to use, in part, recapping the STRIPLETS™ after use, and ejecting the STRIPLETS™ out of the turret. The second motor 1356b drives the gears responsible for, in part in and conjunction with the gears driven by first motor 1356a, uncapping the STRIPLETS™, moving the STRIPLETS™ to perform the lancing function, orienting the STRIPLETS™ from a lancing position to a sensing position, and, in part, recapping the STRIPLETS™. These gears and their operation in each of the aforementioned functions are now described in greater detail. Each of the motors has electro-optical encoders integrated within it to determine the position and speed of the respective meter components which it drives. Additionally, a plurality of sensors is provided throughout the internal components of the meter, particularly along the path traversed by a STRIPLET™, to sense the physical position, both linear and rotational, of moving components critical to proper advancement and movement of the STRIPLETS™. The combination of motor encoding with sensor positioning in a closed loop control system ensures that the STRIPLETS™ are accurately advanced and manipulated to perform the various meter functions.

As best illustrated in FIG. 38B, the sub-assembly of gears and associated components involved in lifting the tub and, thus, sealing the cartridge, include an output pinion gear 1376 driven by motor 1356a, which in turn drives a larger follower tub lift gear 1366 rotatably mounted on an axial mount or shaft 1368 extending from back plate 1342, a tub lift follower arm 1370 having a fixed end rotatably coupled to tub lift arm 1354 and a movable end coupled to a roller bearing 1372 which sits and is movable within grooved face cam 1366a of tub lift gear 1366. The cam may alternately be configured as a disk edge cam. As the movable end of the follower arm 1370 moves within cam 1366a, it rotates the fixed end of the follower arm, thereby rotating shaft 1368 which in turn lifts (closed position) or drops (open position) the tub, depending on the direction in which the follower arm is traveling within the grooved cam. In the lifted or closed position, the tub surface engages against the cartridge's seal and moves against the opposing force imposed by the spring loaded piston 1315 within the closed cartridge door 1306. When the tub is in the dropped or opened position, the spring force imposed by piston 1315 holds the cartridge body against datum stops (not shown) within the cartridge cavity 1345, precisely positioning the bottommost STRIPLET™ for feeding with respect to the apparatus. In this position, there is no seal, allowing a single STRIPLET™ to be fed from the cartridge into the apparatus. The movement of tub 1352 is constrained to vertical linear movement by the frictional engagement between its vertical side walls and the internal structure of the conjoined chasses. Alternately, the tub may be guided in a linear fashion by pins, shafts or other sliding elements. While the lifting of the tub and sealing of the cartridge has been described as operating in an automatic manner, these functions may be accomplished by manual action of the user applied to a system of gears and levers as described above. In an alternate embodiment, the tub may be fixed with respect to the device and the cartridge may be movable relative to the tub. Additionally, a system of one or more sensors within the device may be used to detect whether or not the tub is fully lifted and the seal fully engaged.

The sub-assembly of gears and associated components involved in advancing the STRIPLET™ out of the cartridge into turret 1364 and out of the turret through exit slot 1318 is also driven by first electric motor 1356a. The advancing components include articulated chain 1346 which is linearly driven by a sprocket 1348 to various points within chain guides 1350a, 1350b of front chassis 1340. In alternate embodiments, chain 1346 may be a continuous, yet bendable strip of a material such as plastic or metal or a composite of both, or may be a combination of rigid transverse elements connected axially by one or more continuous flexible connectors. The final link 1346a in chain 1346 serves as a pusher mechanism to push, guide and fix the bottommost STRIPLET™ at various locations within the assembly 1328. Sprocket 1348 is rotatably driven by a sprocket drive gear 1374 which, in turn, is driven by output pinion gear 1376 of motor 1356a which drives the larger idler or follower gear 1366 containing the tub lift cam 1366a. Because actuation of the advance prime mover 1356a causes idler/follower gear 1366 to rotate, which simultaneously lowers tub 1352 and drives the articulated chain 1346 forward, the two operations are synchronized such that the pusher 1346a does not enter the cartridge's footprint until tub 1352 is in its fully dropped position. Likewise, during chain retraction, the aforementioned mechanical synchronization causes the chain pusher 1346a to retract completely past the cartridge's footprint before the tub lifts to seal against the cartridge. Further, as chain drive sprocket 1348 rotates, chain 1346 is driven forward or backward collinearly with the STRIPLET™. The STRIPLET™ may be advanced with its sensing end leading and its capped lancing end interfacing with the chain pusher, or visa versa.

The constant-force spring (see, e.g., 125 in FIG. 4A) inside cartridge 1450 forces the STRIPLETS™ down against the tub 1352 which in turn forces the tub down against precision stops 1355a, 1355b at the distal end of internal cavity 1345, establishing a datum slide plane for the STRIPLET™. The mechanical stops are configured so that when both the cartridge and the tub are against their respective stops, there is an opening so as to allow one and only one STRIPLET™ to be removed from beneath the cartridge footprint. When the tub "opens", it is mechanically removed from contact with the cartridge seal. At the same time, the pusher pushes a STRIPLET™ from the open end of the cartridge to the open tub, thereby transferring the STRIPLET™ advancement to assembly 1328. When the device has completed an analyte measurement cycle, pusher 1346a is retracted from beneath the cartridge footprint and the cartridge is re-sealed by the tub to prevent moisture degradation of the unused STRIPLETS™. A system of one or more sensors may be provided along the travel path of STRIPLET™ advancement to facilitate moving a STRIPLET™ through precise linear distances. Pusher 1346a may also serve as a sensor flag to precisely indicate STRIPLET™ position.

Figure 37D:
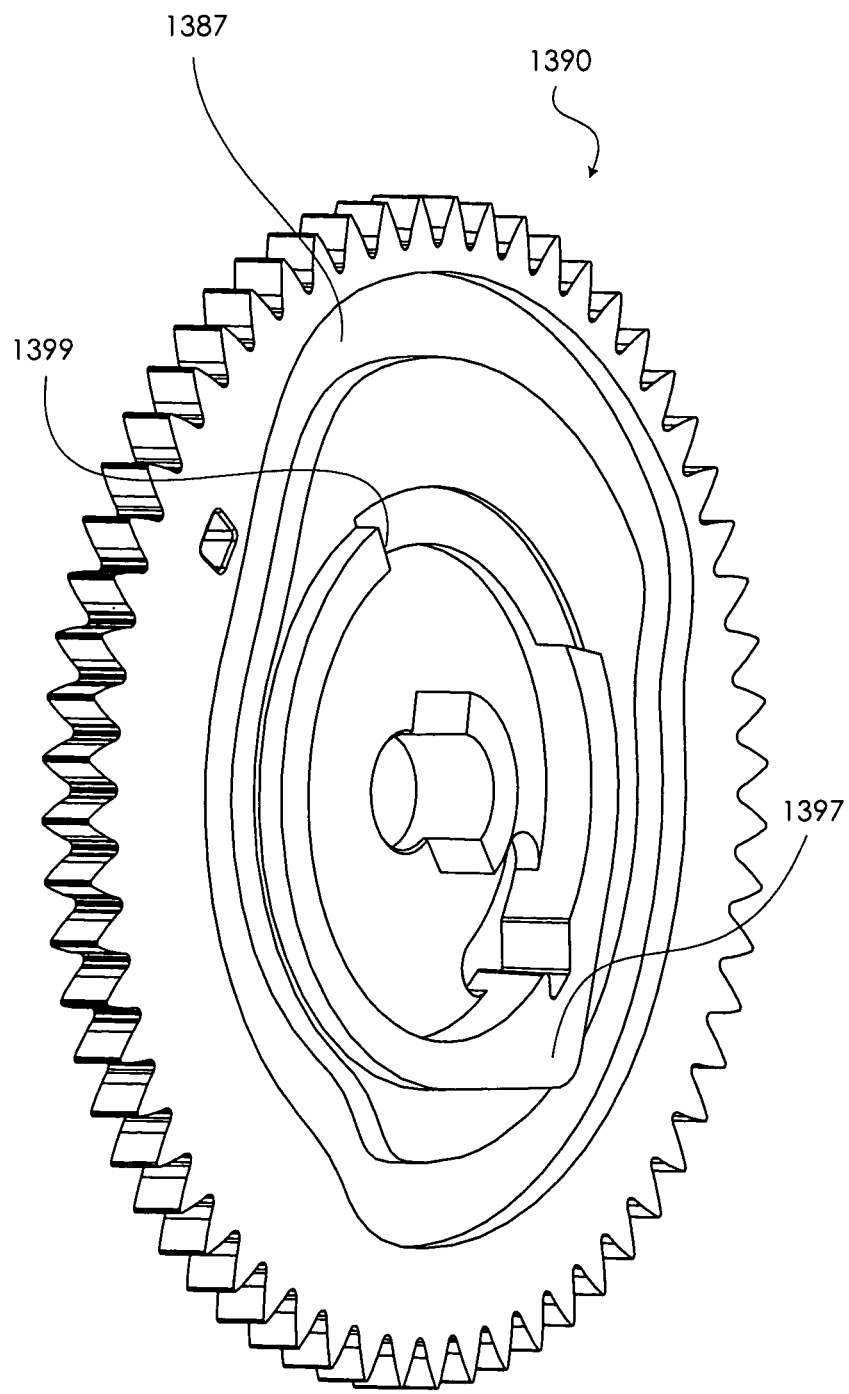
FIGS. 37D-37F enlarged perspective views of certain of the assembly's uncapping and lancing components.
Figure 37E:
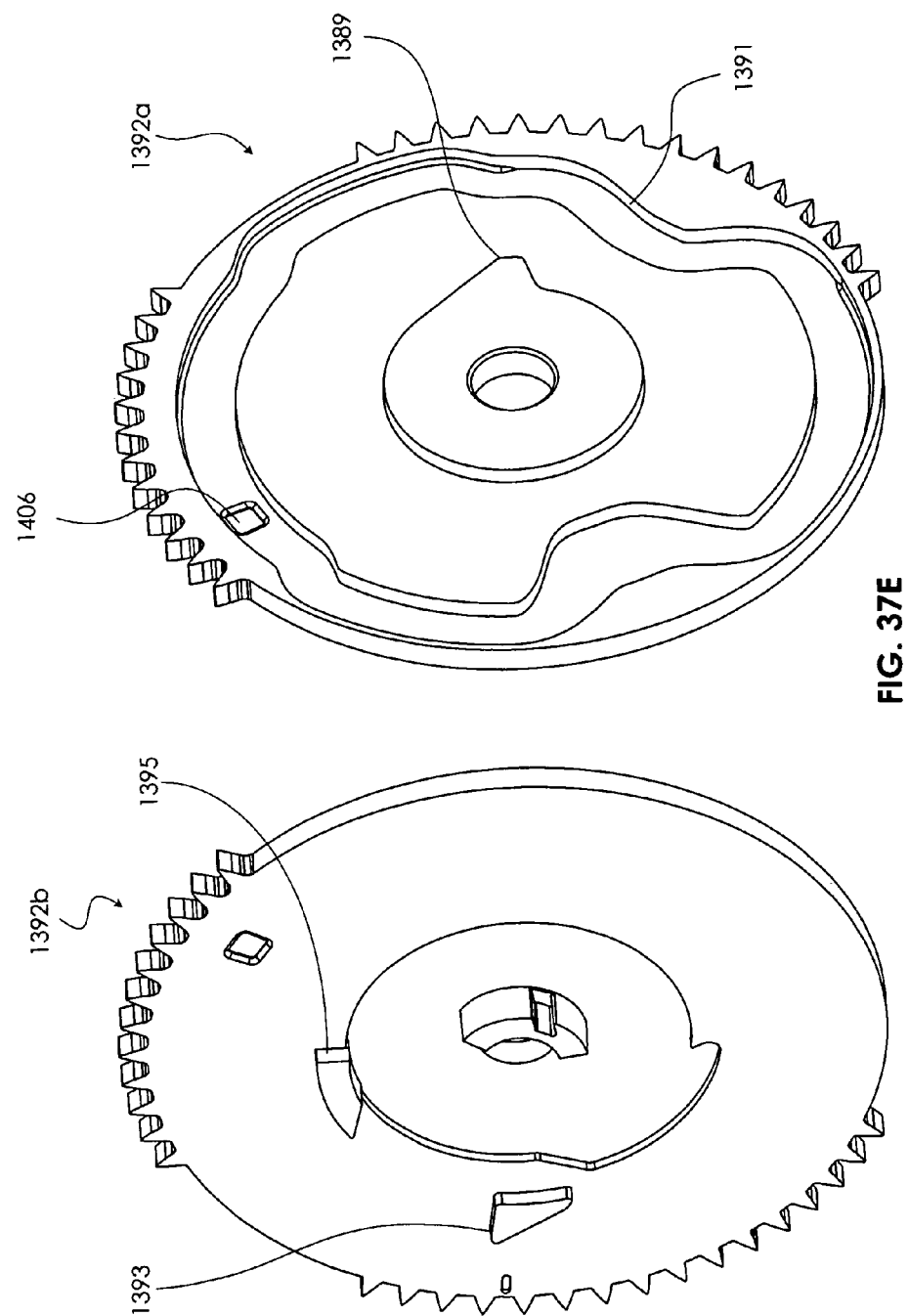
Figure 37F:
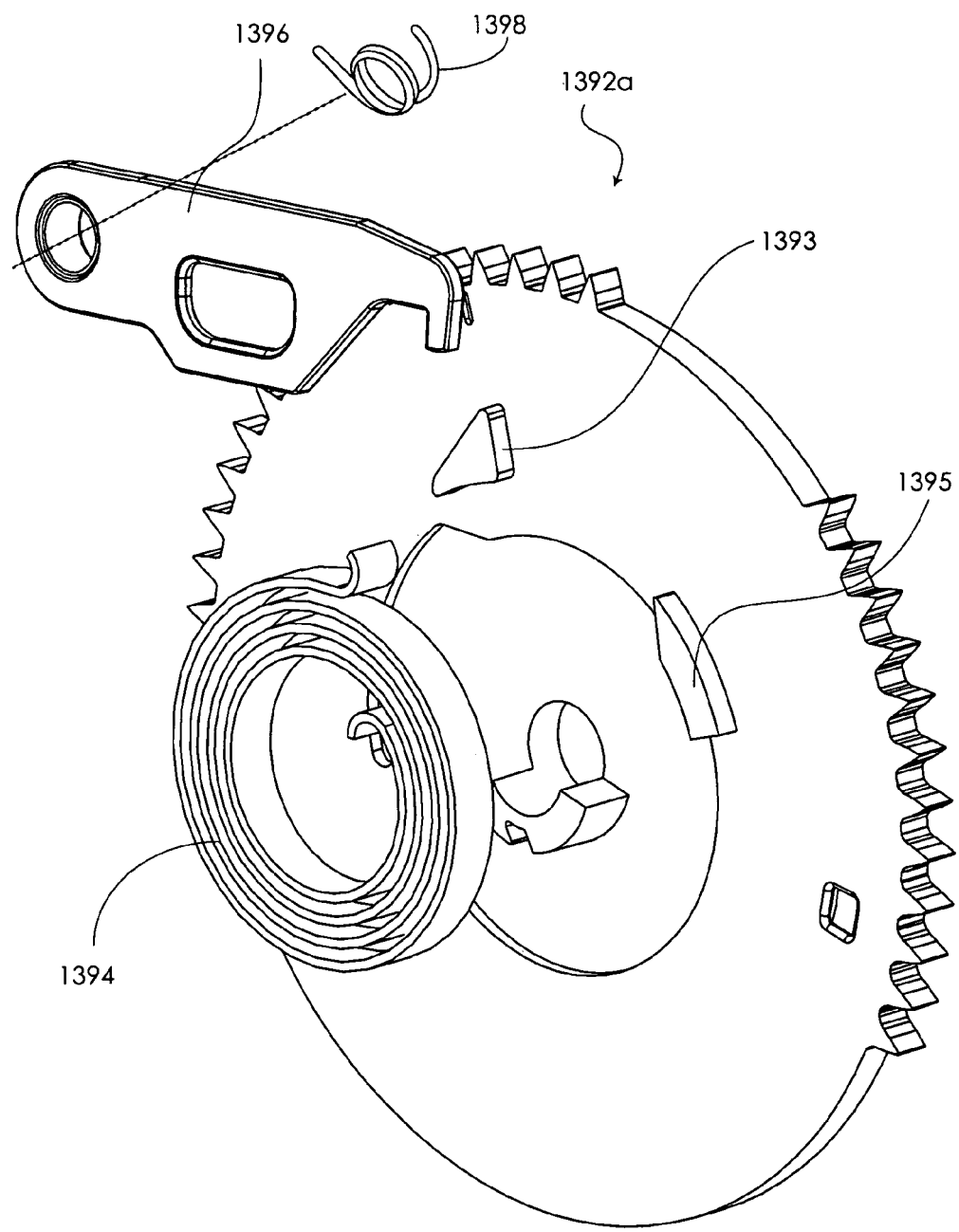
Figure 38E:
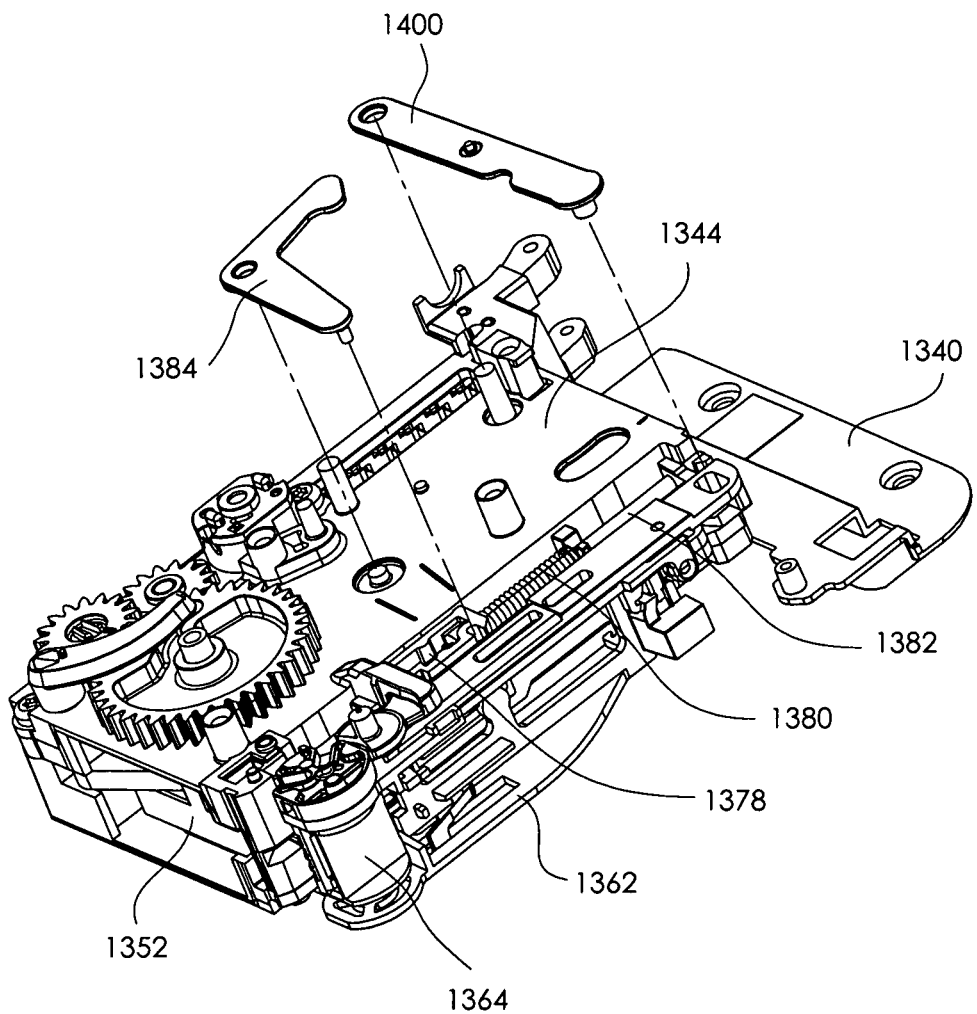
Figure 38F:
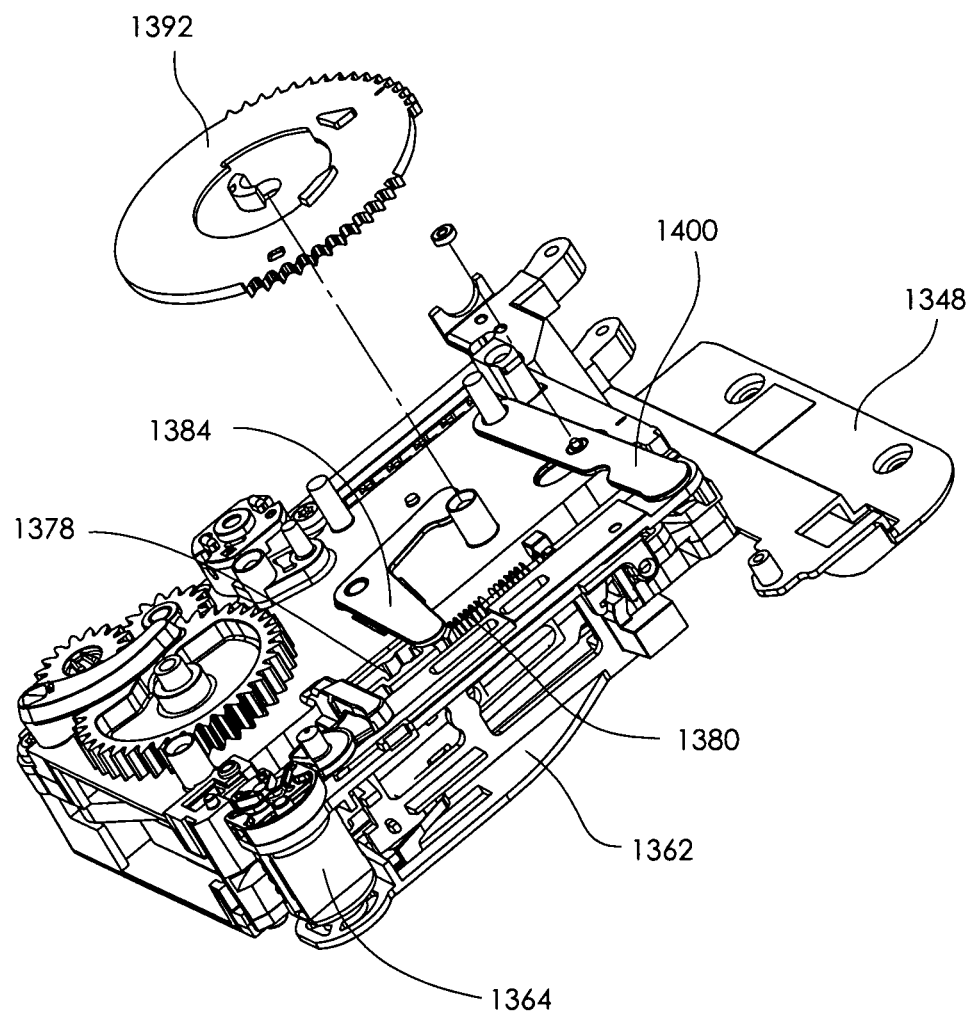
Figure 38G:
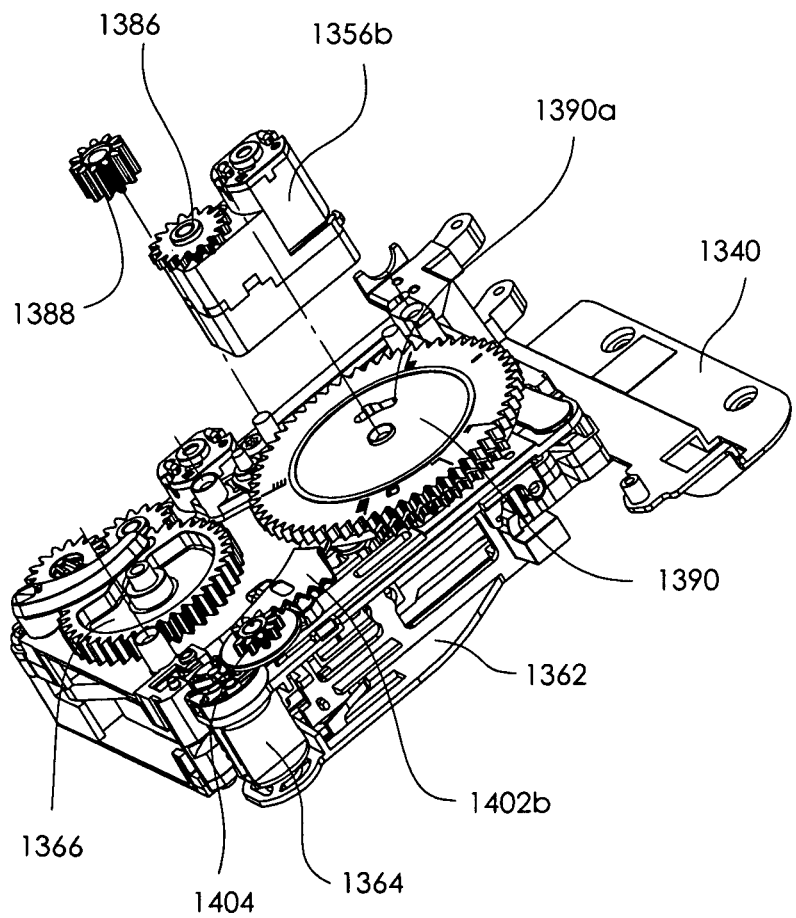

The sub-assembly of gears and associated components for uncapping or arming lancet end of the STRIPLET™ is best illustrated in FIGS. 38C-38E. The uncapping sub-assembly includes, among other components, the second motor 1356b and the STRIPLET™ feeding/advance subsystem described in the preceding paragraph which is used to pull the lancet cap off and push the lancet cap back on the STRIPLET™ lancet. The uncapping sub-assembly also includes uncap lever 1358 which, as described above, moves up and down in a direction perpendicular to STRIPLET™ advance and, when in contact with the lancet cap (not shown), locks the cap to the chain pusher 1346a. The uncap lever 1358 may also swing about a pivot 1362 such that the non-pivoted tip may move forward and backward in the direction parallel to STRIPLET™ advance. An extension spring 1360 biases the end of the uncap lever 1358 down against the STRIPLET™ cap thereby locking the non-pivoting end of the uncap lever into a depression in the STRIPLET™ cap such that the cap may be pulled off and pushed on to the STRIPLET™ lancet. The output pinion gear 1386 of motor 1356b drives an idler gear 1388 which in turn drives a larger main gear 1390 which in turn moves an uncap lever lift follower arm 1384 which lifts the uncap lever 1358 against the downward force of uncap lever spring 1360. Arm 1384 is actuated by a dual-purpose cam 1392 which facilitates both the uncapping/capping actions and the lancing/collecting functions of the device. As best illustrated in FIG. 37E, showing enlarged views of front and back sides 1392a, 1392b, respectively, of cam 1392, the front side 1392a of cam 1392 provides an uncap cam 1389 which guides uncap lever lift follower arm 1384 during the uncapping portion of the point and shoot cycle. An uncap lever lift arm slider 1378 communicates with uncap lever 1358 and uncap lever lift arm 1384 in such a way as to transfer lifting motion to uncap lever 1358 when the uncap lever is swung forward, but leaving it in the down position if the uncap lever is swung back (cap removed). More particularly, a compression spring 1380 (FIG. 38F) holds uncap slider 1378 down such that uncap follower arm 1384 is always in contact with uncap cam 1389. This serves as a clutch, lifting or not lifting the uncap lever 1358 depending on whether the lancet cap is being removed or replaced. This functionality allows the user to perform the function of re-lancing the user's skin with the same lancet should the first try not draw sufficient blood.

The gears and associated components which provide the lancing/collecting (or sensing) sub-assembly, some of which provide functionality to other sub-assemblies, are best illustrated in FIGS. 37D, 37E, 38E-38G and 40A-40F. A second motor 1356b, by way of its output pinion gear 1386, drives idler gear 1388 which in turn drives main gear 1390, one revolution of which defines the complete reorienting, lancing, sensing (collecting) and uncap cycle of the apparatus. Cam 1392, described in part above with respect to the uncapping/capping sub-assembly, is concentrically aligned with, rotates on a common axis with, and is coupled to the main gear 1390 by means of a flat torsion spring or clock spring 1394, which is used to power cam 1392 through the lancing stroke when released from its wound position. At the start of a lancing segment, the cam rotates counterclockwise (as viewed in FIGS. 37C and 37F) in concert with the main gear because of a constant torsional preload (established during the device's assembly) in the clock spring 1394 which tends to pull the two rotating disks together.

Figure 40A:
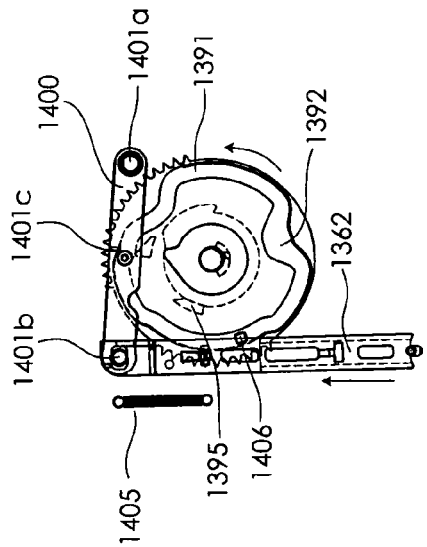
FIGS. 40A-40F, inclusive, illustrate various stages of gear positions involved in the lancing and fluid collecting/sensing functions of the device of FIGS. 36A-36D.

As shown in FIG. 37E, the grooved face on the front side 1392a of cam 1392 provides a lancing/sensing cam 1391 which interacts with a lancing/sensing cam follower 1400 having a free end 1401a and an opposite end 1401b coupled to carriage assembly 1362 (see FIG. 40A). Centrally disposed between ends 1401a, 1401b is pin 1401c which resides within groove 1391 of cam 1392. Because the cam groove 1391 width is only slightly larger than cam follower 1400, the radial location of the groove determines the vertical position of the follower arm tip 1410b. A protrusion 1406 within groove 1391 defines the starting position of a lancing-collecting/sensing cycle with carriage assembly 1362 biased in the "home" position, as shown in FIG. 40A, by a light-weight coil spring 1405 attached to the apparatus chassis. Spring 1405 places a continuous downward force, e.g., of about 2 ounces, on carriage 1362. As cam 1392 rotates in a counter-clockwise direction from the starting position, as viewed from FIGS. 40A-40F, pin 1401c of cam follower 1400 traverses within groove 1391 and the cam follower is pivoted about end 1401b. The force placed on carriage 1362 by cam 1392 is greater than the bias placed on it by sensing spring 1405, causing the carriage to be cam-driven and moving it linearly in a vertical direction transversely to the surface of the user's skin.

Figure 40B:
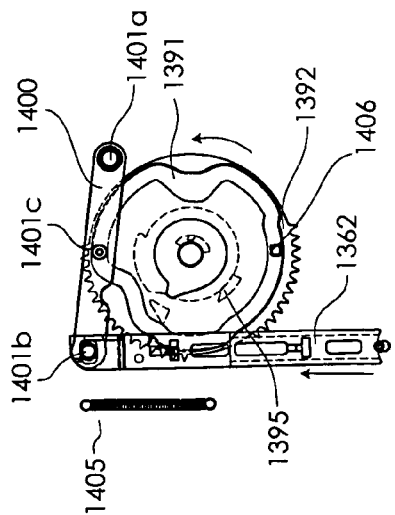
Figure 40C:
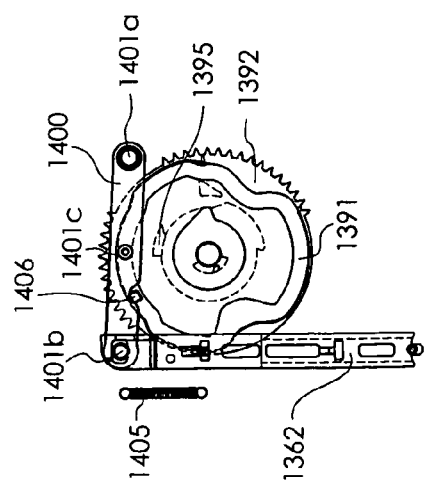
Figure 40D:
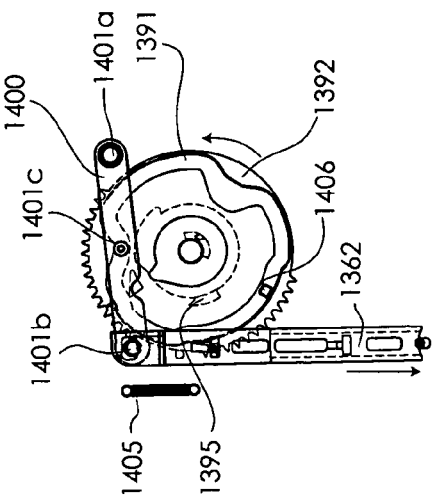
Figure 40F:
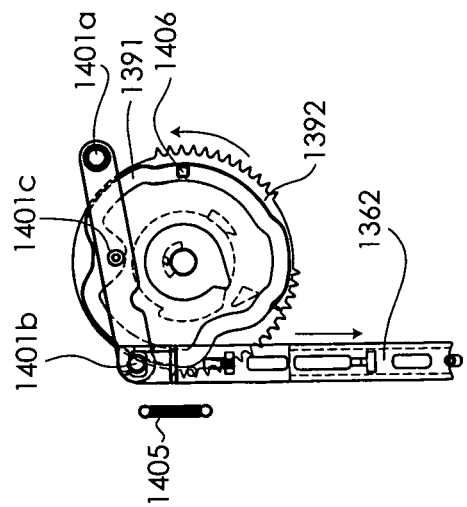
Figure 40E:
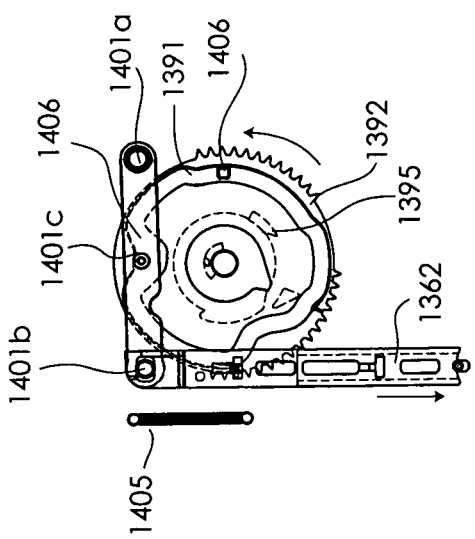

Rotation of main gear 1390 rotates cam 1392 to a first pre-determined angle, as shown in FIG. 40B. At this first pre-determined angle, the lancing cam latch 1396 (see FIG. 37F), biased downward by a torsion spring 1398, biases cam latch 1396 in the clockwise direction which then catches protrusion 1393 on the lancing cam 1392 and prevents the lancing cam from further rotation. However, since the main gear is connected to the lancing cam only through the clock spring 1394, it continues to rotate and, in the process, increases the clock spring torsion. This wind-up segment traverses about 45 degrees of the main gear's rotation. At the end of the wind-up segment, the main gear knock-off dog 1397 is positioned underneath the cam latch 1396, forcing it in the counterclockwise direction until protrusion 1393 is no longer captured. At this point, clock spring 1394 is fully wound and cam 1392 is free to rotate. The wound up clock spring energy is thus released and cam 1392 races to catch up with main gear 1390. After 45 degrees of very fast, accelerating motion, lancing cam stop 1395 hits a mating surface 1399 (see FIG. 37F) on main gear 1390. When the clock spring 1394 is released, the potential energy created in it effects a quick, downward stroke by carriage assembly 1362, as illustrated in FIG. 40C, orienting and moving the STRIPLET™ through the motion required to substantially painlessly lance the skin and extract body fluid. It is noted that, if cam 1392 were directly driven by motor 1356b as the main gear 1390 is, the lancing stroke would be positive but relatively slow, and thus, very painful for the user. As clock spring 1394 unwinds, the upward bias placed on carriage assembly 1362 by coil spring 1405 drives it back upwards, as illustrated in FIG. 40D. Meanwhile, the continued rotation of main gear 1390 to a second pre-determined angle causes a dog or knock-off cam 1397 on the rotating main gear 1390, as shown in FIG. 37D, to contact the spring loaded lancing cam latch 1396 and move in the counterclockwise direction, knocking it off of the lancing cam latch catch 1393 on lancing cam 1392. This action, in turn, knocks lancing cam 1392 off the main gear, thereby causing the lancing cam 1392 to quickly rotate in the clockwise direction to "catch up" with the main gear 1390, at which point the cam and main gear slowly rotate in tandem again to a third pre-determined angle to commence the sensing phase of the device. At this point, pin 1401c on follower arm 1400 is moved to a cut-away portion 1406 within groove 1391, as shown in FIG. 40E, thereby "disengaging" carriage 1362 from being driven by cam 1392. Meanwhile, the STRIPLET-loaded turret 1364 is reoriented by the reorienting sub-assembly, discussed below, with respect to the carriage 1364. The cut-away places cam 1391 in a neutral position relative to carriage 1362 and, as such, the movement of carriage 1362 is effected solely by the light bias of coil spring 1405, being moved slowly downward, as illustrated in FIG. 40F. The sensing end of the STRIPLET™ is thus gently moved against the user's skin at the lancing sight, thereby collecting the body fluid. Motor 1356b, which drives lancing cam 1392, may be stopped when carriage 1392 is fully extended downward to ensure sufficient fluid is collected by the STRIPLET™ for analysis. As the lancing cam 1392 continues to rotate, lancing follower arm 1400 is driven back up to the neutral position with the STRIPLET™ now fully contained within the primary assembly 1328 and oriented to engage with electronic contacts within the meter. Thus, carriage 1362 is cam-driven to effect a fast, positive stroke during the lancing segment/phase, and then spring-driven to effect a slow, gentle stroke during the collecting/sensing segment. The analyte concentration within the body fluid collected by the STRIPLET™ is then detected by the meter electronics and the resulting data displayed for the user.

The purpose of the reorienting sub-assembly is to orient the STRIPLET™ with respect to carriage 1392 in three or more distinct orientations to prepare the STRIPLET™ for lancing, fluid collection/analyte sensing and ejection from the device. Reorientation of the STRIPLET™ may include flipping/rotating the STRIPLET™ about its longitudinal axis and/or transversely to its longitudinal axis. The gears and associated components which provide the reorienting sub-assembly, some of which provide functionality to other subsystems of the apparatus, are best illustrated in FIGS. 37D, 38E-38G and FIGS. 41A-41C.

Second motor 1356b which, by way of its output pinion gear 1386, drives idler gear 1388 which, in turn, drives main gear 1390 which, in turn, by means of a face groove cam track 1387, rotates a broom gear 1402 consisting of a cam follower pin 1402a (residing within track 1387) and a partial toothed gear segment 1402b. Gear segment 1402b communicates with a male Geneva gear 1404 which, in turn, drives a female Geneva gear 1407 (shown partially in phantom from behind the male Geneva gear in FIGS. 41A-41C) by way of two pins 1404a, 1404b on the male gear 1404 which are matingly received within corresponding grooves 1407a, 1407b within the female gear. The female Geneva gear 1407 is directly affixed to an end of the turret 1364 such that rotation of that gear causes the turret to rotate into three discrete functional positions, thereby flipping the STRIPLET™ about the transverse axis of carriage 1362.

Various stages in the reorientation of STRIPLET™ are described in greater detail with reference to FIGS. 41A-41C. In general, main gear 1390 rotates counterclockwise with follower pin 1402a moving in an arc defined by the distance from the pin center to the broom gear axis of rotation, and thus, moving up and down relative to main gear 1390. As follower pin 1402a moves downward relative to main gear 1390, the toothed segment 1402b of broom gear 1402 moves counterclockwise relative to the broom gear axis of rotation. Conversely, as follower pin 1402a moves upward relative to main gear 1390, the toothed segment 1402b rotates clockwise relative to the broom gear axis of rotation 1402c. In the orientation shown in FIG. 37D, as well as in FIG. 41A, follower pin 1402a, situated within cam groove 1387, is positioned midway between its innermost and outermost radial positions, i.e., in the neutral or load position, at which point the STRIPLET™ is advanced into the turret (not shown). As main gear 1390 rotates counterclockwise approximately ⅛ of a rotation (e.g., to approximately 44 degrees in one embodiment) from the home position, broom gear follower pin 1402a is guided at a constant radius with no radial motion. As shown in FIG. 41B, upon further counterclockwise rotation of main gear 1390, from about ⅛ to about ⅕ of a rotation (e.g., to approximately 72 degrees in the one embodiment), cam track groove 1387 and broom gear follower pin 1402a transition radially inward causing broom gear 1402 to rotate clockwise about its fixed axis of rotation 1402c. Meanwhile, gear mesh 1402b between broom gear 1402 and male Geneva 1404 causes the latter to rotate about ¼ turn (e.g., to approximately 90 degrees in the one embodiment) counterclockwise about its axis which, in turn, causes female Geneva gear 1407 to rotate approximately ¼ turn or 90 degrees clockwise about its axis, thereby causing the turret (not shown) to rotate clockwise approximately ¼ turn or 90 degrees to position the lancing end of the STRIPLET™ downward in the lancing position. As main gear 1390 continues to rotate counterclockwise, as shown in FIG. 41C from about ⅕ to about ⅖ of a rotation (e.g., to approximately 154 degrees in the one embodiment), broom gear follower pin 1402a is guided at a constant radius without any radial motion. Upon further counterclockwise rotation of main gear 1390 to about ⅗ of a rotation (e.g., to approximately 209 degrees in the one embodiment), cam track groove 1387 and broom gear follower pin 1402a transition radially outward causing broom gear 1402 to rotate counterclockwise about its fixed axis of rotation. This reverses the motion described above and results in the counterclockwise rotation of female Geneva gear 1407 of about ½ turn or 180 degrees, thereby rotating the turret (not shown) a further ¼ turn or 90 degrees or so in the clockwise direction to position the sensing end of the STRIPLET™ downward in the sensing position (i.e., the lancing end of the STRIPLET™ is now pointing upward). As main gear 1390 continues to rotate counterclockwise to about ¾ of a rotation (e.g., to approximately 274 degrees in the one embodiment), broom gear follower pin 1402*a* is guided at a constant radius without any radial motion. From about ¾ to about ⅘ of a rotation (e.g., to approximately 302 degrees in the one embodiment) of main gear 1390 in the counterclockwise direction, cam track groove 1387 and broom gear follower pin 1402*a* transition radially inward to the medial position, as in FIG. 41A, causing broom gear 1402 to rotate clockwise about its fixed axis of rotation. This, again, reverses the previous motion and rotates female Geneva gear 1407 clockwise about ¼ turn or 90 degrees, thereby rotating the turret (not shown) about ¼ turn or 90 degrees, placing the STRIPLET™ in the neutral position once again. The turret remains in this neutral position as the main gear 1390 completes one full rotation cycle (i.e., 360 degrees) and until the point and shoot cycle of the device is once again initiated by the user.

The cap adjustment sub-assembly is described with reference to FIG. 36D. The effective depth of lancet penetration into the skin of the user is controlled by adjusting the vertical position of expression cap 1312. The lancet penetrates deeper into the subject's skin as the cap 1312 is moved up toward the meter structure, and penetrates less as the cap 1312 is moved away from the meter. The cap is securely fixed into a sliding frame 1322 constrained by features in rear outer housing 1324 and front outer housing 1302 at one end, and by gear retaining plate 1344 and adjustment knob 1324 at the other end, which allow it only to move vertically up and down. Frame 1322 is actuated by a cam groove 1324*b* in adjustment knob 1324 communicating to lift pin 1332 attached to frame 1322. Adjustment knob 1324 is constrained to rotate within feature 1329 fabricated into plate 1327. Additional features within plate 1327 result in a detented action such that the knob remains in one of several pre-determined angular positions, thereby resulting in a similar number of vertical frame positions, thereby determining a similar number of lancing depth settings. These settings are indicated to the user by numbers on knob 1324 and visible though opening or window 1324*c* in front outer housing 1302.

As mentioned previously, the subject devices perform the aforementioned functions in a single "point and shoot" cycle based on the integrated workings of the above-described sub-assemblies. Certain of the primary activities performed by the collective assembly are as follows: The first motor 1356*a* runs so as to drop (open) the tub 1352, thereby breaking the hermetic seal around the bottom end of the STRIPLET™ cartridge and providing an exit path for a single STRIPLET™. The first motor 1356*a* advances the chain 1346 such that its pusher segment 1346*a* interfaces with the bottommost STRIPLET™, pushing it out into turret 1364 where it is secured into place therein by a detent. The second motor 1356*b* drives the uncap lever arm 1358 to engage the cap of the fed STRIPLET™ and locks the cap to the chain 1346. Second motor 1356*b* then runs in reverse so as to pull the protective lancet cap off the STRIPLET™, exposing the lancet. Motor 1356*b*, again, runs in the forward direction so as to rotate the STRIPLET™ such that the lancing end is pointing down towards the skin surface, and continues to run so as to wind up clock spring 1394. Upon being fully wound, the clock spring is released, in turn, driving the lancet end of the STRIPLET™ downward at a high rate of speed to lance the patient's skin and extract bodily fluid, i.e., blood, and then is immediately retracted. Motor 1356*b* continues to rotate the STRIPLET™ 180 degrees such that the sensing/testing end points toward the lancing site with the now-extracted body fluid, and then gently and more slowly moves the sensing end of the STRIPLET™ against the exposed fluid, pausing for fluid collection to take place. Use of the clock spring allows the lancing action to be performed at a much faster rate of speed as opposed to the slower rate at which the sensing action is performed. As such, the former action minimizes pain to the patient and the latter allows a sufficient amount body fluid, e.g., blood, to be drawn onto the sensing portion of the STRIPLET™. The motor continues so as to rotate the STRIPLET™ back to its original position, i.e., the position it was in when it was advanced to turret 1364. First motor 1356*a* then pushes the cap back over the used lancet end of the STRIPLET™. Second motor 1356*b* continues so as to lift the uncap lever 1358, unlocking the cap from the advance chain. First motor 1356*a* continues to push the used, recapped STRIPLET™ through STRIPLET™ ejection port 1318, and then retracts chain 1346 so as to appose pusher 1346*a* with the next or bottommost STRIPLET™ within the cartridge while, at the same time, lifting tub 1352 to seal against the cartridge.

In an alternative embodiment, a medical diagnostic device is provided that carries out the functions of:
(a) storing a plurality of lancets and sensors;
(b) feeding a plurality of lancets and sensors to a system that employs a lancet to form an opening in the skin of a patient and then employs the sensor to collect a sample of biological liquid that emerges from the opening formed in the skin;
(c) forming an opening in the skin of the patient by means of the lancet;
(d) collecting the sample of biological liquid emerging from the opening formed in the skin of the patient by means of the sensor;
(e) analyzing the sample of biological liquid collected by the sensor; and
(f) ejecting the used lancet and the used sensor in a safe manner.

In a further embodiment, a test strip includes a lancet-containing portion and a sensor-containing portion. During the time that the test strip is stored in the medical diagnostic device, a protective cover encloses the lancet of the lancet-containing portion. The medical diagnostic device is capable of removing the protective cover to enable the lancet to form an opening in the skin of the patient and is further capable of re-attaching the protective cover onto the lancet to enable the medical diagnostic device to eject the used test strip in a safe manner.

In another embodiment, a lancing/collecting assembly receives a test strip that includes both a lancet-containing portion and a sensor-containing portion. By means of various operations, the lancing/collecting assembly is configured to (a) orient the lancet-containing portion of the test strip in such a manner that the lancet of the lancet-containing portion of the test strip can be advanced toward a lancing and testing site on the skin of the patient in order to form an opening therein, (b) arm the lancet of the lancet-containing portion of the test strip, (c) trigger the armed lancet of the lancet-containing portion of the test strip so that the lancet forms an opening in the skin of the patient at the lancing and testing site, (d) orient the sensor-containing portion of the test strip in such a manner that the sensor-containing portion of the test strip can be advanced toward the opening formed in the skin of the patient to collect a sample of biological liquid emerging from the opening in the skin of the patient at the lancing and testing site which remains proximate to a lancing and testing port of an analyte, e.g., glucose, monitoring apparatus; and (e) advance the sensor of the sensor-containing portion of the test strip so that sufficient quantity of the sample of biological liquid can be collected for analysis to determine a parameter of the biological liquid, e.g., a body analyte, e.g., glucose, level.

The lancing/collecting assembly may also incorporate an analyzer that is capable of analyzing the sample of biological liquid collected from the opening in the skin of the patient.

In another embodiment, a storing/dispensing assembly is provided for a plurality of test strips, each of which includes a lancet-containing portion and a sensor-containing portion.

In a further embodiment, a method for using a medical diagnostic device includes:
(a) feeding one of multiple test strips, each of the test strips having a lancet-containing portion and a sensor-containing portion, to a lancing/collecting assembly that employs a lancet of the lancet-containing portion to form an opening in the skin of a patient, and then employs a sensor of the sensor-containing portion to collect a sample of biological liquid that emerges from the opening formed in the skin;
(b) forming an opening in the skin of the patient by means of a lancet in the lancet-containing portion;
(c) collecting a sample of biological liquid emerging from the opening formed in the skin of the patient by means of the sensor of the sensor-containing portion;
(d) analyzing the sample of biological liquid collected by the sensor of the sensor-containing portion; and
(e) ejecting the used test strip in a safe manner.

The medical diagnostic device of this embodiment can perform a plurality of diagnostic tests, e.g., 25 tests, before the device requires refilling with test strips. The medical diagnostic device can perform the functions of storing and dispensing test strips, lancing the skin of a patient, collecting a sample of biological liquid, analyzing the sample of biological liquid collected, and disposing of used test strips. In the case of collection of an inadequate quantity of sample, the medical diagnostic device enables re-lancing.

In accordance with another embodiment, the medical diagnostic device requires only a small volume of sample to carry out a complete test, e.g., 0.3 microliter (see, e.g., U.S. Pat. Nos. 7,058,437, 6,618,934, 6,591,125 and 6,551,494, which are hereby incorporated by reference).

The test strip combines a lancet and a sensor in a single small unit. After the skin of the patient is pierced and a sample of biological liquid, e.g., blood, appears, the test strip is moved into position for collecting a sample of the liquid, and the liquid enters the sample application zone of the sensor-containing portion of the test strip without manipulation of the test strip by the user.

Further features and advantages include the small, readily portable and storable size of the integrated meter. The integrated meter is small enough to be handheld, and easily handled by a self-care diabetic. In some embodiments, the meter is less than 5" tall, less than 3" wide, and less than 1.5" deep. In some of these embodiments, the meter is less than 4" tall and in one embodiment, just under 3.5" tall. In some embodiments, the meter is less than 2.6" wide, such as between approximately 2.5" and 2.6" wide, and just under 1.5" deep. The meter may be rectangular, or one or both sides may be contoured concave or convex, as may the top and/or bottom, and the front and back faces.

In some embodiments, the meter may be plugged in, but is also powered by a battery which is located substantially opposite to where the STRIPLETS™ are accessed, i.e., disposed oppositely in at least one dimension of the meter. The battery may be provided in a compartment at the top and back of the meter, which is opposite the STRIPLET™ access near the front and bottom of the meter, i.e., disposed oppositely in at least two dimensions. In some embodiments, the STRIPLET™ is exposed from lancing and testing and ejection at one side of the meter, while the battery compartment is at the other side, i.e., disposed opposite the STRIPLET™ access in all three dimensions.

The STRIPLET™ is also small in size. Generally the STRIPLET™ is less than 2 mm×less than 1 mm×less than 0.3 mm, and in some embodiments, less than 1.5 mm×less than 0.75 mm×less than 0.2 mm, e.g., approximately 1 mm×0.5 mm×0.1 mm.

The meter and STRIPLET™ are advantageously ideal for alternative site testing, i.e., away from the fingertips, where smaller amount of blood are available than at the fingertips, such as less than 1 microliter, and even less than 0.5 microliters, or less than 0.3 microliters, or less than 0.2 microliters, or even 0.1 microliters (100 nanoliters). See for example U.S. Pat. No. 6,284,125 which describes this feature in more detail and in incorporated by reference.

The system includes, in some embodiments, calibration one or more schemes. A calibration module, whether it be a bar code, a RFID tag, a label, or otherwise may be located on a STRIPLET™ and/or on a STRIPLET™ container. U.S. application Ser. No. 11/350,398, which is assigned to the same assignee and incorporated by reference, provides further examples. There may be contact pads that may be shorted together or kept apart during the test strip manufacturing process in order to communicate a calibration code to the meter. There may be a set of contact pads and a varying resistance between the two pads where the resistance is changed during the manufacturing process of the test strip to communicate a calibration code to the meter. There may be an electrical memory that is readable and writable by the meter, which communicates a calibration code to the meter. A calibrator can carry other information such as STRIPLET™ expiration and/or a STRIPLET™ number count down.

In addition, a data processing terminal may include a personal computer, a portable computer such as a laptop or a handheld device (e.g., personal digital assistants (PDAs)), and the like, each of which may be configured for data communication with the integrated meter, or a receiver associated therewith, via a wired or a wireless connection. Such data processing terminal may be connected to a data network for storing, retrieving and updating data corresponding to a detected analyte level of a user.

The data processing terminal may include an infusion device such as an insulin infusion pump or the like, which may be configured to administer insulin to patients, and which may be configured to communicate with the integrated meter for receiving, among others, the measured analyte level and/or transmitting insulin dose values or other information relating to a diabetes care or other health care regimen. Alternatively, a receiver unit may be especially provided for receiving communications from the integrated meter, and may be configured to integrate an infusion device therein or otherwise communicate therewith. The receiver unit may be configured to administer insulin therapy to patients, for example, for administering and modifying basal profiles, as well as for determining appropriate boluses for administration based on, among others, the detected analyte levels received from the integrated meter.

Additionally, the integrated meter may be configured for bi-directional wireless communication, or may be configured in a network of devices that communication via a network hub. The integrated meter may be configured to communicate (that is, transmit data and/or receive data) from multiple devices via a wired or wireless communication link. The communication link may include one or more of an RF communication protocol, an infrared communication protocol, a Bluetooth enabled communication protocol, an 802.11x wireless communication protocol, or an equivalent wireless communication protocol which provides secure, wireless communication of several units (for example, per HIPPA requirements) while avoiding potential data collision and interference.

The present invention is not limited to the embodiments described above herein, which may be amended or modified without departing from the scope of the present invention as set forth in the appended claims, and structural and functional equivalents thereof. The Background section is incorporated by reference into the detailed description as disclosing alternative embodiments.

In methods that may be performed according to embodiments herein and that may have been described above and/or claimed below, the operations have been described in selected typographical sequences. However, the sequences have been selected and so ordered for typographical convenience and are not intended to imply any particular order for performing the operations.

What is claimed is:

1. An analyte testing apparatus, comprising:
   a housing;
   one or more analyte testing structures that are rotatable about 180° from a first position to a second position provided in the housing, wherein each structure comprises a lancet and an analyte test sensor;
   a port in the housing for the analyte test structure to contact a lancing site on a subject; and
   a set of components for advancing an analyte testing structure through the port at a first rate for lancing the lancing site, retracting the analyte testing structure, reorienting the analyte testing structure, and advancing the analyte testing structure through the port at a second rate for testing at the lancing site, the second rate slower than the first rate;
   wherein the set of components comprises a gear coupled to a cam, the gear and cam having a first configuration wherein the cam is movable in concert with the gear through a first biasing element, wherein the movement of the cam in concert with the gear stores potential energy in the first biasing element;
   the gear and cam having a second configuration wherein the cam is independently movable with respect to the gear through a release of the potential energy stored in the first biasing element, wherein the independent movement of the cam provides the advancing of the analyte testing structure through the port at the first rate for lancing;
   the gear and cam having a third configuration wherein the cam is in a neutral position relative to the analyte testing structure, wherein the analyte testing structure is advanced through the port at the second rate for testing by a second biasing element, and
   wherein the set of components comprises a carriage including a turret, wherein the analyte testing structure is disposed in the turret during the advancing for lancing the lancing site, the reorienting, and the advancing for testing the lancing site; wherein the turret rotates for reorienting the analyte testing structure; wherein the cam is coupled to the carriage to advance the carriage at the first rate; and wherein the second biasing element is coupled to the carriage to advance the carriage at the second rate.

2. The apparatus of claim 1, further comprising a cartridge held within an interior space within the housing, the cartridge containing a plurality of analyte testing structures.

3. The apparatus of claim 2, wherein the cartridge comprises at least one guide rail for relative positioning within the housing with respect to the set of components.

4. The apparatus of claim 2, further comprising a seal which generally maintains the analyte testing structures within the cartridge free from exposure to ambient air, and wherein the apparatus is configured to release the seal temporarily to permit loading of a single analyte testing structures for lancing and testing.

5. The apparatus of claim 4, wherein the seal comprises an elastomeric material.

6. The apparatus of claim 2, further comprising a biasing member at a loading end of the cartridge for biasing the analyte testing structures toward a dispensing end of the cartridge.

7. The apparatus of claim 1, wherein the set of components comprises a turret for holding an analyte testing structure during reorientation.

8. The apparatus of claim 7, wherein the turret is movable relative to the housing in a same direction for both the lancing and the testing.

9. The apparatus of claim 1, wherein each of the one or more analyte testing structures further comprises a cap covering the lancing end; and wherein the set of components includes a mechanism for removing the lancet cap.

10. The apparatus of claim 9, wherein the set of components includes a mechanism for replacing the lancet cap.

11. The apparatus of claim 1, wherein the first biasing element is a torsion spring or a clock spring, the torsion spring or the clock spring advancing the analyte testing structure through the port at the first rate for lancing the lancing site.

12. The apparatus of claim 1, wherein the second biasing element is a coil spring, the coil spring advancing the analyte testing structure through the port at the second rate for testing at the lancing site.

13. The apparatus of claim 12, wherein the coil spring is biased to have an amount of potential energy to provide a force of about 2 ounces.

14. The apparatus of claim 12, wherein a biasing of the coil spring requires force from the cam to be removed in order to advance the analyte testing structure through the port at the second rate for testing at the lancing site.

15. The apparatus of claim 1, wherein the set of components comprises at least one motor for driving certain other components.

16. The apparatus of claim 1, further comprising a plurality of electro-optical encoders associated with the at least one motor for determining the position and speed of the respective components which it drives.

17. The apparatus of claim 16, further comprising a plurality of sensors positioned within the housing along a path traversed by an element, wherein the encoders and sensors function within a closed loop control system.

18. The apparatus of claim 1, wherein the set of components comprises a slot for holding the analyte testing structure during re-orientation of the analyte testing structure.

19. The apparatus of claim 18, wherein the analyte testing structure slot is coupled with a cam that oscillates between points corresponding to different orientations of the analyte testing structure for lancing and testing.

20. The apparatus of claim 19, wherein the oscillation is about a point of unstable equilibrium.

21. The apparatus of any of claims 1, wherein opposite ends of the analyte testing structure are sequentially provided through the port for the lancing and the testing.

22. The apparatus of any of claims 1, wherein the analyte comprises glucose or ketone bodies.

* * * * *